US006855517B2

(12) United States Patent
Salceda et al.

(10) Patent No.: US 6,855,517 B2

(45) Date of Patent: Feb. 15, 2005

(54) COMPOSITIONS AND METHODS RELATING TO BREAST SPECIFIC GENES AND PROTEINS

(75) Inventors: Susana Salceda, San Jose, CA (US); Roberto A. Macina, San Jose, CA (US); Herve E. Recipon, San Francisco, CA (US); Robert Cafferkey, San Jose, CA (US); Yongming Sun, San Jose, CA (US); Chenghua Liu, San Jose, CA (US)

(73) Assignee: diaDexus, Inc., South San Francisco, CA (US)

( * ) Notice: Subject to any disclaimer, the term of this patent is extended or adjusted under 35 U.S.C. 154(b) by 207 days.

(21) Appl. No.: 10/001,887

(22) Filed: Nov. 20, 2001

(65) Prior Publication Data

US 2002/0155464 A1 Oct. 24, 2002

Related U.S. Application Data

(60) Provisional application No. 60/252,563, filed on Nov. 22, 2000, and provisional application No. 60/249,998, filed on Nov. 20, 2000.

(51) Int. Cl.[7] .......................... C12Q 1/68; C07H 21/04

(52) U.S. Cl. ..................................... 435/69.1; 536/23.5

(58) Field of Search ............................ 435/69.1, 252.3, 435/320.1, 810; 536/23.5

(56) References Cited

FOREIGN PATENT DOCUMENTS

| | | | |
|---|---|---|---|
| EP | 1 033 401 A2 | | 9/2000 |
| EP | 1 074 617 A2 | | 7/2001 |
| WO | WO 99/02559 | | 1/1999 |
| WO | WO 99/22027 | | 5/1999 |
| WO | 99/58675 | * | 11/1999 |
| WO | WO 99/58675 | | 11/1999 |
| WO | WO 01/55312 A2 | | 8/2001 |
| WO | WO 01/60860 A2 | | 8/2001 |
| WO | WO 02/40672 A2 | | 5/2002 |
| WO | WO 02/064611 A1 | | 8/2002 |
| WO | WO 02/070539 A2 | | 9/2002 |

OTHER PUBLICATIONS

Lipowsky et al., "Exportin 4:a mediator of a novel nuclear export pathway in higher eukaryotes", The EMBO Journal 2000 19 (16) :4362–4371 reprinted and pp. 1–3 are provided.

Nagase et al., "Prediction of the Coding Sequence of Unidentified Human Genes. XIX. The complete Sequences of 100 New cDNA Clones From Brain Which Code for Large Proteins in vitro", DNA Research 2000 7:347–355.

NiceProt View of Swiss–Prot:Q9C0E2 Feb. 2003.

NiceProt View of Swiss–Prot:Q9ESJ0 Feb. 2003.

NCBI Genbank Accession No. NP_071904 [gi:11967999] Dec. 19, 2000—Jul. 14, 2001 with Revision History—The Revision History of 38570160 which replaced 11967999 is provided.

NCBI Genbank Accession No. BAB21812.KIAA1721 [gi:12697987] Feb. 7, 2001 with Revision History.

NCBI Genbank Accession No. NP_065252 [gi:10048438] Sep. 11, 2000—Jan. 7, 2002 with Revision History.

NCBI Genbank Accession No. BAB14409 [gi:10434878] Sep. 29, 2000 with Revision History.

NCBI Genbank Accession No. AK023108 [gi:10434877] Sep. 29, 2000 with Revision History.

NCBI Genbank Accession No. AK057924 [gi:16553905] Oct. 31, 2000 with Revision History.

NCBI Genbank Accession No. AB051508 [gi:12697986] Feb. 7, 2001 with Revision History.

NCBI Genbank Accession No. NM_022459 [gi:11967998] Dec. 19, 2000—Jul. 14, 2001 with Revision History—The Revision History of 38570159 which replaced 11967998 is provided.

* cited by examiner

*Primary Examiner*—Kenneth R. Horlick

(74) *Attorney, Agent, or Firm*—Licata & Tyrrell P.C.; Nathan P. Letts

(57) ABSTRACT

The present invention relates to newly identified nucleic acids and polypeptides present in normal and neoplastic breast cells, including fragments, variants and derivatives of the nucleic acids and polypeptides. The present invention also relates to antibodies to the polypeptides of the invention, as well as agonists and antagonists of the polypeptides of the invention. The invention also relates to compositions comprising the nucleic acids, polypeptides, antibodies, variants, derivatives, agonists and antagonists of the invention and methods for the use of these compositions. These uses include identifying, diagnosing, monitoring, staging, imaging and treating breast cancer and non-cancerous disease states in breast tissue, identifying breast tissue, monitoring and identifying and/or designing agonists and antagonists of polypeptides of the invention. The uses also include gene therapy, production of transgenic animals and cells, and production of engineered breast tissue for treatment and research.

8 Claims, No Drawings

SEQUENCE LISTING

<160> NUMBER OF SEQ ID NOS: 137

<210> SEQ ID NO 1
<211> LENGTH: 1632
<212> TYPE: DNA
<213> ORGANISM: Homo sapien

<400> SEQUENCE: 1

```
ggtcgcggcc gaggtccttc cccttttttt tttttttttt tttttttttt ttttttgggt     60
ccaaatttac gggttttttt tttgggcaca ataaaaacac tctaaaatct tttttcccac    120
accctttttt ttttaaattt tgcgcacacg gggtgtattt ttgttccaca caaaacatct    180
attcacattg tgtttacacc ctcttatttt ctttgagaaa accacaacat attttattta    240
aatattgtgt ttgtgtcttc tctaaaaacg cctcttattc cctctcccac gtttctcaat    300
ctctttgtgt atattgtgtg tatatttaaa gcacacataa gagatgttat attgtgtgtg    360
tgcacactac tctctctatg ttcaacacac acacacatat atataccccct ctatgggaca    420
catatatata aacaatatat gtgatgacac acacagatct gttatgtgac actatttctc    480
acacacatat ataaagtcta tctctcttct aatatatctc acggtgtata tatcacagtg    540
tattcatcac aggaaatata tatgtgtgtg ctcggcccgc tctatatata tatacactac    600
atatataaca catatatcta taacatctgg tgtatgtggg cttaaaacac gacatataat    660
atatcatgtt atatctaccc acacaggata tgtgtgtaca cacaaagagg gagaagataa    720
tatgtgtata tctctcccct actctctcta aacaacctcc cctctatata cacacaggtg    780
tgtagagaaa gtagttataa ggggagttgt tttcgtgttc tacaaagggg cgcagaacag    840
taacaaatac tgttgtgagg gtgtcgttct catctatcaa tattttccac agctaatatt    900
tcccgcgggt gtatataata tctagagggg agggcaatcg tgggcgtcgt attctcatgt    960
gggagagtaa taatgtcggc tctcttaaag gggggtggttg tagaaccccc ctccctataa   1020
tagtaaaaga tgtttaacac agccaacggg tggctgcttg ttgatgacat aatatcgcac   1080
caccaaatgt gggtgtggtg ggggaggcaa ctacacgacg gagacaaaca aattgcggcg   1140
ggtggcggcc gcccgattct gtatttattc gaacgccgcg cctgtgttgt gttgtgcggc   1200
aactatctgc gcctacttgc ttgctcacca aacaataata tataggcggg agcgggtgct   1260
ggcgaggaga gacacacacg tctttccccg ccgaacaaac aaaacagagg gggcggatga   1320
ctgacgcctg attgtataga aacaaaaacg atcgaacgac gaaggcaacg atccgtctat   1380
tgcgacgtca gacaacgcgc gcctccttct cttccagggg gggggggata gatacttagg   1440
gtagatacta ccgtagtagt atttgtgcgc ggcagcacac gacgaaagac ttactcagag   1500
agtgtctccc ccacccaagg aggtagaaat gaagtgggga ggacgactac ttctacaaac   1560
ataagtaagg gggggtgata ataacgaggg gcgctcagac aacggaggtt ctattacatc   1620
tgtgcgcgcc ga                                                        1632
```

<210> SEQ ID NO 2
<211> LENGTH: 163
<212> TYPE: DNA
<213> ORGANISM: Homo sapien

<400> SEQUENCE: 2

```
gagagaacac taggggcagg ttcctgagca ggcggcggcg ctgggaggag aatgtatgcg     60
agacctctta tataattgat tgacgcaaac ttgtcctcct ctaagaggag agagtctgct    120
```

```
taagcgtaag tttgccagtg caaaaagcca taataataag tat                    163


<210> SEQ ID NO 3
<211> LENGTH: 666
<212> TYPE: DNA
<213> ORGANISM: Homo sapien
<220> FEATURE:
<221> NAME/KEY: misc_feature
<222> LOCATION: (166)..(166)
<223> OTHER INFORMATION: a, c, g or t
<221> NAME/KEY: misc_feature
<222> LOCATION: (332)..(332)
<223> OTHER INFORMATION: a, c, g or t

<400> SEQUENCE: 3

cttttatttt tttttttttt tttttttttt tttttttttt ttttttcccc ttttttaatt     60

ttaaaattag gcccacgggg gggattttta taaacctcta tttattttcc aacaaatttt    120

gtggtccaaa tataaaactc atttttttct accttacaca acttgncctt ctttattctc    180

atttttaaat gatggatata cctcacaact ctctgcgtct caaaccaaat tctttttttc    240

ttaaacagtg acgcgtggta aactctccta tacccttatc tatttccccc gcggtgggaa    300

aaattagcct tttcaaaatg tgttctcccc antcttgtgg cttattaaaa ggtggggaat    360

tccctttctt tgtgggacgc ccctatactg tttgtctctg gctctccttt taggcccgag    420

gagaatttct tcctcccagg tgagagagag gcgggtttca ccgcagtata taaaccgcca    480

aagctggggc ggatacgtcg gtggtccact agccgtgttc cccttggttg tgaaaatttg    540

ttattcccgc cctcacaatt ctcccccccca aatactccac ccaccccaac ccgcagcgga    600

gtacggacaa cgacgacacc acgacgataa tacgaacaaa gcaacctaac atcgaacact    660

acacaa                                                               666


<210> SEQ ID NO 4
<211> LENGTH: 1107
<212> TYPE: DNA
<213> ORGANISM: Homo sapien

<400> SEQUENCE: 4

cccccccccc ccccctcctc ccgatgtgtt caccctatag ggcgcaattg ggcctctaga     60

ttctgctcga gcggcgcagt gtgatggatc ggccgcccgg gcaggttttt tttttttttt    120

tttttttttt tttttttttt tttttttttt tttttttttt ttttttgggg gggccccctt    180

ttttttttccc cccccccccc cctttttttt ttccgggggg gggggcccta ctaaagacag    240

ccggctaccg aaaaaaatac acctagggtt tattttcacc cccaatcacc atggttgtcg    300

acccccccag gggggctct ctttcttttt cccaactctc ccaaccgacg tggttttcct    360

ccccctacc gtcgtggggg gtaccccgtg cgccacagtc ggtgtgttcc cgctgtgtgg    420

taggaaagtg tgtttctctc ccgcctcacc gaccttcttc ccacccacac aaacatatgc    480

agcagcgcca agaacacaaa ctcgttccga ccggacggcc cggacggaac gggcgatgtg    540

aggctcgacg caaccatatg caagggacgg catcacagag cccgaccagg atcgcagcca    600

gcgatcgcac ggacgaacag cgcatcgcgc cgccgcacca cccacccggc ccgcaggggg    660

agatcaatac atgcggccgt gcagcctcca agggcccaac caccaagctc ggcgcggaat    720

caggacggac catgacgcac accgaacgac gaagaccaaa gcaacatctc gccacgaacg    780

cccaaagacc gcgattgcac aggcacccaa cgtgtatccg aaggatgagc gactgacacc    840

aacacacctg tggcctgcct tgatgctgca cggcgcgaaa cggagatcct gccggtcgtc    900
```

```
gccacgcgta cccacagaaa gccaacaagc gacacgacac cacaacacac cgaagcagct    960

cacggaggaa gagatgcaaa gaacaacgac aaatgaacac aaaaaacgac cacaaacaga   1020

gatgagtaca accgacaaac aaaaaaagca agactcaaac acacaccgag cagtaagtgc   1080

gatacagcaa agagaccaga caaccaa                                        1107


<210> SEQ ID NO 5
<211> LENGTH: 720
<212> TYPE: DNA
<213> ORGANISM: Homo sapien
<220> FEATURE:
<221> NAME/KEY: misc_feature
<222> LOCATION: (364)..(364)
<223> OTHER INFORMATION: a, c, g or t
<221> NAME/KEY: misc_feature
<222> LOCATION: (429)..(429)
<223> OTHER INFORMATION: a, c, g or t
<221> NAME/KEY: misc_feature
<222> LOCATION: (459)..(459)
<223> OTHER INFORMATION: a, c, g or t
<221> NAME/KEY: misc_feature
<222> LOCATION: (637)..(637)
<223> OTHER INFORMATION: a, c, g or t
<221> NAME/KEY: misc_feature
<222> LOCATION: (654)..(654)
<223> OTHER INFORMATION: a, c, g or t

<400> SEQUENCE: 5

ccgcccgggc aggtccctcc tttttttttt tttttttttt tttttttttt ccttttttaa     60

aaaatattaa ctttgttttt taatcattgg gagggggggc cccgaagaag ggggtagggg    120

ccccagggaa gggggggtc tgtgaaaata ataaccaaaa atgtgttgaa agaaaagggg    180

gggtgtttaa aagcggccgt ggccaggggg tctcccccgg gttctcgctt tctgtgggaa    240

ggggacgcgc cttgtgagga agggagttct gtatgcaacg cctattagtc ttggtgcctc    300

ccaattcact attataaaaa atttctgtga aaacttctta gcttgcccat ctcgggtggt    360

gggntgtctc tagttctttc tcatctcatg tgcgggccag aggcacccca gggggctcct    420

ctcgtagcnt cctgtggtgg aaaggggaca gccatagtnt cgcgtgatat ctctcatgta    480

aatagcgctg gggggcgtat aaactcgtgt gggggcacat atagcgcgtg tgttgccgcg    540

tgggtgaggt ggaagcatgt gtgggttttc tgtgcgcgcg cctcacacat attacccccc    600

aacaactcat tacgtggtaa agcaaaaaag cgatgtntgg cagtgagcag gganaacggg    660

gtcacaagta gtacaaacaa gcaaagctga atgacaaaaa aacgaggtga aaaaaaagaa    720


<210> SEQ ID NO 6
<211> LENGTH: 927
<212> TYPE: DNA
<213> ORGANISM: Homo sapien

<400> SEQUENCE: 6

atggggaccc tctgagtgtc caacaatctc tgaggcagca tcccagcctc ctctctctcc     60

cagcctgtct gtaactggtg aatggtgatg tgtttcctgg ctgagaactg tgtttacagt    120

aagtctctgc cctccagtga actttttaag ggcaggagcc atctttgtaa gcccagcact    180

tgcctgggca ccagacacat gtagtatgtt ttcagtaatc gtggctgttc actagctgct    240

tgattgaaca ttatttgtgt gtaataatgt cattaaatta tgagaaaata aatacttagc    300

aattgaaaaa aaaaaaaaaa aaaaaaaaaa aggcgtgggg gaaaacgggg ccaagcgtgt    360

aacccgggtg gggaaaagtg ggtataccgc ggccccaaaa tgtcccccac ctcaccaata    420
```

-continued

```
gcgccagcca caaggagaga cggagcacac agccaacaat gagcagagca acgacaacag    480

aaaagagacc aaagcagaac acagacgaag gacccgacag caacaagaga gaccaccaga    540

agtgaagcga cagcgacgaa acagagcacg agcaacgaaa cgcaacagca aagagcagca    600

aaagcgtcag agacgaaagg ccgacagccg ggaatagaag gaaggcacag gcaacgccgt    660

gagccgacac aagaccaggg tgcgacacca agagccagca cagcgagtga aacagaagcg    720

agaagcgaaa aaaaaggacg cagcagacgg cagctggaag gcggacgaga cggagactga    780

gacgcagcac ggcggcgcgc gcacgggccg cggagtaggg agaacacgag aaagagcaga    840

caagcaccag cagggaggaa agaaacagcg cagaaggccc cgaccggcac gagccgacaa    900

gacacgccga acacacggac ggcagag                                        927
```

```
<210> SEQ ID NO 7
<211> LENGTH: 451
<212> TYPE: DNA
<213> ORGANISM: Homo sapien

<400> SEQUENCE: 7

tttttttttt tttttttttt ttttttttgg ggccaaaatc cgggcttata ttttgggcca     60

aaggaaaccg gctaaaattt attcccaagc cttttgtgtt taaggttggc aagggggggtt   120

ttggtcccca aaaccccttc cagttgtgtt aacccactta ttttattggg gaaacaacca    180

aatattatta ttacaaattg ggtggggcgt ctaaaaaacg cccaattccc ccccaaggtc    240

taaacctctt ggtgacattg gggaattatt tatgcgcaaa tggaagagtt atttgggggt    300

gatcactcct aatgttaaac cagagcgaca gagatatacg catctagagg gcgaagaata    360

aaaaaatggg cgcaggatct gtatgcgcaa ttatcccaga ataacgtttc cttaaatata    420

caggtatcca gcccccaaag tagggggcg c                                   451
```

```
<210> SEQ ID NO 8
<211> LENGTH: 651
<212> TYPE: DNA
<213> ORGANISM: Homo sapien

<400> SEQUENCE: 8

gcccgggcag gtcccctccc tttttttttt tttttttttt tttttttttt tttggtaggg     60

gaaaattttt ttttttaagg gggtttccca aaaaaaaaat ttttcaggga ataaaaaaata   120

aaatctttaa aatttttccc ggttttattt tccccccccc cccccaaaag ctttttgggg    180

aaaaaaaaaa tttcagtcta aaaacacccc tggatttgtc ggtgggcgga tcaagagagg    240

tggacagaat tagtctgccc tcctctcaca acagacaact cctcgtgtgg ggtgtggtcc    300

tccctctcag agggagaggg gagtgggaag tgccgcctcc cacatattca cttgttgggt    360

gcaaggggac gagataaaaa aaaacggcgg ggcgggaaca ctcaggaggc gccatcatgc    420

gtgtgtccgc cgttgtgtgt gagaaaatgt ggtgtctacc gccgcgcgcc acaaatatct    480

cccacacaca aatatatcga gcgcaaacga acaacgggag gaggcggagc agccgacgaa    540

cacggagcag ggcaggtgag gaaaagcccg ggcaaacagg agacacagga agcaaccgaa    600

gaggcgtaag ggatagaaag aaggacggga cgagagcaac gaaaagcgcg c             651
```

```
<210> SEQ ID NO 9
<211> LENGTH: 103
<212> TYPE: DNA
<213> ORGANISM: Homo sapien
<220> FEATURE:
<221> NAME/KEY: misc_feature
```

<222> LOCATION: (6)..(6)
<223> OTHER INFORMATION: a, c, g or t

<400> SEQUENCE: 9
atggtngggt tggtctgcat tcagtgatgc aagtagggat ctttgcgtag gtcggtctga 60
agtgtggctt tatatttgat ccacacacgt ggtcttttaa cca 103

<210> SEQ ID NO 10
<211> LENGTH: 452
<212> TYPE: DNA
<213> ORGANISM: Homo sapien

<400> SEQUENCE: 10
tggtcgcggc gaggtaccta tttcatgaca aaataggcag ttttaaaaga ataaacaagc 60
taggtgtggt ggctcatgcc tgtaatccta gcactttggg aagccaaagc tgatggatcg 120
cttgagccca ggagtttgag accagcctgg gcaacatggc aaaaccccat ctctacaaaa 180
aatacaaaaa gtaggccggg cacggtggtt cacacctgta atcccggcat tttgggaggc 240
cgagataggt ggatcacctg aagtcaggtg tttgagacca gcctggccaa catggtggaa 300
cccaatctct actaaaaata caaaaaaact agccggatat ggtggcgggt gcctgtaatc 360
tcagctactt gagaggctga ggcaggagaa tcgcttgaac ttgggagcag aggtgagctg 420
agtgcagtga gccaagacca tgccattaca ct 452

<210> SEQ ID NO 11
<211> LENGTH: 576
<212> TYPE: DNA
<213> ORGANISM: Homo sapien
<220> FEATURE:
<221> NAME/KEY: misc_feature
<222> LOCATION: (318)..(318)
<223> OTHER INFORMATION: a, c, g or t

<400> SEQUENCE: 11
acgcctgtag tcccagctac tcaggaggct ggggcaggag aattgcttga acccaggagg 60
aagaggttgc agtgagccaa gatcatgcca catcactcca acctgggcaa cagaacaaga 120
acccatctca aacaaacaaa caaacaaaaa aaaaaaactc tggtctcctt aaggatatgt 180
taccggctcc atggcagact agagaattaa ttgtgtttgg aaccctttta ccgtgcaaaa 240
ctgtgaaaat gtgctagaaa aacccaagac atgaacgaat taaattacct gtgggtggga 300
caacacaccg ggccttgntg cctttttgct ttattacatt ggctacagta agctaaggtt 360
tagaaaaggc taggcttggg ttggtattct ggaaccacat tggaatctcc ttttcggggc 420
gctcaggtgg taggagaagg gcaccacgcc caagattcct tattagggaa ttgaattacc 480
ttcaaatcct tggtgggtcc tggaagattc tctataaggg aaacggattt taaaaacccc 540
acctggggtg cccatttttt ttaaaacaaa aaaaac 576

<210> SEQ ID NO 12
<211> LENGTH: 707
<212> TYPE: DNA
<213> ORGANISM: Homo sapien
<220> FEATURE:
<221> NAME/KEY: misc_feature
<222> LOCATION: (390)..(390)
<223> OTHER INFORMATION: a, c, g or t
<221> NAME/KEY: misc_feature
<222> LOCATION: (497)..(497)
<223> OTHER INFORMATION: a, c, g or t

<400> SEQUENCE: 12

```
tttttttttt tttttttttt tggaccaaaa tccaggctta attattggac caaggaaaac     60

agctaaaatt tattcccaag ctggtgtagt taaagttggc aaagggggat tttggtcccc    120

aaaacacttt caaggtttta acaccctaat tttatttgga aggaaccaac atattattat    180

ttcaacaatt ggttgggctt ctaaaaaacg cccattcccc tccaggtcta aaccctttgg    240

tgatatttgg attattaacg caatgagaat gtatatttgt ggtgcacaac tctatgtata    300

acaacaacgc agaaatatag acgccactag aaggcagcat ataaaaaaca aatatctggc    360

gcccaccaga cactgttatt cgccatattn ttccccaaga tataacgcta tctctttaag    420

atatccccag gttttcccga ggcttccccc aaaagagtat ttggggttgg gcccccctat    480

aatataaaga cactttnaca ccctttttat ctgtgtgagt gtgggctcta cacacaaaac    540

aatattaaga gttatttcac gacaacagct gtgtttccta cacaaagagg ggacagagtg    600

tttatagtct ccccactctc ctcaaatctc ctccatttaa agaggtgtgg agagagtcta    660

gaggggatgc ttaaagaccc aacaattaag gtgtggggtc tcttttc                  707
```

<210> SEQ ID NO 13
<211> LENGTH: 448
<212> TYPE: DNA
<213> ORGANISM: Homo sapien

<400> SEQUENCE: 13

```
agggtgcttc tgggcgtcat gcctctgctt cctggatcgc ttgcctcttt cttctcgctc     60

acttgcgttg acctctcgtt gcgcctctct tcctccctct gccccctgtc tttgcctcct    120

tgccctcccc ccatccctgt ccccctcgcc cgtccctccc tcttcttcgc cgctttctcg    180

cccctctcct cgctcgcttt ccggtcgcct ctttcgtcgc actacgtcct gctacccgac    240

gaccgcttcc gcgatgtgcc tgccgtacct cgcacatcca cccccccctt ttccaccgct    300

tcacgccttc tccggcttca tcccacctcg aaactccgcc cctatcaccc gccgaacacc    360

gcaccttgtt gcaacacccc ttcccaccta cccgcacacg cacccgtccc tccctcccgc    420

cacctacccc tttccccact agcttccg                                       448
```

<210> SEQ ID NO 14
<211> LENGTH: 689
<212> TYPE: DNA
<213> ORGANISM: Homo sapien

<400> SEQUENCE: 14

```
cgagcggcgc ccgggcaggt cccccttttt tttttttttt tttttttttt tttttttttt     60

tttttttttt taaaaaaaag ggattggttt tttaatttgg gggggggggg ccccaaaagg    120

ggggaggggg ccccggggag gggggggcg ggggaagata attgacagaa gtcggttggt    180

acgtgaaggg tgcgtgttgt ttagtgaaac gaccgcgccg gccacggggg gtcccaccgg    240

gccgcctctt ctgtggaaag gggacctctc tgtatgggag gaggtctcct gtatccccct    300

tttcttgggc ccccacttca ttttaagaaa ttgtctgaga ctttcctgct cccccccacc    360

tgggtggggg cccgatctct accatagagg cggcggcaga gagacccccg gggggctccc    420

ttctgtgtgt taccttgtgg tggcaggggg cagtcaaaat gaatcgtgtg aatttatcaa    480

gaacagaggt ggggggacaa cacagtgggc ggcaaccaag gtgtgttcgc cgcgtggttg    540

gagaaaattg gtttcctccg ccctcaaata ttctccccaa aaatattgtg ctttaccata    600

gtgctgcagg atgtaggtga cacaatgcag cacatccaac actaaagtag cagatcatca    660
```

-continued

```
ccccataaca aatcagaaaa aataagtcg                                    689


<210> SEQ ID NO 15
<211> LENGTH: 1032
<212> TYPE: DNA
<213> ORGANISM: Homo sapien

<400> SEQUENCE: 15

cgggcgcccg ggcgggtaaa gtcctagatg agtctagact aggcatatgc tttgggataa     60

ataagagaat aactccgatt cagtatgccc caatgcatag caatgccatg tgcatattta    120

ctctataaga aatcatacag atagggtccc gggtatggta gattgtccat aataggttca    180

ttacgttatg tcacgcccca acaattagac aagtggtaag gccgaactcc tactacggta    240

gttggctcag actataccca taagcgcgta tactgttaga aatgatagat tgtcaggtta    300

taatatcaac ggaatgagcg gttacgagat aatgcgttct tcggtcatga caggagcgta    360

ttgtctccct ttgataaatt tgtggttgcc tctttctatt gcgcattgat ttcgctctta    420

tagatcagtg atttccttcc cgacactagt gtcggtagtt gtcgcgtgac tattccgact    480

agtgatgcct tggtttgcct ccttcagtgc gcatcttgta gcccctgttt aagctctctc    540

ctgatgataa tcggaagtta ggtcagactt aaatggtaat tcgcaggaag agtggagagt    600

agaatggaga aggggcacga gtaaatcggt tggaagcatt ttagaggcca tttggaaaaa    660

tttcccgggt gcctaggttg ctgtccggac ttcaggagtc taaacggtct cgtggttcgt    720

ctaagggggt tgtgatagcg cgcccatttt taattacaac agtgcttgct tatagctaat    780

ctgaaaaaca caactggcac ggtgcatccc ttcttccgtt ggcaatttca ttttgagtat    840

cccagacgtt cctacgaatt gttttaacct gaagaattgg gcctaaatgt ttggggtccc    900

ctcccaagtg gtgactctgg tggttctcgt aggggggggg tggggtaggg ggtaccttag    960

cttttttat acctgaaagg cttgggcgta attccatggt ccataaggct gttccctgtg   1020

gtgaaattgg tt                                                     1032


<210> SEQ ID NO 16
<211> LENGTH: 678
<212> TYPE: DNA
<213> ORGANISM: Homo sapien

<400> SEQUENCE: 16

acagatagaa aattctgcat gtttgcagtg actagaatca gatagtagtg tggtggtttt     60

ttttttata atcattatga acgagggga gcttgcaggt aagggcttct gggcggggtt    120

tggaaaacgc agaaaggcaa taaatggaac acaaagtgtt tggtggtaat atattcctgg    180

cctgtgtctt ctttcacctc agagttggaa atcaggtttt ggcgaggtaa agctgggcaa    240

aaaaacaaga aacacaaatg gttcaaaact ggggtggtgg tgggtggggt gggaatttcc    300

cctctggctt aaataggtag ttctccagct agtacactat ttatgttact tttttctccc    360

tttcctttc tcacagggcc accagaaaac tggaatctgg taagataacg gaggggagac    420

atgacttggt cttggcaaca ctcgggggtg gattttatgg tatccctgtg ggacaccttt    480

taaaagctat tttcacccag tttctggtca aggcgaattt ttcaggaccc tactagtggc    540

gctacgaacc ttttcccgtg ggccctttac cggcgcaata gcacgccttc cggatattac    600

ctcatccctc agtaaataat atccgccatt tctccacaca acacacaaaa aaaaacgggg    660

ggcaccggcg caagcgcc                                                678
```

<210> SEQ ID NO 17
<211> LENGTH: 1441
<212> TYPE: DNA
<213> ORGANISM: Homo sapien
<220> FEATURE:
<221> NAME/KEY: misc_feature
<222> LOCATION: (143)..(143)
<223> OTHER INFORMATION: a, c, g or t

<400> SEQUENCE: 17

```
cgtggctcgc gggcgcggta ccaagctccc cccagatctc ccccatacat cagccacgaa     60
gcaagtcgtg ggtaggtatg gtgagtgggg gaaatcaggc actgttagtg gtacacaggt    120
ggatcccgtc gtatcctgta tgntacctcg cttgtgagcc atttgatctg ggcatccgtt    180
cccagtcctg ttcccaaccg tccattgcaa ggcaagcagg gagagcaagt gtgaacgtcg    240
tagagatcct cttcattcct ctacgttccc cgagccctag gcctggagag gcgaaggctt    300
ggcggtactc attgggtcat acgctggtgc tccttggtgt gcaagactct gttgatcgcg    360
cctcacatac ttccgacaca tacactaccg gaagccatcg ccatttccct cacaaatgag    420
tgacaagtag ggacgttctc tgagcggtca tacaagtggc tcgttcaggc ttgttcttcc    480
cgtgtggatt gcctatgcca tgggtgcaca tacgctggag tgcaatccat agctaaccca    540
ggtgattata cgacatttac ctgaaagtcc aacacagaag ccagcgacgt tagccagcta    600
ctataccctc gttgcgattc aagaaacgtc cgacctagac agactctacg agccgttaca    660
aataccgcaa tgcattagac caacgaacca aaaaagtaag cccatccaga aacatagaag    720
gagcctaacg acatcagaat gcgcgcgaac caagaaacac agagacgtcc aagacatacg    780
ctcgaaacaa aacaacgagc gatccagggg gggacacaat aagtatacca catgggcaag    840
aatcacacac tcaagtaccg aagcgctgaa aagccatctc caatagaggg ccacagaaac    900
accaaccgca atggaagccc gaatgccaac ggggaccaca gtctgtaccc cgttagaacg    960
gacaaaaaaa acgcacacta aaggaccaga actacggggg accagacgcc aggcggaatc   1020
actgcgcaaa gaacacccca acggaccctc ccaaatgcat ggcgcaaaac cgcgcggacc   1080
attgccaagg caagagaaca tgcgataagt aacagaaaca cccgcacaag accatgagac   1140
agaaacaagg gaatcacccc cgcccaaacc accacgttga ggaatcacca acgaataaac   1200
aacaacacac cgagcataga caagggaata acgagaaaca gcaaactagc aaaccactgg   1260
acacaagaga aagaatagca aaggccacaa ggaccgatga acacacacaa aaaagcagga   1320
acaacagaac aaacagaaac aaagcaacac atacagagga ggacagcagc ataaccgcac   1380
aagaccgaag gaggatgaaa acgagaaggt gagccactaa taggaagaaa gcacccgcaa   1440
g                                                                   1441
```

<210> SEQ ID NO 18
<211> LENGTH: 581
<212> TYPE: DNA
<213> ORGANISM: Homo sapien

<400> SEQUENCE: 18

```
gcggccgccg ggcaggtccc cccccctttt tttttttttt tttttttttt ttatttaaaa     60
aaaaaaagcc ccaaaaggga aattttgaac aaaataagga ctcccttccc ctccaaaaat    120
aaaaaatggg gggggttggt tggattgggg ggcaaccaat ttaaaactcg tgtttttccc    180
cctagggagg ttagggagaa gtatatttcc caattttccc caaacggggt gttatgaggt    240
aaagtcctgt gagaacgaaa ggggtgaggc ccttaaatct gtcatatatt ataaacgtga    300
```

-continued

```
tttcctctct acgagcggtg gtggattttt ggaatttcct tattctttgt ggtctttata    360

gccccccata ttttatagag caccaaatgt agtgtgggct ccataattcc aacatagtta    420

cttggggtgt tactactaga agtgcacccc gtgataatcc actttctcca agataactcc    480

ccgtgaagcg tgggcggtta cacaggggct cactagcgtg ttcccgggtg gtgatcatgg    540

ttatccgcgt cacatttcca cacaaattag atgcgaaaaa c                        581
```

<210> SEQ ID NO 19
<211> LENGTH: 901
<212> TYPE: DNA
<213> ORGANISM: Homo sapien

<400> SEQUENCE: 19

```
atggcgtggg tgagcctgat gctatggtga ctactcaata atgcgtgcgt catgccgttc     60

cgtcggaact gataagtgac caggcaagca aataacatga aatcggacaa acagacgcgg    120

gtaataaggc ggatcattgc agtattgatg cgctctatcc gacttcctcg tctccacatg    180

acatcgacat gcagacttcg gatcgttacg tcttgacggt agacgccgag gtactcagac    240

tcacctccaa taggcgcgta aatacggttt atccacagta attcagggga taacggcagg    300

gaaaagacac atgttgagcc aaatggcaca agggaaaact gtgcacggga cacccgaaaa    360

aaaagcggcc gcgtttgttt aggtgttata tccaatatgt gctaccgaaa tcccactaaa    420

tgaagtatat tcacaaaaaa ttcgactgca tcaagagttc agaggatggg cgaaatccca    480

gaagagggac ataattaaag gaaaaaccat agctgtattc ccacatgtta aaactcacct    540

cgatgcgcat catcctggtt cctgaaccaa ttgctgatat acagggatac ctgattcggc    600

attttctacc ctttcgagca aagcgtgggg cactttctca tttgactcac gcctgtaggt    660

tattttcaac atacggatag ataggtcgta gcgcatccaa ggtagggttg tgtgcataaa    720

cccccaggtt tagctcgaac gcatgcctat cggagactat ggattgagcc gcccgataag    780

cacactttag cccatgcgag agcactggta agattacagc aggagattaa agcagcgaaa    840

agagatctaa gtgtagacac taagatagta gaaaaaggta tggtatgagc cataaaacaa    900

a                                                                    901
```

<210> SEQ ID NO 20
<211> LENGTH: 658
<212> TYPE: DNA
<213> ORGANISM: Homo sapien
<220> FEATURE:
<221> NAME/KEY: misc_feature
<222> LOCATION: (123)..(123)
<223> OTHER INFORMATION: a, c, g or t
<221> NAME/KEY: misc_feature
<222> LOCATION: (128)..(128)
<223> OTHER INFORMATION: a, c, g or t
<221> NAME/KEY: misc_feature
<222> LOCATION: (183)..(184)
<223> OTHER INFORMATION: a, c, g or t
<221> NAME/KEY: misc_feature
<222> LOCATION: (197)..(197)
<223> OTHER INFORMATION: a, c, g or t
<221> NAME/KEY: misc_feature
<222> LOCATION: (199)..(199)
<223> OTHER INFORMATION: a, c, g or t
<221> NAME/KEY: misc_feature
<222> LOCATION: (204)..(204)
<223> OTHER INFORMATION: a, c, g or t
<221> NAME/KEY: misc_feature
<222> LOCATION: (209)..(210)
<223> OTHER INFORMATION: a, c, g or t
<221> NAME/KEY: misc_feature
<222> LOCATION: (216)..(216)

-continued

<223> OTHER INFORMATION: a, c, g or t
<221> NAME/KEY: misc_feature
<222> LOCATION: (221)..(221)
<223> OTHER INFORMATION: a, c, g or t
<221> NAME/KEY: misc_feature
<222> LOCATION: (234)..(234)
<223> OTHER INFORMATION: a, c, g or t
<221> NAME/KEY: misc_feature
<222> LOCATION: (260)..(260)
<223> OTHER INFORMATION: a, c, g or t
<221> NAME/KEY: misc_feature
<222> LOCATION: (270)..(270)
<223> OTHER INFORMATION: a, c, g or t
<221> NAME/KEY: misc_feature
<222> LOCATION: (274)..(276)
<223> OTHER INFORMATION: a, c, g or t
<221> NAME/KEY: misc_feature
<222> LOCATION: (285)..(285)
<223> OTHER INFORMATION: a, c, g or t
<221> NAME/KEY: misc_feature
<222> LOCATION: (294)..(295)
<223> OTHER INFORMATION: a, c, g or t
<221> NAME/KEY: misc_feature
<222> LOCATION: (300)..(300)
<223> OTHER INFORMATION: a, c, g or t
<221> NAME/KEY: misc_feature
<222> LOCATION: (302)..(302)
<223> OTHER INFORMATION: a, c, g or t
<221> NAME/KEY: misc_feature
<222> LOCATION: (304)..(305)
<223> OTHER INFORMATION: a, c, g or t
<221> NAME/KEY: misc_feature
<222> LOCATION: (310)..(311)
<223> OTHER INFORMATION: a, c, g or t
<221> NAME/KEY: misc_feature
<222> LOCATION: (316)..(316)
<223> OTHER INFORMATION: a, c, g or t
<221> NAME/KEY: misc_feature
<222> LOCATION: (318)..(319)
<223> OTHER INFORMATION: a, c, g or t
<221> NAME/KEY: misc_feature
<222> LOCATION: (324)..(325)
<223> OTHER INFORMATION: a, c, g or t
<221> NAME/KEY: misc_feature
<222> LOCATION: (331)..(332)
<223> OTHER INFORMATION: a, c, g or t
<221> NAME/KEY: misc_feature
<222> LOCATION: (336)..(337)
<223> OTHER INFORMATION: a, c, g or t
<221> NAME/KEY: misc_feature
<222> LOCATION: (460)..(462)
<223> OTHER INFORMATION: a, c, g or t
<221> NAME/KEY: misc_feature
<222> LOCATION: (492)..(493)
<223> OTHER INFORMATION: a, c, g or t
<221> NAME/KEY: misc_feature
<222> LOCATION: (521)..(522)
<223> OTHER INFORMATION: a, c, g or t

<400> SEQUENCE: 20
acaggttggc aggaccacct ccgcctactt ctccaccatc cctagcatgt ccagaccgct 60
gatatccaca gcatacacac catgacccag atgagcagct catgcgccag ttggcacctt 120
ccntgcgnag atcacaagta gagtgacacg tggcacgtgg cttagcacga agagtgtact 180
gcnntccagc atagacncnt gtgnatgcnn taccantgcg natgggtctt actntggcct 240
tccccctttt cttccacagn actacagagn tgtnnnccct gtagngcgtc tccnnctcgn 300
gnannacagn ntgccntnnc aaanntcctg nnaccnncaa tgggacccag cccatggcgc 360
gacacgacga ctgggttggc acggccacaa actgccacct ttactacgac gacttttcct 420
tattggcctg gcgaacgcgc tgtgtttcct cccccacaan nntttgtttc gtcgacatac 480
ttccaccctc gnnttttaat agacatggtc tcgaacctcg nntcttgacc caaaaacaaa 540

```
acaacacaca aaacaaacaa acggcttggg cgcgtaatcc ggtgggccaa agcggggtcc    600

ccgtgggggga cattgggtaa ccgggtccaa aattcccaca aaattcgcgg acaaagtg     658


<210> SEQ ID NO 21
<211> LENGTH: 969
<212> TYPE: DNA
<213> ORGANISM: Homo sapien
<220> FEATURE:
<221> NAME/KEY: misc_feature
<222> LOCATION: (447)..(447)
<223> OTHER INFORMATION: a, c, g or t

<400> SEQUENCE: 21

gcgtggtcgc ggccgaggta cccgtgcgca cggaggacgc cgagttccat gtcccggagc     60

cctggacatc tgacgtactg ccgtgggttg atgcactccg cagcggacga aggagctgca    120

gtcgaaggcg gctcgcaaga agtcttgaag agggctcaag agtaaccgtt gttcccactc    180

tatgcagaag aagtatggcc aagtcctcca tgtgtgatcg ccggttgcag cacggtgtgc    240

atgatgatgg aaatggggca acggagtcgg gaatgcgtgg tgtgacatgg tccccggagg    300

aaccgtcctg gcaagtatcc gtctcctcgc tggaagctgt cttagtgaag tggggcgatc    360

gcatttgctc cgtccactag cattctccca gtcgcacatc tagcgtgtgt ccaccatgca    420

gtgagccatg cggcctgttg ccatccnctt gagacgttgg gggctgtaac gtcagagcag    480

gattaagacg gttctctcaa cttgttgcgc gtcctggata tgtggacaca ggggtgctac    540

ctttgtccct aggccttgtc ttcaaaagaa agtaaaaagg aaacaagcat ttgagggatc    600

gtttaacaac agagagaaac agacagaaga atgagaacac ataagacaag tccctctgga    660

ggcgacaacc tcagcggggg gccaggagag gctgtgggga ccccccgggt gtgtgagaca    720

atgtgggtgg ggagcacctc gcgggtgctc cttcaccaag aagaatttcc acccgccacc    780

agcgaacata atcaggcgac cagaagagaa agacaaaaaa agcgaggcca gagtaacagt    840

cgagaccgag cgacgaaggc gggggcacgc aggagcacat gggaggagat tggcaggacg    900

aggagaagac caagaaaagg ccaaccgaat aaatagccgc tccagagggg aggcagaaaa    960

gggggaaa                                                             969


<210> SEQ ID NO 22
<211> LENGTH: 709
<212> TYPE: DNA
<213> ORGANISM: Homo sapien
<220> FEATURE:
<221> NAME/KEY: misc_feature
<222> LOCATION: (243)..(243)
<223> OTHER INFORMATION: a, c, g or t
<221> NAME/KEY: misc_feature
<222> LOCATION: (617)..(617)
<223> OTHER INFORMATION: a, c, g or t

<400> SEQUENCE: 22

tttttttttt tttttttttt tttttttttt tttttccccg tggtttaaaa actttaattt     60

tttttgggct tttacaaaaa tttttaaaac attttaaaaa aacccccccc ttccccccatt   120

tccggttccc cgggcggggg gtaaaagggg gacaagggtt ttttcaccgg ttgtggcctt    180

cggggtttgg gagggcttta aaaccaccca ctctccgcca aacaatcttt gtgcgacgtt    240

ttnctatatc ttgtgtgttt aacaataaca acgagagtaa tatctccccc tcgtgtagtg    300

tcgcaacacc cgtggctcca cgccacttct ctctccaaca acacgtgctt gggggtgtgt    360

acccgcgagg cggctcaaga gcgcgtggtc gccgctggga gtgggaacaa gttgggtctc    420
```

-continued

```
atctagcgcg cctcacacaa tctcccccac caaccaatca tctcgacgag accacacagc    480

cggcgtgctg cagccagacc acgcgaaagt ccagagaaag atgcaagacc aagcacgaac    540

gaataaagag caacagacaa ggaccaaacg cagcgaacaa gcaagctagc aagacgacca    600

agcagcacag aaccagnaga gcaccaacaa gcaagacaga caaacgcaag ccagcaggag    660

acacaaacgc aaagcaaaca caacagaaca acctaagata cgcaagtag                709
```

<210> SEQ ID NO 23
<211> LENGTH: 402
<212> TYPE: DNA
<213> ORGANISM: Homo sapien

<400> SEQUENCE: 23

```
gaaggggtgt agtgtaaaga acaaagctaa tattataata ttcaattttt gtgaaggaag     60

tatgaatgaa atagtagtca tatccttcat aatgaagggg cagtgattag ttacaatgag    120

aagattgatg attatcttga tcaaaatgaa atgataatat tgataatgta aaatatgtct    180

ttatctttgc gtgtcattgt gttaaggtgt gtattctatt tgtcatggaa ttcttaattc    240

aaatacatgt tctatataaa gagtatgctc ctattggatg aaaaaaacct aaaaaaaacaa    300

aaaaaaaaaa aaaaaaaaaa aaaaaggttg ggggaactgg gcaaaggtgc cccgggggga    360

attggttatc ggtcaaaatc cacaaaaaat aggaggaaag tg                       402
```

<210> SEQ ID NO 24
<211> LENGTH: 1441
<212> TYPE: DNA
<213> ORGANISM: Homo sapien
<220> FEATURE:
<221> NAME/KEY: misc_feature
<222> LOCATION: (155)..(155)
<223> OTHER INFORMATION: a, c, g or t
<221> NAME/KEY: misc_feature
<222> LOCATION: (247)..(247)
<223> OTHER INFORMATION: a, c, g or t
<221> NAME/KEY: misc_feature
<222> LOCATION: (394)..(394)
<223> OTHER INFORMATION: a, c, g or t
<221> NAME/KEY: misc_feature
<222> LOCATION: (533)..(533)
<223> OTHER INFORMATION: a, c, g or t

<400> SEQUENCE: 24

```
gagcggccgc cgggcaggtt tttttttttt tttttttaat tggatcaaaa ttcaggggtt     60

aattatggag caaggaaaag cggctaaaac ttaatcccaa gcctgtgtgt gttagtttaa    120

gagttgtgca agaggtgggc atagtgggtc tcacnaaaac acatctcaga gtggttttaa    180

accacatatt tattgtgaag aaacaaaatt atatttaaaa tgtgtggtgt ggcgctctct    240

ataaaanagg cccatattct ccctctccaa ggtctctata aaccttgtgt ggtaattgtg    300

tgatatatta taagcgacac atgtgagagg tttatattgt gtgcgttacc aatctcatat    360

gtgttaaaac aagcgcagag aaatatagac gcanctataa gggcgagaga aatatataac    420

aatatgtgtg gcgcacagag agcggttatg tgtgcacata ttctctcaca cagagatata    480

gcgacattct ctcttatata aaattctcac gggtattcta cagcgctctc tcnacacaag    540

agatgatgtg gggtgtgcgc cgccataata tatatgagag acacttccta taacacatat    600

atatatatga tgggtgatgc gcgcgtaata caaacaaaaa aatataataa tatatataac    660

acggaaacac atgatgtgtg ctacacaaag aggaggggag atgatgtgtt gtagatgtgc    720

cacacaactg tctctcatat actctctctt tatacaaaga gaggtgtggg agagagatgc    780
```

-continued

```
tacaaggagg gtgatgagct gtaaaacgaa cgcgcaaaat atatatacat gatgggtgag    840

ggagtgcatc cttatatttt tctctccata aaatattccc ccggttgttt actaattcac    900

tattctcaca tattccgggg ggcgtctcct ctgggagata tatgcgcccc ttatagggg    960

ggtgctcacc cccccatttt tattacaggt gttctacaag aagggggggt tctggggtac   1020

aatctgggcc ccacctggtg gggggggggg cggaactctt gtggaaccac atcttggggc   1080

gccccccaaa ttttatttta tccccccctcg ttggggttgc catttttttcc cccttttttc   1140

tgccacaaac tggtgcgcgg gggggtgggg ggagacaatc ttttccccag aaaacaacag   1200

ggggggtgag gggcgtttgg acgaggaaaa cacaaaacaa caattcctcc ccaaattccg   1260

aaaaaacctc ctcttctcga gggggggctc gaggagggtc ccgaggaata tgttggggcc   1320

aacaccacga gtggattaca cacatggttt cccccccccg ggggagaagg gggggggca    1380

ctttctcaca aaatacagag gggggtacgg ggggggcgaa ccaaggggga gttaatactc   1440

g                                                                   1441
```

<210> SEQ ID NO 25
<211> LENGTH: 854
<212> TYPE: DNA
<213> ORGANISM: Homo sapien

<400> SEQUENCE: 25

```
cgtggtcgcg gcgaggtccc ccccctttttt tttttttttt tttttttttt tttttttttt    60

tttttttttt ttttaaaaag aaaaaacggg ggaggggggg gggggggggg gggggagcga   120

tgaagaaggg gggcgaaggg gagaccagac agcggggggg ctcgtcccgc ggcgcgagcg   180

agggaggtta tcgtgagctg cgtaggagag gggtgggggg cgggccaccc ccgggggtgg   240

ggggagaaac tagtcagcag cggggtacat tagcgggggc gtcaacagta cagtagggcg   300

gccgcccccg tagaagcagc ggcgacggag tatatctgta tgcacagcga ggcagaacag   360

gcgtggcatc acacaccaca caagagagag agagtctccc ccaccgaggt gagataaaag   420

agagggggag gatgtaggag ggaggatcca cagccgggat ggcgtagcaa gacatactcc   480

accacaaaac atccttcgga ggtggcgagc aaccacgccg taaggaagag cctctactct   540

cgaagaaaga gagagacaat ccagatagaa ccgcagcaga gggagagagc gaggccacct   600

cccacaagaa aaaaagaaga gagcaagcga caagcgggca aacaacgcaa accacaaggg   660

tgagaagaaa tatataccaa cccgggtggg aaaaaacaat tagcaaacaa actgcactac   720

tgcccacgat aaaaaaactg gctggcgaga caccaagcgc gtgcaacaaa agctagtata   780

cccggcgggg gggaacaaag cagtacgacg ccgcacacaa ataccccccc caacaacaac   840

ttaacagcaa aaga                                                     854
```

<210> SEQ ID NO 26
<211> LENGTH: 1672
<212> TYPE: DNA
<213> ORGANISM: Homo sapien
<220> FEATURE:
<221> NAME/KEY: misc_feature
<222> LOCATION: (568)..(568)
<223> OTHER INFORMATION: a, c, g or t
<221> NAME/KEY: misc_feature
<222> LOCATION: (1050)..(1050)
<223> OTHER INFORMATION: a, c, g or t
<221> NAME/KEY: misc_feature
<222> LOCATION: (1364)..(1364)
<223> OTHER INFORMATION: a, c, g or t

<400> SEQUENCE: 26

-continued

```
ccgcccgggc aggtcccccc cctttttttt tttttttttt tttttttttg aagaaatttt     60

tggatcaaaa agggggccct taaaattccc ggggggggccg tgatttccct atatttaagc   120

gtggggggaa aaaaaaatct caaattttac gcgtgattaa ttggttagtg tgcctccaaa   180

tgtgaattct agtgtgaccc ctctctgtgt tcacaatata aatatagaag agagcctata   240

atatattctc tcaaaacaca atatagagaa actctgctgt gcgcccacaa aacacacact   300

gtgtgtggtg tcgtctttat cacttgtgtg tgaactgtga gtctctcacc ccaagagaag   360

agagagtgtg ttactaagag gtgtgataaa gtagtttgtg tgagagttat agagtgtctc   420

tctctccaca aatatatatg actctctctg tgtgtgttat acaaaacatc tctctcttct   480

ctctctatat atgatgtgtg tatatatata tgatgagagt gtatatgatg tgtgtctacc   540

gatgtgtctc attctattat tataaaanca ctcctttata tatagaagaa tttctatatc   600

tatatatctc tcactctctc tatatctctc tctctacagt gtgtggcgga cacatatatc   660

tataacatat gatgtgtggg gggcgcgtgt gtagtaacaa tatatatata ttctatgtgt   720

gtgtctctct catcactgtg tgtgtgtctc gtgtgacaca aagagtgtgt gtgtacacag   780

tgtgtgtata tcaccctctg cgagcgttta tctcaccaca tatctctgtg tgggggacac   840

cctctgtgag agagaccact cttatgagag ggggaggcgt cccttatatc tcctcttatt   900

cacagcagag agagaagagt cctcgagagg ggggcgcaaa ttgttgtaga gggggggagg   960

acaccccccc ttatttttct tctgttctat actttgctcc cccctctctg atgagaaaaa  1020

atacgccgcc gtggggtgtg gcaacagccn ccctgttgtt gtgggaaaac atctcacacc  1080

acgagaggat ggtttttttcc gccgaggtct tttcctcaca caacaaatac aaaagtaaat  1140

aaacaccaca agcacgagac gacaaaaaaa cacatcaaac acaccaaata caaaaaaaca  1200

aaaaaaagag ccgccggcgg gggggggga gggaaacaca acaaagccag gggggggaac  1260

acaaaaaaga cgaggagtta accaccagcg gagggagagg tacaaaccaa agagggttgg  1320

tgtatcaacc cgcggcgcgc gacaacaaaa aaattcccac ccanacaaca gatattcatt  1380

tatgtcatca tccgtcatca caacttatac gtaaatacag atgctcataa actaatttga  1440

ttactaaaat ccactaaaag attatcaatg acttagaact aaagtaaata cgatactcat  1500

gaattatcta attcttatat acaactcaca ctacagctaa catatataca ctactacaca  1560

tcacacaact aaagcaaata ctctaacatc gttcacccaa caacaacaac agtaaccaaa  1620

taactgctac atattacata tatatcattc catatattct tgaatacaca aa          1672
```

<210> SEQ ID NO 27
<211> LENGTH: 698
<212> TYPE: DNA
<213> ORGANISM: Homo sapien

<400> SEQUENCE: 27

```
gcggccgccc gggcatggtc cccctttttt tttttttttt tttttttttt tttttttttt     60

tttaaaaaat gctttttttt tttcttttgg gggggtgggg cccccggggg gggggggggcc   120

ccaggagaag gaggtgggcc ctgggagaaa ttaattaaaa aaaagtactg tgaaaagaaa   180

agggtgggtg gtgttaaagt cgcatggccc aaggtggcgc tccctaagcg ctacgcgttc   240

tcatgagaga aggtgaaaaa cctctttgat agaaaagaga tctcatgtga gaaaacgcca   300

tatagcttgt gggccccacc atatctagac atattataaa aaaatctcgc tttgaaaaac   360

acactctata gcgtgtaacc accactcgcg tgtggtgggg tgtctccgag atttctctct   420
```

```
actacaacta gagagcgcgg acacagagtg taaacaccac gagtgggtct ccccttgggg    480

tgctccatgg tgtgaaaaaa gagagcacac atataagatc tcgcgtgtat atctcacaaa    540

taaaaaagtc cttggtgggc gataaacctc cgagggcaca caaaaagagt gtgttctccc    600

gccgtgtgtg tgaaaaaagt gtgtatatcc cccgcgccca cacaaaattc tccacacaaa    660

aaatattttg gccgaaacaa aaaattggtg taacaaaa                            698


<210> SEQ ID NO 28
<211> LENGTH: 393
<212> TYPE: DNA
<213> ORGANISM: Homo sapien

<400> SEQUENCE: 28

accagaagga accctccagt cctgctctct ggccacacct gtgcaggcag ctgagaggca     60

gcgtgcagcc ctactgtccc ttactggggc agcagagggc ttcggaggca gaagtgaggc    120

ctggggtttt ggggggaaag gtcagctcag tgctgttcca ccttttaggg aggttactga    180

ggggaccagg atgggagaat gaggagtaaa atgctcacgg caaagtcagc agcactggta    240

agccaagact gagaaataca aggttgcttg tctgacccca atctgcttga aacctgactc    300

tgcttctctc atttgtcttc ctaccctact cacataattc actcattgac tcactcattc    360

accagatatt tattgacctg ctattataag ctt                                  393


<210> SEQ ID NO 29
<211> LENGTH: 3470
<212> TYPE: DNA
<213> ORGANISM: Homo sapien

<400> SEQUENCE: 29

gcacgagcct gtgcctcctc ctcgtccctc gccgcgtccg cgaagcctgg agccggcggg     60

agccccgcgc tcgccatgtc gggcgagctc agcaacaggt tccaaggagg gaaggcgttc    120

ggcttgctca aagcccggca ggagaggagg ctggccgaga tcaaccggga gtttctgtgt    180

gaccagaagt acagtgatga agagaacctt ccagaaaagc tcacagcctt caaagagaag    240

tacatggagt ttgacctgaa caatgaaggc gagattgacc tgatgtcttt aaagaggatg    300

atggagaagc ttggtgtccc caagacccac ctggagatga agaagatgat ctcagaggtg    360

acaggagggg tcagtgacac tatatcctac cgagactttg tgaacatgat gctggggaaa    420

cggtcggctg tcctcaagtt agtcatgatg tttgaaggaa aagccaacga gagcagcccc    480

aagccagttg gccccccctcc agagagagac attgctagcc tgccctgagg accccgcctg    540

gactccccag ccttcccacc ccatacctcc ctcccgatct tgctgccctt cttgacacac    600

tgtgatctct ctctctctca tttgtttggt cattgagggt ttgtttgtgt tttcatcaat    660

gtctttgtaa agcacaaatt atctgcctta aaggggctct gggtcgggga atcctgagcc    720

ttgggtcccc tccctctctt cttccctcct tccccgctcc ctgtgcagaa gggctgatat    780

caaaccaaaa actagagggg gcagggccag ggcagggagg cttccagcct gtgttcccct    840

cacttggagg aaccagcact ctccatcctt tcagaaagtc tccaagccaa gttcaggctc    900

actgacctgg ctctgacgag gaccccaggc cactctgaga agaccttgga gtagggacaa    960

ggctgcaggg cctctttcgg gtttccttgg acagtgccat ggttccagtg ctctggtgtc   1020

acccaggaca cagccactcg ggccccgct gccccagctg atccccactc attccacacc   1080

tcttctcatc ctcagtgatg tgaaggtggg aaggaaagga gcttggcatt gggagccctt   1140

caagaaggta ccagaaggaa ccctccagtc ctgctctctg gccacacctg tgcaggcagc   1200
```

-continued

```
tgagaggcag cgtgcagccc tactgtccct tactggggca gcagagggct tcggaggtag   1260
aagtgaggcc tggggttttg gggggaaagg tcagctcagt gctgttccac cttttaggga   1320
ggatactgag gggaccagga tgggagaatg aggagtaaaa tgctcacggc aaagtcagca   1380
gcactggtaa gccaagactg agaaatacaa ggttgcttgt ctgaccccaa tctgcttgaa   1440
acctgactct gcttctctca tttgtcttcc taccctactc acataattca ctcattgact   1500
cactcattca ccagatattt attgacctgc tattataagc tttacatcct cccatgttgt   1560
cctggcatgt gcagtataca cggtctaact catctctccc cagatctctc agaaccttga   1620
gcttgggaat tgaactgggg tcacctgtgt cctttcttat ggactcgcag gattttagaa   1680
ccctaatgca ccctggaggg tagctgggcc agacttctca tttcacaggt gaggagactg   1740
gtgccccaca gggattaagt gccttgccca aggtcaggct tatctccaga gggaggtgcc   1800
ctggactggg gcccagatgt tcagggaccc tgcctacacc tcatttccag tgtgggctgc   1860
cttagttagt tatgagaaca gggaagggct gggaagagac agcctccaag gtcaacactt   1920
ggagagggtt tcacttgctc tgaagaccct ggtccaggat tcgccctctc ccatgccttc   1980
aagtcagcat caggcttagg gcaaagacca ggcctctgaa gctgcctctt gtaattcatg   2040
caggaagatg tcaaagtcag ccccatcttg gctgatcagg gtgttcagcc ttaaccccac   2100
ctgtgttctg aagtctctta ccctacctgc tcaggactga gacagttatt cactgaacat   2160
atttattaag cacttgctgt aggccaacag ttaagaatcc aataatgaaa tggacagatt   2220
catggaactt agagtccaat aggaaagtga gacccagaca atgacaatga gataaatgtt   2280
aggaaggggg aggtatgggg tgacttccct gcagtcctgg gggcctagat gggcccaaga   2340
ctgggtgaga gtcttggcag agcctttgca acaccttaag tggacaggac tgggaggtct   2400
tggtggttgg agccaacgtg ggttccctgc ggctccttag tcacctctga tagcagattg   2460
agggaggaaa acaggtaagg catgaggaaa tggccaggtt gggttaaccc actggtttca   2520
accagttcag gaatgaggtt atttggccat gactggctga tcttgagctc aaggatctgc   2580
ttcaaatgca cacaggccta gttgaagttt aaaccccagc aaaacattcc tccctgtaaa   2640
tggaaaatcc tacttctacc cccaccctgc cctgtttttt gttttttttt tccccaagat   2700
cattagatgt cctcacccct cctcactgcc tctcctctct gggacaggct gggacctttg   2760
aggaagataa agccttcctt gactacccat catattcagt gtccctgttc ctcactcaga   2820
gaggaaggca gaaccagtca ggcttatttc agtaagttcc acagttctac aagactgcag   2880
gaattctcct taagggagga gagcaagcag gtgtggcccc agcttctgga aatggcagaa   2940
gagagggttt tctcattgaa tgggggtggg ggctcgtgtg tcctgggaaa ccccatcagt   3000
cccttcattt cttgagactc aactcctggg aggagagggt ctcaagagtt gtccctggaa   3060
ggagggcggg ggcagtctgc atctatttca ggttgtggct cttggttcta ggactcttac   3120
ttctctggct aagggctcag cttcttggga cttcaaccat cttctttctg aaagaccaaa   3180
tctaatgtaa ccagtaacgt gaggactgcc aagtatggct ttgtccctat gactcagagg   3240
agggtttgtc gggcaaattc aggtggatga agtatgtgtg tgcgtgtgca tgggagtgtg   3300
cgtggactgg gatatcatct ctacagcctg caaataaacc agacaaactt accaacgtct   3360
tgattggtgt attttggggc tggttctggg ctcagcaaat tgcgaactag ctaatatagt   3420
aagagattaa aaaaaaaaaa aaaaaaaaaa aaaaaaaaat tgcgtcggcc              3470
```

<210> SEQ ID NO 30

-continued

<211> LENGTH: 484
<212> TYPE: DNA
<213> ORGANISM: Homo sapien

<400> SEQUENCE: 30
gatggaatgg ccttgaaaga ttttagtgca tgcacttgac ttagatagga tctttactga 60
cccttgctta cttaggagtg gcagagttaa ttggtggttc agatattaag ggctactgt 120 cactctgata tgtagctttt ctatcatctc tgtaacttag cttcaagtaa ctagaagagt 180
aatctaaaaa aaataattag cctttaatca gattgcctgc agtgtttctt ggtcacttta 240
aagctgtgac tttgcatgat tgctaggtaa gttcacttaa gaaataggaa attcaaatta 300
tttatgtttc aagtattttt gaacaggtgg taaaatgaaa ttgattttta tcatctttga 360
atgaaagtaa cagcagatat tcaatgagtg acttattttg tggacatttt tgtcctttgg 420
atatgatgtc atagagtcac aatatatttt cagccttttt tgagaaataa gtgatttaga 480
catc 484

<210> SEQ ID NO 31
<211> LENGTH: 1299
<212> TYPE: DNA
<213> ORGANISM: Homo sapien

<400> SEQUENCE: 31
gttaaatgga tgttatgtca tatgcaatgt tgataggtat atgtggattt caagactttc 60
ctacttagat atttctttag aagttcctta ttgagggtaa tgatgttttt aaagaacata 120
gaacattctt tatgttttaa aagaatcatg ccttcattaa gtaggcttta ttctaagttt 180
ggaactgaga ctgttatgct tttaaagtct ccaacagaga ggttaaggag ttaacctggg 240
gcatgccaga actgggatgg aatggccttg aaagatttta gtgcattgca cttgacttag 300
ataggatctt tactgaccct tgcttactta ggagtggcag agttaattgg tggttcagat 360
attaaggggc tactgtcact ctgatatgta gcttttctat catctctgta acttagcttc 420
aagtaactag aagagtaatc taaaaaaaat aattagcctt taatcagatt gcctgcagtg 480
tttcttggtc actttaaagc cgtgactttg catgattgct aggtaagttc acttaagaaa 540
taggaaattc aaattattta tgtttcaagt atttttgaac aggtggtaaa atgaaattga 600
tttttatcat ctttgaatga aagtaacagc agatattcaa tgagtgactt attttgtgga 660
catttttgtc ctttggatat gatgtataga gtcacaatat attttcagcc tttttttgaga 720 aataagtgat ttagacatct tacacagtta ctgagcacct ggtacagtga agatctctca 780
agaatgattt gtgtgatgta gttcggtgga tcatccagca gagggcagta gagccagagc 840
catagtaaaa gttatagtaa agttgctctt agcaacttga gtcttactta gatttaattt 900
tgcatagaac caaaagttca gtttagtagc cattttcttt aaagtcaggc tgtagtggtt 960
ccgaaatgaa aattaggccc tgattttatg taagatgatg tccaatcttt aattgacacc 1020
ttaaaaatat taaaagatta tgataggatc aggaaggagt ttttgaaaat gcaatttgta 1080
gtttttaaca agtgatgtag aataaataaa aagaagtact ttttaaaaag taagtataaa 1140
attattttcc agttaactat gggatataaa tgattgcttt aatacaggta ttcctaacct 1200
gtacagcatt tcctaacctg ctctgtgaaa aacaaagaaa taaaacttag tgctctcttt 1260
aaaaaaaaaa aaaaaaaaaa aaaaaaattt ggtgcggcc 1299

<210> SEQ ID NO 32
<211> LENGTH: 771

-continued

<212> TYPE: DNA
<213> ORGANISM: Homo sapien

<400> SEQUENCE: 32

```
cgtggtcgcg gcgaggtacc aagtgtgaac tggggtcatt cggtctgtga tctcgttgca     60
ctgctccaag tctggctgtg tccaggcggt ccatgttgaa aatggaggat ggctgctgac    120
ttctgactgg ctgagcagtg ggttccttca ggttccttgg ccaaccctcc tcccctgccc    180
acaacttctc caaacaaagc aggctgtttg ctcacttctt caaaaggagg aatgataacc    240
caaatctgcc caagtgacac ttgagaaggt tttggctggg gttcctggtg gatttcttac    300
tacctaacgc ccaagaaaac caactaagga ctctcaaacc atacctggtg gggttcttc     360
gctcaacctc ttcttcccta ggtcaaagcc actatcatct gatgtgttag ggatgggttc    420
tgattggcag aaattaatca gctcccaatg ggagcccacg gaactaagta gggtcccaag    480
aaaaaaaacg ggagctattt cacagagctg agcttctgcc aaatttcatt cctcaaacct    540
ttcaggaggg gtggttggcg tttctaaatg tttatgggat ttgagttgca ggtgtccact    600
taactgacta ctttgataac aatgtcagat tttaactata aaacgacatt ccttgtgcat    660
ttttatattg attcctattt ttttttagat taacgttaaa tgtttcccct agtcttcctt    720
ctactgtata gagcttggta tcatgtcata cgttccgtgt gaatgttcgt c             771
```

<210> SEQ ID NO 33
<211> LENGTH: 4908
<212> TYPE: DNA
<213> ORGANISM: Homo sapien

<400> SEQUENCE: 33

```
atgggagatg tggtcaaaag atacaaaatt tcagttaaga ggaataagtt gggcaacatg     60
ttgccaggtc gaattggatt ccagtatggc ttgcggtggc ctaccaaggc cgcgaggggc    120
ggccggcaga gcgacgcgga accccgccgg cgcggacccc ggaccccaac gccgcccgcc    180
cagccgcgga cgcccctgcc cggagccctc gccgcccggg ccgccctcga gggccgggag    240
cggcgcccgg cggccgcgcc cgcaggccct gcctctgctg gaaccttccc aggcccctcc    300
gacctgaaag cccagcccct cctgctgccg ctgctgccgc caccacgcag ggtagccgca    360
gaggcccagg aatcttggca ggcgtgggga ggcagcgggt ggcgggtggc gctccggaaa    420
aggctgcaaa tgcgaaccag aagcacgtcc acggacgcca tgctggggac tctgacaccc    480
ctgtcttcgc tgctgctgct gctacatggt gctggtgctg ggtgtgggc cgcgggcgtc     540
ctctggtggc ggggccggtg gggcggcggg ctatgcccca gtgaagtaca tccagcccat    600
gcagaaagga cctgtgggac cgcccttccg tgagggcaaa ggccagtacc tggaaatgcc    660
tctaccgctg ctgccgatgg acctgaaggg agagcccggc cccccctggga agcccgggcc    720
tcggggtccc cctggccccc ctggcttccc aggaaaacca ggcatgggaa agccaggact    780
ccatgggcag cctggccctg ctgggccccc tggcttctcc cggatgggca aggctggtcc    840
cccagggctc cctggcaagg tcgggccacc agggcagccg gggcttcggg gggagccagg    900
aatacgaggg gaccagggcc tccggggacc cccaggaccc cctggcctcc cgggcccctc    960
aggcattact atccctggaa aaccaggtgc ccaaggggtg ccagggcccc caggattcca   1020
gggggaacca gggccccagg gggagcctgg gcccccaggt gatcgaggcc tcaaggggga   1080
taatggagtg ggccagcccg ggctgcctgg ggccccaggg caggggggtg cccccggccc   1140
ccccggcctc cctggtccag ctggcttagg caaacctggt ttggatgggc ttcctggggc   1200
```

-continued

```
cccaggagac aagggtgagt ctgggcctcc tggagttcca ggccccaggg gggagccagg   1260
agctgtgggc ccaaaaggac ctcctggagt agacggtgtg ggagtcccag gggcagcagg   1320
gttgccagga ccacagggcc catcaggggc caaaggggag ccaggaaccc ggggcccccc   1380
tgggctgata ggccccactg gctatgggat gccaggactg ccaggcccca agggggacag   1440
gggcccagct ggggtcccag gactcttggg ggacaggggt gagccagggg aggatgggga   1500
cccaggggag cagggcccac agggtcttgg gggtcccccct ggacttcctg ggtctgcagg   1560
gcttcctggc agacgtgggc cccctgggcc taagggtgag gcagggcctg gaggaccccc   1620
aggagtgcct ggcattcgag gtgaccaggg gcctagtggc ctggctggga aaccaggggt   1680
cccaggtgag aggggacttc ctggggccca tggacccccct ggaccaactg ggcccaaggg   1740
tgagccgggt ttcacgggtc gccctggagg accaggggtg gcaggagccc tggggcagaa   1800
aggtgacttg gggctccctg ggcagcctgg cctgaggggt ccctcaggaa tcccaggact   1860
ccagggtcca gctggcccta ttgggcccca aggcctgccg ggcctgaagg gggaaccagg   1920
cctgccaggg ccccctggag aggggagagc aggggaacct ggcacggctg ggcccacggg   1980
gcccccaggg gtccctggct cccctggaat cacgggccct ccggggcctc ccgggccccc   2040
gggacccccct ggtgcccctg gggccttcga tgagactggc atcgcaggct tgcacctgcc   2100
caacggcggt gtggagggtg ccgtgctggg caagggggggc aagccacagt ttgggctggg   2160
cgagctgtct gcccatgcca caccggcctt cactgcggtg ctcacctcgc ccttccccgc   2220
ctcgggcatg cccgtgaaat ttgaccggac tctctacaat ggccacagcg gctacaaccc   2280
agccactggc atcttcacct gccctgtggg cggcgtctac tactttgctt accatgtgca   2340
cgtcaagggc accaacgtgt gggtggccct gtacaagaac aacgtgccgg ccacctatac   2400
ctacgatgag tacaagaagg gctacctgga ccaggcatct ggtggggccg tgctccagct   2460
gcggcccaac gaccaggtct gggtgcagat gccgtcggac caggccaacg gcctctactc   2520
cacggagtac atccactcct ccttttcagg attcttgctc tgccccacat aacccgcggg   2580
gggtgtcctg ctgccctggc ctcctcccct ttagtggtag agcgaccttt tcaattacaa   2640
agaacctcct ggaaaaaaaa acaaaagctg aacagaggcg gccgtggcct tggcccgagg   2700
agactaactt gctttctccc tgcatgcagg ctgagattgt ttctggaagg ggctggcctg   2760
agtttctttc cccaaatgt ctgtgcagtg tcagggctgc accccatagg ccctgaggca   2820
cacagcccag ccccttgtga gtcctggcct ctgctgggcc ctgaaggagc tgagagggag   2880
ctcaactccc caccccgcca cgtgggggaga cagcccttcc cactggctcc ctgatggcac   2940
ctgctggagg aaaggggcac ggcctccctc acagcccttg gctggggctc ctccagctcc   3000
ccctgggacc tccagcatat gacagtggac taaggactgt ggggttttcc tccaagggga   3060
agggagaaga ggggaccatc gaggtggcga gtgtggacac cctgccagga ctgcagcccc   3120
catggtgatg ctgtggcatc agacatgtcc gtggtgggca cagtgcctgt tgccctggga   3180
aagggcaacc tccctttcac tgctccagtg gcagccatgg ggaaggcagt ttgtgagggc   3240
ttggggcaca gacctggggc aggaggcagc tcttcacgtt catccctgtc tctcccgggc   3300
tgcccccgcc agctctggct gtttagcttg agggcagcac agaggcccct gggacaccta   3360
caggccagaa agatcaacct ctgtgaagtg tctagaagta tctagtgcag atggtggcgg   3420
aggcagaatc gaccatcagc aaacatgagc actcttccct ttctcccctt ccacctgctg   3480
cgggctgggc tggttttctc aatacaaaat tgtaagagga tccttgtcac cccagccagg   3540
tatccccaag gcagagcacc tctcgtttgg ccctctgaac aaggtgcacg cgagctgggg   3600
```

-continued

```
gatgaagacg gctcccactt ccttttcctt aataagaacc atatggtggg tgtatgtgtg   3660
tacaagaggg gttcatctgt gggggcttcc tctccttcca ccctctggtt ccaatttcct   3720
gttctaagca ggactagggc ccaggaggct aaggctggga gagaaagggt gccaacaggt   3780
cccttgggaa tgagttggct ctggacgttt ctgccctgtt ccccgatcag agctcctctg   3840
caggaaacag gcaggatgcc cctcccaacc cctcagtccc tacgtcaaac ggagtggata   3900
aggctgagat gagtgctggg agtggtggac attcctgctc gtgcaaagat ggccactttc   3960
cccgcagctg cagggcctcg cgctcggccc tcgccaggcc agccccactc cttgtaccaa   4020
gtgtgaactg ggtcattcg gtctgtgatc tcgttgcact gctccaagtc tggctgtgtc   4080
caggcggtcc atgttgaaaa tggaggatgg ctgctgactt ctgactggct gagcagtggg   4140
ttccttcagg ttccttgcca accctcctcc cctgcccaca acttctccaa acaaagcagg   4200
ctgtttgctc acttcttcaa aaggaggaat gataacccaa atctgcccaa gtgacacttg   4260
agaaggtttt ggctggggtt cctggtggat ttcttactac ctaacgccca agaaaaccaa   4320
ctaaggactc tcaaaccata cctggtgggg gttcttcgct caacctcttc ttccctaggt   4380
caaagccact atcatctgat gtgttaggga tgggttctga ttggcagaaa ttaatcagct   4440
cccaatggga gcccacggaa ctaagtaggg tcccaagaaa aaaaacggga gctatttcac   4500
agagctgagc ttctgccaaa tttcattcct caaacctttc aggaggggtg gttggcgttt   4560
ctaaaatgtt tatgggattt gagttgcagg tgtccactta actgactagc tttgataaac   4620
aatgtcagat tttaactatg aaaacgacat taccttgtgc atttttatat tgattcctat   4680
ttttttttta agattaaagt ttaaatgttt tccactagtc atttcacttc taacttggta   4740
taggaagctt agctctctac atacctatca tgtgccctgt atcacagaag attcaggaaa   4800
aatgcacttg ggaatcaaag aaaatggaac ttctttttga aaagacaagc aaccatgtta   4860
actgtattga cacatcctca ataaaacctg ttgtataaaa aaaaaaaa               4908
```

<210> SEQ ID NO 34
<211> LENGTH: 251
<212> TYPE: DNA
<213> ORGANISM: Homo sapien

<400> SEQUENCE: 34

```
actgcaaatg tccctatgac ttctttgctt tctcttatac caaacatgca ggtatttaat     60
tgtttaatga gggttgagtg gagttatgtg tcgcttttat tcggattgac gaaaatcaac    120
cataattttc aagggatctt catgggttgt gactggaagc tgaccttagt cttgcgtctc    180
atcctttatg atgttgagaa atcatctaat ttctcagaac tttttcttat ctctaacaca    240
gttattacca t                                                         251
```

<210> SEQ ID NO 35
<211> LENGTH: 1331
<212> TYPE: DNA
<213> ORGANISM: Homo sapien

<400> SEQUENCE: 35

```
aaaaaaagaa agtaatttta aactcactgg cttgaaatgt gtgctttctg tacaatgaag     60
ttattgcttt ccatatatcc ttgaatcttc agattaacga aatgaacaaa ttttcggtta    120
tagatcagct ctcaaacact aaagtcctta atggcaaggt cttttctgat agcttcatgg    180
atagtattga tgatcagatt tcttctgtgt tattgtctta aaaataagca tttgaacctt    240
```

-continued

```
aatttaaatt cttttctttt ccatttagag atatgttttt ttctttacct tcataccttt    300
ctatttcttg ctaatttcta tcactaattc cttataattg tccctgctcc ccttcttgat    360
ctcttcaggg ggaatactag gcagttttgt atcttctgat ctcgtaccct gagacttcat    420
ctgaatgtgc tctgccgcct tcttatctga actagatgaa ttggccataa ttatgaatag    480
gaatattaat gaaccagagg acatactagt cacatgttat tatacactaa aaaataggaa    540
gtcatcttga aaggcagtta atgtactgca aatgtcccta tgacttcttt gctttctctt    600
ataccaaaca tgcaggtatt taatttgttt aatgagggtt gagtggagtt atgtgtcgct    660
tttattcgga ttgacgaaaa tcaaccataa ttttcaaggg atcttcatgg gttgtgactg    720
gaagctgacc ttagtcttgc gtctcatcct ttatgatgtt gagaaatcat ctaatttctc    780
agaacttttt cttatctcta acacagttat taccataata atattgtctc catttatcat    840
acaggatcat tatgaaagta aaatgaagta gtatatatga aaatgctttt taaacacaaa    900
agctttatac aaaatattgt tgaatttaaa taaggtaaat ctttttttagt ttatatattt    960
gcagactata cttgttggtt aaattgggca atttaacgtt catagggaat ttggctccta   1020
ggtcctcctt tcgaagagca aaccggacgt accctatttt ttgctaggtg aactattttc   1080
gggcattcgc aacttaattc cctcggtttg gggtgcacat tactctaaat cgctggggct   1140
gatcttacct ggactgttta aggtcggcca gatcccttgt tgagtgccaa ttgcgataac   1200
aatagagccc cgacaaaatg agaacttctt tctgcataac gggggcacag gggcgcaaga   1260
gtgattgcgc caaaagagtc tagccagttt ccctcgcaaa gaaaattatc tcaccctcat   1320
tgactactcg a                                                        1331
```

<210> SEQ ID NO 36
<211> LENGTH: 224
<212> TYPE: DNA
<213> ORGANISM: Homo sapien

<400> SEQUENCE: 36

```
ccgggcaggt accattgttc tcttctgatg gtctgtttac taaaaaataa aaacttcaca     60
aacgtgtaaa aaatagattt gccatttaaa atgtgctttt caagtttgac tttttaggat    120
acaattaatt cactaaatac agaacttaac taaggacaaa aatttaaaga tcagcattct    180
ttcccttccc atcacgctca acttaacatg aagaactgta aaca                     224
```

<210> SEQ ID NO 37
<211> LENGTH: 1547
<212> TYPE: DNA
<213> ORGANISM: Homo sapien

<400> SEQUENCE: 37

```
tttttttttt ttcaagaaaa aaaaatcact ttaattgagg aacactttca gtttgtgaca     60
aaattatgct gtgaatcagg tgttgcaaat tatggcccac tgcctgcttt tgtgtaagtt    120
ttattggaac acagctacat tcagtccatg gctgctttta gaatacaaca gtagacttta    180
acatttggaa cagggaacag aaaccagagc catacagcta ataaacttga aaatatttac    240
aagttgatgc tttacaaaat ccatctgctg acccctgctc tgtaccattg ttctcttctg    300
atggtctgtt tactaaaaaa taaaaacttc acaaacatgt aaaaaataga tttgccattt    360
aaaatgtgct tttcaagttt gactttttag gatgcaatta attcactaaa tacagaactt    420
aactaaggac aaaaatttaa agatcagcat tctttccctt cccatcacgc tcaacttaac    480
atgaagaact gtaaacatcc taagcttaca acaaacctat ctagttagac ttcagttaac    540
```

```
cacttacaca tccccctccc ccatgaacta tttggaaaaa gctgcaggcg taatattgga    600
tccctaaata ctttattctc cttataccat tatcagaccc aagtatcatc taatagtcca    660
taatcaaact gcctaaagca gtttctacac tgtcttttta actatttcaa actatcaagg    720
tccgcatttt cttccttaga acttttagtc tttttcttcc ccaaaatatt tgagtccatg    780
ccagttgcct ttagttgtac ccaaataatg gtttgtctgt ttactaaaag tagtactctt    840
aaatttaaat ttagtgttat ttttgttgtc atcgttcctt cttcctcatg tggttgtgca    900
ggcagagctt gagcatccag atttcaaaat taaaaattta aagataatct agtttaatat    960
atagtagttg aatcacctta agtctagact gctgtatgag cacccattat ctttcactat   1020
attccatcat ccccctcccc catgaactat ttggaaaaag ctgcaggcgt aatattggat   1080
ccctaaatac tttattctcc ttataccatt atcagaccca agtatcatct aatagtccat   1140
aatcaaactg cctaaacagt ttctacactg tctttttaac tatttcaaac tatcaaggtt   1200
cgcattttct tccttagaac ttttagtctt tttcttcccc aaaatatttg agtccatgcc   1260
agttgccttt agttgtaccc aaataatggt ttgtctattt cctaaaagta gtactcttaa   1320
atttaaattt agtgttattt ttgttgtcat tgttccttct tcctcatgtg gttgtgcagg   1380
cagagcttga gcatccagat ttcaaaatta aaaaataaaa gataatctag tttaatatat   1440
agtagttgaa tcaccttaag tctagactgc tgtatgagca cccattatct ttcactatat   1500
tccatcatcc cccaacatat ccacagtaga tgaagggcag tttgctc                 1547
```

<210> SEQ ID NO 38
<211> LENGTH: 710
<212> TYPE: DNA
<213> ORGANISM: Homo sapien

<400> SEQUENCE: 38

```
gagatcacca ctatagggca atgttcctct agatgctgct cgagcggcgc agtgtgatgg     60
atcgtggtcg cggcgaggta cttatgtttt taaaaatatt cagtcatttc ctactataat    120
cctcatgtat ccatgtaact gactcaaaaa tacttcagcc acagaaagct aaaactgagc    180
aaatctcatt cttcttttcc atcccctttg catgtggctg gcatttagta atgattaata    240
atatggccag ctgaataaca gaggtttgag acacaattct ttctcaaagg agtcagctaa    300
gctgggtcta cttatggaca aacatctaaa tgtgtggaag tatctgatat ttgacaatgg    360
taaatttcca cttagctagc tagcattgtc agacttcaat ctcctcatgg ctctggccgt    420
cctgttttaa gcatgataat tgttggccac atctcacata gttctcattg agtgagtcca    480
taaataaaca gggttttttt tttttttaaa gagcagccaa gcacaaagtg gtgaccttgt    540
tgacttttta tgcgactttg tcatatgttc ctaaccccca ataaaagcaa tgtggcatca    600
actataaaaa aaaaaaacaa aaaaaaaaaa ggttgggggt aaccggggcc aaaagcggtc    660
cccggggttg aattgttttt ccgcccaaat tcccaccatt ggaaaaaaaa               710
```

<210> SEQ ID NO 39
<211> LENGTH: 2399
<212> TYPE: DNA
<213> ORGANISM: Homo sapien

<400> SEQUENCE: 39

```
tatggatatg cttattaatg cacttgtttc aaaatcccaa attgcacaaa tgtgttaata     60
ttttaagaaa caaaatgaat cctacaagga gaatgatttt tagccacaca tagggttgga    120
```

-continued

```
tcttgagagt gacctacaga ataaaagtac ttttaaaata aagtagtcag aggctattca    180
aagggtaaaa taatcatagt accacattgg tccacttgac actaaccaat cgatcatttt    240
tttttaatca agaaagctag attctatcag ataaaatcac tgcttctaaa gagtttaaat    300
ctagttagaa aaagttatag aaatgtttgc aaagataagt aacagataga gtcagtagag    360
gataagatca aaaacaaaac caagcaaaag atgagttcag gggagtttgc catcaagttg    420
gcaaaactga cttacttagg gaagaaagtt ataaaacagg aaaatatgag atgaaccttg    480
agtgatgtgg aagatttaga taaatggaaa ggaaggagaa aatggagttc tttaggtggt    540
tgtaattgga ggaggaaatg aatacacaca tcttgttgac ttaaacccag acattcagca    600
gctctctata catatctgga aaagactgca cagtcacctc ctgtctctca ccccaggtat    660
tacttagaat tattatcata tttcccttcc tttaaagtaa gtaagggtga ttggtgacaa    720
tatggagaac tatgattttt ccattaacct aataataatt ggtatttatt gagttctgtt    780
aagcatttta catattaact cacttaagcc tttcaacagc cttgcaaaat aggtattatt    840
atccccattt tacaggcaag aaaactgagg tttaagtaac ttgccgaagt gccatataca    900
gggctcacat tcagtattgc agttgcaaag ctcatgatct atagtgccaa gttgcaatat    960
tgtagtcaat gtcacaatta ttaccccttt ttatattcct tgatattttt ccatggcaaa   1020
caattagcta tttcatttaa taatcaccta aaacttttca gtcttctgat taaaattacg   1080
ctggagtgat agaatgtatt ttcatgatag aaattgggaa aaaaaatggg gaatgaagtt   1140
tatcagcatt tcagacttgt tttttttttt tttttttttg caagactttg atgagattgt   1200
tcacttttgt ctatgtaaaa tcccaaatcc ttgagaataa aaaaggggga ggtttaagtc   1260
acttgttgca atgccctttt taatagaggc aataaatcta aaggccataa atttagagtg   1320
acttacagaa gatcgaactt tggagtgtgg cagagtaagg gatggaaacc gggccctcca   1380
gttcactatc agtagctttt gcactggtct gcccttccta aattaagtat gcacttcaat   1440
ttgatgagtg gaaacagtct atctgggcag taaccaggga gctttgtgcc tagtagattg   1500
cttctgttct gcacttcttt ggtttcccac ctcaatgtaa aaaatagcta gcaatgaagt   1560
ccagaagttg tcaatggttc atccccagaa gaatgcataa tgtccaaagt tgtatgtgta   1620
tgatgtcttc aatggtatta agttatttca aattcttagt tcacctacat aaatcatttc   1680
taacaagcat cttcttaacc aactttatgc acagtgtatg tttgtaagtg cttctgcacg   1740
aatgtttata catgactgtt tccatagtac ttatgttttt aaaaatattc agtcatttcc   1800
tactataatc ctcatgtatc catgtaactg actcaaaaat acttcagcca cagaaagcta   1860
aaactgagca aatctcattc ttcttttcca tccccttttgc atgtggctgg catttagtaa   1920
tgattaataa tatggccagc tgaataacag aggtttgaga cacaattctt tctcaaagga   1980
gtcagctaag ctgggtctac ttatggacaa acatctaaat gtgtggaagt atctgatatt   2040
tgacaatggt aaatttccac ttagctagct agcattgtca gacttcaatc tcctcatggc   2100
tctggccgtc ctgttttaag catgataatt gttggccaca tctcacatag ttctcattga   2160
gtgagttcat aaataaacag ggtttttttt tttttttaaa gagcagccaa gcacaaagtg   2220
tgactttgtt gacattttat gtgactttgt catatgttcc taacccccaa taaaagcaat   2280
gttgcatcaa ctgtgaaaaa aaaaaaaaaa aaaaaaaaag gttgggggta accggggcca   2340
aaagcggtcc ccggggttga attgtttttc cgcccaaatt cccaccattg gaaaaaaaa    2399
```

<210> SEQ ID NO 40
<211> LENGTH: 538

-continued

```
<212> TYPE: DNA
<213> ORGANISM: Homo sapien

<400> SEQUENCE: 40

cgtggtcgcg gcgaggtaca gagtatgtag tgggcatctg ttgaatgaat gcttttccca     60

gtagcagtgt attcatacaa tattaatata attgtcccct gggcttacgg ataaagaatg    120

aaagcatcaa gtgcccagtg agtgagaccc aggtgttctt cctccacccc tagtggtccc    180

ctgggcaggt cttttttttt tggtaacact caccaggtct gttctgtagt caatcatgtg    240

atggactgtg tcggtgaact gtgcaggaca ctgttctcat agtgttcatt agcgacagag    300

taaacatgtt tgccatgcaa gggttatttg gcatctgcat ttaagtgata atgttgaatc    360

aatgaaaagg tgttgattaa gcagtagttg tagatatgct aagtttttca aattactaat    420

atcaagtgga gattgttttt acttttaagg gtatggcttt ggtgatagca taaataatgg    480

ttttcctttt tggtaatgta acattactgg ctggcaactt tggtattccc atagactg      538


<210> SEQ ID NO 41
<211> LENGTH: 1643
<212> TYPE: DNA
<213> ORGANISM: Homo sapien

<400> SEQUENCE: 41

ggcctttgca cattgaagtc ggcactgctt tggtgccttt tttgtttttt ggctcggtgt     60

tttgactgca agtctttttg gatagaattt tatagttaga aagtagctaa cacttgggtt    120

ttataggcac aaaaaacaag tcttatacta gctgtacttt attttttgag ttcttattaa    180

tgaggaacat ccacttttgc attgacagtg atttcaagat tgctttatca gcctttaaag    240

gattcttgac tagtcgtgca catcagaact gccaggtccc cagtggttct gaagcagtaa    300

gctttgggtg ggctctggca tcagcacttt cactaagctt cacagataat tctgatgcat    360

actccaggcc tgaaccactg atcaatttga aacatgcata acaaagcaaa tcattcagag    420

agacaggtcg ttgctccgga gtgatacaga tctggcagta cccagccctt gtgtgtgtgc    480

gttagctcag cacctgccca cactgcgagc cccgtagga tgtgccttgt ccttccctgt     540

ttcagcactt aacacactac ctggtacaga gtatgtagtg ggcatctgtt gaatgaatgc    600

ttttcccagt agcagtgtat tcatacaata ttaatataat tgtcccctgg cttacagata    660

aaaatgaaag catcaagtgc ccagtgagtg agacccaggt gttcttcctc cacccctagt    720

ggtcccctgg gcaggtcttt tttttttgt aacactcacc agtctgttct gtagtcaatc     780

attgattgac ttgtctgtga acttgcagga actgtttcat agtttcatta gcacagagta    840

aacatgtttg ccatgcaagg ttattttgca tctgcattta agtgataatg ttgaatcaat    900

gaaaagtgtt gattaagcag tagttgtaga tatgctaagt ttttcaaatt actaatatca    960

agtggagatt gtttttactt ttaagggtat tgcttttgtg atagcataaa taatggtttt   1020

cctttttgt aatgtaaatt aattgctggc aacttttgta ttcccataga ctggggaagc    1080

ttaattgcct ttacaagtac ttatgtacaa ctttgtatca aattttctgt aatagtttat   1140

gctttagtac tatatatgta ctaataattt tatctgactt ctgtttatat catttgtaca   1200

attacatggt tgtaaaactt ttcctcaata tccttctatt tttatatatc tttctttctt   1260

tctattcctt tctaatcttt attatattat tttaatctct ttcatttttt tctactctct   1320

tctcttctat ctttctaatt cacgatttct actctattat attttttcta ttactccata   1380

tttatgtcta ttatcttatt ctaattatac ttttttctct tttacttttc ttattatctc   1440
```

-continued

```
tccttctaac tttatctctc tttctttatt tgatcttttc ttttattttc tatattattc   1500

ttttttttt ttactcttct cttttatttg tcttatttct ctcaattatt catatttatt   1560

ctctctctta ctttctacat attcttactc ttatttttta taccttcttc ttatttacct   1620

tcctatcctt tcttgtttct cct                                           1643
```

<210> SEQ ID NO 42
<211> LENGTH: 711
<212> TYPE: DNA
<213> ORGANISM: Homo sapien

<400> SEQUENCE: 42

```
cgtggtcgcg ggccgaggta ctacgcataa tgttaatagc tgagatgtta aagaatttga     60

agtctaaaat ataaaagatg aatataccca tattaatcct atgttaagat gctctggaaa    120

taaaggcctt attcccttac acatgcgatt tttgtaagat aatatataca cagtatattt    180

taaatgtttg tgtgggtggt ctgtgtagtt actccccata caacaaagct gacaaaattt    240

ttaatttaca caatgtattc tgcattttca aatgtttatg ttgtgtatat agcaaagaaa    300

ttatcttact gatatgcgtt gaccaaatcc catggagaaa agacatctca tttgaggttc    360

cccttcctct catgtgtttg attttttgga aggtgataca gtatgtgggt aaccatgcaa    420

atgtttatga ataactttac tgaagtgatt ccatccgtat tctgttctaa tacttggaga    480

atgaccttca tatttatata ttttatttct ttgtttcaac tatccagtga taattcagga    540

aatgtttcct ttttttttt ttttacaaaa accttttact gtgtcacatg ttgtataatg    600

taaggtgacc gtgttcataa agtctctttt agaaaaaaaa aaaaaaaaaa ggggggggta    660

ccctgggcaa agggcccggg ggaatggttc cgccaattca ctgaaaaaaa a             711
```

<210> SEQ ID NO 43
<211> LENGTH: 5520
<212> TYPE: DNA
<213> ORGANISM: Homo sapien

<400> SEQUENCE: 43

```
aaataaaagt aaaaagattt caaaataatt cagacataaa aggagtgaca ttctgataca     60

tggatggagc tggagaatat tatgcttagt gaaataagcc agatacaacc ttttgtacaa    120

aaatacaaaa ttgtatgatc tcatttatat gaggtagtta gaagaggcaa ctctatggag    180

acagaaagta gaatagaggt taccagggct gtgaggggag aggtgaatgg ggagtttaat    240

gaatacagag tttctgtttg gaatggtgaa aaaattctgg agatggataa tagtgatggt    300

tgaacaatat tttgaatata tttaatgcca cagaattgta cacttaaaaa tggttaaaat    360

ggtaaatttt acacgatatg tatctgtatc tatatatatc tctctctata tctatatatc    420

ttaccagaat acaaaattta ataacacact ccgaaaacct ttacagatga ggaaactgaa    480

gaaaactgtc tacaggggag gagttaagaa tttgcccagg attattcagc tgggaatttg    540

cattcgggat ccaaacttag ttctgtttca ctacatatta tctactccat attatctgtt    600

ctgtgttatc tgctggcttt ctgggtgatt aaagatatgt cagctccgag aagaatgagt    660

ttatttgaat cattcagaaa gttacattta aaagtaggta attgtagttt gatggaaggt    720

acagtgtgaa accctagaca gactaaaggt taactttgag gatttctttc tcagccagag    780

tggtaatagt atgcatttga gaggggagga gagtagagtt ctaaggatgt ggtctttgga    840

gacagtttct tgggttccag tccctgagct accaatttgt gtctggggtg ttatcctctt    900

gatgtcttag catccctatc tgtaaattgg tgaggataat gataacatct gataaggtgg    960
```

-continued

```
ttgtgaggat taaaggaatt gatacatgtg aaatccttag aactgtacct ggcaaaaagt   1020
gtttgataaa tgattttcag ttattgtgcc gatattattt tagagttgat gtactttctc   1080
attaatggaa ccaaacactt ctcaagttaa aattacgtgc ttaggactgg taagttacaa   1140
aaatggtacc acacgtttta tctatttcaa tttagaaatg tctgttgatt aaatgtgttc   1200
gctttaaact actgaaacaa tgtagacatt tataaaatga aagcgtattg atccctgtta   1260
tctcattcgc tacctttaac ggtttggtgt atattcttcc ccaaattttc aaatatattc   1320
atatatgaat atgtattttt acatacattt tataaaaatg ggaccaagtt atttggttct   1380
aacatggctt ttttttaagg tcaatacaaa gatctgtttt attaaaaaat aattgatatt   1440
cctttagggc tcactatatg cttggtactc ttctaagtca ttattttata tagatactat   1500
aatatcgaga gatggagaga ttaagtaaca actagttagt ggtaaaggaa ggattttaat   1560
ttgggtacgt tagcttcaaa gtcctgatct cccagccagg gatcattttt ggtaaggcct   1620
gtgagctgga aacgttaaca cttttaaaag agttgtaaaa caataccacc ccacttccct   1680
gaagaacata taagggagac tagataccgc ctgccaagcc taaaatactt accatgtggc   1740
cctttacaga gaaagtttgc tgccccttgc tctaagccat ccagctgtac ctctttggtg   1800
taagggggt gcatagtatt ccagtttatg aatgtgcatt acgcagcaaa ccaatctgtt   1860
gtgattgaca ttgttttctc tcctgaaaag aagtgaacat ccttatgtat ctttgaacat   1920
ttgtgtgaca attttctata gagttggctc tttcaagatt ttgaacattt ctagttttaa   1980
taggtgttgt caagttatat taatttttag ttaaaacaac aactgtattg aagtataatt   2040
tacatacaat aaaaagcaca catttgaagg gtatgatttg aggagttttg acaaatgtat   2100
gcacctgcac cgctgcctgg atcaagatct ataatggttg ccatcatctc agagtccttt   2160
catcctcttt tacagtcatt ctctcaactt tttttttttt tccctccaag atggagtctt   2220
gctctgtcac ccaggctgga gtgcaatggc atgatctcgg ctcaccgcaa cctctgcctc   2280
ctgggttcaa gcaattctcc tgcctcagtc tcccgagtag ctgggattac aggcgtctgc   2340
caccacaccc agctaatttt tgtagtttta ggcgagatct cagctcactg caaccttgac   2400
ctcctgggct caatcaaacc tctcacctca gcctcccaag tagctaggac cacaggcatg   2460
taccaccatg cccagctaac atttattatt aatatttttt tgtagagatg gggttttcct   2520
gtgtcgccca ggatggtttc caactcctgg gctcaaatga ttctgccttg gcctcccaaa   2580
gtgttgggat tacaggcatg agccgcggca cctgacttgt agtaaactct ctgaattaat   2640
attccattgt aggcatgtgc tacagttttt aaattcattt acccatggat ggacacatag   2700
gactgttgtc agctgttgat aaagctgcta tcaccatttg tatgtctttc ctggacatgt   2760
tttagtggta aatattgatt ttactttgta agaaaccgtt aaactctttt ccaaaatagt   2820
tgtaccattt taaattgaaa gttacagttg taactgtgca ggagttacag tttcttcaca   2880
ttttcattga cacttcgtgt tgccagtctt ttaaattttg gccatcaaat gagtattaag   2940
tatctcattg tgggtttgtg tttctcagat gatcaatgat gttggaacat cttttcatat   3000
gcttattggc catttgtgta cttttttttgg ttcaagcctt ttgtcccttt aaaaaattgg   3060
attgtttgtc tggttgagtg gtaagaggtc tttatatgtt ctgggtacat agtcacatta   3120
tctgtcagat tgtgttgcca atattttatt gttcattttt gtttgatttt gtgtattttt   3180
aatactataa agatcaagtt aaaactttaa tatgggaagc ataatcagat aaattatgtg   3240
aaacaaattg tccttaattc acgagtcatt taattagtgt aacaaaatgt tatgcatttg   3300
```

-continued

```
cagaaacttg taaactaaaa ggatattatt catatgctgt taggtgtatg gatgataact   3360
tttattaatt aaactagttt tgaaaattat tgtatttagt aattctcttc attttgcata   3420
attcaaacct tttcatttat tagtgagtta agccttaaat tttttcttca aaggataaat   3480
gagaatatta aaagtaaaaa gtgaccttga tcttagaatg ggtatgtag aaatgatgat   3540
tgccaaactt agtttcccta ctttgacaat caagtaaaat tttttttttt ttttttttgag   3600
acggagtctt gctctgtccc ccaggctgga gtgcggtggc gcgatctcgg ctcactgcaa   3660
gctctgcctc ctgggttcac gctgttctcc tgcctaagcc tcccgtaaat tttttttatta   3720
tagaaatgga tggcttttca gattatatat acttggtttc tatacactat tttatttttg   3780
taaagtagca gttcttttgc tcaacacctg aaatgccccc acaataaatt tttagttttt   3840
cttcaatatt caagtaatac ataactttttc cttttcctgt ttaacaaaga aaaaaaatat   3900
ataaagcaag ctgttggacc tccattgggt gttgtttacc accactgtag gtgatcgtgg   3960
cattgtccac ctcagtcttc tcatggctgt ggattcaagt tatgaaattc ctgaaggtag   4020
cattccaggt agtctgtaga acagcccaaa ctctctgaat tagtattatc tctgataggt   4080
gtttttttta ttctttgctt ttttatttga gacggggttt tgctctgtca cccagcctgg   4140
atttcagtgg cacaatcttg gcttactgca acctccacct cctgggctga aacaatcctc   4200
ccacatcagt ctcctgagta gctgggacca caggcacatg ccaccatgcc cagctaattt   4260
tttatatttt tgttagagac agagtttcac tatgttgccc aggttggtct caagattccc   4320
gagctcaagc gatgttccca ccttggcctc ccaaagtgct aggaccacag gcatgagcca   4380
ctgtgcccag cctagtttct tttctgtatg ctttttttac aaaactgtga gccacagagg   4440
ttgaccactt agccaatttg ttgctagaag ggagaaaaaa atctccaact agcctccaga   4500
caaaacatac tcaaattcaa acagcagtta gttttaatta acatacagaa gtaattttag   4560
actttcagat ttctatgctg actagaacac tttgcaggct gaagctgaca ttattaccaa   4620
atacttcatt taagtacata ctctgaagtg tcaggcttcc agtatatata gcaacgctct   4680
gagagacaaa ctgggctcat atgacggggt tgcattttat tttcttaaca ggtctttaaa   4740
ttgggcagtt ctgaaattct gtttggtcag ttctagatgg tacgtcatgt gaatgcaacc   4800
aagcactgta gttgaaattg tgttatgcca ctactcatat gttgtcttag gtactacgca   4860
taatgttaat agctgagatg ttaaagaatt tgaagtctaa aatataaaag atgaatatac   4920
ccatattaat cctatgttaa gatgctctgg aaataaaggc cttattccct tacacatgcg   4980
atttttgtaa gataatatat acacagtata ttttaaatgt ttgtgtgggt ggtctgtgta   5040
gttactcccc atacaacaaa gctgacaaaa tttttaattt acacaatgta ttctgcattt   5100
tcaaatgttt atgttgtgta tatagcaaag aaattatctt actgatatgc gttgaccaaa   5160
tcccatggag aaaagacatc tcatttgagg ttccccttcc tctcatgtgt ttgatttttt   5220
ggaaggtgat acagtatgtg ggtaaccatg caaatgttta tgaataactt tactgaagtg   5280
attccatccg tattctgttc taatacttgg agaatgacct tcatatttat atattttatt   5340
tctttgtttc aactatccag tgataattca ggaaatgttt cctttttttt tttttttttac   5400
aaaaactttt tatttgtaaa atgtttgtaa taatgtaaag gtgaacatgt tcaataaaaa   5460
tcatatatta aaagtttaaa aaaaaaaaaa aaaaaaaaaa aaaaaaaaaa aaaaggcggc   5520
```

<210> SEQ ID NO 44
<211> LENGTH: 369
<212> TYPE: DNA
<213> ORGANISM: Homo sapien

<400> SEQUENCE: 44

```
atgatagatc atataggcga atgggcctct agatcatgct cgagcggcgc agtgtgatgg      60
atgcgtggcg cggcgaggtg gttgattgag gttaaatcat caaccactag ccccccttcca    120
aaatcagcga gatatttgat gattaagtga ttcattgggt atgttctggc tactgatgtt    180
actgaaatct gcaatcgtgt atgtttttta atttgttgct tttgtatttg taattttatg    240
acatttcgaa gtttctgtgt cttaactctt tttaattaat tttctgcacg ttgctttttt    300
ctctttgttt ttaattccat acagagtatt caattcttga aacacattaa aataatttgc    360
ttgctaggg                                                              369
```

<210> SEQ ID NO 45
<211> LENGTH: 1019
<212> TYPE: DNA
<213> ORGANISM: Homo sapien
<220> FEATURE:
<221> NAME/KEY: misc_feature
<222> LOCATION: (21)..(21)
<223> OTHER INFORMATION: a, c, g or t
<221> NAME/KEY: misc_feature
<222> LOCATION: (284)..(383)
<223> OTHER INFORMATION: a, c, g or t

<400> SEQUENCE: 45

```
gcgcttccct gggagtaagt nctcctccag tccctgtcac tggacttgtg ccttagggct      60
tggggacaaa cactcaggga aggccctttg catggatggg acagtgcctg gctgcctgga    120
ggagagctaa gcagttagga gatagtctac tctagaaaac taagaattat tttaaggcaa    180
agaccatgct ctgatcaacc agagaagata ctatcaatag cccaggacta tcacagctga    240
atggaatggg atgggacatt ggtgtctctg tcaactgatg aacnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnngaattgt cctttggttg ccttagttac cagagttgaa    420
tgaatgtaca catttcggta gtgggggggc agagcggata acccccttcct tgtctgtttc    480
ctttgagaaa ggacactcca ccttttcaaa ggtacttaaa gccatcttta cagattgctt    540
gtaatgtaag gaaagagtca tgtcctttgg attgattgag gttaaatcat caaccactag    600
ccccctttca aaatcagcga gatatttgat gattaagtga ttcattgggt atgttctggc    660
tactgatgtt actgaaatct gcaatcgtgt atgtttttta atttgttgct tttgtatttg    720
taattttatg acatttcgaa gtttctgtgt cttaactctt tttaattaat tttctgcacg    780
ttgctttttt tctctttgtt tttaattcca tacagagtat tcaattcttg aaacacatta    840
aaataatttg cttgctaggg tatggtttat tttataatta cattcctagt cttgtgtggt    900
tattgtaatg atgtctggtc ctaatttctc tgcccgtatg aaaaagaacc ccttgcctgt    960
tgatcctaaa tataatttgg aaattaaaaa aacacacaca caaacaccaa aacaaaaag    1019
```

<210> SEQ ID NO 46
<211> LENGTH: 589
<212> TYPE: DNA
<213> ORGANISM: Homo sapien

<400> SEQUENCE: 46

```
tggtcgcggc cgaggtgtgg cagtgtgtct tcctgctctc ctcctgccct cgaaggagga      60
ctgggaagat ttccacgctg agattcccag gcgcaaactg cagctgatgc gttcctcgag    120
gttctctttg agatggaaac gagccggctg ctcgtgttca tttctgtttt gcttttctac    180
```

```
tgttgaatga ataccaccac agtgaaggga ttattggaat gttttcgaaa cacaaaataa    240

ccattttgta acttctgctg tatagttttc ttttcctgtg gatggagtgt gtaactacag    300

cacacattta aatgaaatct ctgttaatcg cctctgcact atcttagcaa atattttaaa    360

cctaaagcta aatgttgaaa taaaggtgta gagcattact gagatgcaaa tggagctctc    420

tctggctcct aattaatgac ctgcaaaaaa aagatcaaaa aaaaaaaagt ttggggttat    480

ctcactggct catacgtatg ttccctgttt gaatttgttt tccggttcaa atttccacac    540

aatttcgcac aagtgggcag aaaacgagaa cgggagaaag aggaaagga                589
```

<210> SEQ ID NO 47
<211> LENGTH: 675
<212> TYPE: DNA
<213> ORGANISM: Homo sapien

<400> SEQUENCE: 47

```
gtcaacgtct attttggggg gagctgggaa tatttggagt tctacatgcg acctggagga     60

atttatcctg gggccggggt gacatctggg gtcccctagt gagtggcagt gtgtcttcct    120

gctctcctcc tgccctcgaa ggaggactgg gaagatttcc acgctgagat tcccaggcgc    180

aaactgcagc tgatgcgttc ctcgaggttc tctttgagat ggaaacgagc cggctgctcg    240

tgttcatttc tgttttgctt ttctactgtt gaatgaatac caccacagtg aagggattat    300

tggaatgttt tcgaaacaca aaataaccat tttgtaactt ctgctgtata gttttctttt    360

cctgtggatg gagtgtgtaa ctacagcaca catttaaatg aaatctctgt taatcgcctc    420

tgcactatct tagcaaatat tttaaaccta aagctaaatg ttgaaataaa ggtgtagagc    480

attactgaga tgcaaatgga gctctctctg gctcctaatt aatgacctgc aaaaaaaaga    540

tcaaaaaaaa aaaagtttgg ggttatctca ctggctcata cgtatgttcc ctgtttgaat    600

ttgttttccg gttcaaattt ccacacaatt tcgcacaagt gggcagaaaa cgagaacggg    660

agaaagagga aagga                                                     675
```

<210> SEQ ID NO 48
<211> LENGTH: 420
<212> TYPE: DNA
<213> ORGANISM: Homo sapien

<400> SEQUENCE: 48

```
actggtggta ggttacatta gtggatcaca cacagtgtac tacttggccc tgtaaaatgg     60

tgcctgtgga ctagggtgag tttggataag tatgtatgta tgtatgagtt atagcaaaat    120

gaagtagatt gaatcaagtc catgcaaaag cagtaaaaca gttattaatt gttaattttt    180

taaaaattaa aacgttaata aaacagtttg taatgttttg ctagtgtctt ttataaaatg    240

atgtaagtta cagtggaagt cttcacagga cttgtgtctt tcctggaact attgaaatgt    300

aatttaggat gatttgatct tccatctcaa gttgtcaaca tggctgtgtc attctggctt    360

acatatgttt tatttaacaa aattctagtc aagggataag gccttaatga agacaagctt    420
```

<210> SEQ ID NO 49
<211> LENGTH: 846
<212> TYPE: DNA
<213> ORGANISM: Homo sapien

<400> SEQUENCE: 49

```
cgatgttgcc tctagatgct gtcgagcggc gcagtgtgat ggatcggccg ccgggcaggt     60
```

-continued

```
acaacaacca cttctcagta gaaagttaag aataacattt aaaaacatat tcatgtttta    120
gagaatgaat gtgccatcgt tgtatattaa ataaaaataa aagattaacc agctataaga    180
acactacaat tacaactaga gtggcagtgt tttttaacta ataaaagtat acatgtttat    240
aagtgcagta tacctgaaat cttgatgttt gtcaatactt atggttgctt caaagataaa    300
tttatgtgat tatttttgaa agatgtgtat taatttaaat aatacccaga aaaattataa    360
cttaaaaatt gcagttttca atatgagaat catttatgtg tgtaaatact caactaagaa    420
aaatcaaaag tgtggtataa tattacaaga aaaaatattc aaaatggaaa gtccatttat    480
gaatgtatta atattaaaat ccaaagttat gtttttttat aatgtctaca ttataatgtt    540
tacaaaggcc ataaaatcat ttcagaaagt tctcatcctc cagatatgac caataaaact    600
tcatttccta gaaaaaagaa gaaatgttat aatttatacc aagatgaagt aagatttgga    660
attacgtata cttacacctt cattttggat ttgattttga atgcatgctt aaaattctga    720
tattcatatg acttatttac catcaaaatt gatttgattt tttgctctca ctttctatat    780
gttcttgtcc aaaaaaaaaa aaaactgggt tatctgcctc ttccttgatt ttctcaccca    840
aaaaat                                                               846
```

<210> SEQ ID NO 50
<211> LENGTH: 2347
<212> TYPE: DNA
<213> ORGANISM: Homo sapien
<220> FEATURE:
<221> NAME/KEY: misc_feature
<222> LOCATION: (207)..(230)
<223> OTHER INFORMATION: a, c, g or t

<400> SEQUENCE: 50

```
gggcattgga aagctacttg tttatctgat acatccgcta ggtttaagaa atttgtttct     60
caatagctga gattaaatag gaagctctaa ccttagtttt ctgatttctt ttttaagttc    120
agactatatt ctaaacgaat gatcagaggt aggtgatcaa ggaattaaat tgaaagcaga    180
agtagtaatt tcaacaaaac caagcannnn nnnnnnnnnn nnnnnnnnnn gatggatttt    240
ggctctgtcg ccaggctgga ttacagtgag ccaattttcg cggccatttg cacttccagc    300
ctgtgggaga cagggcaagg cttcttgtct caaaaaaaag aaaatataaa tggaaatacc    360
agaatcaccc cttgatagag aattccattt ggcaaagtac aaacaaccac ttctcagtag    420
aaagttaaga ataacattta aaaacatatt catgttttag agaacgaatg tgccatcgtt    480
gtatattaaa taaaaataaa agattaacca gctataagaa cactacaatt acaactagag    540
tggcagtgtt ttttaactaa taaaagtata catgtttata agtgcagcat acctgaaatc    600
ttgatgtttg tcaatactta tggttgcttc aaagataaat ttatgtgatt atttttgaaa    660
gatgtgtatt aatttaaata atacccagaa aaattataac ttaaaaattg cagttttcaa    720
tatgagaatc atttatgtgt gtaaatactc aactaagaaa aatcaaaagt gtggtataat    780
attacaagaa aaaatattca aaatggaaag tccatttatg aatgtattaa tattaaaatc    840
caaagttatg tttttttata atgtctacat tataatgttt acaaaggcca taaaatcatt    900
tcagaaagtt ctcatcctcc agatattgac caataaaact tcatttccta gaaaaaagaa    960
gaaatgttat aatttataca aagatgaagt aagattttgg aattacgtat acttacacct   1020
tcattttgga tttgattttt gaatggatgc ttaaaattct gatattcaac taatgactta   1080
gttttaccat caaaaaattt agattatgat ttttttgcat ctcacttttc ataataaatg   1140
taatatagat acaatttatt ctgttttttg ttgatgttat tattgtttcc actgctattg   1200
```

-continued

```
aaatcgttct tttaaccatg aatgtgcaga atcagttgat tttccatgtg acagcttctg   1260
ctaggaatct gcagtggaac tggaagtatt tgcaatgaaa gaactttttt ctttaattaa   1320
aatagaattc ccatagaatc aacaattcct cctggtcatc aaacgcgagg tttttcctgt   1380
acttggtaga gcagagtgtg tgtgtgtttg tgcgttgtgt gtgtgttgtt tggtgagaat   1440
gatgagagct gagcattgtg aaaatacagg cgggggtggg gtaacagagc tgggtagggg   1500
tccagggcgc ttagattgcc ttattgtcca ggcttagatg cctcttaccc agagccatca   1560
ggtgtaccct atatagctcc agcctttctg cctactcctg agaagataaa ctgggatcct   1620
gcagtctgga ttcctagaag gagatggaaa gcccagccat atccccagtt tgacttgacc   1680
agtagtaaaa ctagcactac agtttgatcc ctttttacct ccttgaatat cttcaattca   1740
tcaaggatct gtaaagaagg agaggtacaa gatatatgaa acccaaatct caaaacaatg   1800
atttagtgaa tttcccatga actttaaaca gtgattgctt caaaatttcc aagagccata   1860
ctctccctcc agctgctgtg tgtgtgtgtg tgtgtataaa tgcacactat tttaacctaa   1920
aatggtgccc tgtggctgcc attctctaac tcttgcatac ttaaacattt attcttggtc   1980
aaattaaaac ctcatgcatt tccaaagata taaatgcctt gcctggagaa gttagatctt   2040
gcaagtctca ggagggccga gatggtttgt cttatgccta tagctgttta tgtcccacca   2100
gtgggtgttt gtttcattag gtgccgtttc cagccaaatg ttctcattct tcacatcttc   2160
aatgttgagt agcaaacaga agaacatcct tcttagcata atattgcttc actggactga   2220
ttgtgaactc aaaatacctc ttgtttcttg tgaagggttt gccttttgta aacaatataa   2280
gatcactttt ggtcaaccac cctgtctgaa tttatctggg ctgctataat aaagtatcat   2340
aaactgg                                                             2347
```

<210> SEQ ID NO 51
<211> LENGTH: 150
<212> TYPE: DNA
<213> ORGANISM: Homo sapien

<400> SEQUENCE: 51

```
cgagcggcgc ccgggcaggt acatgttttt aaaaaatgac tacatgtttc acctggtcct     60
attttgctat ttggaccata cttttaagtg aattgatctt acatacatgt taagtctgat    120
ttatctcccc acatttttaa acactaaatg                                     150
```

<210> SEQ ID NO 52
<211> LENGTH: 1748
<212> TYPE: DNA
<213> ORGANISM: Homo sapien

<400> SEQUENCE: 52

```
ccctttcgag cggccgcccg ggcaggtaca agtttttatg tgggtgtgta taggtagatg     60
cctatcttac cgatatatgg aatggagtta tagtaacttg tagcgtcttt ctctgctgac    120
tccaactgta tgtcagttct gagtctgttt tggttgatta ttttctttac gtgtcatgct    180
tttctgcttc gttgtatgcc tggcagtctt tgactggatg ctgaatttta cttcatgggt    240
gttaaatatt ttcgtattgt tataaacctt aaactttcag agacgtagtt aagttactta    300
aacagtctga tactttcagg tcttgctttt atgatttgtt aggcagacct ggaccaatgc    360
ttagttgagg gctaattttt ctttttcttt ttgagacgga atctcgctct ccctccaggc    420
tgaagtgcag tggtgtgatc tcagctcact gcaacctctg cctcccgggt tcacacgagt    480
```

-continued

```
cttctgcctc agcctcctga gtaagctggg actacaggca cgtgccacca cacccagcta    540

atttttgtgt ttttagtaga gacggggttt caccatgttg gccaggatgg tctcgaaccc    600

ctgacctcaa gtgatcagcc cacctcagct tcccaaagtg ctgggattac aggtgtgatc    660

cactgcaccc ggccggcatt atgattttgt gtactcttga aatggttatc tttgtggatg    720

attttttttt ttaagctgaa acttacctca tgaataactt gattaaagta gtaggtgatt    780

aaaatttcaa tagaatcaaa tgagacaaaa attttaaact gactcatttg agtttcaact    840

ttacagtcat tgaccataaa gcacactaaa aatgtaagtt atttttaaat acatctgaaa    900

taaaaatact tactaaaaag gaagaagccg aagatgtata tttagaccag cacacaattt    960

tgatttcaat tagccttatt ctaatattta gcttttagat ctttcataca cattttcacg   1020

tactttgcaa ttgagaccag aaagacttgt aggtctttct gcagaatgag tgggtccttg   1080

caaagtgagt gggaaactta ctcctagatc agaaatgttt gcctctctga gtaaaatgtt   1140

tctttcagat gagccataga gggggcacct tttactcaac ttttctttgt tttgaaactt   1200

tgtttcccat actgttttca gccttttgtt tataattaga aattgtgaga agcttcattt   1260

agtgtttaaa aatgtgggga gataaatcag acttaacatg tatgtaagat caattcactt   1320

aaaagtatgg tccaaatagc aaaaatagga ccaggtgaaa catgtagtca tttttaaaa    1380

acatgtactt ggtcttttgt gtgtgtctgt tttattccat tagaataaat gtgtccttga   1440

tgtaaatgca aagcatttct tcctgattaa attgtagatg tagactttac aatataattc   1500

aataataaaa agtaattaac ctctaaaaaa aaaagagaaa aaaaacaaaa aaaaacactt   1560

gttggggcgg cgcgggcccg gagaaaagtt tttaaaacac ttctgttggg gcggggcgcc   1620

cgggtgtagg gccccggcac aggggtgcaa ggagaaaccg ggccggcacg gcgctggttc   1680

cccaaaaaaa gccgtggcac ggggctcgaa aaccgagggc cgggcacagg ctctcacggg   1740

ccggcgta                                                            1748
```

<210> SEQ ID NO 53
<211> LENGTH: 459
<212> TYPE: DNA
<213> ORGANISM: Homo sapien

<400> SEQUENCE: 53

```
gggaaactaa caatgttcag ctgttcctgg acttcagaac cacagaactg agatgataaa     60

tgagtggtgt ttcaagttgc taagttgtgg tcattgctta cagtaatgta aactaataca    120

caagtgtaag tttgttttct taaagaagaa aaaaacgggg aaggaggtaa gtgttaaagg    180

atcaaaactc tgacaaaagg ctggttgcag aacatgacag gttgttgcac tggaaactat    240

ttgtcatgca agtttatgtt aaaataagta gcttttgagg actttcattt ttggtcttgt    300

aaacatgcca tttaatattg tccaactgat aatacttttt gcaacagaaa ctgttaaaac    360

ctttaaagca atattactgt agagaagaag tatgtgtatg aaacctgtga ggatactaaa    420

agatctacta gttctcagca taataatgac gtttgacaa                           459
```

<210> SEQ ID NO 54
<211> LENGTH: 217
<212> TYPE: DNA
<213> ORGANISM: Homo sapien

<400> SEQUENCE: 54

```
gagacagaca tatgggcgaa tgggccctag atgctgctcg agcggcgcag tgtgatggat     60

aaaattaaaa taaaaacaac tgaaggatat atgccaagat aaaccaaaat taatacagtg    120
```

```
atcacagcac agttcttaaa caaaagtggc atacaatcta aaaatatctc tttttctaga    180

aatactatta tgtaatctag ttcaattatg gaagctt                             217


<210> SEQ ID NO 55
<211> LENGTH: 2054
<212> TYPE: DNA
<213> ORGANISM: Homo sapien

<400> SEQUENCE: 55

ttttttttt gacaaacagg tgtatgcatt tattcctttt taggaacaat atctaaaaaa      60

agaaccgccc tctgccctcc cccaaaaaag acaaagattc acacagacac atcgggatat    120

atgtacaacg taataaaccc catcctaaag aagcaactgg gataaccccc aggggataca    180

gaatcagaat tgtaaaaatc atagtgaagt ttgcttgctg taaagcctga gaattttttt    240

tcagttgggt cttcttgcaa ggttgggata cctgcaaaga tttgaaaaac ctaatttttt    300

tttttttttt tttttgctac agtctttaga ctaagcatgc aagacatacg actaagtgca    360

actgagtgaa atgttttttt tttaaatttt aatcattccc taaaggtttg aactgaggta    420

tgcgtactaa cagtttctca tgctgttatc tttactcatg tctagctaca catgctgaga    480

atgaactaat ctaccagatt tttatcctct tttgaatacc aaactaacca gcaaccactc    540

agtttagaag cacagggccc ccttcccatg accctgtctg gctactgcct gcacatcatg    600

aagctgcctg gaaaagtttt tttttttttt tttttttttt tttttttttt ttttttaaag    660

tcttgcgtga ccacagactg ccctttatac agaaagcaga gtgaagcttc aaaagtaact    720

gccagagaag tttttgtacc aagcttatga gtggatggga gtgttacttt tctttaaatg    780

aaaaatgctg accaaagcct aatcggaaaa aaaggaaaaa ttaaaaataa aaacaaactg    840

aaggatatat gccaagataa accaaaatta atacagtgat cacagcacag ttcttaaaca    900

aaagtggcat acaatctaaa aatatctctt tttctagaaa tactattatg taatctagtt    960

caattatgga agcttttctg tcctgactct aaactgtctc ctttattgga tactctaatt   1020

gcagtggcat acattcattt tttttttgag atgggactcc cttccttctg tagctccttt   1080

aatattgtgt cctattttta tctgcagtag ccccataaaa tctctttaag agaatgagtt   1140

ttggtctctg tagaggtaca caaaaagaaa aaggaaaaat aactactaga aaaaagtaac   1200

aactttggtt ccattatcta cttggtcttc taaatttacg atgaaggagc agttctcttt   1260

ctcaggttgc aatagcctat cgcttgtcat ttgcctctaa attcttttgc ctcctttgat   1320

caacaataag aggatatttg gcttcatcag ataaagcata aaacagagaa cataatttac   1380

ctttgtgtaa tatctttggt aattttagaa aaaaggtaca aagaaagaat ataaattaag   1440

cttcgaaagg ctctcgaact aaaaaaaact acagtcctat ataaataaat gacaggaaag   1500

tgggtgcaga gctgaagtgt ggaggggttc taaggactga ggttgtactg acctgtaacc   1560

atcacatttc tgcataccat gtttgggacc cccccaaagc ccagggccta catgatatct   1620

tctatgagtt tttgtgatac tgggttggtg atataatatt gcataacaaa ctgcagtacc   1680

aaatttgcat atttgaaatt aacactttag catttgctga actcagccct cgttaactcc   1740

cttaacaagt tcaatctgaa atcgaatttg cattcaaaca gtttaatgcc accaagtagg   1800

tctgaactaa tgtataaact cagcgccgcc gccgccaccc ctactttcag ggcagctgct   1860

cggggaagcc ggtttttttt tttggcccat tttgccaaac caaaacccta cccacacccc   1920

gttatcgcca gagcacccca ggcccctggc aacttggttc cacaagggag agccttccaa   1980
```

-continued

```
ggccatattg tccagtctaa ttaatatgag cttttttttt tttttcagtg ctgtcgctac   2040

cttaggaccg ttat                                                      2054


<210> SEQ ID NO 56
<211> LENGTH: 221
<212> TYPE: DNA
<213> ORGANISM: Homo sapien

<400> SEQUENCE: 56

aaagaaaaag aataattgag ataggtattt actttcgtgc acagtaataa atctagctga     60

gctgctacac cttgctttgc aaagatgttt acataaaata aatcatctct tatcaagtta    120

caatggtaat ttcttgaaat gtagatatga aagctataca cttaatccac tgaaatttcc    180

ttctaatttt ttaatctgta attagaccat caccataagg a                        221


<210> SEQ ID NO 57
<211> LENGTH: 3055
<212> TYPE: DNA
<213> ORGANISM: Homo sapien

<400> SEQUENCE: 57

tctaattttt ggttaattta tagccacacc ctaaagtgaa aaagtgccaa cacaggccaa     60

ttggaatccc acaatttcca cgagcccaaa aaaaaaaaac atgtatttta gagttcatct    120

ttggcaaaat ctttggttca gggtactagt tgtttaaaag ttgattcata ttcttacctt    180

gtgctgagaa aggttgcatt gctgcccctt atacacatgc tgcagcttga tgttaaagaa    240

tttttattct ttctgaagaa ctaattaatg tttaaagcaa ctgtttaata tgatggcatg    300

tgtgtgtgtg cgtgcgtgtg tatgttctga gtccacttct tttttcctaa ataacactac    360

agggattttg tcatattaga tttaatttat aatttgaaaa atcatctagt gtgtgaccta    420

caggcttaga aatggtatag tcaaagacat tttatccaca tttctaatag tggacttgat    480

taagtagata agatcagcat ctgtttatgg tagtaggaga aatagccaaa gttgaggatt    540

ttatgtatgt tttcctgttt acctggaaaa tagcaattaa ttggattttt tggtaaagat    600

tgccttctgt ataatgtttg gattatataa aattgcaaaa atgataacag cccgctttac    660

tgtactaagc ctgttacttt catgacgtgt gagcagaatg ccttattttg taatcttgtt    720

taacttgttg ctactgggac ttgatttact gtggcactag ttaagtaagt taaaaaaaag    780

ttaaaccctc tcattattaa agaggaaagg cgatggtgat gtctgtagta caatataaac    840

cataattgtg atttacctta agtaggtata actcttatgg gatatacagt atagtttttg    900

tgaatcttta catgatagca ttatcttttt ataatttttt ttcctaagat aaacaaatgc    960

atagttttct tctatgggtg atagaaacag ctttttgaag taatgaaaac ctcaaaagat   1020

catgttgatt cttaattttt gccttttgca taagcctctt tataacatgt atctttaaaa   1080

caattaagtc tttaggaatg tgtaaccaga actatgttag tattgcttat aaaactttag   1140

ttaggttcaa tatatacata tatacatctc tatataggta tatagatttg cattttgtct   1200

tgtaaaattt tatttgaata aattcttcct gtaggtaatg ggaaacaaaa ttaatagttc   1260

atatgtcact catagcattt ctatatttga aagtagccca atataaaact tttgattcta   1320

aaattaaacc agcagcctat tacaagcaca ttctttgatt gagtcattgg ttataaactt   1380

actaaatgca gagaaagcag ccaatttagg aaacttctga gttggtggga cactgttgat   1440

taataatgta ctgtatgaat taagtgatgc tttaactttg attttacatt ttaaagttaa   1500

aatgtgggca ttatgtcagc aaacttaagg gcattatgtc agcaagctaa aacatttttt   1560
```

```
ttcctgtgct tttaatgtat ctctttacat gatctgagag aggattcaag ttgatagaaa   1620
tagctgaggg gaaaaggggg aacatcttgg gatgaagctt gtccttatgg tgatggttta   1680
attacagatt aaaaaattag aaggaaattt cagtggatta agtgtatagc tttcatatct   1740
acatttcaag aaattaccat tgtaacttga taagagatga tttattttat gtaaacatct   1800
ttgcaaagca aggtgtagca gctcagctag atttattact gtgcacgaaa gtaaatacct   1860
atctcaatta ttctttttct tttccaatat aaagtttgct gaatgtacaa gaagagttta   1920
tcacttagga tatagaattt ttttaggggt tgggggaggg gatctgttag gaaactgtta   1980
cctataaaca aagattgact ggattcgatc caaaagataa aacttgaagc tattctggaa   2040
ctaacatgga aaaatgaaat ggctattgtt taaaaaaatg atagaaatac attgttgatg   2100
ggatatgagt taagtttatt ttctacaaac tgtaattgat gaggacatgg ataatatctt   2160
catgtttctg agaagtaatc tgtatgtggg gggaggggat aataaatatt tctaaccaaa   2220
aaaaaaaaaa aaaaaaaaaa aaaaaaaaaa aaaaaaaaaa aaaaaaaaaa aaaaaaaaaa   2280
aaaagggggg ggggcgccaa aaaatatccc cccggggggc gccccattcg cgcccaccct   2340
ttttttgtga aaaagggggc ccccatgggg ggtcttatta aaccaggggg gggcgcgcta   2400
aacagggggg ggggaacaac tacgcctgtg gggcacttgt ggggaagacg aggcaccccc   2460
tacactcggg gggggggccg aaacaatggg ggggcaacca ccactccaga aagttatgta   2520
agacgcgtaa gggggataaa tacacaaact agcggcgtgg agctggtggg tggcagccca   2580
caggcgcgta tatttgcgaa gcagaaaaga agttgggcta cccgagcgta tcgtattgac   2640
gacctttctt tcgcggggct ccgtgagtta ttacgtcgaa ccaaaagtca aaagcgacca   2700
agagacaacg aagcgagcca ggtatgaaca cgagggcacg actgacggca agacgacacg   2760
aagggaaggc aacaaagcaa aggagacaca cccacaagaa gcgagcaaac cgccacacac   2820
ggaagacaag gcccgaaacg acgagcgaaa gagagcgaca aagacagaag aagaatagat   2880
acaaaaacgc ggggccacaa agcagcgcac aaagcaggcg aacaacacac aacaacacgc   2940
acgaccaaca acgacgacag cacaagcaga gatccaagac agacacgaga ccaagagcag   3000
acagccgaga gcactaaggc ccggagacga acacacacgg tgaccgaaca agcac        3055
```

<210> SEQ ID NO 58
<211> LENGTH: 831
<212> TYPE: DNA
<213> ORGANISM: Homo sapien
<220> FEATURE:
<221> NAME/KEY: misc_feature
<222> LOCATION: (76)..(300)
<223> OTHER INFORMATION: a, c, g or t

<400> SEQUENCE: 58

```
ttttaaaaga cgtgcttgtt tccaagtgct ttttacatac atttatcttt tacagttctc     60
acaaacttgc ccatannnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
atgaccgcaa gaggcagtac ttgtggacag ctcagacacg ttgtccatcg gaacagcgtg    360
gaccacagcg agaagacttc cgagtccaga tcagtaccag cgagagagac gaagggcatc    420
gagccaaaca tctcccaaag agggcgagaa cactaccgag atactcacag cagaaggtca    480
```

-continued

```
gtgagggaat aaaacgcccg gaaaagcaac atatgatgaa gcccactaga cgcgagaaag    540

aggccccaag gataaccgga aagcaacaga gcacgacgtc acggccggcg aggaagagaa    600

acacaataag aacaacagac acacgcacat ggagcgaaag ccagttcacg cgaagaaacg    660

gtgcgaaagg catcagaagc acaacgaagg gatgggcaaa aaaaccacgg cacagaggat    720

gtagtcaaac agattaccca gggaggatat acacaccagc ataagctccc ctcaagtcgc    780

cccacatgtc cgaagccaga ccgcatagcg gacaacctga cgacaacatc c             831
```

<210> SEQ ID NO 59
<211> LENGTH: 220
<212> TYPE: DNA
<213> ORGANISM: Homo sapien

<400> SEQUENCE: 59

```
aaaatggcca aggtgaatat atagtcattt atttgtgcaa aaatgccaaa gaaatgctga     60

gatgtcttct gtaaaaaaca gtaaattact ggttttacct atccctaacc cttatttgac    120

acaactatct aaaatgttca ctagttaacc aaacatttac tcagcatgtg aatccatgct    180

aagttgagga tcaaaggtgc gaagagaaga tattctttat                           220
```

<210> SEQ ID NO 60
<211> LENGTH: 2626
<212> TYPE: DNA
<213> ORGANISM: Homo sapien

<400> SEQUENCE: 60

```
cttattgtgc ggtagggtgt cttcccccct ccttggtgtt ttccccccgg tgttttcctc     60

tggtgtggac ccgctgttgt tgcccacacg ttgtttcggc tgatctcctc actgttgtgg    120

ggcccgcgcc cggcgtccct acaagcattg ggttcttcta gaagccctct tctttcgcgg    180

gggggctgct atgtgtgggc tccccacagt cagatgtttt gtttttgttg tagcgtgttg    240

ctgtggctgc cgccgcgctc tcgccgtgtt cttctcttgt agaattctgt taaaaactag    300

gaaagtgttc taagttgcaa aagggaagtc tttgatacag ttcatgattc tttttaaata    360

catatgaagt ttaacaaaat atatacatga atgtgttcaa gtagaaaatg tgaaatatac    420

attatagatt tgttgtattg cacttgggca aatcataatt gctcacttca gcatattcaa    480

accgaatcac aacatagtct ttgaaagttg acattataac ttagccttgt actcaaacat    540

tttaagaaat gttttgatgc cttaatcttc accaaaggaa tcaaacccaa atactaactt    600

ggccatatgt ttaaatacca ctaaaggcag ggaggtaaag tgttgtaggg tgcttaaaat    660

atactaagaa gggatttggc aattttccat tcacagtatt tccaatataa aagactcatc    720

ctatttatca aactcacaaa agttggggga aaatatcact tgggaaaaaa tttcactgaa    780

ttgctatcaa aggaagcaat gaagttactt gacaaactat tgacaggatg tctagttcaa    840

aatagaatct tcattgaggc taactgtagc acagtatgtg atacataaac aaaattcaaa    900

tattaaaatt ctaaataaaa aaattttccc cactagtata aagtagaagt tctatagtgg    960

aaataacaat gaaaacagat gaaaaatcag tgaagaaata gagggaggta ctactaaaat   1020

tttgtgtttg agaggaaaaa gagaaaggta aaaaataatt ctgggaatat ttaaatcagt   1080

aattgaatac atgtagtgat gtctttaaag caccttcaag aaagacctct ttcattttgg   1140

atgacaatac attaggataa atgaaatatg tgaatatggc aattttccat aaaaacaaag   1200

gagactatgg agactgtctg gttcctgatt tggccataca aaatatagaa aattcaagtg   1260

acccaggttc cacagtccca attctgtcaa attccgatcc aacaatttgt aaaatggata   1320
```

-continued

```
acatctgtat acttccactg tatatgaaaa agaatgagca gctcataggg ctacttaaaa   1380
aaaaaaatgg ccaaggtgaa tatatagtca tttatttgtg caaaaatgcc aaagaaatgc   1440
tgagatgtct tctgtaaaaa acagtaaatt actggtttta cctatcccta acccttattt   1500
ttgacacaac tatctaaaat gttcactagt taaccaaaca tttactcagc atgtgaatcc   1560
atgctaagtt tgaggataaa aggatgcaga agagaaagat attctttatt acaagctttc   1620
caacatcatg atcaaaatta caaataattt tcaaggctgt tgtaagaagt caacattaaa   1680
tgttaagttt aagcatagat tactactatt tatgaaacag atttcttcct tttgaaaggt   1740
gtgtataaaa tgtgatgtaa atcaaatcta cttatccttc tcctgcagtg caaaattact   1800
tgtacttttg ggaagataa ttccctaata aactaaatta aggtctcttg gatagaaatt   1860
cagtttctct cttcatacag ccacaaaggg tactatcttt tcattcagtc ccttaagcag   1920
cttactcttc aatgccaaca aaactttatt ttttaaatag tcttaaaagt gcttaaggga   1980
gttctggttc ctctttttag cctgcacagt ttaagatcaa tggtaaaggt aggaaataat   2040
cataagggca ctggaagaag gaatgagtct aaataatgta taatgactgt tccgccatac   2100
caattttgtc atggtgatta ttcactaatt ttataggaga gtgtattgag atctgctaca   2160
gcttcttgga tctttgaagc actgctgaat tacatacaca aagcagagca gatgtcagca   2220
cctgattaat cagtactcta ctactggcta gattccccag gcaagtcact taaattatct   2280
ccaaacagct tcctcatctg taaaataagg ataaaaattc cttcctcaca gagatgttat   2340
gagaattaga ggagatttga aaatgctccg tcaatcataa aatcatgcaa aattattcct   2400
ttgtagaaat ttgaggatta aatgtaataa catgaaggcc acactaaccg cctggcacat   2460
aaatacttaa taaaagttat tccccattct cactcttctg tgtaatttgc agttaggaaa   2520
tataaatcaa agacaccctt gtcagactca catccatttg gctttaacta gaactgtcct   2580
tccctgctcc ttttcttttt tttttttttt ttggatacat atcttt                  2626
```

<210> SEQ ID NO 61
<211> LENGTH: 586
<212> TYPE: DNA
<213> ORGANISM: Homo sapien

<400> SEQUENCE: 61

```
gcgtggcgcg ccgaggtatc gcactccagc ctgggtgcag agcgaaactc tgtctcaaaa     60
aaagaaagga agtggcatat ttggtaaatt gataaattac cactgtcaaa ttatattggt    120
gagtctatat ctattgttgt ccccagatgt tgcctttgca agaattagtg taaaattgga    180
aaaaatactc aatgttgaaa gctgtcattg ttgagatctt tatgaaatta ttgtgcccat    240
gtccaagttt gaattagaga tacacagcac acaatcattt ctgttaccac ttttggaata    300
tctagcatta gccttgatag ttttgtgtgg tgtgtttgag tatatctgaa ctgttagtta    360
tatttggtta atttattaaa agatgtgtgt taaaccttaa tatttatgca gtgtttaagt    420
attttggaat atatttgaaa taaattatcc agtgtcttag atacaaaaaa cacacccaca    480
cacaacaaca aaaacagcct gggggacccc ggggccaaaa ccggtcccgg ggggaaattt    540
ggtttcccgc ccaaatttcc caacattggc aaaaaaagcg cacccc                   586
```

<210> SEQ ID NO 62
<211> LENGTH: 856
<212> TYPE: DNA
<213> ORGANISM: Homo sapien -continued

<400> SEQUENCE: 62

```
ttttcattaa tgttttattt tttagagaat cactttaagc aattaaataa ccatttatct     60
aaaacactgg ataatttatt tcaaatatat tccaaatact taaacactgc ataaatatta    120
aggtttaaca cacatctttt aataaattaa ccaaatataa ctaacagttc agatatactc    180
aaaacacacc acacaaaact atcaaggcta atgctagata ttccaaaagt ggtaacagaa    240
atgattgtgt gctgtgtatc tctaattcaa acttggacat gggcacaata atttcataaa    300
gatctcaaca atgacagctt tcaacattga gtatttttc caattttaca ctaattcttg    360
caaaggcaac atctggggac aacaatagat atagactcac caatataatt tgacagtggt    420
aatttatcaa tttaccaaat atgccacttc ctttcttttt ttgagacaga gtttcgctct    480
tgcacccagg ctggagtgcg atggtgcgat ctcggctcac cgcaaccccc gcctcccggg    540
ctcaagcgac tctcctgcct cagcccccg agtagatggg actacagacc tgggccacca    600
cacccggcta actttgcact tccagtagag atggggtctc tccatgtggg ccaggccggt    660
ctccaacccc tgacctcaag cgatccgccc gccccggcct cccaaagtgc tgggaccaca    720
gacgtgagcc actggacccg gccgcatttt tttttttttt ttttaattga gactgagcct    780
cactctattg cccaggctgg agaacagtag cacaatctcg gctcactgca acatccctct    840
ctcaggttca accgat                                                    856
```

<210> SEQ ID NO 63
<211> LENGTH: 276
<212> TYPE: DNA
<213> ORGANISM: Homo sapien

<400> SEQUENCE: 63

```
ttggtctctt gaatttgtat tttgtctttt gtctagcttt cccacaaaaa aacattgttg     60
atttgaggat ataataatgt tttaatcttt ttaaaatata agtggttatt ctctgacttg    120
gtaactatgt tctgaaaaca ctgcatttaa gaatttttaa aaattggttt tctaaaatta    180
aaatgtccaa attaggcata ttgctgagct caaattgatg tgaaatgcca tggttccagt    240
tgaattttaa gcatattttc atttagatat aaaata                              276
```

<210> SEQ ID NO 64
<211> LENGTH: 8904
<212> TYPE: DNA
<213> ORGANISM: Homo sapien

<400> SEQUENCE: 64

```
atggcggcgg cgctggggcc cccagaagtg atcgctcagc tggagaacgc ggctaaagtt     60
ctgatggtga ggacgccgcg cccctcagac cccgggattc gcgggccccc ggtcggccct    120
gccactccag gccttgctgc tcgctgggct ggcgactggc aagggcctgc agggagcctg    180
gaagtggagg aggaggtggc ggtggcgtgg cgcaggattc ttcagcctac tttcctcctg    240
ccgtcgtccc ctccttccag gagctgtccc cttcccctgg ctgcccagca ccccagtcgg    300
gcgtgggaat atagtggtgt agcaaagaga atttcttcac cttacaccct gccccacaga    360
ctgggtcgca gagcaaggcg ccgggaagga gttggggtta tccccgcagg gcttcgggcc    420
tctcatatac tagtccttct gtctggaatg cttttcttcc ctgtcacttc atccttcagt    480
tctctcagta gtcagtttct cagggaagcc ttccttagcc tgcctgaaag tataccctgg    540
gtgatagatt ggattggatt ggattggatc ggatcggatc ggatcggatt ggattatatt    600
gtatttattt ttaagagaca gggcagctgt caaaatggaa gttcagggtc actagaggtt    660
```

```
ggcacatgtc tccagggtaa acacatgagt gcttgcattc atctttggat ccctgcgttc    720
gcttctgttt tagcttttga tgattcctta atttcttctg ccacagccat aatggaagca    780
gttgtccgag agtggattct cttggaaaaa ggtagcatcg agtctctgcg aacattcctt    840
ttaacctatg tcttacaaag gcccaacctt caaaagtatg ttcgggaaca gattctacta    900
gcagtagcag taattgtaaa aagaggatca ttagataaat caattgactg caaaagcatt    960
tttcatgaag tcagccagtt gattagtagt ggcaatccca ctgtgcaaac tctggcctgt   1020
tctattctga ctgcgctatt gagtgaattt tcaagttcaa gtaaaactag caacattgga   1080
ttgagcatgg aattccatgg taactgcaaa aagagttttt caggaagaag accttcgtca   1140
gatcttcatg ttaactgttg aagttctgca ggagttcagc aggcgggaaa acctcaatgc   1200
tcagatgtct tcagtatttc agcgttacct tgcactcgcc aatcaagtct tgagctggaa   1260
ctttcttcct ccaaatttgg gcagacatta tatagctatg tttgaatcct cgcaaaatgt   1320
gctgttgaag ccaacagagt cctgcgggag actcttctgg acagcagagt tatggagctt   1380
ttcttcacag tacatcgaaa aatccgagaa gcattcagat atggcaccaa gattctctgc   1440
agtgccttgc ccagttagct tctcttcatg gacccatctt cccagatgaa ggatcacaag   1500
ttgattatct agcacacttc attgagggat tactgaatac tatcaatgga attgaaatag   1560
aagattctga agctgtgggg atctccagca ttatcagcaa cctgataacc gtgttcccac   1620
gaaatgtttt aactgccatt ccaagtgaac ttttctcctc ctttgttaac tgcctcacac   1680
acctcacttg ttcttttggg cgaagtgctg cattggaaga agtgcttgat aaagatgaca   1740
tggtatacat ggaagcatat gataaattgt tggagtcctg gttaactttg gttcaagatg   1800
acaaacattt ccataaaggc ttttttaccc aacatgcagt tcaagttttc aattcctata   1860
ttcagtgcca cctagctgct ccagatggca caagaaattt gactgccaat ggtgtggcct   1920
ctcgtgagga ggaagaaata agtgaacttc aagaggatga tcgagaccag ttttctgatc   1980
aactggccag tgtaggaatg ctaggaagaa ttgctgcaga acactgtata cctcttctga   2040
caagtttatt agaagaaaga gtaacaagac tccatggtca gttacaacga catcagcaac   2100
agttacttgc ttcaccgggt tcaagcactg ttgacaacaa aatgcttgat gatctctatg   2160
aagatattca ctggcttatt ttagttacag gctacctctt agctgatgat actcagggag   2220
agactccgct aatacctcca gaaataatgg aatattccat taagcattca tctgaagttg   2280
acattaatac aacacttcaa attttgggat ctccaggaga aaaggcttct tccatcccag   2340
ggtacaacag aacagattct gtgattaggc tgttgtctgc cattctcaga gtttcagaag   2400
ttgaatctcg agcaataaga gcagatctca ctcatctact aagtccccag atgggcaaag   2460
atattgtttg gtttttaaaa cgctgggcaa agacttatct cctggtggat gaaaaactgt   2520
atgatcagat aagtctgcca ttcagtacag cgttcggagc agatacagag ggttctcagt   2580
ggataattgg ctacctctta caaaaagtca tcagtaacct ctcagtctgg agtagtgagc   2640
aggaccttgc aaatgacact gtgcagctcc ttgtcacttt ggtggaaaga agagaaaggg   2700
caaacttagt aattcaatgt gagaactggt ggaatttagc taagcagttt gcaagccgaa   2760
gcccacctct taatttcttg tcaagtcctg tgcagaggac attgatgaag gctctagtct   2820
taggaggttt tgcacatatg gacacagaaa ccaaacagca gtattggaca gaggttcttc   2880
agccacttca gcagcgattc ttaagagtga taaaccaaga aaacttccag cagatgtgtc   2940
agcaagagga agtcaagcag gaaatcactg ccacactaga ggccctgtgt ggcattgctg   3000
```

-continued

```
aggctaccca gattgacaac gtagcaatcc tgtttaattt tttaatggac ttccttacca   3060
attgcattgg attgatggaa gtttacaaga ataccccaga gactgtcaat ctcattatag   3120
aagtttttgt tgaagttgca cataaacaga tatgctatct tggagagtcc aaagctatga   3180
acttatatga agcctgcctt actttgttgc aagtgtattc taagaataat ttagggcggc   3240
aaagaataga tgttacagca gaagaagagc aataccaaga cctgcttctc attatggaac   3300
ttcttactaa cctgctgtca aaagaattca tagatttcag tgatacagat gaagtgttta   3360
gaggacatga gccaggtcaa gcagcaaaca gatctgtgtc agcagcggat gttgtgttgt   3420
atggagtaaa cctaattctg cccttgatgt cacaggatct cttgaagttt ccaacccttt   3480
gtaatcagta ctacaaatta atcacattta tctgtgagat tttcctgaa aaaataccac    3540
agcttcctga ggatctgttt aaaagtctga tgtactccct agaattagga atgacatcaa   3600
tgagttcgga ggtttgccag ctttgcctgg aggccttgac accgttagct gaacagtgtg   3660
caaaagcaca agaaacagac tcaccacttt ttctagcaac acggcacttt cttaagctgg   3720
tttttgatat gctggttttg caaaagcaca acacagagat gaccactgcg gctggcgaag   3780
ctttctacac gttggtgtgt ttgcaccagg ctgaatattc tgaactggtc gaaacattac   3840
tatcaagtca gcaagaccca gttatttacc agagattagc agatgccttc aacaagctca   3900
ctgcaagcag cactcctcct acgctggatc ggaagcagaa gatggccttc ttaaagagtt   3960
tagaagaatt tatggcaaat gttggtggtc tcctttgtgt aaaataaaca acagaacttt   4020
atgcttaatt tagatccttt ctgcaaagtg cactgaattg ctgaaagttg acttgagtct   4080
tgtcctattc ctcagttcat ttggccattt tggattttgg agagcctgaa actttgatat   4140
gtatgtaata cagtgaaaca ggagaggtca acttggcatc agcttctgct gttaagtgtt   4200
agccacaatc tgtcatatat atgtctttta gattctgaat ggtgatttaa aattttcaaa   4260
atgaaattcc atatatgtgc aaacagatat gggcaccacg aaatacatat gcagtgcctt   4320
ttttcctttt aacataggtg gctagccaaa gtttagaatt tttgtcatta aatatgaaat   4380
ggatatatgc taggcagtgt ttctcaaaat ctccacagat cgcctgcatc acttgaggag   4440
ctggtgaaaa ggcagattct taggcccaac tgtagacctt cagagtcaga atgtctggtt   4500
gttgggccca ggagtcttca tgttaataag cttctccctt tcgtcacccc aaaagttttg   4560
aatcaatgaa agagacattg aaaactctta agaggttttg tgctttctag cttttcctcc   4620
ctttgatgat tgggttttat aattcagcag gaaggggaaa catcatcagg ggtttgttgg   4680
ctttttctta gcttgctttc ttgcttgctt gctttcttgc ttttcttgct ttctgtctct   4740
ctctttcttt tctctctctc tctcacatca acccagtgct gcaggttttg tgtaatacaa   4800
gtcactaatc atactctgat gcctgaactt gaggaggaaa atacatgtat atttttgttc   4860
cgtaaaaata accttaggaa ctgtagccat ttcattgcct taattttaag aggaaaatac   4920
aaaaacagct gatttgtttt agtaagaaac cacgtcttga tgcttcagag ttggtttagg   4980
gtgttagctg ctatgaacct gttgcccctt tcgatcgtgt atttatgtag gtttatcagt   5040
gaaatgaaag gcttgtttcc gtctagtcta actttttgag tgtgtttcta tccagccaca   5100
tagcccatat ctactctaaa tggcttgctt aagcaataat tattttaaag gatgtgaatc   5160
actgattcac acagactatt gcacgttggg gcattagggg caataattct tatccagaca   5220
tgggagccag tgaatttaat ttcagagatt aaaaattcac tttagatcct ctagtttgat   5280
ctcttaatca ggatttttat acagctgcca ggctccccta attcagtgtg ccagcttaca   5340
atgtggaaat gaaagctaat ttatacacag caggcatatg aaactccact cattgcagta   5400
```

-continued

```
ctttcacagc acagtgacag gtagaggact ctggcacagg tgcactcatg aaactctgct   5460
tccaccatgt tcctgacacc tatctattaa accattctgc aaatacggtt tttctacctg   5520
attgcatata gcatatgtgt cattacatgt gatgctgtgc aaaactttgt ataattctgt   5580
gttattaaca gttaacaaaa ctggagcatc tgaattacat ccaacctgtg catgtgatgt   5640
taggtagatg tgaatgcagg gccttgggcc ataacttaca tttctctcaa tttgattagc   5700
tttgagtcac aattaagggg aagcaaaaac atcttgaaaa gactgctagg aaggaaatta   5760
atatcagtca tccagaagta cacgtttctg tattttaaaa aatactttga tgcatttatt   5820
tttaggtgtt tttttttcc ccttaaaaaa cttgaagtga tatgcagcag taatctattt   5880
gttttgcatt gttcttggtg ttttgtgttt cccagatccc tcaagctttc tcagctgttg   5940
cgaattatgt gtatctgtgt gtgtgctaag tacagtctct ttaccaaagg gcactgaaac   6000
acacaattga ctggacaggt ccacgcgcca tgacaaaact ataatcaagt tattaaaact   6060
aaagaggagt gggaaaggaa tgccttggta agtaaaaagg catctatatt taataacttt   6120
tatccagatg gcaacatatt tgcaaaattt gcccagatcc tattacaata ctaaaaatag   6180
aaaatttcac ctccatattc ctgaggtgta atttcattag actagtttta gtttaaaaag   6240
accttcttca gattggacca aataatactt ataagatcag cagaatgttg aatattagct   6300
cactggggtg gggagaagcc actaccattt tttaggtgat ggggatgcca ctgagttgca   6360
acggctagac cttttcaggg tggttgtgtc catgtttgcc tgattggatg cttattcact   6420
ttgtgttttc ttttgtttta ttttgtccaa ttttgtcttt agctgtgttt attaacttct   6480
ccggtcttgt tttgttttaa tgctcttggc ccagtgggtg tcaagaacac tggcttaatt   6540
caagtcagtt gattttttt ctattaaaac tgttgttaaa atattttta aaacaaaaac   6600
attatttgtg ccctctttta tatatgtcaa agggacactg tcaagtattt catttttaga   6660
tttttgtttt ataaaatttc tgttgttcat atagtatcct ttaacctcta gttttccata   6720
catcctttgt ttgtttctca ttttatttc cttgacccat ttatttccca aggcacaatc   6780
actaaagact ttgtactttc acagtctgtt aatgtggtag cacctgtaac tgtgttcttg   6840
ttctgttaaa aggattgatt tgcttttata gtccttgtgc tggatgagtg gctgcctcag   6900
tagcaaaact acctgacagt atttgacagt gtcctttcca gcaccattat ttgggtcttt   6960
cagggtggcc atctctgtta gaagacagta gcatgttaac atcactgcat tgagtttttg   7020
tctggtgtaa agtatgactt ttaatgtaaa caaactgcag gtttttttca aactaatttt   7080
aagaatttag tcttatttcg ttgtaaactg tgtatctaat tatattacat tactctgttc   7140
agatgggatg gttactacca cttgtccatg attttcattt gaaaagcaag tatctatatc   7200
atttcccccc agtcagcatt atttaacact ccccttaact gtctttgaac tttctctttt   7260
aacaaaaatg tcaagtcttt acagttgtaa tatcaccatg tttcccattt ctgttaatac   7320
ttctatgaac ccctaaagta ttgaagggaa ctagctgtca gtttcaagga ttacaagttt   7380
gagtctccta gtattcaaca tcattctgaa ccctgaaata atatttttct ctgttaaaca   7440
atttttatct gtttgccacc tctgttgtta gaggtggttg tcaattgacc ttactaagtt   7500
agctgtcttt gatgaggaat tattgttatt ggttcctgaa taaaacatta accttttaag   7560
tcagaaggaa cctcggtact tcttaaggtt tgtttgtgtt ttctaaaacc agagaataag   7620
gaactgattt ggctatgagg tttaacatta taattttctg taagctttcc cacaaaaaaa   7680
cattgttgat ttgaggatat aataatgttt taatcttttt aaaatataag tggttattct   7740
```

-continued

```
ctgacttggt aactatgttc tgaaaacact gcatttaaga atttttaaaa attggttttc   7800

taaaattaaa atgtccaaat taggcatatt gctgagctca aattgatgtg aaatgccatg   7860

gttccagttg aattttaagc atattttcat ttagatataa aatatatgaa gtatgctttg   7920

ttgattatag tgagaaccca tgacatagtt aaccaaagaa tatgtttggt tcaaataaaa   7980

atagaagctt aatactgggc attcatactt tttaaagaga atgaatgaag aaatcggttt   8040

cctgctgtag ttctctatgg gtaagtctta gtaaagacga gaatgctgaa gtcggccgtg   8100

gcgattccct cctaggaact gggaggtgtg gcttgcccat tacccgcttg aagctcacat   8160

ctttaccctc ctctcccact gtggtttgat cttcacctat tcccaggccc tcccagcaat   8220

tggagaggtg tctttttttt tggttttggt tttttttctc cccgtctgca ttcttaggcc   8280

tcttagctat taggaactgt cagatacata ctagtagcta attttcctag cctgaaatta   8340

tatactgcat ctgcactatg tacctactag ggatctgacc tcaagtgttt tctgagccca   8400

ggcttcctgg tgtggtgtct tttaccacat aaaattatta caaattgcaa atgttggtat   8460

tgtgatttga ttatctgtac aaagaaagaa gctctatgca gtgagtttgt ggtttaatgg   8520

tcacaaaaat gttagcactg ctaccactca gcacgtgtaa aatttttaa atttataaat   8580

attaaaattt taaacttaca ctaagacttt tcagttttat ttaaagaccc agggatgagt   8640

gtactgttta aatatttacc tctattaaca taactaatga aggtataaaa ttgcatttag   8700

tttttcagaa gatgctgcaa tatgatttta ggaaataagg ctatgtattg agccagttat   8760

aggctgaata tcaggttgat aaaattttat ttgtattttt aaaattcata aatgggagtt   8820

aaaatgtgtc ttttcactaa atatttttat tacaaaaaaa aaaaaaaaaa aaaaaaaaaa   8880

aaaaaaaaaa aaaaaactgc ggcc                                          8904
```

<210> SEQ ID NO 65
<211> LENGTH: 241
<212> TYPE: DNA
<213> ORGANISM: Homo sapien

<400> SEQUENCE: 65

```
acggtgcctg gcacattaat tcctttcctc ttttcccctc actgccaaat gagctattgc     60

cactcacttg atatgcaaac actggctgtc tagtatggaa aaatattttt ctggctgtag    120

acttgagttt gattaccaaa ttgatttctg tgaattacat ttcaattctg tgcagaactt    180

tttgacagcc ctttaatcac catgtatcca ataaatattt attaaagaca tattctgtga    240

c                                                                    241
```

<210> SEQ ID NO 66
<211> LENGTH: 368
<212> TYPE: DNA
<213> ORGANISM: Homo sapien

<400> SEQUENCE: 66

```
ccaataaatt gaatactgaa tatttggaca attgcctctc tctaagtgct ctagaagctt     60

ctagagggaa ggaatcttgt cttatacatt aaaaaaaaaa aaaaaaaagt cttatccagt    120

ctgaagtacg gtgcctggca cattaattcc tttcctcttt tcccctcact gccaaatgag    180

ctattgccac tcacttgata tgcaaacact ggctgtctag tatggaaaaa tatttttctg    240

gctgtagact tgagtttgat taccaaattg atttctgtga attacatttc aattctgtgc    300

agaacttttt gacagccctt taatcaccat gtatccaata aatatttatt aaagacatat    360

tctgtgac                                                             368
```

-continued

<210> SEQ ID NO 67
<211> LENGTH: 745
<212> TYPE: DNA
<213> ORGANISM: Homo sapien

<400> SEQUENCE: 67

```
tggtcgcggc cgaggtacta atttttgctc ccaccagctg gagggggagg ggccaaattt     60
ccatatttgc aaatctggga gacgaacaat ggtgtgtttt ttatgcctct tattacgaat    120
gagtttgaac atcttttcaa atatttaaga gtcacctgta gctcattttc cataaactgt    180
cagttcatat cctttgccca cttttttatt ggcttttggt ctttttcctg ttgagttgta    240
aaagcacttt tcatgttaag ggaatttgct ctttgtctat tatatggtta tactgtcatt    300
taaacatggt ggcatagttg cttatagaat gtctgaacca tatgcgtcat tgttagatat    360
ttatattggg tctcatttct cttgtattat atactgggat gttttccctg ctttttctgt    420
ccccatcaac aacacacaaa acacacacac cccaaacccc ggcgcggaaa acacaggggc    480
acctacctgc cccccggggg gtgacaccgt ccgatcaccg cggctccaaa attccccaca    540
gcacaactat cgccgacgca acagggccac tgaataccgc cacagagcga cacgcgacga    600
cttcacaccg cgaccgtacg acgcacacgg caacacaaag acgcgccgag gcaaccacat    660
acggacacgc gagaacggca gatggcgacc acgcgccaaa cccaccaaga gcacaacaca    720
cagaaccacg cacaacgcac gccca                                          745
```

<210> SEQ ID NO 68
<211> LENGTH: 1064
<212> TYPE: DNA
<213> ORGANISM: Homo sapien
<220> FEATURE:
<221> NAME/KEY: misc_feature
<222> LOCATION: (93)..(93)
<223> OTHER INFORMATION: a, c, g or t

<400> SEQUENCE: 68

```
ctctaacttg ggtttttttt ttttaaactt agtgcaattt ggaaatcttt ctacatcaaa     60
attttaaaat ctgccctttc cctctttctt ttnaacagct gcctagtatt tcaccgtatg    120
actgctctgt aattgatcta acagttgtag aacacttagg ttatttcctg tcttttgcta    180
tttcaacagt gctgtaatga atatccttgg tcaggcatca tttttcatac gtgggagtga    240
atctttaaga aaaccaggag tggatttgca aggtcaaggg gaatatgcag tttgaacttg    300
gataaataag gcaaattatc ccccttaaa tgttgtacta atttttgctc ccaccagctg     360
gagggggagg ggccaaattt ccatatttgc aaatctggga gacgaacaat ggtgtgtttt    420
ttatgcctct tattacgaat gagtttgaac atcttttcaa atatttaaga gtcacctgta    480
gctcattttc cataaactgt cagttcatat cctttgccca cttttttatt ggcttttggt    540
ctttttcctg ttgagttgta aaagcacttt tcatgttaag ggaatttgct ctttgtctat    600
tatatggtta tactgtcatt taatatggtg gcatagttgc ttatagaatg tctgaaccat    660
atgcgtcatt gttagatatt tatattgggt ctcatttctc ttgtattata tactgggatg    720
ttttccctgc tttttctgtc cccatcaaca acacacaaaa cacacacacc ccaaaccccg    780
gcgcggaaaa cacaggggca cctacctgcc ccccgggggg tgacaccgtc cgatcaccgc    840
ggctccaaaa ttccccacag cacaactatc gccgacgcaa cagggccact gaataccgcc    900
acagagcgac acgcgacgac ttcacaccgc gaccgtacga cgcacacggc aacacaaaga    960
```

-continued

```
cgcgccgagg caaccacata cggacacgcg agaacggcag atggcgacca cgcgccaaac   1020

ccaccaagag cacaacacac agaaccacgc acaacgcacg ccca                    1064
```

<210> SEQ ID NO 69
<211> LENGTH: 549
<212> TYPE: DNA
<213> ORGANISM: Homo sapien

<400> SEQUENCE: 69

```
agatgatgac tcatatggcg aatgggcact aatgcatgct cgagcggcgc agtgtgatgg     60

attggtcgcg gcggaggtac tcttgaggac attttgtcag attaactata acagtgtagt    120

gtagttttta aaatgcagtg aaaagtttag ctgtctggaa gtcaaattta tccaatgttc    180

agacttctgt tactacttaa tatgaagcca ccatgctggc tggacagaat taatttcatt    240

catgttatgg agaattctat attacaaatc tggtccccta taatatgaac aggagcagtc    300

agaaatatac aaagggttaa atagggtaaa gacttggcca agaaaggaaa ggccttagtt    360

ctaccataga gtatcttctc taattaaaat gacgggaaat atatggaagc agaaaccagc    420

acaaagcact acccatctag aaataatctt tcagttaaaa aacaactctc aaaaccagca    480

ctcatttctc taagataggt tataagtatt ttacgatttc tgtgttatat taacatctgg    540

ttaaaggta                                                            549
```

<210> SEQ ID NO 70
<211> LENGTH: 774
<212> TYPE: DNA
<213> ORGANISM: Homo sapien

<400> SEQUENCE: 70

```
ttttttttt aactggttgt aaaaaaggtt tatttgtgac aaaaagttaa gtactaaagc     60

taaaaacata taaattcagg tcaggctata ttaaaataca cacataccct tctttgcaaa    120

attattaaag gttgaattaa acagatgctt taaataaaat aaagtactct tgaggacatt    180

tttgtcagat taactataac agtgtagtgt agtttttaaa attgcagttg aaaagtttag    240

ctgtcttgga agtcaaattt atccaattgt tcagacttct gttactactt aatatgaagc    300

caccatgctg gcttggacag aattaatttc attcatgtta tggagaattc tatattacaa    360

atctggtccc ctataatatg aacagtgagc agtcagaaat atacaaaggg ttaaataggg    420

taaagacttt ggccaagaaa ggaaaggcct tagttctacc atagagtatc ttctctaatt    480

aaaatgactg ggaaatatat ggaagcagaa accagcacaa agcactaccc atctagaaat    540

aatctttcag ttaaaaaaca actctcaaaa ccagcactca tttctctaag ataggttata    600

agtattttac gatttcttgt tatattaaat tgagttaaag gtactgacaa gtcaatatgc    660

aaatgggttt aaacactaat ttgatttctc ttctgactag ctctggagag ctgtgacatc    720

tggatgttgg tgcccagttg gtgtggagtg tgtagttttg ttatgaaagt tctc          774
```

<210> SEQ ID NO 71
<211> LENGTH: 881
<212> TYPE: DNA
<213> ORGANISM: Homo sapien
<220> FEATURE:
<221> NAME/KEY: misc_feature
<222> LOCATION: (601)..(601)
<223> OTHER INFORMATION: a, c, g or t

<400> SEQUENCE: 71

```
cggccgaggt acattgaaac cccatatacc cttcacctag attcaccagt gttagcgcct     60
```

-continued

```
ggtgatattt tccatatcta tgtatatgtg tgggatgtga atatatttct ttttctttcc    120

gttgcttctg gctaaacgtt gagacctcat gatacttcac ccccatatat atcagcatgt    180

atctcccagg atgaagaata ctcttccatg aaatcataat acaattatca cagtaaacat    240

gtttcaacac aactatctaa gttagggtct atattaaaaa ctcctcagtt atcatactaa    300

tgcccacatg tttctccatt tgttgatcat cccatcatga ttagattaag tagtttgtca    360

ggaatacaac ataggtgaag ttgtatcctc atgtatcaca tcaggagata ttctgtcacc    420

cattataagt aatattaact ttaattactt gatatatggg ttttctgctg tgcaacaaat    480

taccacaaac tgagcatgta ttgcatgtga aacaacaccc ttgtagttct gtagattata    540

aatctggctg ggtttccctg ctcaagattt tacaaggcca aagtcaaggt cttggccggg    600

nctaggctct tacctggagg ctctggggaa gaatctgttt ccaaggctca ttcaggttgt    660

gaccgaattt agtttccttg tggcaggccc aggggctcac acctgtaaaa ccagcagttt    720

gggaggccga gggggggtgg atcacttgtg atcaggggtt tgggaccagc tggcaacatg    780

tggaatggtg ctcctctaaa ataccaaaat agccgggtgg gggagcgcgt atcacgatat    840

ccgggggggg gggggttgtg taccccttcc tcctaggagg g                        881
```

```
<210> SEQ ID NO 72
<211> LENGTH: 1735
<212> TYPE: DNA
<213> ORGANISM: Homo sapien
<220> FEATURE:
<221> NAME/KEY: misc_feature
<222> LOCATION: (1024)..(1024)
<223> OTHER INFORMATION: a, c, g or t

<400> SEQUENCE: 72

atataatcct tagccagtct ataaaagatc tctggtctgc ataggcagta gcttggactg     60

tccattctaa tctaccccaa tagtttatct tatttacagt ttttatttat agtttctttt    120

acttagtagt tattacaata aataacatcg acccaataca actatctaag atagggccct    180

tattcaaaat gccttttttac cagctaaaac tgtttaaata ttgctaacac ctgaaactat    240

agttcgaaca caggtattta tgggagcagg gaaaaaagaa caaaaaacag ttaacaagca    300

tattctgtaa aaattgttag gattttgttt tgcttaatac atttttaaaa aatgttcttc    360

ctcaattttt tactttgaac aatttcaaac ctacagaaaa gttgaatgaa ttagtacata    420

gaaaccccat ataccttca cctagattca ccagtgttag cgcctggtga tattttccat    480

atctatgtat atgtgtggga tgtgaatata tttctttttc tttccgtttg cttcttggct    540

aaactgtttg agacctcatg atacttcacc cccatatata tcagcatgta tctcccagga    600

tgaagaatac tcttccatga aatcataata caattatcac agtaaacatt gtttcaacac    660

aactatctaa gttagggtct atattaaaaa ctcctcagtt atcatactaa tgcccacatg    720

tttctccatt ttgtttggat ccatcccatc atggattagg attaatggta tttttgtcag    780

ggaatacaac ataggtgaag ttgtaatcct catggtatca catcaggaga tattctggtc    840

acccattata agtaatatta actttaatta cttgatatat gggttttctg ctgtgcaaca    900

aattaccaca aactgagcat gtattgcatg tgaaacaaca cccttgtagt tctgtagatt    960

ataaatctgg ctgggtttcc ctgctcaaga ttttacaagg ccaaagtcaa ggtcttggcc   1020

gggnctaggc tcttacctgg aggctctggg gaagaatctg tgtccaagct cattcagttg   1080

ctggcagaat ccagttcctt ggggttgtag gactgatgtc cccatttatt gctgaatatc   1140
```

-continued

```
cactgagggt tactctcagc tcctgtaagc tgcttttggg ttctttccac atggacccct   1200

ccatcttcaa agccaggaat ggaagatttc tctcatattg aatatcttct ctctgacttc   1260

tccttgtatt atcaactgga gaaaacactc tgcttttaaa gcattctcct cccaatgagt   1320

gggaaatccc ctccttcctt tctagcactg tttctgtgac tcctggagag gtgctcagga   1380

ggtagaccca tggcctgcat tcaccgctga agctgaaggc tgccttggcg aagacaggtt   1440

ttgtcaaagt agtggctgtg aatgtgacct tacgtaaaaa taaggtttct gcggatggta   1500

tcaagaagag gttatgagag ggccctttat ccactgcgac tggtgccctt ataagaggaa   1560

aattttgacc cagaggcaca caaggagagc tccatgtgac aatagaggga cagattggag   1620

ggatgcagct gcaagcaaag gaacgccgag gattgacggc caccatcaga agcttggtgc   1680

aagacaccgt cctctcacct ggattattgc cgaagctgct aacttgtctc tccat        1735
```

```
<210> SEQ ID NO 73
<211> LENGTH: 429
<212> TYPE: DNA
<213> ORGANISM: Homo sapien
<220> FEATURE:
<221> NAME/KEY: misc_feature
<222> LOCATION: (231)..(231)
<223> OTHER INFORMATION: a, c, g or t
<221> NAME/KEY: misc_feature
<222> LOCATION: (245)..(246)
<223> OTHER INFORMATION: a, c, g or t

<400> SEQUENCE: 73

actttttag tatttacctg ttacaaagga cattgtgttt cctgtcatgt aaaaccagct     60

attttagtta ctattgtact ctagaaaaga gctgtagatt tatgttaaac tcgtacttac    120

gaacaattgt aattagttct aaaaggcatg aactcagctc ctaatcgtca ctgtatagtc    180

ctgaatttgt agaactagag ttaattccct ttcttggaaa cttttccttt ntgtgtctct    240

caagnntagt tactttttc cttacctaaa agggttgtct gtcacaacca agtctccctt    300

cgaaccatta acaacttttc ctggtgtatt cgacaacaaa aaaaacaaaa aacaaaaaaa    360

aaggctgggg gaacacaggg ccacaggggt ccccgggggg agaaactggg catacccggc    420

ctacaaaat                                                            429
```

```
<210> SEQ ID NO 74
<211> LENGTH: 563
<212> TYPE: DNA
<213> ORGANISM: Homo sapien
<220> FEATURE:
<221> NAME/KEY: misc_feature
<222> LOCATION: (49)..(49)
<223> OTHER INFORMATION: a, c, g or t

<400> SEQUENCE: 74

gatgattatc actataggca cttcggtctc taatgctgct cgagcggcnc cagttgtatg     60

gatccgcccg ggcaggtctt attcatacac atttcacttg gctttttacc cctaggaaat    120

aattgtccaa gtatatatct cgtcttcttt cttgtaactt tgattaaact gcttacttca    180

acttacaaca ttgtaaagcc agaatacctc attttaacag tgaaaaaaaa tatgatgacc    240

tgatgtgttc tcttgtattt gatttgaact acctaaatag gcttaactgt aataataaat    300

atacaatttt ggcaggcatt ttttcctttg tttggatgaa cattttgtta ttggtccact    360

tctaattttg tcttaaagag ttataactca gtgtcaataa aacatcttgt tatattaagt    420

tattggcaaa aaaaaaccac aaacaaaaaa acaaaaaaaa cctttgggat tacccaagtg    480
```

```
gccatatact atttccctgt gtttctaaaa ttgtgtttct ctccgcttca acattttccc    540

acaaaaattt caccaacaaa agt                                            563
```

<210> SEQ ID NO 75
<211> LENGTH: 1775
<212> TYPE: DNA
<213> ORGANISM: Homo sapien

<400> SEQUENCE: 75

```
ttacaaccat tgccttggga cacacagagt gaactgtttg agtgataagt aatttaggta     60

gaaactttac ccttaatttc aaatgatacc aaacagctca ttactacccc aagggacgct    120

ctccgtagct tctggattcc ccagtttcct tctagaaaca aggactccaa tagcactata    180

accctaaaca ggccctaacc cagaagaata caccacaaaa tgcgattgat tttctcaaaa    240

tatcacagtc ttagacacta tacaaataat tcaagaaaat tctttctacc ctgcagtgga    300

tatagtattc tattatattc tccagcaaaa cttttaggac ttttcaaact catttctaag    360

ccaaatagtt tagataaata tttaccctta tatttggggg gaattcaggc tcaccatttg    420

ccgaggcaag cccatcaaca gtctagaggc atattctgtg tcattccttc ccgtctcctt    480

catagaatac tactttttcc ttttgtctcc tggccattct ccatcatctg ctgattattg    540

ctaaccacag gatgctgggc aaagcttaca gtgataggca catgtgttca gtgatgtcca    600

atacactctt atcacagtgg ttattgcttc ttactctttt caaatgcatt attctacccc    660

tcaacctaca tccaatcatt agaactatac ctgactggag cccagaactt gggaccaata    720

cttaattcaa atagcagggg cttgctcaca aacattaagc ccaaaaagaa gcacagcact    780

ttgaaaagtc aaataggcct ttggtagctc tgtacatttg caattttaca tttgttatta    840

gtttatagca ctaataacac ttcagtcgtg aatctacagt ctcaatatga taagtcttag    900

aacatgttct agaaatagtg gtaccttgct gctattatac ttagtaactt ataccccaat    960

ataataataa gtattaaata cagattgtgt atgcattctt tgtgtgtata tgccaactgt   1020

actacttaac ctcactgatg agcaattaga aaaatacaca aattgtcata gtgaaaataa   1080

gtcttggtca attcagatga tacgtgaacc tgataaatgc tctaatagat atgctatttt   1140

gtcctgtatt gcttgtttta cagtatggtg catgttgttt gctaagtaaa atgataataa   1200

taataaagta taccaatttt aaggttagaa ttaaaatttt gcacatatgc ttcttgatat   1260

tctgaaatgt attctgtggc ttaattatct tattcataca catttcactt ggctttttac   1320

ccctaggaaa taattgtcca agtatatatc tcgtcttctt tcttgtaact ttgattaaac   1380

tgcttacttc aacttacaac attgtaaagc cagaatacct cattttaaca gtgaaaaaaa   1440

atatgatgac ctgatgtgtt ctcttgtatt tgatttgaac tacctaaata ggcttaactg   1500

taataataaa tatacaattt tggcaggcat tttttccttt gtttggatga acattttgtt   1560

attggtccac ttctaatttt gtcttaaaga gttataaact cagtgtcaat aaaacatctt   1620

gttatattaa gttattggca aaaaaaaacc acaaacaaaa aaacaaaaaa aacctttggg   1680

attacccaag tggccatata ctatttccct gtgtttctaa aattgtgttt ctctccgctt   1740

caacattttc ccacaaaaat ttcaccaaca aaagt                              1775
```

<210> SEQ ID NO 76
<211> LENGTH: 511
<212> TYPE: DNA
<213> ORGANISM: Homo sapien

<400> SEQUENCE: 76

```
atgatatata tagcgaatgg cctctaatca tctcgagcgc gcatgtgatg gatccggcgc     60
cggcaggtac tgatctaacc aagatatttt gtttttctca tccaccagtc actttctcag    120
tcctttctgt atcccttgca aatttgaaca aagctttttt tttttttttt tttttttttt    180
tttatggcca aaatattttt tttttcccaa aatttattta attccctttt tttctttttt    240
attggttaaa ataacttttg aaaaaatcgt tcttttgaaa aatatgaggt ccatattttt    300
acaacggcca cctttgaata tagttccaca gtttgccgcc aaaaatatcc tctctttaaa    360
acaaaggggg gtttctttgg aattgcccat atttttatct tgccaaaaaa aagctctgcg    420
agtatctcct tgtatatata gctgtgttcc tctgtgtgaa tttgtttttc cgtctacaca    480
tttcccacac aatcatcaaa gaaaaggata g                                   511
```

```
<210> SEQ ID NO 77
<211> LENGTH: 646
<212> TYPE: DNA
<213> ORGANISM: Homo sapien

<400> SEQUENCE: 77

gggattacag gcatgagcca ctgcacccgg ccactttttt tttttaaaga aaaatgctct     60
gcatggattg gagacacagc aataactact gttgccatgg aagggttaac agtgtaggag    120
ctggtttatc agtccgcttt gacatacagc taaaggaaat ttatgtttgg gggaaaaagg    180
ccctctgttc actttaaaat tcagtgtgga cttatgccaa agggggctgt ttaagttgaa    240
agaagccaag ttaagtttgg cctcttgcct ggaatcactt gaattctgaa atttcactgc    300
gacggacatg tgccttgtca cattttccat tgcttaatcc tgaagttggg tgcaagtctc    360
tctgcaccta ttaaaaagtg atgtatatac ttccttctta ttctgttgag ttgtatagaa    420
tggtcttttg tatttaacac tttgtaattt tcacaatatt ttttaattta aataaataaa    480
cactttttc cctcctgcga aaaaaaaaaa aaggctgggc gtatcgtggc aaagctgtgc    540
ctgggtgaat ggtttccgct ccatcccatc tcgcagcaaa aaaatgtgtc gaaaccgaag    600
acaaacaaac ggggagagac aaaaagacag aaagacaaat aactaa                   646
```

```
<210> SEQ ID NO 78
<211> LENGTH: 493
<212> TYPE: DNA
<213> ORGANISM: Homo sapien
<220> FEATURE:
<221> NAME/KEY: misc_feature
<222> LOCATION: (264)..(264)
<223> OTHER INFORMATION: a, c, g or t
<221> NAME/KEY: misc_feature
<222> LOCATION: (250)..(250)
<223> OTHER INFORMATION: a, c, g or t
<221> NAME/KEY: misc_feature
<222> LOCATION: (308)..(308)
<223> OTHER INFORMATION: a, c, g or t
<221> NAME/KEY: misc_feature
<222> LOCATION: (311)..(312)
<223> OTHER INFORMATION: a, c, g or t

<400> SEQUENCE: 78

ggtgatagtc atatagggcg atgggcctct agatgctgct cgagcggcgc caggtgatgg     60
atcgaggtac tgaataggaa agggaagttt tattggaacc ttctaagagg aaatcaacca    120
ggaccaaaga gccttaaagg acacacagca atgcacggca cttcccttcc ccagctggct    180
gccctaggtg atttctcaag ctccttgggg gactgtgttt ctcatctgga atcaatgtgt    240
gtatgagttn tgtctggtag gatngctgac tctgtccaac agatatcact gtggaattga    300
```

```
ataaattngt nngaaagaac caaaaaaaaa aacaaaaaaa caaacaaaaa ggcgggggt    360

aatcctgggg cctaaggcgg gttcccgggg gtggaattgg gtttccccgg ccccacaatt   420

cccccaacaa ctttcacggg aagcaagttg caacaaaagg caaaagaaaa aagaagaaaa   480

ggaaagagaa aca                                                      493
```

<210> SEQ ID NO 79
<211> LENGTH: 704
<212> TYPE: DNA
<213> ORGANISM: Homo sapien

<400> SEQUENCE: 79

```
cacttaggag ttattagtgc taaaaagggg accgtgcaag gcagcagagt tacatggttc    60

ttcaaatcat gtctgaacct attcttggaa tcttctctat aataagggaa gttctcttac   120

cccactgcca catacctctg ttttaaaaga taagtccact aactgtgagt aaaaatgata   180

tatataggca ttaaccacac actttaatgg gtataatttc ctggctgcct cccttcctca   240

gcccattagg ttaaacacca aagaaagact ggtgtgtact gaataggaaa gggaagtttt   300

atttggaacc ttctaagagg aaatcaacca ggaccaaaga gccttaaagg acacacagca   360

atgcacagcc acttcccttc cccagcttgg ctgccctagg tgatttctca agctccttgg   420

gggactgttg tttctcatct ggaatcaatg tgtgtatgag ttttgtctgg taggattgct   480

gactctgtcc aacagatatc actgtgaatt gaataaattt gttgaaagag aaaaaaaaaa   540

aaaaaaaaaa aaaaaaaaaa aggcgggggg taatcctggg gcctaaggcg ggttcccggg   600

ggtggaattg ggtttccccg gccccacaat tcccccaaca actttcacgg gaagcaagtt   660

gcaacaaaag gcaaaagaaa aaagaagaaa aggaaagaga aaca                    704
```

<210> SEQ ID NO 80
<211> LENGTH: 455
<212> TYPE: DNA
<213> ORGANISM: Homo sapien

<400> SEQUENCE: 80

```
gatcgatata taggcgactc ggtcctctaa tgctgctcga gcggcgcagt tgtgatggat    60

gcgcccgggc aggtcggcga gggaggaaga agcgcggaga gccgttaagt ccatgccggt   120

gtggtggcgg cggcggagac tgcgggccgt agctgggttc tgcgagcata taggttgctg   180

tagataatgt tcttagctgt caatgtttaa aaatacttct gcttcgttac ctcaagtgtg   240

gcatgcagca ttttggaagg aaaattgaag acgtgttcaa gaaaacatga acagaagcaa   300

atgatgaaaa tgagcatttt acttgatgtt gatacatcac aataaattat ggagaaaaaa   360

aaaaaaaaaa aaaaaaaagc tttggggtaa ccttggccaa actttttccc tgtgtgaatt   420

ttttttccgc tcaaattccc caaaaaattt gaaca                              455
```

<210> SEQ ID NO 81
<211> LENGTH: 1756
<212> TYPE: DNA
<213> ORGANISM: Homo sapien

<400> SEQUENCE: 81

```
atggctgatt tcaggcctgg gatagaaaat atagcagatg gacttggggt atggtctaac    60

aaatggcctg tgtcaaaagg acataggagc aaccttgaag ggacccccag tgacaaaaga   120

tgtaagcagg agggggccat aaatcagggc ctggagttcg gtggcatcaa aagagttaga   180
```

-continued

```
gctaagtctg ggtgtcactg cgtaaagcgg aggccctggg gagtggacgc gttttcacgg    240

aggcatatta agtcgggaaa agacatagaa gcctgtggaa aagcgttaaa gccggtgcac    300

tcagcccccc ttcgcacccg cggaggggcg gggccgcgta ccggaagagg cggggccacc    360

ggagtgccta agagctgtct tccgatgtcg ctcttccttt cccgcgcgac cggtcgaggg    420

aggaagaagc gcgaagagcc gttagtcatg ccggtgtggt ggcggcggcg gagactgcgg    480

gcccgtagct gggctctgcg agcatatagg ttgctgtaga tgaatgttct tagctgtcat    540

gtttaaaaat acttctgctt cgttacctca agtgtggcat gcagcatttt ggaaggaaaa    600

ttgaagacgt gttcaagaaa acatgaacag aagcaaatga tgaaaatgag cattttactt    660

gatgttgata acatcacaat aaattatgga gaaaaataca tatttggcta acttttaatt    720

gctgaacaat aaagtgtttt cttttaaaaa aataacaaca gaacaaaaaa actcccgagg    780

aataagtctc ctcctctcct cttcccctcc ttttaaaaca ttggcgcata gaaaggcata    840

tgcagggact tataagggtg gaaaagacct cctctttagt gaatgtttgt ggttgcccaa    900

gtgaatagaa gtgtgtttcc cacggtgtgc aacaaaactc tagtgggcta catagggggg    960

gaccttggaa tgcacactgt aaagacctgg ggggtcaatg aaacgctttt ggtggcacac   1020

ggccatgtag ggccactatc tcacagaggt tgagcgcacg aaatgcgtgg gataccacat   1080

ctaacgcgat ctacccaagt gggtgccgtt gtgggaacac cggtttgtaa agcaacagag   1140

gggaactatg aaaaatcacg gagagagatt tttcccaata tataaaccac tgcggattaa   1200

acgcctataa aaggctgtaa gaacggcccc tataaggaga ggacacggcc agtcagaacc   1260

caaaacacgg ggggggctcc tttaggacag gctgcgagac gaccacacac cacaagggtg   1320

tggccgaccc tcaaacggga aagggtagaa cccccagggg agggtcctcc ccaggccccc   1380

gggggaaaac acactacggt gggacgcatc tgagacagag gagactcgag ggaataaaac   1440

gcctcggcaa aagagaaaca cgtgtggcgg tcatagaacg agcccagtcg ccgacaaatt   1500

cgatgggtcg tcggccccgg tggggacaca ggagaagaaa taccccagac agatgagggg   1560

ttttatccaa aaggcgccat gtgtgcatca tcacgacgtg ggacagggga gaaaggggag   1620

tcacccaaaa gagtagggct gccaggtggg gccaagtcac tgcagaaagg gacccgggga   1680

tctgtgaaat tcgcgccacc tgttgcgacg agagagaatg agaagcggga tcatacggcc   1740

gacccatgag gaacct                                                   1756
```

<210> SEQ ID NO 82
<211> LENGTH: 71
<212> TYPE: PRT
<213> ORGANISM: Homo sapien

<400> SEQUENCE: 82

```
Met Phe Asn Thr Ala Asn Gly Trp Leu Leu Val Asp Asp Ile Ile Ser
1               5                   10                  15

His His Gln Met Trp Val Trp Trp Gly Arg Gln Leu His Asp Gly Asp
            20                  25                  30

Lys Gln Ile Ala Ala Gly Gly Gly Arg Pro Ile Leu Tyr Leu Phe Glu
        35                  40                  45

Arg Arg Ala Cys Val Val Leu Cys Gly Asn Tyr Leu Arg Leu Leu Ala
    50                  55                  60

Cys Ser Pro Asn Asn Asn Ile
65                  70
```

<210> SEQ ID NO 83

-continued

<211> LENGTH: 16
<212> TYPE: PRT
<213> ORGANISM: Homo sapien

<400> SEQUENCE: 83

Met Ala Phe Cys Thr Gly Lys Leu Thr Leu Lys Gln Thr Leu Ser Ser
1 5 10 15

<210> SEQ ID NO 84
<211> LENGTH: 47
<212> TYPE: PRT
<213> ORGANISM: Homo sapien

<400> SEQUENCE: 84

Met Leu Gly Cys Phe Val Arg Ile Ile Val Val Val Ser Ser Leu Ser
1 5 10 15

Val Leu Arg Cys Gly Leu Gly Trp Val Glu Tyr Leu Gly Gly Arg Ile
20 25 30

Val Arg Ala Gly Ile Thr Asn Phe His Asn Gln Gly Glu His Gly
35 40 45

<210> SEQ ID NO 85
<211> LENGTH: 181
<212> TYPE: PRT
<213> ORGANISM: Homo sapien

<400> SEQUENCE: 85

Met Val Val Asp Pro Pro Arg Gly Gly Ser Leu Ser Phe Ser Gln Leu
1 5 10 15

Ser Gln Pro Thr Trp Phe Ser Ser Pro Leu Pro Ser Trp Gly Val Pro
20 25 30

Arg Ala Pro Gln Ser Val Cys Ser Arg Cys Val Val Gly Lys Cys Val
35 40 45

Ser Leu Pro Pro His Arg Pro Ser Ser His Pro His Lys His Met Gln
50 55 60

Gln Arg Gln Glu His Lys Leu Val Pro Thr Gly Arg Pro Gly Arg Asn
65 70 75 80

Gly Arg Cys Glu Ala Arg Arg Asn His Met Gln Gly Thr Ala Ser Gln
85 90 95

Ser Pro Thr Arg Ile Ala Ala Ser Asp Arg Thr Asp Glu Gln Arg Ile
100 105 110

Ala Pro Pro His His Pro Pro Gly Pro Gln Gly Glu Ile Asn Thr Cys
115 120 125

Gly Arg Ala Ala Ser Lys Gly Pro Thr Thr Lys Leu Gly Ala Glu Ser
130 135 140

Gly Arg Thr Met Thr His Thr Glu Arg Arg Arg Pro Lys Gln His Leu
145 150 155 160

Ala Thr Asn Ala Gln Arg Pro Arg Leu His Arg His Pro Thr Cys Ile
165 170 175

Arg Arg Met Ser Asp
180

<210> SEQ ID NO 86
<211> LENGTH: 209
<212> TYPE: PRT
<213> ORGANISM: Homo sapien

<400> SEQUENCE: 86

Met Pro Ser Val Cys Ser Ala Cys Leu Val Gly Ser Cys Arg Ser Gly

```
1               5                   10                  15

Pro Ser Ala Leu Phe Leu Ser Ser Leu Leu Val Leu Val Cys Ser Phe
            20                  25                  30

Ser Cys Ser Pro Tyr Ser Ala Ala Arg Ala Arg Ala Ala Val Leu Arg
        35                  40                  45

Leu Ser Leu Arg Leu Val Arg Leu Pro Ala Ala Val Cys Cys Val Leu
    50                  55                  60

Phe Phe Arg Phe Ser Leu Leu Phe His Ser Leu Cys Trp Leu Leu Val
65                  70                  75                  80

Ser His Pro Gly Leu Val Ser Ala His Gly Val Ala Cys Ala Phe Leu
                85                  90                  95

Leu Phe Pro Ala Val Gly Leu Ser Ser Leu Thr Leu Leu Leu Leu Phe
            100                 105                 110

Ala Val Ala Phe Arg Cys Ser Cys Ser Val Ser Ser Leu Ser Leu His
        115                 120                 125

Phe Trp Trp Ser Leu Leu Leu Leu Ser Gly Pro Ser Ser Val Phe Cys
    130                 135                 140

Phe Gly Leu Phe Ser Val Val Val Ala Leu Leu Ile Val Gly Cys Val
145                 150                 155                 160

Leu Arg Leu Ser Leu Trp Leu Ala Leu Leu Val Arg Trp Gly Thr Phe
                165                 170                 175

Trp Gly Arg Gly Ile Pro Thr Phe Pro His Pro Gly Tyr Thr Leu Gly
            180                 185                 190

Pro Val Phe Pro His Ala Phe Phe Phe Phe Phe Phe Phe Phe Phe Asn
        195                 200                 205

Cys


<210> SEQ ID NO 87
<211> LENGTH: 29
<212> TYPE: PRT
<213> ORGANISM: Homo sapien

<400> SEQUENCE: 87

Met Arg Lys Trp Lys Ser Tyr Leu Gly Val Ile Thr Pro Asn Val Lys
1               5                   10                  15

Pro Glu Arg Gln Arg Tyr Thr His Leu Glu Gly Glu Glu
            20                  25


<210> SEQ ID NO 88
<211> LENGTH: 78
<212> TYPE: PRT
<213> ORGANISM: Homo sapien

<400> SEQUENCE: 88

Met Arg Val Ser Ala Val Val Cys Glu Lys Met Trp Cys Leu Pro Pro
1               5                   10                  15

Arg Ala Thr Asn Ile Ser His Thr Gln Ile Tyr Arg Ala Gln Thr Asn
            20                  25                  30

Asn Gly Arg Arg Arg Ser Ser Arg Arg Thr Arg Ser Arg Ala Gly Glu
        35                  40                  45

Glu Lys Pro Gly Gln Thr Gly Asp Thr Gly Ser Asn Arg Arg Gly Val
    50                  55                  60

Arg Asp Arg Lys Lys Asp Gly Thr Arg Ala Thr Lys Ser Ala
65                  70                  75


<210> SEQ ID NO 89
```

-continued

<211> LENGTH: 61
<212> TYPE: PRT
<213> ORGANISM: Homo sapien

<400> SEQUENCE: 89

```
Met Pro Val Ile Leu Ala Leu Trp Glu Ala Lys Ala Asp Gly Ser Leu
1               5                   10                  15

Glu Pro Arg Ser Leu Arg Pro Ala Trp Ala Thr Trp Gln Asn Pro Ile
            20                  25                  30

Ser Thr Lys Asn Thr Lys Ser Arg Pro Gly Thr Val Val His Thr Cys
        35                  40                  45

Asn Pro Gly Ile Leu Gly Gly Arg Asp Arg Trp Ile Thr
    50                  55                  60
```

<210> SEQ ID NO 90
<211> LENGTH: 42
<212> TYPE: PRT
<213> ORGANISM: Homo sapien

<400> SEQUENCE: 90

```
Met Gly Ser Cys Ser Val Ala Gln Val Gly Val Met Trp His Asp Leu
1               5                   10                  15

Gly Ser Leu Gln Pro Leu Pro Pro Gly Phe Lys Gln Phe Ser Cys Pro
            20                  25                  30

Ser Leu Leu Ser Ser Trp Asp Tyr Arg Arg
        35                  40
```

<210> SEQ ID NO 91
<211> LENGTH: 52
<212> TYPE: PRT
<213> ORGANISM: Homo sapien

<400> SEQUENCE: 91

```
Met Leu Pro Ser Ser Gly Val Tyr Ile Ser Ala Leu Leu Leu Tyr Ile
1               5                   10                  15

Glu Leu Cys Thr Thr Asn Ile His Ser His Cys Val Asn Asn Pro Asn
            20                  25                  30

Ile Thr Lys Gly Phe Arg Pro Gly Gly Glu Trp Ala Phe Phe Arg Ser
        35                  40                  45

Pro Thr Asn Cys
    50
```

<210> SEQ ID NO 92
<211> LENGTH: 143
<212> TYPE: PRT
<213> ORGANISM: Homo sapien

<400> SEQUENCE: 92

```
Met Pro Leu Leu Pro Gly Ser Leu Ala Ser Phe Phe Ser Leu Thr Cys
1               5                   10                  15

Val Asp Leu Ser Leu Arg Leu Ser Ser Ser Leu Cys Pro Leu Ser Leu
            20                  25                  30

Pro Pro Cys Pro Pro Pro Ile Pro Val Pro Leu Ala Arg Pro Ser Leu
        35                  40                  45

Phe Phe Ala Ala Phe Ser Pro Leu Ser Ser Leu Ala Phe Arg Ser Pro
    50                  55                  60

Leu Ser Ser His Tyr Val Leu Leu Pro Asp Asp Arg Phe Arg Asp Val
65                  70                  75                  80

Pro Ala Val Pro Arg Thr Ser Thr Pro Pro Phe Ser Thr Ala Ser Arg
```

-continued

```
                85                  90                  95

Leu Leu Arg Leu His Pro Thr Ser Lys Leu Arg Pro Tyr His Pro Pro
            100                 105                 110

Asn Thr Ala Pro Cys Cys Asn Thr Pro Ser His Leu Pro Ala His Ala
        115                 120                 125

Pro Val Pro Pro Ser Arg His Leu Pro Leu Ser Pro Leu Ala Ser
    130                 135                 140


<210> SEQ ID NO 93
<211> LENGTH: 83
<212> TYPE: PRT
<213> ORGANISM: Homo sapien

<400> SEQUENCE: 93

Met Lys Trp Gly Pro Lys Lys Arg Gly Ile Gln Glu Thr Ser Ser His
1               5                   10                  15

Thr Glu Arg Ser Pro Phe His Arg Arg Gly Gly Pro Val Gly Pro Pro
            20                  25                  30

Val Ala Gly Ala Val Val Ser Leu Asn Asn Thr His Pro Ser Arg Thr
        35                  40                  45

Asn Arg Leu Leu Ser Ile Ile Phe Pro Arg Pro Pro Pro Pro Arg Gly
    50                  55                  60

Pro Leu Pro Pro Phe Gly Ala Pro Pro Pro Gln Ile Lys Lys Pro Ile
65                  70                  75                  80

Pro Phe Phe


<210> SEQ ID NO 94
<211> LENGTH: 73
<212> TYPE: PRT
<213> ORGANISM: Homo sapien

<400> SEQUENCE: 94

Met Glu Leu Arg Pro Ser Leu Ser Gly Ile Lys Lys Ala Lys Val Pro
1               5                   10                  15

Pro Thr Pro Pro Pro Pro Tyr Glu Asn His Gln Ser His His Leu Gly
            20                  25                  30

Gly Asp Pro Lys His Leu Gly Pro Ile Leu Gln Val Lys Thr Ile Arg
        35                  40                  45

Arg Asn Val Trp Asp Thr Gln Asn Glu Ile Ala Asn Gly Arg Arg Asp
    50                  55                  60

Ala Pro Cys Gln Leu Cys Phe Ser Asp
65                  70


<210> SEQ ID NO 95
<211> LENGTH: 37
<212> TYPE: PRT
<213> ORGANISM: Homo sapien

<400> SEQUENCE: 95

Met Ser Pro Leu Arg Tyr Leu Thr Arg Phe Gln Phe Ser Gly Gly Pro
1               5                   10                  15

Val Arg Lys Gly Lys Gly Glu Lys Ser Asn Ile Asn Ser Val Leu Ala
            20                  25                  30

Gly Glu Leu Pro Ile
        35


<210> SEQ ID NO 96
<211> LENGTH: 151
```

```
<212> TYPE: PRT
<213> ORGANISM: Homo sapien

<400> SEQUENCE: 96

Met Phe Ser Cys Leu Gly Asn Gly Pro Arg Gly Phe Ala Pro Cys Ile
1               5                   10                  15

Trp Glu Gly Pro Leu Gly Cys Ser Leu Arg Ser Asp Ser Ala Trp Arg
            20                  25                  30

Leu Val Pro Arg Ser Ser Gly Pro Leu Val Cys Val Phe Phe Val Arg
        35                  40                  45

Ser Asn Gly Val Gln Thr Val Val Pro Val Gly Ile Arg Ala Ser Ile
    50                  55                  60

Ala Val Gly Val Ser Val Ala Leu Tyr Trp Arg Trp Leu Phe Ser Ala
65                  70                  75                  80

Ser Val Leu Glu Cys Val Ile Leu Ala His Val Val Tyr Leu Leu Cys
                85                  90                  95

Pro Pro Leu Asp Arg Ser Leu Phe Cys Phe Glu Arg Met Ser Trp Thr
            100                 105                 110

Ser Leu Cys Phe Leu Val Arg Ala His Ser Asp Val Val Arg Leu Leu
        115                 120                 125

Leu Cys Phe Trp Met Gly Leu Leu Phe Trp Phe Val Gly Leu Met His
    130                 135                 140

Cys Gly Ile Cys Asn Gly Ser
145                 150


<210> SEQ ID NO 97
<211> LENGTH: 60
<212> TYPE: PRT
<213> ORGANISM: Homo sapien

<400> SEQUENCE: 97

Met Ile Thr Thr Arg Glu His Ala Ser Glu Pro Leu Cys Asn Arg Pro
1               5                   10                  15

Arg Phe Thr Gly Ser Tyr Leu Gly Glu Ser Gly Leu Ser Arg Gly Ala
            20                  25                  30

Leu Leu Val Val Thr Pro Gln Val Thr Met Leu Glu Leu Trp Ser Pro
        35                  40                  45

His Tyr Ile Trp Cys Ser Ile Lys Tyr Gly Gly Leu
    50                  55                  60


<210> SEQ ID NO 98
<211> LENGTH: 59
<212> TYPE: PRT
<213> ORGANISM: Homo sapien

<400> SEQUENCE: 98

Met Trp Arg Arg Gly Ser Arg Ile Glu Arg Ile Asn Thr Ala Met Ile
1               5                   10                  15

Arg Leu Ile Thr Arg Val Cys Leu Ser Asp Phe Met Leu Phe Ala Cys
            20                  25                  30

Leu Val Thr Tyr Gln Phe Arg Arg Asn Gly Met Thr His Ala Leu Leu
        35                  40                  45

Ser Ser His His Ser Ile Arg Leu Thr His Ala
    50                  55


<210> SEQ ID NO 99
<211> LENGTH: 133
<212> TYPE: PRT
```

-continued

```
<213> ORGANISM: Homo sapien

<400> SEQUENCE: 99

Met Cys Asp Trp Glu Asn Ala Ser Gly Arg Ser Lys Cys Asp Arg Pro
1               5                   10                  15

Thr Ser Leu Arg Gln Leu Pro Ala Arg Arg Arg Ile Leu Ala Arg Thr
            20                  25                  30

Val Pro Pro Gly Thr Met Ser His His Ala Phe Pro Thr Pro Leu Pro
        35                  40                  45

His Phe His His His Ala His Arg Ala Ala Thr Gly Asp His Thr Trp
    50                  55                  60

Arg Thr Trp Pro Tyr Phe Phe Cys Ile Glu Trp Glu Gln Arg Leu Leu
65                  70                  75                  80

Leu Ser Pro Leu Gln Asp Phe Leu Arg Ala Ala Phe Asp Cys Ser Ser
                85                  90                  95

Phe Val Arg Cys Gly Val His Gln Pro Thr Ala Val Arg Gln Met Ser
            100                 105                 110

Arg Ala Pro Gly His Gly Thr Arg Arg Pro Pro Cys Ala Arg Val Pro
        115                 120                 125

Arg Pro Arg Pro Arg
    130


<210> SEQ ID NO 100
<211> LENGTH: 22
<212> TYPE: PRT
<213> ORGANISM: Homo sapien

<400> SEQUENCE: 100

Met Gln Asp Gln Ala Arg Thr Asn Lys Glu Gln Gln Thr Arg Thr Lys
1               5                   10                  15

Arg Ser Glu Gln Ala Ser
            20


<210> SEQ ID NO 101
<211> LENGTH: 52
<212> TYPE: PRT
<213> ORGANISM: Homo sapien

<400> SEQUENCE: 101

Met Phe Tyr Ile Lys Ser Met Leu Leu Leu Asp Glu Lys Asn Leu Lys
1               5                   10                  15

Lys Gln Lys Lys Lys Lys Lys Lys Lys Lys Arg Leu Gly Glu Leu Gly
            20                  25                  30

Lys Gly Ala Pro Gly Gly Ile Gly Tyr Arg Ser Lys Ser Thr Lys Asn
        35                  40                  45

Arg Arg Lys Val
    50


<210> SEQ ID NO 102
<211> LENGTH: 80
<212> TYPE: PRT
<213> ORGANISM: Homo sapien

<400> SEQUENCE: 102

Met Phe Cys Gly Gly Val Cys Leu Ala Thr Pro Ser Arg Leu Trp Ile
1               5                   10                  15

Leu Pro Pro Thr Ser Ser Pro Ser Leu Leu Ser His Leu Gly Gly Gly
            20                  25                  30
```

```
Asp Ser Leu Ser Leu Val Trp Cys Val Met Pro Arg Leu Phe Cys Leu
        35                  40                  45

Ala Val His Thr Asp Ile Leu Arg Arg Arg Cys Phe Tyr Gly Gly Gly
    50                  55                  60

Arg Pro Thr Val Leu Leu Thr Pro Pro Leu Met Tyr Pro Ala Ala Asp
65                  70                  75                  80


<210> SEQ ID NO 103
<211> LENGTH: 120
<212> TYPE: PRT
<213> ORGANISM: Homo sapien

<400> SEQUENCE: 103

Met Leu His Gln Phe Phe Val Ser Ala Lys Ile Phe Phe Val Trp Arg
1               5                   10                  15

Ile Leu Cys Gly Arg Gly Gly Tyr Thr His Phe Phe His Thr His Gly
            20                  25                  30

Gly Arg Thr His Ser Phe Cys Val Pro Ser Glu Val Tyr Arg Pro Pro
        35                  40                  45

Arg Thr Phe Leu Phe Val Arg Tyr Thr Arg Glu Ile Leu Tyr Val Cys
    50                  55                  60

Ser Leu Phe Ser His His Gly Ala Pro Gln Gly Glu Thr His Ser Trp
65                  70                  75                  80

Cys Leu His Ser Val Ser Ala Leu Ser Ser Cys Ser Arg Glu Lys Ser
                85                  90                  95

Arg Arg His Pro Thr Thr Arg Glu Trp Trp Leu His Ala Ile Glu Cys
            100                 105                 110

Val Phe Gln Ser Glu Ile Phe Leu
        115                 120


<210> SEQ ID NO 104
<211> LENGTH: 28
<212> TYPE: PRT
<213> ORGANISM: Homo sapien

<400> SEQUENCE: 104

Met Arg Glu Ala Glu Ser Gly Phe Lys Gln Ile Gly Val Arg Gln Ala
1               5                   10                  15

Thr Leu Tyr Phe Ser Val Leu Ala Tyr Gln Cys Cys
            20                  25


<210> SEQ ID NO 105
<211> LENGTH: 150
<212> TYPE: PRT
<213> ORGANISM: Homo sapien

<400> SEQUENCE: 105

Met Ser Gly Glu Leu Ser Asn Arg Phe Gln Gly Gly Lys Ala Phe Gly
1               5                   10                  15

Leu Leu Lys Ala Arg Gln Glu Arg Arg Leu Ala Glu Ile Asn Arg Glu
            20                  25                  30

Phe Leu Cys Asp Gln Lys Tyr Ser Asp Glu Glu Asn Leu Pro Glu Lys
        35                  40                  45

Leu Thr Ala Phe Lys Glu Lys Tyr Met Glu Phe Asp Leu Asn Asn Glu
    50                  55                  60

Gly Glu Ile Asp Leu Met Ser Leu Lys Arg Met Met Glu Lys Leu Gly
65                  70                  75                  80

Val Pro Lys Thr His Leu Glu Met Lys Lys Met Ile Ser Glu Val Thr
```

```
                85                  90                  95

Gly Gly Val Ser Asp Thr Ile Ser Tyr Arg Asp Phe Val Asn Met Met
            100                 105                 110

Leu Gly Lys Arg Ser Ala Val Leu Lys Leu Val Met Met Phe Glu Gly
        115                 120                 125

Lys Ala Asn Glu Ser Ser Pro Lys Pro Val Gly Pro Pro Pro Glu Arg
    130                 135                 140

Asp Ile Ala Ser Leu Pro
145                 150


<210> SEQ ID NO 106
<211> LENGTH: 61
<212> TYPE: PRT
<213> ORGANISM: Homo sapien

<400> SEQUENCE: 106

Met Ser Lys Ser Leu Ile Ser Gln Lys Arg Leu Lys Ile Tyr Cys Asp
1               5                   10                  15

Ser Met Thr Ser Tyr Pro Lys Asp Lys Asn Val His Lys Ile Ser His
            20                  25                  30

Ser Leu Asn Ile Cys Cys Tyr Phe His Ser Lys Met Ile Lys Ile Asn
        35                  40                  45

Phe Ile Leu Pro Pro Val Gln Lys Tyr Leu Lys His Lys
    50                  55                  60


<210> SEQ ID NO 107
<211> LENGTH: 32
<212> TYPE: PRT
<213> ORGANISM: Homo sapien

<400> SEQUENCE: 107

Met Gly Ser Asp Trp Gln Lys Leu Ile Ser Ser Gln Trp Glu Pro Thr
1               5                   10                  15

Glu Leu Ser Arg Val Pro Arg Lys Lys Thr Gly Ala Ile Ser Gln Ser
            20                  25                  30


<210> SEQ ID NO 108
<211> LENGTH: 638
<212> TYPE: PRT
<213> ORGANISM: Homo sapien

<400> SEQUENCE: 108

Met Pro Leu Pro Leu Leu Pro Met Asp Leu Lys Gly Glu Pro Gly Pro
1               5                   10                  15

Pro Gly Lys Pro Gly Pro Arg Gly Pro Pro Gly Pro Pro Gly Phe Pro
            20                  25                  30

Gly Lys Pro Gly Met Gly Lys Pro Gly Leu His Gly Gln Pro Gly Pro
        35                  40                  45

Ala Gly Pro Pro Gly Phe Ser Arg Met Gly Lys Ala Gly Pro Pro Gly
    50                  55                  60

Leu Pro Gly Lys Val Gly Pro Pro Gly Gln Pro Gly Leu Arg Gly Glu
65                  70                  75                  80

Pro Gly Ile Arg Gly Asp Gln Gly Leu Arg Gly Pro Pro Gly Pro Pro
                85                  90                  95

Gly Leu Pro Gly Pro Ser Gly Ile Thr Ile Pro Gly Lys Pro Gly Ala
            100                 105                 110

Gln Gly Val Pro Gly Pro Pro Gly Phe Gln Gly Glu Pro Gly Pro Gln
        115                 120                 125
```

```
Gly Glu Pro Gly Pro Pro Gly Asp Arg Gly Leu Lys Gly Asp Asn Gly
    130                 135                 140

Val Gly Gln Pro Gly Leu Pro Gly Ala Pro Gly Gln Gly Gly Ala Pro
145                 150                 155                 160

Gly Pro Pro Gly Leu Pro Gly Pro Ala Gly Leu Gly Lys Pro Gly Leu
                165                 170                 175

Asp Gly Leu Pro Gly Ala Pro Gly Asp Lys Gly Glu Ser Gly Pro Pro
            180                 185                 190

Gly Val Pro Gly Pro Arg Gly Glu Pro Gly Ala Val Gly Pro Lys Gly
        195                 200                 205

Pro Pro Gly Val Asp Gly Val Gly Val Pro Gly Ala Ala Gly Leu Pro
    210                 215                 220

Gly Pro Gln Gly Pro Ser Gly Ala Lys Gly Glu Pro Gly Thr Arg Gly
225                 230                 235                 240

Pro Pro Gly Leu Ile Gly Pro Thr Gly Tyr Gly Met Pro Gly Leu Pro
                245                 250                 255

Gly Pro Lys Gly Asp Arg Gly Pro Ala Gly Val Pro Gly Leu Leu Gly
            260                 265                 270

Asp Arg Gly Glu Pro Gly Glu Asp Gly Asp Pro Gly Glu Gln Gly Pro
        275                 280                 285

Gln Gly Leu Gly Gly Pro Pro Gly Leu Pro Gly Ser Ala Gly Leu Pro
    290                 295                 300

Gly Arg Arg Gly Pro Pro Gly Pro Lys Gly Glu Ala Gly Pro Gly Gly
305                 310                 315                 320

Pro Pro Gly Val Pro Gly Ile Arg Gly Asp Gln Gly Pro Ser Gly Leu
                325                 330                 335

Ala Gly Lys Pro Gly Val Pro Gly Glu Arg Gly Leu Pro Gly Ala His
            340                 345                 350

Gly Pro Pro Gly Pro Thr Gly Pro Lys Gly Glu Pro Gly Phe Thr Gly
        355                 360                 365

Arg Pro Gly Gly Pro Gly Val Ala Gly Ala Leu Gly Gln Lys Gly Asp
    370                 375                 380

Leu Gly Leu Pro Gly Gln Pro Gly Leu Arg Gly Pro Ser Gly Ile Pro
385                 390                 395                 400

Gly Leu Gln Gly Pro Ala Gly Pro Ile Gly Pro Gln Gly Leu Pro Gly
                405                 410                 415

Leu Lys Gly Glu Pro Gly Leu Pro Gly Pro Pro Gly Glu Gly Arg Ala
            420                 425                 430

Gly Glu Pro Gly Thr Ala Gly Pro Thr Gly Pro Pro Gly Val Pro Gly
        435                 440                 445

Ser Pro Gly Ile Thr Gly Pro Pro Gly Pro Pro Gly Pro Pro Gly Pro
    450                 455                 460

Pro Gly Ala Pro Gly Ala Phe Asp Glu Thr Gly Ile Ala Gly Leu His
465                 470                 475                 480

Leu Pro Asn Gly Gly Val Glu Gly Ala Val Leu Gly Lys Gly Gly Lys
                485                 490                 495

Pro Gln Phe Gly Leu Gly Glu Leu Ser Ala His Ala Thr Pro Ala Phe
            500                 505                 510

Thr Ala Val Leu Thr Ser Pro Phe Pro Ala Ser Gly Met Pro Val Lys
        515                 520                 525

Phe Asp Arg Thr Leu Tyr Asn Gly His Ser Gly Tyr Asn Pro Ala Thr
    530                 535                 540
```

```
Gly Ile Phe Thr Cys Pro Val Gly Gly Val Tyr Tyr Phe Ala Tyr His
545                 550                 555                 560

Val His Val Lys Gly Thr Asn Val Trp Val Ala Leu Tyr Lys Asn Asn
                565                 570                 575

Val Pro Ala Thr Tyr Thr Tyr Asp Glu Tyr Lys Lys Gly Tyr Leu Asp
            580                 585                 590

Gln Ala Ser Gly Gly Ala Val Leu Gln Leu Arg Pro Asn Asp Gln Val
        595                 600                 605

Trp Val Gln Met Pro Ser Asp Gln Ala Asn Gly Leu Tyr Ser Thr Glu
    610                 615                 620

Tyr Ile His Ser Ser Phe Ser Gly Phe Leu Leu Cys Pro Thr
625                 630                 635


<210> SEQ ID NO 109
<211> LENGTH: 78
<212> TYPE: PRT
<213> ORGANISM: Homo sapien

<400> SEQUENCE: 109

Met Thr Ser Leu Leu Ser Leu Ile Pro Asn Met Gln Val Phe Asn Cys
1               5                   10                  15

Leu Met Arg Val Glu Trp Ser Tyr Val Ser Leu Leu Phe Gly Leu Thr
            20                  25                  30

Lys Ile Asn His Asn Phe Gln Gly Ile Phe Met Gly Cys Asp Trp Lys
        35                  40                  45

Leu Thr Leu Val Leu Arg Leu Ile Leu Tyr Asp Val Glu Lys Ser Ser
    50                  55                  60

Asn Phe Ser Glu Leu Phe Leu Ile Ser Asn Thr Val Ile Thr
65                  70                  75


<210> SEQ ID NO 110
<211> LENGTH: 19
<212> TYPE: PRT
<213> ORGANISM: Homo sapien

<400> SEQUENCE: 110

Met Gly Arg Glu Arg Met Leu Ile Phe Lys Phe Leu Ser Leu Val Lys
1               5                   10                  15

Phe Cys Ile


<210> SEQ ID NO 111
<211> LENGTH: 36
<212> TYPE: PRT
<213> ORGANISM: Homo sapien

<400> SEQUENCE: 111

Met Thr Lys Ser His Lys Lys Ser Thr Arg Ser Pro Leu Cys Ala Trp
1               5                   10                  15

Leu Leu Phe Lys Lys Lys Lys Asn Pro Val Tyr Leu Trp Thr His Ser
            20                  25                  30

Met Arg Thr Met
        35


<210> SEQ ID NO 112
<211> LENGTH: 36
<212> TYPE: PRT
<213> ORGANISM: Homo sapien

<400> SEQUENCE: 112
```

-continued

```
Met Gln Met Pro Asn Asn Pro Cys Met Ala Asn Met Phe Thr Leu Ser
1               5                   10                  15

Leu Met Asn Thr Met Arg Thr Val Ser Cys Thr Val His Arg His Ser
            20                  25                  30

Pro Ser His Asp
        35
```

<210> SEQ ID NO 113
<211> LENGTH: 66
<212> TYPE: PRT
<213> ORGANISM: Homo sapien

<400> SEQUENCE: 113

```
Met Trp Val Thr Met Gln Met Phe Met Asn Asn Phe Thr Glu Val Ile
1               5                   10                  15

Pro Ser Val Phe Cys Ser Asn Thr Trp Arg Met Thr Phe Ile Phe Ile
            20                  25                  30

Tyr Phe Ile Ser Leu Phe Gln Leu Ser Ser Asp Asn Ser Gly Asn Val
        35                  40                  45

Ser Phe Phe Phe Phe Phe Thr Lys Thr Phe Tyr Cys Val Thr Cys Cys
    50                  55                  60

Ile Met
65
```

<210> SEQ ID NO 114
<211> LENGTH: 101
<212> TYPE: PRT
<213> ORGANISM: Homo sapien

<400> SEQUENCE: 114

```
Leu Phe Tyr Leu Arg Arg Gly Phe Ala Leu Ser Pro Ser Leu Asp Phe
1               5                   10                  15

Ser Gly Thr Ile Leu Ala Tyr Cys Asn Leu His Leu Leu Gly Ala Asn
            20                  25                  30

Asn Pro Pro Thr Ser Val Ser Ala Val Ala Gly Thr Thr Gly Thr Cys
        35                  40                  45

His His Ala Gln Leu Ile Phe Ile Phe Leu Leu Glu Thr Glu Phe His
    50                  55                  60

Tyr Val Ala Gln Val Gly Leu Lys Ile Pro Ser Ser Ser Asp Val Pro
65                  70                  75                  80

Thr Leu Ala Ser Gln Ser Ala Arg Thr Thr Gly Met Ser His Cys Ala
                85                  90                  95

Gln Pro Ser Phe Phe
            100
```

<210> SEQ ID NO 115
<211> LENGTH: 48
<212> TYPE: PRT
<213> ORGANISM: Homo sapien

<400> SEQUENCE: 115

```
Met Asn His Leu Ile Ile Lys Tyr Leu Ala Asp Phe Gly Arg Gly Leu
1               5                   10                  15

Val Val Asp Asp Leu Thr Ser Ile Asn His Leu Ala Ala Pro Arg Ile
            20                  25                  30

His His Thr Ala Pro Leu Glu His Asp Leu Glu Ala His Ser Pro Ile
        35                  40                  45
```

-continued

```
<210> SEQ ID NO 116
<211> LENGTH: 53
<212> TYPE: PRT
<213> ORGANISM: Homo sapien

<400> SEQUENCE: 116

Met Asn Thr Ser Ser Arg Leu Val Ser Ile Ser Lys Arg Thr Ser Arg
1               5                   10                  15

Asn Ala Ser Ala Ala Val Cys Ala Trp Glu Ser Gln Arg Gly Asn Leu
            20                  25                  30

Pro Ser Pro Pro Ser Arg Ala Gly Gly Glu Gln Glu Asp Thr Leu Pro
        35                  40                  45

His Leu Gly Arg Asp
    50


<210> SEQ ID NO 117
<211> LENGTH: 41
<212> TYPE: PRT
<213> ORGANISM: Homo sapien

<400> SEQUENCE: 117

Met Asp Leu Ile Gln Ser Thr Ser Phe Cys Tyr Asn Ser Tyr Ile His
1               5                   10                  15

Thr Tyr Leu Ser Lys Leu Thr Leu Val His Arg His His Phe Thr Gly
            20                  25                  30

Pro Ser Ser Thr Leu Cys Val Ile His
        35                  40


<210> SEQ ID NO 118
<211> LENGTH: 88
<212> TYPE: PRT
<213> ORGANISM: Homo sapien

<400> SEQUENCE: 118

Met Cys Ile Asn Leu Asn Asn Thr Gln Lys Asn Tyr Asn Leu Lys Ile
1               5                   10                  15

Ala Val Phe Asn Met Arg Ile Ile Tyr Val Cys Lys Tyr Ser Thr Lys
            20                  25                  30

Lys Asn Gln Lys Cys Gly Ile Ile Leu Gln Glu Lys Ile Phe Lys Met
        35                  40                  45

Glu Ser Pro Phe Met Asn Val Leu Ile Leu Lys Ser Lys Val Met Phe
    50                  55                  60

Phe Tyr Asn Val Tyr Ile Ile Met Phe Thr Lys Ala Ile Lys Ser Phe
65                  70                  75                  80

Gln Lys Val Leu Ile Leu Gln Ile
                85


<210> SEQ ID NO 119
<211> LENGTH: 25
<212> TYPE: PRT
<213> ORGANISM: Homo sapien

<400> SEQUENCE: 119

Met Thr Thr Cys Phe Thr Trp Ser Tyr Phe Ala Ile Trp Thr Ile Leu
1               5                   10                  15

Leu Ser Glu Leu Ile Leu His Thr Cys
            20                  25


<210> SEQ ID NO 120
<211> LENGTH: 109
```

```
<212> TYPE: PRT
<213> ORGANISM: Homo sapien

<400> SEQUENCE: 120

Cys Phe Tyr Asp Leu Leu Gly Arg Pro Gly Pro Met Leu Ser Ala Gly
1               5                   10                  15

Leu Ile Phe Leu Phe Leu Phe Glu Thr Glu Ser Arg Ser Pro Ser Arg
            20                  25                  30

Leu Lys Cys Ser Gly Val Ile Ser Ala His Cys Asn Leu Cys Leu Pro
        35                  40                  45

Gly Ser His Glu Ser Ser Ala Ser Ala Ser Ala Val Ala Gly Thr Thr
    50                  55                  60

Gly Thr Cys His His Thr Gln Leu Ile Phe Val Phe Leu Val Glu Thr
65                  70                  75                  80

Gly Phe His His Val Gly Gln Asp Gly Leu Glu Pro Leu Thr Gln Val
                85                  90                  95

Ile Ser Pro Pro Gln Leu Pro Lys Val Leu Gly Leu Gln
            100                 105


<210> SEQ ID NO 121
<211> LENGTH: 66
<212> TYPE: PRT
<213> ORGANISM: Homo sapien

<400> SEQUENCE: 121

Met Ser Asn Val Ile Ile Met Leu Arg Thr Ser Arg Ser Phe Ser Ile
1               5                   10                  15

Leu Thr Gly Phe Ile His Ile Leu Leu Leu Tyr Ser Asn Ile Ala Leu
            20                  25                  30

Lys Val Leu Thr Val Ser Val Ala Lys Ser Ile Ile Ser Trp Thr Ile
        35                  40                  45

Leu Asn Gly Met Phe Thr Arg Pro Lys Met Lys Val Leu Lys Ser Tyr
    50                  55                  60

Leu Phe
65


<210> SEQ ID NO 122
<211> LENGTH: 41
<212> TYPE: PRT
<213> ORGANISM: Homo sapien

<400> SEQUENCE: 122

Met Pro Leu Leu Phe Lys Asn Cys Ala Val Ile Thr Val Leu Ile Leu
1               5                   10                  15

Val Tyr Leu Gly Ile Tyr Pro Ser Val Val Phe Ile Leu Ile Leu Ser
            20                  25                  30

Ile Thr Leu Arg Arg Ser Ser Ser Ile
        35                  40


<210> SEQ ID NO 123
<211> LENGTH: 28
<212> TYPE: PRT
<213> ORGANISM: Homo sapien

<400> SEQUENCE: 123

Met Ser Ser Val Lys Asn Ser Lys Leu Leu Val Leu Pro Ile Pro Asn
1               5                   10                  15

Pro Tyr Leu Thr Gln Leu Ser Lys Met Phe Thr Ser
            20                  25
```

<210> SEQ ID NO 124
<211> LENGTH: 58
<212> TYPE: PRT
<213> ORGANISM: Homo sapien

<400> SEQUENCE: 124

Met Leu Gly Asn Leu Gly Gly Lys Pro Asn Phe Pro Pro Gly Pro Val
1               5                   10                  15

Leu Ala Pro Gly Ser Pro Arg Leu Phe Leu Leu Leu Cys Val Gly Val
            20                  25                  30

Phe Phe Val Ser Lys Thr Leu Asp Asn Leu Phe Gln Ile Tyr Ser Lys
        35                  40                  45

Ile Leu Lys His Cys Ile Asn Ile Lys Val
    50                  55

<210> SEQ ID NO 125
<211> LENGTH: 98
<212> TYPE: PRT
<213> ORGANISM: Homo sapien

<400> SEQUENCE: 125

Phe Leu Phe Leu Arg Gln Ser Phe Ala Leu Ala Thr Gln Ala Gly Val
1               5                   10                  15

Arg Trp Cys Asp Leu Gly Ser Pro Gln Pro Pro Pro Pro Gly Leu Lys
            20                  25                  30

Arg Leu Ser Cys Leu Ser Pro Pro Ser Arg Trp Asp Tyr Arg Pro Gly
        35                  40                  45

Pro Pro His Pro Ala Asn Phe Ala Leu Pro Val Glu Met Gly Ser Leu
    50                  55                  60

His Val Gly Gln Ala Gly Leu Gln Pro Leu Thr Ser Ser Asp Pro Pro
65                  70                  75                  80

Ala Pro Ala Ser Gln Ser Ala Gly Thr Thr Asp Val Ser His Trp Thr
                85                  90                  95

Arg Pro

<210> SEQ ID NO 126
<211> LENGTH: 45
<212> TYPE: PRT
<213> ORGANISM: Homo sapien

<400> SEQUENCE: 126

Met Lys Ile Cys Leu Lys Phe Asn Trp Asn His Gly Ile Ser His Gln
1               5                   10                  15

Phe Glu Leu Ser Asn Met Pro Asn Leu Asp Ile Leu Ile Leu Glu Asn
            20                  25                  30

Gln Phe Leu Lys Ile Leu Lys Cys Ser Val Phe Arg Thr
        35                  40                  45

<210> SEQ ID NO 127
<211> LENGTH: 1088
<212> TYPE: PRT
<213> ORGANISM: Homo sapien

<400> SEQUENCE: 127

Asp Asp Ser Leu Ile Ser Ser Ala Thr Ala Ile Met Glu Ala Val Val
1               5                   10                  15

Arg Glu Trp Ile Leu Leu Glu Lys Gly Ser Ile Glu Ser Leu Arg Thr
            20                  25                  30

-continued

```
Phe Leu Leu Thr Tyr Val Leu Gln Arg Pro Asn Leu Gln Lys Tyr Val
        35                  40                  45

Arg Glu Gln Ile Leu Leu Ala Val Ala Val Ile Val Lys Arg Gly Ser
    50                  55                  60

Leu Asp Lys Ser Ile Asp Cys Lys Ser Ile Phe His Glu Val Ser Gln
65                  70                  75                  80

Leu Ile Ser Ser Gly Asn Pro Thr Val Gln Thr Leu Ala Cys Ser Ile
                85                  90                  95

Leu Thr Ala Leu Leu Ser Glu Phe Ser Ser Ser Ser Lys Thr Ser Asn
            100                 105                 110

Ile Gly Leu Ser Met Glu Phe His Gly Asn Cys Lys Arg Val Phe Gln
        115                 120                 125

Glu Glu Asp Leu Arg Gln Ile Phe Met Leu Thr Val Glu Val Leu Gln
    130                 135                 140

Glu Phe Ser Arg Arg Glu Asn Leu Asn Ala Gln Met Ser Ser Val Phe
145                 150                 155                 160

Gln Arg Tyr Leu Ala Leu Ala Asn Gln Val Leu Ser Trp Asn Phe Leu
                165                 170                 175

Pro Pro Asn Leu Gly Arg His Tyr Ile Ala Met Phe Glu Ser Ser Gln
            180                 185                 190

Asn Val Leu Leu Lys Pro Thr Glu Ser Leu Arg Glu Thr Leu Leu Asp
        195                 200                 205

Ser Arg Val Met Glu Leu Phe Phe Thr Val His Arg Lys Ile Arg Glu
    210                 215                 220

His Ser Asp Met Ala Gln Asp Ser Leu Gln Cys Leu Ala Gln Leu Ala
225                 230                 235                 240

Ser Leu His Gly Pro Ile Phe Pro Asp Glu Gly Ser Gln Val Asp Tyr
                245                 250                 255

Leu Ala His Phe Ile Glu Gly Leu Leu Asn Thr Ile Asn Gly Ile Glu
            260                 265                 270

Ile Glu Asp Ser Glu Ala Val Gly Ile Ser Ser Ile Ile Ser Asn Leu
        275                 280                 285

Ile Thr Val Phe Pro Arg Asn Val Leu Thr Ala Ile Pro Ser Glu Leu
    290                 295                 300

Phe Ser Ser Phe Val Asn Cys Leu Thr His Leu Thr Cys Ser Phe Gly
305                 310                 315                 320

Arg Ser Ala Ala Leu Glu Glu Val Leu Asp Lys Asp Asp Met Val Tyr
                325                 330                 335

Met Glu Ala Tyr Asp Lys Leu Leu Glu Ser Trp Leu Thr Leu Val Gln
            340                 345                 350

Asp Asp Lys His Phe His Lys Gly Phe Phe Thr Gln His Ala Val Gln
        355                 360                 365

Val Phe Asn Ser Tyr Ile Gln Cys His Leu Ala Ala Pro Asp Gly Thr
    370                 375                 380

Arg Asn Leu Thr Ala Asn Gly Val Ala Ser Arg Glu Glu Glu Glu Ile
385                 390                 395                 400

Ser Glu Leu Gln Glu Asp Asp Arg Asp Gln Phe Ser Asp Gln Leu Ala
                405                 410                 415

Ser Val Gly Met Leu Gly Arg Ile Ala Ala Glu His Cys Ile Pro Leu
            420                 425                 430

Leu Thr Ser Leu Leu Glu Glu Arg Val Thr Arg Leu His Gly Gln Leu
        435                 440                 445
```

-continued

```
Gln Arg His Gln Gln Gln Leu Leu Ala Ser Pro Gly Ser Ser Thr Val
    450                 455                 460

Asp Asn Lys Met Leu Asp Asp Leu Tyr Glu Asp Ile His Trp Leu Ile
465                 470                 475                 480

Leu Val Thr Gly Tyr Leu Leu Ala Asp Asp Thr Gln Gly Glu Thr Pro
                485                 490                 495

Leu Ile Pro Pro Glu Ile Met Glu Tyr Ser Ile Lys His Ser Ser Glu
            500                 505                 510

Val Asp Ile Asn Thr Thr Leu Gln Ile Leu Gly Ser Pro Gly Glu Lys
        515                 520                 525

Ala Ser Ser Ile Pro Gly Tyr Asn Arg Thr Asp Ser Val Ile Arg Leu
    530                 535                 540

Leu Ser Ala Ile Leu Arg Val Ser Glu Val Glu Ser Arg Ala Ile Arg
545                 550                 555                 560

Ala Asp Leu Thr His Leu Leu Ser Pro Gln Met Gly Lys Asp Ile Val
                565                 570                 575

Trp Phe Leu Lys Arg Trp Ala Lys Thr Tyr Leu Leu Val Asp Glu Lys
            580                 585                 590

Leu Tyr Asp Gln Ile Ser Leu Pro Phe Ser Thr Ala Phe Gly Ala Asp
        595                 600                 605

Thr Glu Gly Ser Gln Trp Ile Ile Gly Tyr Leu Leu Gln Lys Val Ile
    610                 615                 620

Ser Asn Leu Ser Val Trp Ser Ser Glu Gln Asp Leu Ala Asn Asp Thr
625                 630                 635                 640

Val Gln Leu Leu Val Thr Leu Val Glu Arg Arg Glu Arg Ala Asn Leu
                645                 650                 655

Val Ile Gln Cys Glu Asn Trp Trp Asn Leu Ala Lys Gln Phe Ala Ser
            660                 665                 670

Arg Ser Pro Pro Leu Asn Phe Leu Ser Ser Pro Val Gln Arg Thr Leu
        675                 680                 685

Met Lys Ala Leu Val Leu Gly Gly Phe Ala His Met Asp Thr Glu Thr
    690                 695                 700

Lys Gln Gln Tyr Trp Thr Glu Val Leu Gln Pro Leu Gln Gln Arg Phe
705                 710                 715                 720

Leu Arg Val Ile Asn Gln Glu Asn Phe Gln Gln Met Cys Gln Gln Glu
                725                 730                 735

Glu Val Lys Gln Glu Ile Thr Ala Thr Leu Glu Ala Leu Cys Gly Ile
            740                 745                 750

Ala Glu Ala Thr Gln Ile Asp Asn Val Ala Ile Leu Phe Asn Phe Leu
        755                 760                 765

Met Asp Phe Leu Thr Asn Cys Ile Gly Leu Met Glu Val Tyr Lys Asn
    770                 775                 780

Thr Pro Glu Thr Val Asn Leu Ile Ile Glu Val Phe Val Glu Val Ala
785                 790                 795                 800

His Lys Gln Ile Cys Tyr Leu Gly Glu Ser Lys Ala Met Asn Leu Tyr
                805                 810                 815

Glu Ala Cys Leu Thr Leu Leu Gln Val Tyr Ser Lys Asn Asn Leu Gly
            820                 825                 830

Arg Gln Arg Ile Asp Val Thr Ala Glu Glu Glu Gln Tyr Gln Asp Leu
        835                 840                 845

Leu Leu Ile Met Glu Leu Leu Thr Asn Leu Leu Ser Lys Glu Phe Ile
    850                 855                 860

Asp Phe Ser Asp Thr Asp Glu Val Phe Arg Gly His Glu Pro Gly Gln
```

-continued

```
865                 870                 875                 880

Ala Ala Asn Arg Ser Val Ser Ala Ala Asp Val Val Leu Tyr Gly Val
                885                 890                 895

Asn Leu Ile Leu Pro Leu Met Ser Gln Asp Leu Leu Lys Phe Pro Thr
            900                 905                 910

Leu Cys Asn Gln Tyr Tyr Lys Leu Ile Thr Phe Ile Cys Glu Ile Phe
        915                 920                 925

Pro Glu Lys Ile Pro Gln Leu Pro Glu Asp Leu Phe Lys Ser Leu Met
    930                 935                 940

Tyr Ser Leu Glu Leu Gly Met Thr Ser Met Ser Ser Glu Val Cys Gln
945                 950                 955                 960

Leu Cys Leu Glu Ala Leu Thr Pro Leu Ala Glu Gln Cys Ala Lys Ala
                965                 970                 975

Gln Glu Thr Asp Ser Pro Leu Phe Leu Ala Thr Arg His Phe Leu Lys
            980                 985                 990

Leu Val Phe Asp Met Leu Val Leu  Gln Lys His Asn Thr  Glu Met Thr
        995                 1000                1005

Thr Ala  Ala Gly Glu Ala Phe  Tyr Thr Leu Val Cys  Leu His Gln
    1010                1015                1020

Ala Glu  Tyr Ser Glu Leu Val  Glu Thr Leu Leu Ser  Ser Gln Gln
    1025                1030                1035

Asp Pro  Val Ile Tyr Gln Arg  Leu Ala Asp Ala Phe  Asn Lys Leu
    1040                1045                1050

Thr Ala  Ser Ser Thr Pro Pro  Thr Leu Asp Arg Lys  Gln Lys Met
    1055                1060                1065

Ala Phe  Leu Lys Ser Leu Glu  Glu Phe Met Ala Asn  Val Gly Gly
    1070                1075                1080

Leu Leu  Cys Val Lys
    1085


<210> SEQ ID NO 128
<211> LENGTH: 33
<212> TYPE: PRT
<213> ORGANISM: Homo sapien

<400> SEQUENCE: 128

Met Glu Lys Tyr Phe Ser Gly Cys Arg Leu Glu Phe Asp Tyr Gln Ile
1               5                   10                  15

Asp Phe Cys Glu Leu His Phe Asn Ser Val Gln Asn Phe Leu Thr Ala
            20                  25                  30

Leu


<210> SEQ ID NO 129
<211> LENGTH: 154
<212> TYPE: PRT
<213> ORGANISM: Homo sapien

<400> SEQUENCE: 129

Met Val Ile Leu Ser Phe Lys His Gly Gly Ile Val Ala Tyr Arg Met
1               5                   10                  15

Ser Glu Pro Tyr Ala Ser Leu Leu Asp Ile Tyr Ile Gly Ser His Phe
            20                  25                  30

Ser Cys Ile Ile Tyr Trp Asp Val Phe Pro Ala Phe Ser Val Pro Ile
        35                  40                  45

Asn Asn Thr Gln Asn Thr His Thr Pro Asn Pro Gly Ala Glu Asn Thr
    50                  55                  60
```

```
Gly Ala Pro Thr Cys Pro Pro Gly Gly Asp Thr Val Arg Ser Pro Arg
65                  70                  75                  80

Leu Gln Asn Ser Pro Gln His Asn Tyr Arg Arg Arg Asn Arg Ala Thr
                85                  90                  95

Glu Tyr Arg His Arg Ala Thr Arg Asp Asp Phe Thr Pro Arg Pro Tyr
            100                 105                 110

Asp Ala His Gly Asn Thr Lys Thr Arg Arg Gly Asn His Ile Arg Thr
        115                 120                 125

Arg Glu Asn Gly Arg Trp Arg Pro Arg Ala Lys Pro Thr Lys Ser Thr
    130                 135                 140

Thr His Arg Thr Thr His Asn Ala Arg Pro
145                 150


<210> SEQ ID NO 130
<211> LENGTH: 37
<212> TYPE: PRT
<213> ORGANISM: Homo sapien

<400> SEQUENCE: 130

Met Phe Arg Leu Leu Leu Leu Leu Asn Met Lys Pro Pro Cys Trp Leu
1               5                   10                  15

Asp Arg Ile Asn Phe Ile His Val Met Glu Asn Ser Ile Leu Gln Ile
            20                  25                  30

Trp Ser Pro Ile Ile
        35


<210> SEQ ID NO 131
<211> LENGTH: 72
<212> TYPE: PRT
<213> ORGANISM: Homo sapien

<400> SEQUENCE: 131

Met Ile Ser Trp Lys Ser Ile Leu His Pro Gly Arg Tyr Met Leu Ile
1               5                   10                  15

Tyr Met Gly Val Lys Tyr His Glu Val Ser Thr Phe Ser Gln Lys Gln
            20                  25                  30

Arg Lys Glu Lys Glu Ile Tyr Ser His Pro Thr His Ile His Arg Tyr
        35                  40                  45

Gly Lys Tyr His Gln Ala Leu Thr Leu Val Asn Leu Gly Glu Gly Tyr
    50                  55                  60

Met Gly Phe Gln Cys Thr Ser Ala
65                  70


<210> SEQ ID NO 132
<211> LENGTH: 43
<212> TYPE: PRT
<213> ORGANISM: Homo sapien

<400> SEQUENCE: 132

Met Pro Ser Phe Ser Pro Arg Gly Pro Leu Trp Pro Cys Val Pro Pro
1               5                   10                  15

Ala Phe Phe Phe Val Phe Cys Phe Phe Cys Cys Arg Ile His Gln Glu
            20                  25                  30

Lys Leu Leu Met Val Arg Arg Glu Thr Trp Leu
        35                  40


<210> SEQ ID NO 133
<211> LENGTH: 61
```

<212> TYPE: PRT
<213> ORGANISM: Homo sapien

<400> SEQUENCE: 133

```
Met Asp Pro Pro Gly Gln Val Leu Phe Ile His Ile Ser Leu Gly Phe
1               5                   10                  15

Leu Pro Leu Gly Asn Asn Cys Pro Ser Ile Tyr Leu Val Phe Phe Leu
            20                  25                  30

Val Thr Leu Ile Lys Leu Leu Thr Ser Thr Tyr Asn Ile Val Lys Pro
        35                  40                  45

Glu Tyr Leu Ile Leu Thr Val Lys Lys Asn Met Met Thr
    50                  55                  60
```

<210> SEQ ID NO 134
<211> LENGTH: 75
<212> TYPE: PRT
<213> ORGANISM: Homo sapien

<400> SEQUENCE: 134

```
Met Arg Ser Ile Phe Leu Gln Arg Pro Pro Leu Asn Ile Val Pro Gln
1               5                   10                  15

Phe Ala Ala Lys Asn Ile Leu Ser Leu Lys Gln Arg Gly Val Ser Leu
            20                  25                  30

Glu Leu Pro Ile Phe Leu Ser Cys Gln Lys Lys Ala Leu Arg Val Ser
        35                  40                  45

Pro Cys Ile Tyr Ser Cys Val Pro Leu Cys Glu Phe Val Phe Pro Ser
    50                  55                  60

Thr His Phe Pro His Asn His Gln Arg Lys Gly
65                  70                  75
```

<210> SEQ ID NO 135
<211> LENGTH: 74
<212> TYPE: PRT
<213> ORGANISM: Homo sapien

<400> SEQUENCE: 135

```
Met Glu Asn Val Thr Arg His Met Ser Val Ala Val Lys Phe Gln Asn
1               5                   10                  15

Ser Ser Asp Ser Arg Gln Glu Ala Lys Leu Asn Leu Ala Ser Phe Asn
            20                  25                  30

Leu Asn Ser Pro Leu Trp His Lys Ser Thr Leu Asn Phe Lys Val Asn
        35                  40                  45

Arg Gly Pro Phe Ser Pro Lys His Lys Phe Pro Leu Ala Val Cys Gln
    50                  55                  60

Ser Gly Leu Ile Asn Gln Leu Leu His Cys
65                  70
```

<210> SEQ ID NO 136
<211> LENGTH: 31
<212> TYPE: PRT
<213> ORGANISM: Homo sapien

<400> SEQUENCE: 136

```
Met His Gly Thr Ser Leu Pro Gln Leu Ala Ala Leu Gly Asp Phe Ser
1               5                   10                  15

Ser Ser Leu Gly Asp Cys Val Ser His Leu Glu Ser Met Cys Val
            20                  25                  30
```

<210> SEQ ID NO 137

-continued

```
<211> LENGTH: 56
<212> TYPE: PRT
<213> ORGANISM: Homo sapien

<400> SEQUENCE: 137

Met Leu Ala Glu Pro Ser Tyr Gly Pro Gln Ser Pro Pro Pro Pro Pro
1               5                   10                  15

His Arg His Gly Leu Asn Gly Ser Pro Arg Phe Phe Leu Pro Arg Arg
            20                  25                  30

Pro Ala Arg Ala His Pro Ser Gln Leu Arg Arg Ser Ser Ser Ile Arg
        35                  40                  45

Gly Pro Ser Arg Leu Tyr Ile Asp
    50                  55
```

COMPOSITIONS AND METHODS RELATING TO BREAST SPECIFIC GENES AND PROTEINS

This application claims the benefit of priority from U.S. Provisional Application Ser. No. 60/249,998 filed Nov. 20, 2000 and U.S. Provisional Application Ser. No. 60/252,563 filed Nov. 22, 2000, each of which are herein incorporated by reference in their entirety.

FIELD OF THE INVENTION

The present invention relates to newly identified nucleic acid molecules and polypeptides present in normal and neoplastic breast cells, including fragments, variants and derivatives of the nucleic acids and polypeptides. The present invention also relates to antibodies to the polypeptides of the invention, as well as agonists and antagonists of the polypeptides of the invention. The invention also relates to compositions comprising the nucleic acids, polypeptides, antibodies, variants, derivatives, agonists and antagonists of the invention and methods for the use of these compositions. These uses include identifying, diagnosing, monitoring, staging, imaging and treating breast cancer and non-cancerous disease states in breast tissue, identifying breast tissue and monitoring and identifying and/or designing agonists and antagonists of polypeptides of the invention. The uses also include gene therapy, production of transgenic animals and cells, and production of engineered breast tissue for treatment and research.

BACKGROUND OF THE INVENTION

Excluding skin cancer, breast cancer, also called mammary tumor, is the most common cancer among women, accounting for a third of the cancers diagnosed in the United States. One in nine women will develop breast cancer in her lifetime and about 192,000 new cases of breast cancer are diagnosed annually with about 42,000 deaths. Bevers, *Primary Prevention of Breast Cancer*, in BREAST CANCER, 20–54 (Kelly K Hunt et al., ed., 2001); Kochanek et al., 49 Nat'l. Vital Statistics Reports 1, 14 (2001).

In the treatment of breast cancer, there is considerable emphasis on detection and risk assessment because early and accurate staging of breast cancer has a significant impact on survival. For example, breast cancer detected at an early stage (stage T0, discussed below) has a five-year survival rate of 92%. Conversely, if the cancer is not detected until a late stage (i.e., stage T4), the five-year survival rate is reduced to 13%. *AJCC Cancer Staging Handbook* pp. 164–65 (Irvin D. Fleming et al. eds., $5^{th}$ ed. 1998). Some detection techniques, such as mammography and biopsy, involve increased discomfort, expense, and/or radiation, and are only prescribed only to patients with an increased risk of breast cancer.

Current methods for predicting or detecting breast cancer risk are not optimal. One method for predicting the relative risk of breast cancer is by examining a patient's risk factors and pursuing aggressive diagnostic and treatment regiments for high risk patients. A patient's risk of breast cancer has been positively associated with increasing age, nulliparity, family history of breast cancer, personal history of breast cancer, early menarche, late menopause, late age of first full term pregnancy, prior proliferative breast disease, irradiation of the breast at an early age and a personal history of malignancy. Lifestyle factors such as fat consumption, alcohol consumption, education, and socioeconomic status have also been associated with an increased incidence of breast cancer although a direct cause and effect relationship has not been established. While these risk factors are statistically significant, their weak association with breast cancer limited their usefulness. Most women who develop breast cancer have none of the risk factors listed above, other than the risk that comes with growing older. NIH Publication No. 00-1556 (2000).

Current screening methods for detecting cancer, such as breast self exam, ultrasound, and mammography have drawbacks that reduce their effectiveness or prevent their widespread adoption. Breast self exams, while useful, are unreliable for the detection of breast cancer in the initial stages where the tumor is small and difficult to detect by palpitation. Ultrasound measurements require skilled operators at an increased expense. Mammography, while sensitive, is subject to over diagnosis in the detection of lesions that have questionable malignant potential. There is also the fear of the radiation used in mammography because prior chest radiation is a factor associated with an increase incidence of breast cancer.

At this time, there are no adequate methods of breast cancer prevention. The current methods of breast cancer prevention involve prophylactic mastectomy (mastectomy performed before cancer diagnosis) and chemoprevention (chemotherapy before cancer diagnosis) which are drastic measures that limit their adoption even among women with increased risk of breast cancer. Bevers, supra.

A number of genetic markers have been associated with breast cancer. Examples of these markers include carcinoembryonic antigen (CEA) (Mughal et al., 249 JAMA 1881 (1983)) MUC-1 (Frische and Liu, 22 J. Clin. Ligand 320 (2000)), HER-2/neu (Haris et al., 15 Proc.Am.Soc.Clin.Oncology. A96 (1996)), uPA, PAI-1, LPA, LPC, RAK and BRCA (Esteva and Fritsche, *Serum and Tissue Markers for Breast Cancer*, in BREAST CANCER, 286–308 (2001)). These markers have problems with limited sensitivity, low correlation, and false negatives which limit their use for initial diagnosis. For example, while the BRCA1 gene mutation is useful as an indicator of an increased risk for breast cancer, it has limited use in cancer diagnosis because only 6.2% of breast cancers are BRCA1 positive. Malone et al., 279 JAMA 922 (1998). See also, Mewman et al., 279 JAMA 915 (1998) (correlation of only 3.3%).

Breast cancers are diagnosed into the appropriate stage categories recognizing that different treatments are more effective for different stages of cancer. Stage TX indicates that primary tumor cannot be assessed (i.e., tumor was removed or breast tissue was removed). Stage T0 is characterized by abnormalities such as hyperplasia but with no evidence of primary tumor. Stage Tis is characterized by carcinoma in situ, intraductal carcinoma, lobular carcinoma in situ, or Paget's disease of the nipple with no tumor. Stage T1 is characterized as having a tumor of 2 cm or less in the greatest dimension. Within stage T1, Tmic indicates microinvasion of 0.1 cm or less, T1a indicates a tumor of between 0.1 to 0.5 cm, T1b indicates a tumor of between 0.5 to 1 cm, and T1c indicates tumors of between 1 cm to 2 cm. Stage T2 is characterized by tumors from 2 cm to 5 cm in the greatest dimension. Tumors greater than 5 cm in size are classified as stage T4. Within stage T4, T4a indicates extension of the tumor to the chess wall, T4b indicates edema or ulceration of the skin of the breast or satellite skin nodules confined to the same breast, T4c indicates a combination of T4a and T4b, and T4d indicates inflammatory carcinoma. *AJCC Cancer Staging Handbook* pp. 159–70 (Irvin D. Fleming et al. eds., $5^{th}$ ed. 1998). In addition to standard staging, breast tumors may be classified according to their estrogen receptor and progesterone receptor protein status. Fisher et al., 7 Breast Cancer Research and Treatment 147 (1986). Additional pathological status, such as HER2/neu status may also be useful. Thor et al., 90 J.Nat'l.Cancer Inst. 1346 (1998); Paik et al., 90 J.Nat'l.Cancer Inst. 1361 (1998); Hutchins et al., 17 Proc.Am.Soc.Clin.Oncology A2 (1998).; and Simpson et al., 18 J.Clin.Oncology 2059 (2000).

In addition to the staging of the primary tumor, breast cancer metastases to regional lymph nodes may be staged. Stage NX indicates that the lymph nodes cannot be assessed (e.g., previously removed). Stage NO indicates no regional lymph node metastasis. Stage N1 indicates metastasis to movable ipsilateral axillary lymph nodes. Stage N2 indicates metastasis to ipsilateral axillary lymph nodes fixed to one another or to other structures. Stage N3 indicates metastasis to ipsilateral internal mammary lymph nodes. Id.

Stage determination has potential prognostic value and provides criteria for designing optimal therapy. Simpson et al., 18 J. Clin. Oncology 2059 (2000). Generally, pathological staging of breast cancer is preferable to clinical staging because the former gives a more accurate prognosis. However, clinical staging would be preferred if it were as accurate as pathological staging because it does not depend on an invasive procedure to obtain tissue for pathological evaluation. Staging of breast cancer would be improved by detecting new markers in cells, tissues, or bodily fluids which could differentiate between different stages of invasion. Progress in this field will allow more rapid and reliable method for treating breast cancer patients.

Treatment of breast cancer is generally decided after an accurate staging of the primary tumor. Primary treatment options include breast conserving therapy (lumpectomy, breast irradiation, and surgical staging of the axilla), and modified radical mastectomy. Additional treatments include chemotherapy, regional irradiation, and, in extreme cases, terminating estrogen production by ovarian ablation.

Until recently, the customary treatment for all breast cancer was mastectomy. Fonseca et al., 127 Annals of Internal Medicine 1013 (1997). However, recent data indicate that less radical procedures may be equally effective, in terms of survival, for early stage breast cancer. Fisher et al., 16 J. of Clinical Oncology 441 (1998). The treatment options for a patient with early stage breast cancer (i.e., stage Tis) may be breast-sparing surgery followed by localized radiation therapy at the breast. Alternatively, mastectomy optionally coupled with radiation or breast reconstruction may be employed. These treatment methods are equally effective in the early stages of breast cancer.

Patients with stage I and stage II breast cancer require surgery with chemotherapy and/or hormonal therapy. Surgery is of limited use in Stage III and stage IV patients. Thus, these patients are better candidates for chemotherapy and radiation therapy with surgery limited to biopsy to permit initial staging or subsequent restaging because cancer is rarely curative at this stage of the disease. *AJCC Cancer Staging Handbook* 84, ¶. 164–65 (Irvin D. Fleming et al. eds., 5$^{th}$ ed. 1998).

In an effort to provide more treatment options to patients, efforts are underway to define an earlier stage of breast cancer with low recurrence which could be treated with lumpectomy without postoperative radiation treatment. While a number of attempts have been made to classify early stage breast cancer, no consensus recommendation on postoperative radiation treatment has been obtained from these studies. Page et al., 75 Cancer 1219 (1995); Fisher et al., 75 Cancer 1223 (1995); Silverstein et al., 77 Cancer 2267 (1996).

As discussed above, each of the methods for diagnosing and staging breast cancer is limited by the technology employed. Accordingly, there is need for sensitive molecular and cellular markers for the detection of breast cancer. There is a need for molecular markers for the accurate staging, including clinical and pathological staging, of breast cancers to optimize treatment methods. Finally, there is a need for sensitive molecular and cellular markers to monitor the progress of cancer treatments, including markers that can detect recurrence of breast cancers following remission.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

SUMMARY OF THE INVENTION

The present invention solves these and other needs in the art by providing nucleic acid molecules and polypeptides as well as antibodies, agonists and antagonists, thereto that may be used to identify, diagnose, monitor, stage, image and treat breast cancer and non-cancerous disease states in breast; identify and monitor breast tissue; and identify and design agonists and antagonists of polypeptides of the invention. The invention also provides gene therapy, methods for producing transgenic animals and cells, and methods for producing engineered breast tissue for treatment and research.

Accordingly, one object of the invention is to provide nucleic acid molecules that are specific to breast cells and/or breast tissue. These breast specific nucleic acids (BSNAs) may be a naturally-occurring cDNA, genomic DNA, RNA, or a fragment of one of these nucleic acids, or may be a non-naturally-occurring nucleic acid molecule. If the BSNA is genomic DNA, then the BSNA is a breast specific gene (BSG). In a preferred embodiment, the nucleic acid molecule encodes a polypeptide that is specific to breast. In a more preferred embodiment, the nucleic acid molecule encodes a polypeptide that comprises an amino acid sequence of SEQ ID NO: 82 through 137. In another highly preferred embodiment, the nucleic acid molecule comprises a nucleic acid sequence of SEQ ID NO: 1 through 81. By nucleic acid molecule, it is also meant to be inclusive of sequences that selectively hybridize or exhibit substantial sequence similarity to a nucleic acid molecule encoding a BSP, or that selectively hybridize or exhibit substantial sequence similarity to a BSNA, as well as allelic variants of a nucleic acid molecule encoding a BSP, and allelic variants of a BSNA. Nucleic acid molecules comprising a part of a nucleic acid sequence that encodes a BSP or that comprises a part of a nucleic acid sequence of a BSNA are also provided.

A related object of the present invention is to provide a nucleic acid molecule comprising one or more expression control sequences controlling the transcription and/or translation of all or a part of a BSNA. In a preferred embodiment, the nucleic acid molecule comprises one or more expression control sequences controlling the transcription and/or translation of a nucleic acid molecule that encodes all or a fragment of a BSP.

Another object of the invention is to provide vectors and/or host cells comprising a nucleic acid molecule of the instant invention. In a preferred embodiment, the nucleic acid molecule encodes all or a fragment of a BSP. In another preferred embodiment, the nucleic acid molecule comprises all or a part of a BSNA.

Another object of the invention is to provided methods for using the vectors and host cells comprising a nucleic acid molecule of the instant invention to recombinantly produce polypeptides of the invention.

Another object of the invention is to provide a polypeptide encoded by a nucleic acid molecule of the invention. In a preferred embodiment, the polypeptide is a BSP. The polypeptide may comprise either a fragment or a full-length protein as well as a mutant protein (mutein), fusion protein, homologous protein or a polypeptide encoded by an allelic variant of a BSP.

Another object of the invention is to provide an antibody that specifically binds to a polypeptide of the instant invention.

Another object of the invention is to provide agonists and antagonists of the nucleic acid molecules and polypeptides of the instant invention.

Another object of the invention is to provide methods for using the nucleic acid molecules to detect or amplify nucleic acid molecules that have similar or identical nucleic acid sequences compared to the nucleic acid molecules described herein. In a preferred embodiment, the invention provides methods of using the nucleic acid molecules of the invention for identifying, diagnosing, monitoring, staging, imaging and treating breast cancer and non-cancerous disease states in breast. In another preferred embodiment, the invention provides methods of using the nucleic acid molecules of the invention for identifying and/or monitoring breast tissue. The nucleic acid molecules of the instant invention may also be used in gene therapy, for producing transgenic animals and cells, and for producing engineered breast tissue for treatment and research.

The polypeptides and/or antibodies of the instant invention may also be used to identify, diagnose, monitor, stage, image and treat breast cancer and non-cancerous disease states in breast. The invention provides methods of using the polypeptides of the invention to identify and/or monitor breast tissue, and to produce engineered breast tissue.

The agonists and antagonists of the instant invention may be used to treat breast cancer and non-cancerous disease states in breast and to produce engineered breast tissue.

Yet another object of the invention is to provide a computer readable means of storing the nucleic acid and amino acid sequences of the invention. The records of the computer readable means can be accessed for reading and displaying of sequences for comparison, alignment and ordering of the sequences of the invention to other sequences.

DETAILED DESCRIPTION OF THE INVENTION

Definitions and General Techniques

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present invention are generally performed according to conventional methods well-known in the art and as described in various general and more specific references that are cited and discussed throughout the present specification unless otherwise indicated. See, e.g., Sambrook et al., *Molecular Cloning: A Laboratory Manual*, 2d ed., Cold Spring Harbor Laboratory Press (1989) and Sambrook et al., *Molecular Cloning: A Laboratory Manual*, 3d ed., Cold Spring Harbor Press (2001); Ausubel et al., *Current Protocols in Molecular Biology*, Greene Publishing Associates (1992, and Supplements to 2000); Ausubel et al., *Short Protocols in Molecular Biology: A Compendium of Methods from Current Protocols in Molecular Biology—4th Ed.*, Wiley & Sons (1999); Harlow and Lane, *Antibodies: A Laboratory Manual*, Cold Spring Harbor Laboratory Press (1990); and Harlow and Lane, *Using Antibodies: A Laboratory Manual*, Cold Spring Harbor Laboratory Press (1999); each of which is incorporated herein by reference in its entirety.

Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

A "nucleic acid molecule" of this invention refers to a polymeric form of nucleotides and includes both sense and antisense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." The term "nucleic acid molecule" usually refers to a molecule of at least 10 bases in length, unless otherwise specified. The term includes single- and double-stranded forms of DNA. In addition, a polynucleotide may include either or both naturally-occurring and modified nucleotides linked together by naturally-occurring and/or non-naturally occurring nucleotide linkages.

The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) The term "nucleic acid molecule" also includes any topological conformation, including single-stranded, double-stranded, partially duplexed, triplexed, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

A "gene" is defined as a nucleic acid molecule that comprises a nucleic acid sequence that encodes a polypeptide and the expression control sequences that surround the nucleic acid sequence that encodes the polypeptide. For instance, a gene may comprise a promoter, one or more enhancers, a nucleic acid sequence that encodes a polypeptide, downstream regulatory sequences and, possibly, other nucleic acid sequences involved in regulation of the expression of an RNA. As is well-known in the art, eukaryotic genes usually contain both exons and introns. The term "exon" refers to a nucleic acid sequence found in genomic DNA that is bioinformatically predicted and/or experimentally confirmed to contribute a contiguous sequence to a mature mRNA transcript. The term "intron" refers to a nucleic acid sequence found in genomic DNA that is predicted and/or confirmed to not contribute to a mature mRNA transcript, but rather to be "spliced out" during processing of the transcript.

A nucleic acid molecule or polypeptide is "derived" from a particular species if the nucleic acid molecule or polypeptide has been isolated from the particular species, or if the nucleic acid molecule or polypeptide is homologous to a nucleic acid molecule or polypeptide isolated from a particular species.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases, or genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, (4) does not occur in nature as part of a larger sequence or (5) includes nucleotides or intemucleoside bonds that are not found in nature. The term "isolated" or "substantially pure" also can be used in reference to recombinant or cloned DNA isolates, chemically synthesized polynucleotide analogs, or polynucleotide analogs that are biologically synthesized by heterologous systems. The term "isolated nucleic acid molecule" includes nucleic acid molecules that are integrated into a host cell chromosome at a heterologous site, recombinant fusions of a native fragment to a heterologous sequence, recombinant vectors present as episomes or as integrated into a host cell chromosome.

A "part" of a nucleic acid molecule refers to a nucleic acid molecule that comprises a partial contiguous sequence of at least 10 bases of the reference nucleic acid molecule. Preferably, a part comprises at least 15 to 20 bases of a reference nucleic acid molecule. In theory, a nucleic acid sequence of 17 nucleotides is of sufficient length to occur at random less frequently than once in the three gigabase human genome, and thus to provide a nucleic acid probe that can uniquely identify the reference sequence in a nucleic acid mixture of genomic complexity. A preferred part is one that comprises a nucleic acid sequence that can encode at least 6 contiguous amino acid sequences (fragments of at least 18 nucleotides) because they are useful in directing the expression or synthesis of peptides that are useful in mapping the epitopes of the polypeptide encoded by the reference nucleic acid. See, e.g., Geysen et al., *Proc. Natl. Acad. Sci. USA* 81:3998–4002 (1984); and U.S. Pat. Nos. 4,708,871 and 5,595,915, the disclosures of which are incorporated herein by reference in their entireties. A part may also comprise at least 25, 30, 35 or 40 nucleotides of a reference nucleic acid molecule, or at least 50, 60, 70, 80, 90, 100, 150, 200, 250, 300, 350, 400 or 500 nucleotides of a reference nucleic acid molecule. A part of a nucleic acid molecule may comprise no other nucleic acid sequences. Alternatively, a part of a nucleic acid may comprise other nucleic acid sequences from other nucleic acid molecules.

The term "oligonucleotide" refers to a nucleic acid molecule generally comprising a length of 200 bases or fewer. The term often refers to single-stranded deoxyribonucleotides, but it can refer as well to single- or double-stranded ribonucleotides, RNA:DNA hybrids and double-stranded DNAs, among others. Preferably, oligonucleotides are 10 to 60 bases in length and most preferably 12, 13, 14, 15, 16, 17, 18, 19 or 20 bases in length. Other preferred oligonucleotides are 25, 30, 35, 40, 45, 50, 55 or 60 bases in length. Oligonucleotides may be single-stranded, e.g. for use as probes or primers, or may be double-stranded, e.g for use in the construction of a mutant gene. Oligonucleotides of the invention can be either sense or antisense oligonucleotides. An oligonucleotide can be derivatized or modified as discussed above for nucleic acid molecules.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms. Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP. The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well-known, this reaction can be prevented selectively, where desired, by removing the 5' phosphates of the other polynucleotide(s) prior to ligation.

The term "naturally-occurring nucleotide" referred to herein includes naturally-occurring deoxyribonucleotides and ribonucleotides. The term "modified nucleotides" referred to herein includes nucleotides with modified or substituted sugar groups and the like. The term "nucleotide linkages" referred to herein includes nucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al. *Nucl. Acids Res*. 14:9081–9093 (1986); Stein et al. *Nucl. Acids Res*. 16:3209–3221 (1988); Zon et al. *Anti-Cancer Drug Design* 6:539–568 (1991); Zon et al., in Eckstein (ed.) *Oligonucleotides and Analogues: A Practical Approach*, pp. 87–108, Oxford University Press (1991); U.S. Pat. No. 5,151,510; Uhlmann and Peyman *Chemical Reviews* 90:543 (1990), the disclosures of which are hereby incorporated by reference.

Unless specified otherwise, the left hand end of a polynucleotide sequence in sense orientation is the 5' end and the right hand end of the sequence is the 3' end. In addition, the left hand direction of a polynucleotide sequence in sense orientation is referred to as the 5' direction, while the right hand direction of the polynucleotide sequence is referred to as the 3' direction. Further, unless otherwise indicated, each nucleotide sequence is set forth herein as a sequence of deoxyribonucleotides. It is intended, however, that the given sequence be interpreted as would be appropriate to the polynucleotide composition: for example, if the isolated nucleic acid is composed of RNA, the given sequence intends ribonucleotides, with uridine substituted for thymidine.

The term "allelic variant" refers to one of two or more alternative naturally-occurring forms of a gene, wherein each gene possesses a unique nucleotide sequence. In a preferred embodiment, different alleles of a given gene have similar or identical biological properties.

The term "percent sequence identity" in the context of nucleic acid sequences refers to the residues in two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183: 63–98 (1990); Pearson, *Methods Mol. Biol.* 132: 185–219 (2000); Pearson, *Methods Enzymol.* 266: 227–258 (1996); Pearson, *J. Mol. Biol.* 276: 71–84 (1998); herein incorporated by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for antisense therapy, hybridization probes and PCR primers.

In the molecular biology art, researchers use the terms "percent sequence identity", "percent sequence similarity" and "percent sequence homology" interchangeably. In this application, these terms shall have the same meaning with respect to nucleic acid sequences only.

The term "substantial similarity" or "substantial sequence similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95–98% of the nucleotide bases, as measured by any well-known algorithm of sequence identity, such as FASTA, BLAST or Gap, as discussed above.

Alternatively, substantial similarity exists when a nucleic acid or fragment thereof hybridizes to another nucleic acid, to a strand of another nucleic acid, or to the complementary strand thereof, under selective hybridization conditions. Typically, selective hybridization will occur when there is at least about 55% sequence identity, preferably at least about 65%, more preferably at least about 75%, and most preferably at least about 90% sequence identity, over a stretch of at least about 14 nucleotides, more preferably at least 17 nucleotides, even more preferably at least 20, 25, 30, 35, 40, 50, 60, 70, 80, 90 or 100 nucleotides.

Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. "Stringent hybridization conditions" and "stringent wash conditions" in the context of nucleic acid hybridization experiments depend upon a number of different physical parameters. The most important parameters include temperature of hybridization, base composition of the nucleic acids, salt concentration and length of the nucleic acid. One having ordinary skill in the art knows how to vary these parameters to achieve a particular stringency of hybridization. In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook (1989), supra, p. 9.51, hereby incorporated by reference.

The $T_m$ for a particular DNA-DNA hybrid can be estimated by the formula:

$$T_m = 81.5°\text{ C.} + 16.6(\log_{10}[Na^+]) + 0.41(\text{fraction G+C}) - 0.63(\%\text{ formamide}) - (600/l)$$

where l is the length of the hybrid in base pairs.

The $T_m$ for a particular RNA-RNA hybrid can be estimated by the formula:

$$T_m = 79.8°\text{ C.} + 18.5(\log_{10}[Na^+]) + 0.58(\text{fraction G+C}) + 11.8(\text{fraction G+C})^2 - 0.35(\%\text{ formamide}) - (820/l).$$

The $T_m$ for a particular RNA-DNA hybrid can be estimated by the formula:

$$T_m = 79.8°\text{ C.} + 18.5(\log_{10}[Na^+]) + 0.58(\text{fraction G+C}) + 11.8(\text{fraction G+C})^2 - 0.50(\%\text{ formamide}) - (820/l).$$

In general, the $T_m$ decreases by 1–1.5° C. for each 1% of mismatch between two nucleic acid sequences. Thus, one having ordinary skill in the art can alter hybridization and/or washing conditions to obtain sequences that have higher or lower degrees of sequence identity to the target nucleic acid. For instance, to obtain hybridizing nucleic acids that contain up to 10% mismatch from the target nucleic acid sequence, 10–15° C. would be subtracted from the calculated $T_m$ of a perfectly matched hybrid, and then the hybridization and washing temperatures adjusted accordingly. Probe sequences may also hybridize specifically to duplex DNA under certain conditions to form triplex or other higher order DNA complexes. The preparation of such probes and suitable hybridization conditions are well-known in the art.

An example of stringent hybridization conditions for hybridization of complementary nucleic acid sequences having more than 100 complementary residues on a filter in a Southern or Northern blot or for screening a library is 50% formamide/6×SSC at 42° C. for at least ten hours and preferably overnight (approximately 16 hours). Another example of stringent hybridization conditions is 6×SSC at 68° C. without formamide for at least ten hours and preferably overnight. An example of moderate stringency hybridization conditions is 6×SSC at 55° C. without formamide for at least ten hours and preferably overnight. An example of low stringency hybridization conditions for hybridization of complementary nucleic acid sequences having more than 100 complementary residues on a filter in a Southern or Northern blot or for screening a library is 6×SSC at 42° C. for at least ten hours. Hybridization conditions to identify nucleic acid sequences that are similar but not identical can be identified by experimentally changing the hybridization temperature from 68° C. to 42° C. while keeping the salt concentration constant (6×SSC), or keeping the hybridization temperature and salt concentration constant (e.g. 42° C. and 6×SSC) and varying the formamide concentration from 50% to 0%. Hybridization buffers may also include blocking agents to lower background. These agents are well-known in the art. See Sambrook et al. (1989), supra, pages 8.46 and 9.46–9.58, herein incorporated by reference. See also Ausubel (1992), supra, Ausubel (1999), supra, and Sambrook (2001), supra.

Wash conditions also can be altered to change stringency conditions. An example of stringent wash conditions is a 0.2×SSC wash at 65° C. for 15 minutes (see Sambrook (1989), supra, for SSC buffer). Often the high stringency wash is preceded by a low stringency wash to remove excess probe. An exemplary medium stringency wash for duplex DNA of more than 100 base pairs is 1×SSC at 45° C. for 15 minutes. An exemplary low stringency wash for such a duplex is 4×SSC at 40° C. for 15 minutes. In general, signal-to-noise ratio of 2× or higher than that observed for an unrelated probe in the particular hybridization assay indicates detection of a specific hybridization.

As defined herein, nucleic acid molecules that do not hybridize to each other under stringent conditions are still substantially similar to one another if they encode polypeptides that are substantially identical to each other. This occurs, for example, when a nucleic acid molecule is created synthetically or recombinantly using high codon degeneracy as permitted by the redundancy of the genetic code.

Hybridization conditions for nucleic acid molecules that are shorter than 100 nucleotides in length (e.g., for oligonucleotide probes) may be calculated by the formula:

$$T_m = 81.5° \text{ C.} + 16.6(\log_{10}[Na^+]) + 0.41(\text{fraction G+C}) - (600/N),$$

wherein N is change length and the $[Na^+]$ is 1 M or less. See Sambrook (1989), supra, p. 11.46. For hybridization of probes shorter than 100 nucleotides, hybridization is usually performed under stringent conditions (5–10° C. below the $T_m$) using high concentrations (0.1–1.0 pmol/ml) of probe. Id. at p. 11.45. Determination of hybridization using mismatched probes, pools of degenerate probes or "guessmers," as well as hybridization solutions and methods for empirically determining hybridization conditions are well-known in the art. See, e.g., Ausubel (1999), supra; Sambrook (1989), supra, pp. 11.45–11.57.

The term "digestion" or "digestion of DNA" refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan. For analytical purposes, typically, 1 μg of plasmid or DNA fragment is digested with about 2 units of enzyme in about 20 μl of reaction buffer. For the purpose of isolating DNA fragments for plasmid construction, typically 5 to 50 μg of DNA are digested with 20 to 250 units of enzyme in proportionately larger volumes. Appropriate buffers and substrate amounts for particular restriction enzymes are described in standard laboratory manuals, such as those referenced below, and they are specified by commercial suppliers. Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well-known methods that are routine for those skilled in the art.

The term "ligation" refers to the process of forming phosphodiester bonds between two or more polynucleotides, which most often are double-stranded DNAS. Techniques for ligation are well-known to the art and protocols for ligation are described in standard laboratory manuals and references, such as, e.g., Sambrook (1989), supra.

Genome-derived "single exon probes," are probes that comprise at least part of an exon ("reference exon") and can hybridize detectably under high stringency conditions to transcript-derived nucleic acids that include the reference exon but do not hybridize detectably under high stringency conditions to nucleic acids that lack the reference exon. Single exon probes typically further comprise, contiguous to a first end of the exon portion, a first intronic and/or intergenic sequence that is identically contiguous to the exon in the genome, and may contain a second intronic and/or intergenic sequence that is identically contiguous to the exon in the genome. The minimum length of genome-derived single exon probes is defined by the requirement that the exonic portion be of sufficient length to hybridize under high stringency conditions to transcript-derived nucleic acids, as discussed above. The maximum length of genome-derived single exon probes is defined by the requirement that the probes contain portions of no more than one exon. The single exon probes may contain priming sequences not found in contiguity with the rest of the probe sequence in the genome, which priming sequences are useful for PCR and other amplification-based technologies.

The term "microarray" or "nucleic acid microarray" refers to a substrate-bound collection of plural nucleic acids, hybridization to each of the plurality of bound nucleic acids being separately detectable. The substrate can be solid or porous, planar or non-planar, unitary or distributed. Microarrays or nucleic acid microarrays include all the devices so called in Schena (ed.), *DNA Microarrays: A Practical Approach* (*Practical Approach Series*), Oxford University Press (1999); *Nature Genet.* 21(1)(suppl.):1–60 (1999); Schena (ed.), *Microarray Biochip: Tools and Technology*, Eaton Publishing Company/BioTechniques Books Division (2000). These microarrays include substrate-bound collections of plural nucleic acids in which the plurality of nucleic acids are disposed on a plurality of beads, rather than on a unitary planar substrate, as is described, inter alia, in Brenner et al., *Proc. Natl. Acad. Sci. USA* 97(4):1665–1670 (2000).

The term "mutated" when applied to nucleic acid molecules means that nucleotides in the nucleic acid sequence of the nucleic acid molecule may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. In a preferred embodiment, the nucleic acid molecule comprises the wild type nucleic acid sequence encoding a BSP or is a BSNA. The nucleic acid molecule may be mutated by any method known in the art including those mutagenesis techniques described infra.

The term "error-prone PCR" refers to a process for performing PCR under conditions where the copying fidelity of the DNA polymerase is low, such that a high rate of point mutations is obtained along the entire length of the PCR product. See, e.g., Leung et al., *Technique* 1: 11–15 (1989) and Caldwell et al., *PCR Methods Applic.* 2: 28–33 (1992).

The term "oligonucleotide-directed mutagenesis" refers to a process which enables the generation of site-specific mutations in any cloned DNA segment of interest. See, e.g., Reidhaar-Olson et al., *Science* 241: 53–57(1988).

The term "assembly PCR" refers to a process which involves the assembly of a PCR product from a mixture of small DNA fragments. A large number of different PCR reactions occur in parallel in the same vial, with the products of one reaction priming the products of another reaction.

The term "sexual PCR mutagenesis" or "DNA shuffling" refers to a method of error-prone PCR coupled with forced homologous recombination between DNA molecules of different but highly related DNA sequence in vitro, caused by random fragmentation of the DNA molecule based on sequence similarity, followed by fixation of the crossover by primer extension in an error-prone PCR reaction. See, e.g., Stemmer, *Proc. Natl. Acad. Sci. U.S.A.* 91: 10747–10751 (1994). DNA shuffling can be carried out between several related genes ("Family shuffling").

The term "in vivo mutagenesis" refers to a process of generating random mutations in any cloned DNA of interest which involves the propagation of the DNA in a strain of bacteria such as *E. coli* that carries mutations in one or more of the DNA repair pathways. These "mutator" strains have a higher random mutation rate than that of a wild-type parent. Propagating the DNA in a mutator strain will eventually generate random mutations within the DNA.

The term "cassette mutagenesis" refers to any process for replacing a small region of a double-stranded DNA molecule with a synthetic oligonucleotide "cassette" that differs from the native sequence. The oligonucleotide often contains completely and/or partially randomized native sequence.

The term "recursive ensemble mutagenesis" refers to an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. See, e.g., Arkin et al., *Proc. Natl. Acad. Sci. U.S.A.* 89: 7811–7815 (1992).

The term "exponential ensemble mutagenesis" refers to a process for generating combinatorial libraries with a high percentage of unique and functional mutants, wherein small groups of residues are randomized in parallel to identify, at each altered position, amino acids which lead to functional proteins. See, e.g., Delegrave et al., *Biotechnology Research* 11: 1548–1552 (1993); Arnold, *Current Opinion in Biotechnology* 4: 450–455 (1993). Each of the references mentioned above are hereby incorporated by reference in its entirety.

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include the promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "vector," as used herein, is intended to refer to a nucleic acid molecule capable of transporting another nucleic acid to which it has been linked. One type of vector is a "plasmid", which refers to a circular double-stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome. Viral vectors that infect bacterial cells are referred to as bacteriophages. Certain vectors are capable of autonomous replication in a host cell into which they are introduced (e.g., bacterial vectors having a bacterial origin of replication). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include other forms of expression vectors that serve equivalent functions.

The term "recombinant host cell" (or simply "host cell"), as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the phrase "open reading frame" and the equivalent acronym "ORF" refer to that portion of a transcript-derived nucleic acid that can be translated in its entirety into a sequence of contiguous amino acids. As so defined, an ORF has length, measured in nucleotides, exactly divisible by 3. As so defined, an ORF need not encode the entirety of a natural protein.

As used herein, the phrase "ORF-encoded peptide" refers to the predicted or actual translation of an ORF.

As used herein, the phrase "degenerate variant" of a reference nucleic acid sequence intends all nucleic acid sequences that can be directly translated, using the standard genetic code, to provide an amino acid sequence identical to that translated from the reference nucleic acid sequence.

The term "polypeptide" encompasses both naturally-occurring and non-naturally-occurring proteins and polypeptides, polypeptide fragments and polypeptide mutants, derivatives and analogs. A polypeptide may be monomeric or polymeric. Further, a polypeptide may comprise a number of different modules within a single polypeptide each of which has one or more distinct activities. A preferred polypeptide in accordance with the invention comprises a BSP encoded by a nucleic acid molecule of the instant invention, as well as a fragment, mutant, analog and derivative thereof.

The term "isolated protein" or "isolated polypeptide" is a protein or polypeptide that by virtue of its origin or source of derivation (1) is not associated with naturally associated components that accompany it in its native state, (2) is free of other proteins from the same species (3) is expressed by a cell from a different species, or (4) does not occur in nature. Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well-known in the art.

A protein or polypeptide is "substantially pure," "substantially homogeneous" or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well-known in the art, such as polyacrylamide gel electrophoresis of a protein sample, followed by visualizing a single polypeptide band upon staining the gel with a stain well-known in the art. For certain purposes, higher resolution may be provided by using HPLC or other means well-known in the art for purification.

The term "polypeptide fragment" as used herein refers to a polypeptide of the instant invention that has an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "derivative" refers to polypeptides or fragments thereof that are substantially similar in primary structural sequence but which include, e.g., in vivo or in vitro chemical and biochemical modifications that are not found in the native polypeptide. Such modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Other modification include, e.g., labeling with radionuclides, and various enzymatic modifications, as will be readily appreciated by those skilled in the art. A variety of methods for labeling polypeptides and of substituents or labels useful for such purposes are well-known in the art, and include radioactive isotopes such as $^{125}I$, $^{32}P$, $^{35}S$, and $^{3}H$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well-known in the art. See Ausubel (1992), supra; Ausubel (1999), supra, herein incorporated by reference.

The term "fusion protein" refers to polypeptides of the instant invention comprising polypeptides or fragments coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "analog" refers to both polypeptide analogs and non-peptide analogs. The term "polypeptide analog" as used herein refers to a polypeptide of the instant invention that is comprised of a segment of at least 25 amino acids that has substantial identity to a portion of an amino acid sequence but which contains non-natural amino acids or non-natural inter-residue bonds. In a preferred embodiment, the analog has the same or similar biological activity as the native polypeptide. Typically, polypeptide analogs comprise a conservative amino acid substitution (or insertion or deletion) with respect to the naturally-occurring sequence. Analogs typically are at least 20 amino acids long, preferably at least 50 amino acids long or longer, and can often be as long as a full-length naturally-occurring polypeptide.

The term "non-peptide analog" refers to a compound with properties that are analogous to those of a reference polypeptide of the instant invention. A non-peptide compound may also be termed a "peptide mimetic" or a "peptidomimetic." Such compounds are often developed with the aid of computerized molecular modeling. Peptide mimetics that are structurally similar to useful peptides may be used to produce an equivalent effect. Generally, peptidomimetics are structurally similar to a paradigm polypeptide (i.e., a polypeptide that has a desired biochemical property or pharmacological activity), but have one or more peptide linkages optionally replaced by a linkage selected from the group consisting of: —$CH_2NH$—, —$CH_2S$—, —$CH_2$—$CH_2$—, —CH═CH-(cis and trans), —$COCH_2$—, —CH(OH)$CH_2$—, and —$CH_2SO$—, by methods well-known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo et al., *Ann. Rev. Biochem.* 61:387–418 (1992), incorporated herein by reference). For example, one may add internal cysteine residues capable of forming intramolecular disulfide bridges which cyclize the peptide.

A "polypeptide mutant" or "mutein" refers to a polypeptide of the instant invention whose sequence contains substitutions, insertions or deletions of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. Further, a mutein may have the same or different biological activity as the naturally-occurring protein. For instance, a mutein may have an increased or decreased biological activity. A mutein has at least 50% sequence similarity to the wild type protein, preferred is 60% sequence similarity, more preferred is 70% sequence similarity. Even more preferred are muteins having 80%, 85% or 90% sequence similarity to the wild type protein. In an even more preferred embodiment, a mutein exhibits 95% sequence identity, even more preferably 97%, even more preferably 98% and even more preferably 99%. Sequence similarity may be measured by any common sequence analysis algorithm, such as Gap or Bestfit.

Preferred amino acid substitutions are those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or finctional properties of such analogs. For example, single or multiple amino acid substitutions (preferably conservative amino acid substitutions) may be made in the naturally-occurring sequence (preferably in the portion of the polypeptide outside the domain(s) forming intermolecular contacts. In a preferred embodiment, the amino acid substitutions are moderately conservative substitutions or conservative substitutions. In a more preferred embodiment, the amino acid substitutions are conservative substitutions. A conservative amino acid substitution should not substantially change the structural characteristics of the parent sequence (e.g., a replacement amino acid should not tend to disrupt a helix that occurs in the parent sequence, or disrupt other types of secondary structure that characterizes the parent sequence). Examples of art-recognized polypeptide secondary and tertiary structures are described in Creighton (ed.), *Proteins, Structures and Molecular Principles*, W. H. Freeman and Company (1984); Branden et al. (ed.), *Introduction to Protein Structure,* Garland Publishing (1991); Thornton et al., *Nature* 354:105–106 (1991), each of which are incorporated herein by reference.

As used herein, the twenty conventional amino acids and their abbreviations follow conventional usage. See Golub et al. (eds.), *Immunology—A Synthesis* $2^{nd}$ Ed., Sinauer Associates (1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the lefthand direction is the amino terminal direction and the right hand direction is the carboxy-terminal direction, in accordance with standard usage and convention.

A protein has "homology" or is "homologous" to a protein from another organism if the encoded amino acid sequence of the protein has a similar sequence to the encoded amino acid sequence of a protein of a different organism and has a similar biological activity or function. Alternatively, a protein may have homology or be homologous to another protein if the two proteins have similar amino acid sequences and have similar biological activities or functions. Although two proteins are said to be "homologous," this does not imply that there is necessarily an evolutionary relationship between the proteins. Instead, the term "homologous" is defined to mean that the two proteins have similar amino acid sequences and similar biological activities or functions. In a preferred embodiment, a homologous protein is one that exhibits 50% sequence similarity to the wild type protein, preferred is 60% sequence similarity, more preferred is 70% sequence similarity. Even more preferred are homologous proteins that exhibit 80%, 85% or 90% sequence similarity to the wild type protein. In a yet more preferred embodiment, a homologous protein exhibits 95%, 97%, 98% or 99% sequence similarity.

When "sequence similarity" is used in reference to proteins or peptides, it is recognized that residue positions that are not identical often differ by conservative amino acid substitutions. In a preferred embodiment, a polypeptide that has "sequence similarity" comprises conservative or moderately conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, *Methods Mol. Biol.* 24: 307–31 (1994), herein incorporated by reference.

For instance, the following six groups each contain amino acids that are conservative substitutions for one another:

1) Serine (S), Threonine (T);
2) Aspartic Acid (D), Glutamic Acid (E);
3) Asparagine (N), Glutamine (Q);
4) Arginine (R), Lysine (K);
5) Isoleucine (I), Leucine (L), Methionine (M), Alanine (A), Valine (V), and
6) Phenylalanine (F), Tyrosine (Y), Tryptophan (W).

Alternatively, a conservative replacement is any change having a positive value in the PAM250 log-likelihood matrix disclosed in Gonnet et al., *Science* 256: 1443–45 (1992), herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Other programs include FASTA, discussed supra.

A preferred algorithm when comparing a sequence of the invention to a database containing a large number of sequences from different organisms is the computer program BLAST, especially blastp or tblastn. See, e.g., Altschul et al., *J. Mol. Biol.* 215: 403–410 (1990); Altschul et al., *Nucleic Acids Res.* 25:3389–402 (1997); herein incorporated by reference. Preferred parameters for blastp are:

| | |
|---|---|
| Expectation value: | 10 (default) |
| Filter: | seg (default) |
| Cost to open a gap: | 11 (default) |
| Cost to extend a gap: | 1 (default |
| Max. alignments: | 100 (default) |
| Word size: | 11 (default) |
| No. of descriptions: | 100 (default) |
| Penalty Matrix: | BLOSUM62 |

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

Database searching using amino acid sequences can be measured by algorithms other than blastp are known in the art. For instance, polypeptide sequences can be compared using FASTA, a program in GCG Version 6.1. FASTA (e.g., FASTA2 and FASTA3) provides alignments and percent sequence identity of the regions of the best overlap between the query and search sequences (Pearson (1990), supra; Pearson (2000), supra. For example, percent sequence identity between amino acid sequences can be determined using FASTA with its default or recommended parameters (a word size of 2 and the PAM250 scoring matrix), as provided in GCG Version 6.1, herein incorporated by reference.

An "antibody" refers to an intact immunoglobulin, or to an antigen-binding portion thereof that competes with the intact antibody for specific binding to a molecular species, e.g., a polypeptide of the instant invention. Antigen-binding portions may be produced by recombinant DNA techniques or by enzymatic or chemical cleavage of intact antibodies. Antigen-binding portions include, inter alia, Fab, Fab', $F(ab')_2$, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide. An Fab fragment is a monovalent fragment consisting of the VL, VH, CL and CH1 domains; an $F(ab')_2$ fragment is a bivalent fragment comprising two Fab fragments linked by a disulfide bridge at the hinge region; an Fd fragment consists of the VH and CH1 domains; an Fv fragment consists of the VL and VH domains of a single arm of an antibody; and a dAb fragment consists of a VH domain. See, e.g., Ward et al., *Nature* 341: 544–546 (1989).

By "bind specifically" and "specific binding" is here intended the ability of the antibody to bind to a first molecular species in preference to binding to other molecular species with which the antibody and first molecular species are admixed. An antibody is said specifically to "recognize" a first molecular species when it can bind specifically to that first molecular species.

A single-chain antibody (scFv) is an antibody in which a VL and VH region are paired to form a monovalent molecule via a synthetic linker that enables them to be made as a single protein chain. See, e.g., Bird et al., *Science* 242: 423–426 (1988); Huston et al., *Proc. Natl. Acad. Sci. USA* 85: 5879–5883 (1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites. See e.g., Holliger et al., *Proc. Natl. Acad. Sci. USA* 90: 6444–6448 (1993); Poljak et al., *Structure* 2: 1121–1123 (1994). One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest. A chimeric antibody is an antibody that contains one or more regions from one antibody and one or more regions from one or more other antibodies.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody has two different binding sites.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature. It is known that purified proteins, including purified antibodies, may be stabilized with non-naturally-associated components. The non-naturally-associated component may be a protein, such as albumin (e.g., BSA) or a chemical such as polyethylene glycol (PEG).

A "neutralizing antibody" or "an inhibitory antibody" is an antibody that inhibits the activity of a polypeptide or blocks the binding of a polypeptide to a ligand that normally binds to it. An "activating antibody" is an antibody that increases the activity of a polypeptide.

The term "epitope" includes any protein determinant capable of specifically binding to an immunoglobulin or T-cell receptor. Epitopic determinants usually consist of chemically active surface groupings of molecules such as amino acids or sugar side chains and usually have specific three-dimensional structural characteristics, as well as specific charge characteristics. An antibody is said to specifically bind an antigen when the dissociation constant is less than 1 $\mu$M, preferably less than 100 nM and most preferably less than 10 nM.

The term "patient" as used herein includes human and veterinary subjects.

Throughout this specification and claims, the word "comprise," or variations such as "comprises" or "comprising," will be understood to imply the inclusion of a stated integer or group of integers but not the exclusion of any other integer or group of integers.

The term "breast specific" refers to a nucleic acid molecule or polypeptide that is expressed predominantly in the breast as compared to other tissues in the body. In a preferred embodiment, a "breast specific" nucleic acid molecule or polypeptide is expressed at a level that is 5-fold higher than any other tissue in the body. In a more preferred embodiment, the "breast specific" nucleic acid molecule or polypeptide is expressed at a level that is 10-fold higher than any other tissue in the body, more preferably at least 15-fold, 20-fold, 25-fold, 50-fold or 100-fold higher than any other tissue in the body. Nucleic acid molecule levels may be measured by nucleic acid hybridization, such as Northern blot hybridization, or quantitative PCR. Polypeptide levels may be measured by any method known to accurately quantitate protein levels, such as Western blot analysis.

Nucleic Acid Molecules, Regulatory Sequences, Vectors, Host Cells and Recombinant Methods of Making Polypeptides

Nucleic Acid Molecules

One aspect of the invention provides isolated nucleic acid molecules that are specific to the breast or to breast cells or tissue or that are derived from such nucleic acid molecules. These isolated breast specific nucleic acids (BSNAs) may comprise a cDNA, a genomic DNA, RNA, or a fragment of one of these nucleic acids, or may be a non-naturally-occurring nucleic acid molecule. In a preferred embodiment, the nucleic acid molecule encodes a polypeptide that is specific to breast, a breast-specific polypeptide (BSP). In a more preferred embodiment, the nucleic acid molecule encodes a polypeptide that comprises an amino acid sequence of SEQ ID NO: 82 through 137. In another highly preferred embodiment, the nucleic acid molecule comprises a nucleic acid sequence of SEQ ID NO: 1 through 81.

A BSNA may be derived from a human or from another animal. In a preferred embodiment, the BSNA is derived from a human or other mammal. In a more preferred embodiment, the BSNA is derived from a human or other primate. In an even more preferred embodiment, the BSNA is derived from a human.

By "nucleic acid molecule" for purposes of the present invention, it is also meant to be inclusive of nucleic acid sequences that selectively hybridize to a nucleic acid molecule encoding a BSNA or a complement thereof. The hybridizing nucleic acid molecule may or may not encode a polypeptide or may not encode a BSP. However, in a preferred embodiment, the hybridizing nucleic acid molecule encodes a BSP. In a more preferred embodiment, the invention provides a nucleic acid molecule that selectively hybridizes to a nucleic acid molecule that encodes a polypeptide comprising an amino acid sequence of SEQ ID NO: 82 through 137. In an even more preferred embodiment, the invention provides a nucleic acid molecule that selectively hybridizes to a nucleic acid molecule comprising the nucleic acid sequence of SEQ ID NO: 1 through 81.

In a preferred embodiment, the nucleic acid molecule selectively hybridizes to a nucleic acid molecule encoding a BSP under low stringency conditions. In a more preferred embodiment, the nucleic acid molecule selectively hybridizes to a nucleic acid molecule encoding a BSP under moderate stringency conditions. In a more preferred embodiment, the nucleic acid molecule selectively hybridizes to a nucleic acid molecule encoding a BSP under high stringency conditions. In an even more preferred embodiment, the nucleic acid molecule hybridizes under low, moderate or high stringency conditions to a nucleic acid molecule encoding a polypeptide comprising an amino acid sequence of SEQ ID NO: 82 through 137. In a yet more preferred embodiment, the nucleic acid molecule hybridizes under low, moderate or high stringency conditions to a nucleic acid molecule comprising a nucleic acid sequence selected from SEQ ID NO: 1 through 81. In a preferred embodiment of the invention, the hybridizing nucleic acid molecule may be used to express recombinantly a polypeptide of the invention.

By "nucleic acid molecule" as used herein it is also meant to be inclusive of sequences that exhibits substantial sequence similarity to a nucleic acid encoding a BSP or a complement of the encoding nucleic acid molecule. In a preferred embodiment, the nucleic acid molecule exhibits substantial sequence similarity to a nucleic acid molecule encoding human BSP. In a more preferred embodiment, the nucleic acid molecule exhibits substantial sequence similarity to a nucleic acid molecule encoding a polypeptide having an amino acid sequence of SEQ ID NO: 82 through 137. In a preferred embodiment, the similar nucleic acid molecule is one that has at least 60% sequence identity with a nucleic acid molecule encoding a BSP, such as a polypeptide having an amino acid sequence of SEQ ID NO: 82 through 137, more preferably at least 70%, even more preferably at least 80% and even more preferably at least 85%. In a more preferred embodiment, the similar nucleic acid molecule is one that has at least 90% sequence identity with a nucleic acid molecule encoding a BSP, more preferably at least 95%, more preferably at least 97%, even more preferably at least 98%, and still more preferably at least 99%. In another highly preferred embodiment, the nucleic acid molecule is one that has at least 99.5%, 99.6%, 99.7%, 99.8% or 99.9% sequence identity with a nucleic acid molecule encoding a BSP.

In another preferred embodiment, the nucleic acid molecule exhibits substantial sequence similarity to a BSNA or its complement. In a more preferred embodiment, the nucleic acid molecule exhibits substantial sequence similarity to a nucleic acid molecule comprising a nucleic acid sequence of SEQ ID NO: 1 through 81. In a preferred embodiment, the nucleic acid molecule is one that has at least 60% sequence identity with a BSNA, such as one having a nucleic acid sequence of SEQ ID NO: 1 through 81, more preferably at least 70%, even more preferably at least 80% and even more preferably at least 85%. In a more preferred embodiment, the nucleic acid molecule is one that has at least 90% sequence identity with a BSNA, more preferably at least 95%, more preferably at least 97%, even more preferably at least 98%, and still more preferably at least 99%. In another highly preferred embodiment, the nucleic acid molecule is one that has at least 99.5%, 99.6%, 99.7%, 99.8% or 99.9% sequence identity with a BSNA.

A nucleic acid molecule that exhibits substantial sequence similarity may be one that exhibits sequence identity over its entire length to a BSNA or to a nucleic acid molecule encoding a BSP, or may be one that is similar over only a part of its length. In this case, the part is at least 50 nucleotides of the BSNA or the nucleic acid molecule encoding a BSP, preferably at least 100 nucleotides, more preferably at least 150 or 200 nucleotides, even more preferably at least 250 or 300 nucleotides, still more preferably at least 400 or 500 nucleotides.

The substantially similar nucleic acid molecule may be a naturally-occurring one that is derived from another species, especially one derived from another primate, wherein the similar nucleic acid molecule encodes an amino acid sequence that exhibits significant sequence identity to that of SEQ ID NO: 82 through 137 or demonstrates significant sequence identity to the nucleotide sequence of SEQ ID NO: 1 through 81. The similar nucleic acid molecule may also be a naturally-occurring nucleic acid molecule from a human, when the BSNA is a member of a gene family. The similar nucleic acid molecule may also be a naturally-occurring nucleic acid molecule derived from a non-primate, mammalian species, including without limitation, domesticated species, e.g., dog, cat, mouse, rat, rabbit, hamster, cow, horse and pig; and wild animals, e.g., monkey, fox, lions, tigers, bears, giraffes, zebras, etc. The substantially similar nucleic acid molecule may also be a naturally-occurring nucleic acid molecule derived from a non-mammalian species, such as birds or reptiles. The naturally-occurring substantially similar nucleic acid molecule may be isolated directly from humans or other species. In another embodiment, the substantially similar nucleic acid molecule may be one that is experimentally produced by random mutation of a nucleic acid molecule. In another embodiment, the substantially similar nucleic acid molecule may be one that is experimentally produced by directed mutation of a BSNA. Further, the substantially similar nucleic acid molecule may or may not be a BSNA. However, in a preferred embodiment, the substantially similar nucleic acid molecule is a BSNA.

By "nucleic acid molecule" it is also meant to be inclusive of allelic variants of a BSNA or a nucleic acid encoding a BSP. For instance, single nucleotide polymorphisms (SNPs) occur frequently in eukaryotic genomes. In fact, more than 1.4 million SNPs have already identified in the human genome, International Human Genome Sequencing Consortium, *Nature* 409: 860–921 (2001). Thus, the sequence determined from one individual of a species may differ from other allelic forms present within the population. Additionally, small deletions and insertions, rather than single nucleotide polymorphisms, are not uncommon in the general population, and often do not alter the function of the protein. Further, amino acid substitutions occur frequently among natural allelic variants, and often do not substantially change protein function.

In a preferred embodiment, the nucleic acid molecule comprising an allelic variant is a variant of a gene, wherein the gene is transcribed into an mRNA that encodes a BSP. In a more preferred embodiment, the gene is transcribed into an mRNA that encodes a BSP comprising an amino acid sequence of SEQ ID NO: 82 through 137. In another preferred embodiment, the allelic variant is a variant of a gene, wherein the gene is transcribed into an mRNA that is a BSNA. In a more preferred embodiment, the gene is transcribed into an mRNA that comprises the nucleic acid sequence of SEQ ID NO: 1 through 81. In a preferred embodiment, the allelic variant is a naturally-occurring allelic variant in the species of interest. In a more preferred embodiment, the species of interest is human.

By "nucleic acid molecule" it is also meant to be inclusive of a part of a nucleic acid sequence of the instant invention. The part may or may not encode a polypeptide, and may or may not encode a polypeptide that is a BSP. However, in a preferred embodiment, the part encodes a BSP. In one aspect, the invention comprises a part of a BSNA. In a second aspect, the invention comprises a part of a nucleic acid molecule that hybridizes or exhibits substantial sequence similarity to a BSNA. In a third aspect, the invention comprises a part of a nucleic acid molecule that is an allelic variant of a BSNA. In a fourth aspect, the invention comprises a part of a nucleic acid molecule that encodes a BSP. A part comprises at least 10 nucleotides, more preferably at least 15, 17, 18, 20, 25, 30, 35, 40, 50, 60, 70, 80, 90, 100, 150, 200, 250, 300, 350, 400 or 500 nucleotides. The maximum size of a nucleic acid part is one nucleotide shorter than the sequence of the nucleic acid molecule encoding the full-length protein.

By "nucleic acid molecule" it is also meant to be inclusive of sequence that encoding a fusion protein, a homologous protein, a polypeptide fragment, a mutein or a polypeptide analog, as described below.

Nucleotide sequences of the instantly-described nucleic acids were determined by sequencing a DNA molecule that had resulted, directly or indirectly, from at least one enzymatic polymerization reaction (e.g., reverse transcription and/or polymerase chain reaction) using an automated sequencer (such as the MegaBACE™ 1000, Molecular Dynamics, Sunnyvale, Calif., USA). Further, all amino acid sequences of the polypeptides of the present invention were predicted by translation from the nucleic acid sequences so determined, unless otherwise specified.

In a preferred embodiment of the invention, the nucleic acid molecule contains modifications of the native nucleic acid molecule. These modifications include nonnative internucleoside bonds, post-synthetic modifications or altered nucleotide analogues. One having ordinary skill in the art would recognize that the type of modification that can be made will depend upon the intended use of the nucleic acid molecule. For instance, when the nucleic acid molecule is used as a hybridization probe, the range of such modifications will be limited to those that permit sequence-discriminating base pairing of the resulting nucleic acid. When used to direct expression of RNA or protein in vitro or in vivo, the range of such modifications will be limited to those that permit the nucleic acid to function properly as a polymerization substrate. When the isolated nucleic acid is used as a therapeutic agent, the modifications will be limited to those that do not confer toxicity upon the isolated nucleic acid.

In a preferred embodiment, isolated nucleic acid molecules can include nucleotide analogues that incorporate labels that are directly detectable, such as radiolabels or fluorophores, or nucleotide analogues that incorporate labels that can be visualized in a subsequent reaction, such as biotin or various haptens. In a more preferred embodiment, the labeled nucleic acid molecule may be used as a hybridization probe.

Common radiolabeled analogues include those labeled with $^{33}$P, $^{32}$P, and $^{35}$S, such as $\alpha$-$^{32}$P-dATP, $\alpha$-$^{32}$P-dCTP, $\alpha$-$^{32}$P-dGTP, $\alpha$-$^{32}$P-dTTP, $\alpha$-$^{32}$P-3'dATP, $\alpha$-$^{32}$P-ATP, $\alpha$-$^{32}$P-CTP, $\alpha$-$^{32}$P-GTP, $\alpha$-$^{32}$P-UTP, $\alpha$-$^{35}$S-dATP, $\alpha$-$^{35}$S-GTP, $\alpha$-$^{33}$P-dATP, and the like.

Commercially available fluorescent nucleotide analogues readily incorporated into the nucleic acids of the present invention include Cy3-dCTP, Cy3-dUTP, Cy5-dCTP, Cy3-dUTP (Amersham Pharmacia Biotech, Piscataway, N.J., USA), fluorescein-12-dUTP, tetramethylrhodamine-6-dUTP, Texas Red®-5-dUTP, Cascade Blue®-7-dUTP, BODIPY® FL-14-dUTP, BODIPY® TMR-14-dUTP, BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, Alexa Fluor® 546-14-UTP (Molecular Probes, Inc. Eugene, Oreg., USA). One may also custom synthesize nucleotides having other fluorophores. See Henegariu et al., *Nature Biotechnol*. 18: 345–348 (2000), the disclosure of which is incorporated herein by reference in its entirety.

Haptens that are commonly conjugated to nucleotides for subsequent labeling include biotin (biotin-11-dUTP, Molecular Probes, Inc., Eugene, Oreg., USA; biotin-21-UTP, biotin-21-dUTP, Clontech Laboratories, Inc., Palo Alto, Calif., USA), digoxigenin (DIG-11-dUTP, alkali labile, DIG-11-UTP, Roche Diagnostics Corp., Indianapolis, Ind., USA), and dinitrophenyl (dinitrophenyl-11-dUTP, Molecular Probes, Inc., Eugene, Oreg., USA).

Nucleic acid molecules can be labeled by incorporation of labeled nucleotide analogues into the nucleic acid. Such analogues can be incorporated by enzymatic polymerization, such as by nick translation, random priming, polymerase chain reaction (PCR), terminal transferase tailing, and end-filling of overhangs, for DNA molecules, and in vitro transcription driven, e.g., from phage promoters, such as T7, T3, and SP6, for RNA molecules. Commercial kits are readily available for each such labeling approach. Analogues can also be incorporated during automated solid phase chemical synthesis. Labels can also be incorporated after nucleic acid synthesis, with the 5' phosphate and 3' hydroxyl providing convenient sites for post-synthetic covalent attachment of detectable labels.

Other post-synthetic approaches also permit internal labeling of nucleic acids. For example, fluorophores can be attached using a cisplatin reagent that reacts with the N7 of guanine residues (and, to a lesser extent, adenine bases) in DNA, RNA, and PNA to provide a stable coordination complex between the nucleic acid and fluorophore label (Universal Linkage System) (available from Molecular Probes, Inc., Eugene, Oreg., USA and Amersham Pharmacia Biotech, Piscataway, N.J., USA); see Alers et al., *Genes, Chromosomes & Cancer* 25: 301–305 (1999); Jelsma et al., *J. NIH Res*. 5: 82 (1994); Van Belkum et al., *BioTechniques* 16: 148–153 (1994), incorporated herein by reference. As another example, nucleic acids can be labeled using a disulfide-containing linker (FastTag™ Reagent, Vector Laboratories, Inc., Burlingame, Calif., USA) that is photo- or thermally-coupled to the target nucleic acid using aryl azide chemistry; after reduction, a free thiol is available for coupling to a hapten, fluorophore, sugar, affinity ligand, or other marker.

One or more independent or interacting labels can be incorporated into the nucleic acid molecules of the present invention. For example, both a fluorophore and a moiety that in proximity thereto acts to quench fluorescence can be included to report specific hybridization through release of fluorescence quenching or to report exonucleotidic excision. See, e.g., Tyagi et al., *Nature Biotechnol*. 14: 303–308 (1996); Tyagi et al., *Nature Biotechnol*. 16: 49–53 (1998); Sokol et al., *Proc. Natl. Acad. Sci. USA* 95: 11538–11543 (1998); Kostrikis et al., *Science* 279: 1228–1229 (1998); Marras et al., *Genet. Anal*. 14: 151–156 (1999); U.S. Pat. Nos. 5,846,726; 5,925,517; 5,925,517; 5,723,591 and 5,538,848; Holland et al., *Proc. Natl. Acad Sci. USA* 88: 7276–7280 (1991); Heid et al., *Genome Res*. 6(10): 986–94 (1996); Kuimelis et al., *Nucleic Acids Symp. Ser*. (37): 255–6 (1997); the disclosures of which are incorporated herein by reference in their entireties.

Nucleic acid molecules of the invention may be modified by altering one or more native phosphodiester internucleoside bonds to more nuclease-resistant, internucleoside bonds. See Hartmann et al. (eds.), *Manual of Antisense Methodology: Perspectives in Antisense Science*, Kluwer Law International (1999); Stein et al. (eds.), *Applied Antisense Oligonucleotide Technology*, Wiley-Liss (1998); Chadwick et al. (eds.), *Oligonucleotides as Therapeutic Agents—Symposium No*. 209, John Wiley & Son Ltd (1997); the disclosures of which are incorporated herein by reference in their entireties. Such altered intemucleoside bonds are often desired for antisense techniques or for targeted gene correction. See Gamper et al., *Nucl. Acids Res*. 28(21): 4332–4339 (2000), the disclosure of which is incorporated herein by reference in its entirety.

Modified oligonucleotide backbones include, without limitation, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, the disclosures of which are incorporated herein by reference in their entireties. In a preferred embodiment, the modified internucleoside linkages may be used for antisense techniques.

Other modified oligonucleotide backbones do not include a phosphorus atom, but have backbones that are formed by short chain alkyl or cycloalkyl intemucleoside linkages, mixed heteroatom and alkyl or cycloalkyl intemucleoside linkages, or one or more short chain heteroatomic or heterocyclic intemucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above backbones include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437 and 5,677,439; the disclosures of which are incorporated herein by reference in their entireties.

In other preferred oligonucleotide mimetics, both the sugar and the intemucleoside linkage are replaced with novel groups, such as peptide nucleic acids (PNA). In PNA compounds, the phosphodiester backbone of the nucleic acid is replaced with an amide-containing backbone, in particular by repeating N-(2-aminoethyl) glycine units linked by amide bonds. Nucleobases are bound directly or indirectly to aza nitrogen atoms of the amide portion of the backbone, typically by methylene carbonyl linkages. PNA can be synthesized using a modified peptide synthesis protocol. PNA oligomers can be synthesized by both Fmoc and tBoc methods. Representative U.S. patents that teach the preparation of PNA compounds include, but are not limited to, U.S. Pat. Nos. 5,539,082; 5,714,331; and 5,719,262, each of which is herein incorporated by reference. Automated PNA synthesis is readily achievable on commercial synthesizers (see, e.g., "PNA User's Guide," Rev. 2, Feb. 1998, Perseptive Biosystems Part No. 60138, Applied Biosystems, Inc., Foster City, Calif.).

PNA molecules are advantageous for a number of reasons. First, because the PNA backbone is uncharged, PNA/DNA and PNA/RNA duplexes have a higher thermal stability than is found in DNA/DNA and DNA/RNA duplexes. The Tm of a PNA/DNA or PNA/RNA duplex is generally 1° C. higher per base pair than the Tm of the corresponding DNA/DNA or DNA/RNA duplex (in 100 mM NaCl). Second, PNA molecules can also form stable PNA/DNA complexes at low ionic strength, under conditions in which DNA/DNA duplex formation does not occur. Third, PNA also demonstrates greater specificity in binding to complementary DNA because a PNA/DNA mismatch is more destabilizing than DNA/DNA mismatch. A single mismatch in mixed a PNA/DNA 15-mer lowers the Tm by 8–20° C. (15° C. on average). In the corresponding DNA/DNA duplexes, a single mismatch lowers the Tm by 4–16° C. (11° C. on average). Because PNA probes can be significantly shorter than DNA probes, their specificity is greater. Fourth, PNA oligomers are resistant to degradation by enzymes, and the lifetime of these compounds is extended both in vivo and in vitro because nucleases and proteases do not recognize the PNA polyamide backbone with nucleobase sidechains. See, e.g., Ray et al., *FASEB J*. 14(9): 1041–60 (2000); Nielsen et al., *Pharmacol Toxicol*. 86(1): 3–7 (2000); Larsen et al., *Biochim Biophys Acta*. 1489(1): 159–66 (1999); Nielsen, *Curr. Opin. Struct. Biol*. 9(3): 353–7 (1999), and Nielsen, *Curr. Opin. Biotechnol*. 10(1): 71–5 (1999), the disclosures of which are incorporated herein by reference in their entireties.

Nucleic acid molecules may be modified compared to their native structure throughout the length of the nucleic acid molecule or can be localized to discrete portions thereof. As an example of the latter, chimeric nucleic acids can be synthesized that have discrete DNA and RNA domains and that can be used for targeted gene repair and modified PCR reactions, as further described in U.S. Pat. Nos. 5,760,012 and 5,731,181, Misra et al., *Biochem*. 37: 1917–1925 (1998); and Finn et al., *Nucl. Acids Res*. 24: 3357–3363 (1996), the disclosures of which are incorporated herein by reference in their entireties.

Unless otherwise specified, nucleic acids of the present invention can include any topological conformation appropriate to the desired use; the term thus explicitly comprehends, among others, single-stranded, double-stranded, triplexed, quadruplexed, partially double-stranded, partially-triplexed, partially-quadruplexed, branched, hairpinned, circular, and padlocked conformations. Padlock conformations and their utilities are further described in Banér et al., *Curr. Opin. Biotechnol*. 12: 11–15 (2001); Escude et al., *Proc. Natl. Acad. Sci. USA* 14: 96(19): 10603–7 (1999); Nilsson et al., *Science* 265(5181): 2085–8 (1994), the disclosures of which are incorporated herein by reference in their entireties. Triplex and quadruplex conformations, and their utilities, are reviewed in Praseuth et al., *Biochim. Biophys. Acta*. 1489(1): 181–206 (1999); Fox, *Curr. Med. Chem*. 7(1): 17–37 (2000); Kochetkova et al., *Methods Mol. Biol*. 130: 189–201 (2000); Chan et al., *J. Mol. Med*. 75(4): 267–82 (1997), the disclosures of which are incorporated herein by reference in their entireties.

Methods for Using Nucleic Acid Molecules as Probes and Primers

The isolated nucleic acid molecules of the present invention can be used as hybridization probes to detect, characterize, and quantify hybridizing nucleic acids in, and isolate hybridizing nucleic acids from, both genomic and transcript-derived nucleic acid samples. When free in solution, such probes are typically, but not invariably, detectably labeled; bound to a substrate, as in a microarray, such probes are typically, but not invariably unlabeled.

In one embodiment, the isolated nucleic acids of the present invention can be used as probes to detect and characterize gross alterations in the gene of a BSNA, such as deletions, insertions, translocations, and duplications of the BSNA genomic locus through fluorescence in situ hybridization (FISH) to chromosome spreads. See, e.g., Andreeff et al. (eds.), *Introduction to Fluorescence In Situ Hybridization: Principles and Clinical Applications*, John Wiley & Sons (1999), the disclosure of which is incorporated herein by reference in its entirety. The isolated nucleic acids of the present invention can be used as probes to assess smaller genomic alterations using, e.g., Southern blot detection of restriction fragment length polymorphisms. The isolated nucleic acid molecules of the present invention can be used as probes to isolate genomic clones that include the nucleic acid molecules of the present invention, which thereafter can be restriction mapped and sequenced to identify deletions, insertions, translocations, and substitutions (single nucleotide polymorphisms, SNPs) at the sequence level.

In another embodiment, the isolated nucleic acid molecules of the present invention can be used as probes to detect, characterize, and quantify BSNA in, and isolate BSNA from, transcript-derived nucleic acid samples. In one aspect, the isolated nucleic acid molecules of the present invention can be used as hybridization probes to detect, characterize by length, and quantify mRNA by Northern blot of total or poly-$A^+$-selected RNA samples. In another aspect, the isolated nucleic acid molecules of the present invention can be used as hybridization probes to detect, characterize by location, and quantify mRNA by in situ hybridization to tissue sections. See, e.g., Schwarchzacher et al., *In Situ Hybridization*, Springer-Verlag New York (2000), the disclosure of which is incorporated herein by reference in its entirety. In another preferred embodiment, the isolated nucleic acid molecules of the present invention can be used as hybridization probes to measure the representation of clones in a cDNA library or to isolate hybridizing nucleic acid molecules acids from cDNA libraries, permitting sequence level characterization of mRNAs that hybridize to BSNAs, including, without limitations, identification of deletions, insertions, substitutions, truncations, alternatively spliced forms and single nucleotide polymorphisms. In yet another preferred embodiment, the nucleic acid molecules of the instant invention may be used in microarrays.

All of the aforementioned probe techniques are well within the skill in the art, and are described at greater length in standard texts such as Sambrook (2001), supra; Ausubel (1999), supra; and Walker et al. (eds.), *The Nucleic Acids Protocols Handbook*, Humana Press (2000), the disclosures of which are incorporated herein by reference in their entirety.

Thus, in one embodiment, a nucleic acid molecule of the invention may be used as a probe or primer to identify or amplify a second nucleic acid molecule that selectively hybridizes to the nucleic acid molecule of the invention. In a preferred embodiment, the probe or primer is derived from a nucleic acid molecule encoding a BSP. In a more preferred embodiment, the probe or primer is derived from a nucleic acid molecule encoding a polypeptide having an amino acid sequence of SEQ ID NO: 82 through 137. In another preferred embodiment, the probe or primer is derived from a BSNA. In a more preferred embodiment, the probe or primer is derived from a nucleic acid molecule having a nucleotide sequence of SEQ ID NO: 1 through 81.

In general, a probe or primer is at least 10 nucleotides in length, more preferably at least 12, more preferably at least 14 and even more preferably at least 16 or 17 nucleotides in length. In an even more preferred embodiment, the probe or primer is at least 18 nucleotides in length, even more preferably at least 20 nucleotides and even more preferably at least 22 nucleotides in length. Primers and probes may also be longer in length. For instance, a probe or primer may be 25 nucleotides in length, or may be 30, 40 or 50 nucleotides in length. Methods of performing nucleic acid hybridization using oligonucleotide probes are well-known in the art. See, e.g., Sambrook et al., 1989, supra, Chapter 11 and pp. 11.31–11.32 and 11.40–11.44, which describes radiolabeling of short probes, and pp. 11.45–11.53, which describe hybridization conditions for oligonucleotide probes, including specific conditions for probe hybridization (pp. 11.50–11.51).

Methods of performing primer-directed amplification are also well-known in the art. Methods for performing the polymerase chain reaction (PCR) are compiled, inter alia, in McPherson, *PCR Basics: From Background to Bench*, Springer Verlag (2000); Innis et al. (eds.), *PCR Applications: Protocols for Functional Genomics*, Academic Press (1999); Gelfand et al. (eds.), *PCR Strategies*, Academic Press (1998); Newton et al., *PCR*, Springer-Verlag New York (1997); Burke (ed.), *PCR: Essential Techniques*, John Wiley & Son Ltd (1996); White (ed.), *PCR Cloning Protocols: From Molecular Cloning to Genetic Engineering*, Vol. 67, Humana Press (1996); McPherson et al. (eds.), *PCR 2: A Practical Approach*, Oxford University Press, Inc. (1995); the disclosures of which are incorporated herein by reference in their entireties. Methods for performing RT-PCR are collected, e.g., in Siebert et al. (eds.), *Gene Cloning and Analysis by RT-PCR*, Eaton Publishing Company/Bio Techniques Books Division, 1998; Siebert (ed.), *PCR Technique:RT-PCR*, Eaton Publishing Company/Bio Techniques Books (1995); the disclosure of which is incorporated herein by reference in its entirety.

PCR and hybridization methods may be used to identify and/or isolate allelic variants, homologous nucleic acid molecules and fragments of the nucleic acid molecules of the invention. PCR and hybridization methods may also be used to identify, amplify and/or isolate nucleic acid molecules that encode homologous proteins, analogs, fusion protein or muteins of the invention. The nucleic acid primers of the present invention can be used to prime amplification of nucleic acid molecules of the invention, using transcript-derived or genomic DNA as template.

The nucleic acid primers of the present invention can also be used, for example, to prime single base extension (SBE) for SNP detection (See, e.g., U.S. Pat. No. 6,004,744, the disclosure of which is incorporated herein by reference in its entirety).

Isothermal amplification approaches, such as rolling circle amplification, are also now well-described. See, e.g., Schweitzer et al., *Curr. Opin. Biotechnol.* 12(1): 21–7 (2001); U.S. Pat. Nos. 5,854,033 and 5,714,320; and international patent publications WO 97/19193 and WO 00/15779, the disclosures of which are incorporated herein by reference in their entireties. Rolling circle amplification can be combined with other techniques to facilitate SNP detection. See, e.g., Lizardi et al., *Nature Genet.* 19(3): 225–32 (1998).

Nucleic acid molecules of the present invention may be bound to a substrate either covalently or noncovalently. The substrate can be porous or solid, planar or non-planar, unitary or distributed. The bound nucleic acid molecules may be used as hybridization probes, and may be labeled or unlabeled. In a preferred embodiment, the bound nucleic acid molecules are unlabeled.

In one embodiment, the nucleic acid molecule of the present invention is bound to a porous substrate, e.g., a membrane, typically comprising nitrocellulose, nylon, or positively-charged derivatized nylon. The nucleic acid molecule of the present invention can be used to detect a hybridizing nucleic acid molecule that is present within a labeled nucleic acid sample, e.g., a sample of transcript-derived nucleic acids. In another embodiment, the nucleic acid molecule is bound to a solid substrate, including, without limitation, glass, amorphous silicon, crystalline silicon or plastics. Examples of plastics include, without limitation, polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, or mixtures thereof. The solid substrate may be any shape, including rectangular, disk-like and spherical. In a preferred embodiment, the solid substrate is a microscope slide or slide-shaped substrate.

The nucleic acid molecule of the present invention can be attached covalently to a surface of the support substrate or applied to a derivatized surface in a chaotropic agent that facilitates denaturation and adherence by presumed noncovalent interactions, or some combination thereof. The nucleic acid molecule of the present invention can be bound to a substrate to which a plurality of other nucleic acids are concurrently bound, hybridization to each of the plurality of bound nucleic acids being separately detectable. At low density, e.g on a porous membrane, these substrate-bound collections are typically denominated macroarrays; at higher density, typically on a solid support, such as glass, these substrate bound collections of plural nucleic acids are colloquially termed microarrays. As used herein, the term microarray includes arrays of all densities. It is, therefore, another aspect of the invention to provide microarrays that include the nucleic acids of the present invention.

Expression Vectors, Host Cells and Recombinant Methods of Producing Polypeptides Another aspect of the present invention relates to vectors that comprise one or more of the isolated nucleic acid molecules of the present invention, and host cells in which such vectors have been introduced.

The vectors can be used, inter alia, for propagating the nucleic acids of the present invention in host cells (cloning vectors), for shuttling the nucleic acids of the present invention between host cells derived from disparate organisms (shuttle vectors), for inserting the nucleic acids of the present invention into host cell chromosomes (insertion vectors), for expressing sense or antisense RNA transcripts of the nucleic acids of the present invention in vitro or within a host cell, and for expressing polypeptides encoded by the nucleic acids of the present invention, alone or as fusions to heterologous polypeptides (expression vectors). Vectors of the present invention will often be suitable for several such uses.

Vectors are by now well-known in the art, and are described, inter alia, in Jones et al. (eds.), *Vectors: Cloning Applications: Essential Techniques* (Essential Techniques Series), John Wiley & Son Ltd. (1998); Jones et al. (eds.), *Vectors: Expression Systems: Essential Techniques* (Essential Techniques Series), John Wiley & Son Ltd. (1998); Gacesa et al., *Vectors: Essential Data*, John Wiley & Sons Ltd. (1995); Cid-Arregui (eds.), *Viral Vectors: Basic Science and Gene Therapy*, Eaton Publishing Co. (2000); Sambrook (2001), supra; Ausubel (1999), supra; the disclosures of which are incorporated herein by reference in their entireties. Furthermore, an enormous variety of vectors are available commercially. Use of existing vectors and modifications thereof being well within the skill in the art, only basic features need be described here.

Nucleic acid sequences may be expressed by operatively linking them to an expression control sequence in an appropriate expression vector and employing that expression vector to transform an appropriate unicellular host. Expression control sequences are sequences which control the transcription, post-transcriptional events and translation of nucleic acid sequences. Such operative linking of a nucleic sequence of this invention to an expression control sequence, of course, includes, if not already part of the nucleic acid sequence, the provision of a translation initiation codon, ATG or GTG, in the correct reading frame upstream of the nucleic acid sequence.

A wide variety of host/expression vector combinations may be employed in expressing the nucleic acid sequences of this invention. Useful expression vectors, for example, may consist of segments of chromosomal, non-chromosomal and synthetic nucleic acid sequences.

In one embodiment, prokaryotic cells may be used with an appropriate vector. Prokaryotic host cells are often used for cloning and expression. In a preferred embodiment, prokaryotic host cells include *E. coli, Pseudomonas, Bacillus* and *Streptomyces*. In a preferred embodiment, bacterial host cells are used to express the nucleic acid molecules of the instant invention. Useful expression vectors for bacterial hosts include bacterial plasmids, such as those from *E. coli, Bacillus* or *Streptomyces*, including pBluescript, pGEX-2T, pUC vectors, col E1, pCR1, pBR322, pMB9 and their derivatives, wider host range plasmids, such as RP4, phage DNAs, e.g., the numerous derivatives of phage lambda, e.g., NM989, λGT10 and λGT11, and other phages, e.g., M13 and filamentous single-stranded phage DNA. Where *E. coli* is used as host, selectable markers are, analogously, chosen for selectivity in gram negative bacteria: e.g., typical markers confer resistance to antibiotics, such as ampicillin, tetracycline, chloramphenicol, kanamycin, streptomycin and zeocin; auxotrophic markers can also be used.

In other embodiments, eukaryotic host cells, such as yeast, insect, mammalian or plant cells, may be used. Yeast cells, typically *S. cerevisiae*, are useful for eukaryotic genetic studies, due to the ease of targeting genetic changes by homologous recombination and the ability to easily complement genetic defects using recombinantly expressed proteins. Yeast cells are useful for identifying interacting protein components, e.g. through use of a two-hybrid system. In a preferred embodiment, yeast cells are useful for protein expression. Vectors of the present invention for use in yeast will typically, but not invariably, contain an origin of replication suitable for use in yeast and a selectable marker that is functional in yeast. Yeast vectors include Yeast Integrating plasmids (e.g., YIp5) and Yeast Replicating plasmids (the YRp and YEp series plasmids), Yeast Centromere plasmids (the YCp series plasmids), Yeast Artificial Chromosomes (YACs) which are based on yeast linear plasmids, denoted YLp, pGPD-2, 2$\mu$ plasmids and derivatives thereof, and improved shuttle vectors such as those described in Gietz et al., *Gene,* 74: 527–34 (1988) (YIplac, YEplac and YCplac). Selectable markers in yeast vectors include a variety of auxotrophic markers, the most common of which are (in *Saccharomyces cerevisiae*) URA3, HIS3, LEU2, TRP1 and LYS2, which complement specific auxotrophic mutations, such as ura3-52, his3-D1, leu2-D1,trp1-D1 and lys2-201.

Insect cells are often chosen for high efficiency protein expression. Where the host cells are from *Spodoptera frugiperda*, e.g, Sf9 and Sf21 cell lines, and expresSF™ cells (Protein Sciences Corp., Meriden, Conn., USA)), the vector replicative strategy is typically based upon the baculovirus life cycle. Typically, baculovirus transfer vectors are used to replace the wild-type AcMNPV polyhedrin gene with a heterologous gene of interest. Sequences that flank the polyhedrin gene in the wild-type genome are positioned 5' and 3' of the expression cassette on the transfer vectors. Following co-transfection with AcMNPV DNA, a homologous recombination event occurs between these sequences resulting in a recombinant virus carrying the gene of interest and the polyhedrin or p10 promoter. Selection can be based upon visual screening for lacZ fusion activity.

In another embodiment, the host cells may be mammalian cells, which are particularly useful for expression of proteins intended as pharmaceutical agents, and for screening of potential agonists and antagonists of a protein or a physiological pathway. Mammalian vectors intended for autonomous extrachromosomal replication will typically include a viral origin, such as the SV40 origin (for replication in cell lines expressing the large T-antigen, such as COS1 and COS7 cells), the papillomavirus origin, or the EBV origin for long term episomal replication (for use, e.g., in 293-EBNA cells, which constitutively express the EBV EBNA-1 gene product and adenovirus E1A). Vectors intended for integration, and thus replication as part of the mammalian chromosome, can, but need not, include an origin of replication functional in mammalian cells, such as the SV40 origin. Vectors based upon viruses, such as adenovirus, adeno-associated virus, vaccinia virus, and various mammalian retroviruses, will typically replicate according to the viral replicative strategy. Selectable markers for use in mammalian cells include resistance to neomycin (G418), blasticidin, hygromycin and to zeocin, and selection based upon the purine salvage pathway using HAT medium.

Expression in mammalian cells can be achieved using a variety of plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses). Useful vectors for insect cells include baculoviral vectors and pVL 941.

Plant cells can also be used for expression, with the vector replicon typically derived from a plant virus (e.g., cauliflower mosaic virus, CaMV; tobacco mosaic virus, TMV) and selectable markers chosen for suitability in plants.

It is known that codon usage of different host cells may be different. For example, a plant cell and a human cell may exhibit a difference in codon preference for encoding a particular amino acid. As a result, human mRNA may not be efficiently translated in a plant, bacteria or insect host cell. Therefore, another embodiment of this invention is directed to codon optimization. The codons of the nucleic acid molecules of the invention may be modified to resemble, as much as possible, genes naturally contained within the host cell without altering the amino acid sequence encoded by the nucleic acid molecule.

Any of a wide variety of expression control sequences may be used in these vectors to express the DNA sequences of this invention. Such useful expression control sequences include the expression control sequences associated with structural genes of the foregoing expression vectors. Expression control sequences that control transcription include, e.g., promoters, enhancers and transcription termination sites. Expression control sequences in eukaryotic cells that control post-transcriptional events include splice donor and acceptor sites and sequences that modify the half-life of the transcribed RNA, e.g., sequences that direct poly(A) addition or binding sites for RNA-binding proteins. Expression control sequences that control translation include ribosome binding sites, sequences which direct targeted expression of the polypeptide to or within particular cellular compartments, and sequences in the 5' and 3' untranslated regions that modify the rate or efficiency of translation.

Examples of useful expression control sequences for a prokaryote, e.g., *E. coli*, will include a promoter, often a phage promoter, such as phage lambda pL promoter, the trc promoter, a hybrid derived from the trp and lac promoters, the bacteriophage T7 promoter (in *E. coli* cells engineered to express the T7 polymerase), the TAC or TRC system, the major operator and promoter regions of phage lambda, the control regions of fd coat protein, or the araBAD operon. Prokaryotic expression vectors may further include transcription terminators, such as the aspA terminator, and elements that facilitate translation, such as a consensus ribosome binding site and translation termination codon, Schomer et al., *Proc. Natl. Acad. Sci. USA* 83: 8506–8510 (1986).

Expression control sequences for yeast cells, typically *S. cerevisiae*, will include a yeast promoter, such as the CYC1 promoter, the GAL1 promoter, the GAL10 promoter, ADH1 promoter, the promoters of the yeast $\alpha$-mating system, or the GPD promoter, and will typically have elements that facilitate transcription termination, such as the transcription termination signals from the CYC1 or ADH1 gene.

Expression vectors useful for expressing proteins in mammalian cells will include a promoter active in mammalian cells. These promoters include those derived from mammalian viruses, such as the enhancer-promoter sequences from the immediate early gene of the human cytomegalovirus (CMV), the enhancer-promoter sequences from the Rous sarcoma virus long terminal repeat (RSV LTR), the enhancer-promoter from SV40 or the early and late promoters of adenovirus. Other expression control sequences include the promoter for 3-phosphoglycerate kinase or other glycolytic enzymes, the promoters of acid phosphatase. Other expression control sequences include those from the gene comprising the BSNA of interest. Often, expression is enhanced by incorporation of polyadenylation sites, such as the late SV40 polyadenylation site and the polyadenylation signal and transcription termination sequences from the bovine growth hormone (BGH) gene, and ribosome binding sites. Furthermore, vectors can include introns, such as intron II of rabbit $\beta$-globin gene and the SV40 splice elements.

Preferred nucleic acid vectors also include a selectable or amplifiable marker gene and means for amplifying the copy number of the gene of interest. Such marker genes are well-known in the art. Nucleic acid vectors may also comprise stabilizing sequences (e.g., ori- or ARS-like sequences and telomere-like sequences), or may alternatively be designed to favor directed or non-directed integration into the host cell genome. In a preferred embodiment, nucleic acid sequences of this invention are inserted in frame into an expression vector that allows high level expression of an RNA which encodes a protein comprising the encoded nucleic acid sequence of interest. Nucleic acid cloning and sequencing methods are well-known to those of skill in the art and are described in an assortment of laboratory manuals, including Sambrook (1989), supra, Sambrook (2000), supra; and Ausubel (1992), supra, Ausubel (1999), supra. Product information from manufacturers of biological, chemical and immunological reagents also provide useful information.

Expression vectors may be either constitutive or inducible. Inducible vectors include either naturally inducible promoters, such as the trc promoter, which is regulated by the lac operon, and the pL promoter, which is regulated by tryptophan, the MMTV-LTR promoter, which is inducible by dexamethasone, or can contain synthetic promoters and/or additional elements that confer inducible control on adjacent promoters. Examples of inducible synthetic promoters are the hybrid Plac/ara-1 promoter and the PLtetO-1 promoter. The PltetO-1 promoter takes advantage of the high expression levels from the PL promoter of phage lambda, but replaces the lambda repressor sites with two copies of operator 2 of the Tn10 tetracycline resistance operon, causing this promoter to be tightly repressed by the Tet repressor protein and induced in response to tetracycline (Tc) and Tc derivatives such as anhydrotetracycline. Vectors may also be inducible because they contain hormone response elements, such as the glucocorticoid response element (GRE) and the estrogen response element (ERE), which can confer hormone inducibility where vectors are used for expression in cells having the respective hormone receptors. To reduce background levels of expression, elements responsive to ecdysone, an insect hormone, can be used instead, with coexpression of the ecdysone receptor.

In one aspect of the invention, expression vectors can be designed to fuse the expressed polypeptide to small protein tags that facilitate purification and/or visualization. Tags that facilitate purification include a polyhistidine tag that facilitates purification of the fusion protein by immobilized metal affinity chromatography, for example using NiNTA resin (Qiagen Inc., Valencia, Calif., USA) or TALON™ resin (cobalt immobilized affinity chromatography medium, Clontech Labs, Palo Alto, Calif., USA). The fusion protein can include a chitin-binding tag and self-excising intein, permitting chitin-based purification with self-removal of the fused tag (IMPACT™ system, New England Biolabs, Inc., Beverley, Mass., USA). Alternatively, the fusion protein can include a calmodulin-binding peptide tag, permitting purification by calmodulin affinity resin (Stratagene, La Jolla, Calif., USA), or a specifically excisable fragment of the biotin carboxylase carrier protein, permitting purification of in vivo biotinylated protein using an avidin resin and subsequent tag removal (Promega, Madison, Wis., USA). As another useful alternative, the proteins of the present invention can be expressed as a fusion protein with glutathione-S-transferase, the affinity and specificity of binding to glutathione permitting purification using glutathione affinity resins, such as Glutathione-Superflow Resin (Clontech Laboratories, Palo Alto, Calif., USA), with subsequent elution with free glutathione. Other tags include, for example, the Xpress epitope, detectable by anti-Xpress antibody (Invitrogen, Carlsbad, Calif., USA), a myc tag, detectable by anti-myc tag antibody, the V5 epitope, detectable by anti-V5 antibody (Invitrogen, Carlsbad, Calif., USA), FLAG® epitope, detectable by anti-FLAG® antibody (Stratagene, La Jolla, Calif., USA), and the HA epitope.

For secretion of expressed proteins, vectors can include appropriate sequences that encode secretion signals, such as leader peptides. For example, the pSecTag2 vectors (Invitrogen, Carlsbad, Calif., USA) are 5.2 kb mammalian expression vectors that carry the secretion signal from the V-J2-C region of the mouse Ig kappa-chain for efficient secretion of recombinant proteins from a variety of mammalian cell lines.

Expression vectors can also be designed to fuse proteins encoded by the heterologous nucleic acid insert to polypeptides that are larger than purification and/or identification tags. Useful fusion proteins include those that permit display of the encoded protein on the surface of a phage or cell, fusion to intrinsically fluorescent proteins, such as those that have a green fluorescent protein (GFP)-like chromophore, fusions to the IgG Fc region, and fusion proteins for use in two hybrid systems.

Vectors for phage display fuse the encoded polypeptide to, e.g., the gene III protein (pIII) or gene VIII protein (pVIII) for display on the surface of filamentous phage, such as M13. See Barbas et al., *Phage Display: A Laboratory Manual*, Cold Spring Harbor Laboratory Press (2001); Kay et al. (eds.), *Phage Display of Peptides and Proteins: A Laboratory Manual*, Academic Press, Inc., (1996); Abelson et al. (eds.), *Combinatorial Chemistry* (Methods in Enzymology, Vol. 267) Academic Press (1996). Vectors for yeast display, e.g the pYD1 yeast display vector (Invitrogen, Carlsbad, Calif., USA), use the α-agglutinin yeast adhesion receptor to display recombinant protein on the surface of *S. cerevisiae*. Vectors for mammalian display, e.g., the pDisplay™ vector (Invitrogen, Carlsbad, Calif., USA), target recombinant proteins using an N-terminal cell surface targeting signal and a C-terminal transmembrane anchoring domain of platelet derived growth factor receptor.

A wide variety of vectors now exist that fuse proteins encoded by heterologous nucleic acids to the chromophore of the substrate-independent, intrinsically fluorescent green fluorescent protein from *Aequorea victoria* ("GFP") and its variants. The GFP-like chromophore can be selected from GFP-like chromophores found in naturally occurring proteins, such as *A. victoria* GFP (GenBank accession number AAA27721), *Renilla reniformis* GFP, FP583 (GenBank accession no. AF168419) (DsRed), FP593 (AF272711), FP483 (AF168420), FP484 (AF168424), FP595 (AF246709), FP486 (AF168421), FP538 (AF168423), and FP506 (AF168422), and need include only so much of the native protein as is needed to retain the chromophore's intrinsic fluorescence. Methods for determining the minimal domain required for fluorescence are known in the art. See Li et al., *J. Biol. Chem.* 272: 28545–28549 (1997). Alternatively, the GFP-like chromophore can be selected from GFP-like chromophores modified from those found in nature. The methods for engineering such modified GFP-like chromophores and testing them for fluorescence activity, both alone and as part of protein fusions, are well-known in the art. See Heim et al., *Curr. Biol*. 6: 178–182 (1996) and Palm et al., *Methods Enzymol.* 302: 378–394 (1999), incorporated herein by reference in its entirety. A variety of such modified chromophores are now commercially available and can readily be used in the fusion proteins of the present invention. These include EGFP ("enhanced GFP"), EBFP ("enhanced blue fluorescent protein"), BFP2, EYFP ("enhanced yellow fluorescent protein"), ECFP ("enhanced cyan fluorescent protein") or Citrine. EGFP (see, e.g, Cormack et al., *Gene* 173: 33–38 (1996); U.S. Pat. Nos. 6,090,919 and 5,804,387) is found on avariety of vectors, both plasmid and viral, which are available commercially (Clontech Labs, Palo Alto, Calif., USA); EBFP is optimized for expression in mammalian cells whereas BFP2, which retains the original jellyfish codons, can be expressed in bacteria (see, e.g,. Heim et al., *Curr. Biol.* 6: 178–182 (1996) and Cormack et al., *Gene* 173: 33–38 (1996)). Vectors containing these blue-shifted variants are available from Clontech Labs (Palo Alto, Calif., USA). Vectors containing EYFP, ECFP (see, e.g., Heim et al., *Curr. Biol.* 6: 178–182 (1996); Miyawaki et al., *Nature* 388: 882–887 (1997)) and Citrine (see, e.g., Heikal et al., *Proc. Natl. Acad. Sci. USA* 97: 11996–12001 (2000)) are also available from Clontech Labs. The GFP-like chromophore can also be drawn from other modified GFPs, including those described in U.S. Pat. Nos. 6,124,128; 6,096,865; 6,090,919; 6,066,476; 6,054,321; 6,027,881; 5,968,750; 5,874,304; 5,804,387; 5,777,079; 5,741,668; and 5,625,048, the disclosures of which are incorporated herein by reference in their entireties. See also Conn (ed.), *Green Fluorescent Protein* (Methods in Enzymology, Vol. 302), Academic Press, Inc. (1999). The GFP-like chromophore of each of these GFP variants can usefully be included in the fusion proteins of the present invention.

Fusions to the IgG Fc region increase serum half life of protein pharmaceutical products through interaction with the FcRn receptor (also denominated the FcRp receptor and the Brambell receptor, FcRb), further described in International Patent Application Nos. WO 97/43316, WO 97/34631, WO 96/32478, WO 96/18412.

For long-term, high-yield recombinant production of the proteins, protein fusions, and protein fragments of the present invention, stable expression is preferred. Stable expression is readily achieved by integration into the host cell genome of vectors having selectable markers, followed by selection of these integrants. Vectors such as pUB6/V5-His A, B, and C (Invitrogen, Carlsbad, Calif., USA) are designed for high-level stable expression of heterologous proteins in a wide range of mammalian tissue types and cell lines. pUB6/V5-His uses the promoter/enhancer sequence from the human ubiquitin C gene to drive expression of recombinant proteins: expression levels in 293, CHO, and NIH3T3 cells are comparable to levels from the CMV and human EF-1a promoters. The bsd gene permits rapid selection of stably transfected mammalian cells with the potent antibiotic blasticidin.

Replication incompetent retroviral vectors, typically derived from Moloney murine leukemia virus, also are useful for creating stable transfectants having integrated provirus. The highly efficient transduction machinery of retroviruses, coupled with the availability of a variety of packaging cell lines such as RetroPack™ PT 67, EcoPack2™-293, AmphoPack-293, and GP2-293 cell lines (all available from Clontech Laboratories, Palo Alto, Calif., USA), allow a wide host range to be infected with high efficiency; varying the multiplicity of infection readily adjusts the copy number of the integrated provirus.

Of course, not all vectors and expression control sequences will function equally well to express the nucleic acid sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must be replicated in it. The vector's copy number, the ability to control that copy number, the ability to control integration, if any, and the expression of any other proteins encoded by the vector, such as antibiotic or other selection markers, should also be considered. The present invention further includes host cells comprising the vectors of the present invention, either present episomally within the cell or integrated, in whole or in part, into the host cell chromosome. Among other considerations, some of which are described above, a host cell strain may be chosen for its ability to process the expressed protein in the desired fashion. Such post-translational modifications of the polypeptide include, but are not limited to, acetylation, carboxylation, glycosylation, phosphorylation, lipidation, and acylation, and it is an aspect of the present invention to provide BSPs with such post-translational modifications.

Polypeptides of the invention may be post-translationally modified. Post-translational modifications include phosphorylation of amino acid residues serine, threonine and/or tyrosine, N-linked and/or O-linked glycosylation, methylation, acetylation, prenylation, methylation, acetylation, arginylation, ubiquination and racemization. One may determine whether a polypeptide of the invention is likely to be post-translationally modified by analyzing the sequence of the polypeptide to determine if there are peptide motifs indicative of sites for post-translational modification. There are a number of computer programs that permit prediction of post-translational modifications. See, e.g., www.expasy.org (accessed Aug. 31, 2001), which includes PSORT, for prediction of protein sorting signals and localization sites, SignalP, for prediction of signal peptide cleavage sites, MITOPROT and Predotar, for prediction of mitochondrial targeting sequences, NetOGlyc, for prediction of type O-glycosylation sites in mammalian proteins, big-PI Predictor and DGPI, for prediction of prenylation-anchor and cleavage sites, and NetPhos, for prediction of Ser, Thr and Tyr phosphorylation sites in eukaryotic proteins. Other computer programs, such as those included in GCG, also may be used to determine post-translational modification peptide motifs.

General examples of types of post-translational modifications may be found in web sites such as the Delta Mass database http://www.abrforg/ABRF/Research Committees/deltamass/deltamass.html (accessed Oct. 19, 2001); "GlycoSuiteDB: a new curated relational database of glycoprotein glycan structures and their biological sources" Cooper et al. Nucleic Acids Res. 29; 332–335 (2001) and http://www.glycosuite.com/(accessed Oct. 19, 2001); "O-GLYCBASE version 4.0: a revised database of O-glycosylated proteins" Gupta et al. Nucleic Acids Research, 27: 370–372 (1999) and http://www.cbs.dtu.dk/databases/OGLYCBASE/ (accessed Oct. 19, 2001); "PhosphoBase, a database of phosphorylation sites: release 2.0.", Kreegipuu et al. Nucleic Acids Res 27(1):237–239 (1999) and http://www.cbs.dtu.dk/databases/PhosphoBase/ (accessed Oct. 19, 2001); or http://pir.georgetown.edu/pirwww/search/textresid.html (accessed Oct. 19, 2001).

Tumorigenesis is often accompanied by alterations in the post-translational modifications of proteins. Thus, in another embodiment, the invention provides polypeptides from cancerous cells or tissues that have altered post-translational modifications compared to the post-translational modifications of polypeptides from normal cells or tissues. A number of altered post-translational modifications are known. One common alteration is a change in phosphorylation state, wherein the polypeptide from the cancerous cell or tissue is hyperphosphorylated or hypophosphorylated compared to the polypeptide from a normal tissue, or wherein the polypeptide is phosphorylated on different residues than the polypeptide from a normal cell. Another common alteration is a change in glycosylation state, wherein the polypeptide from the cancerous cell or tissue has more or less glycosylation than the polypeptide from a normal tissue, and/or wherein the polypeptide from the cancerous cell or tissue has a different type of glycosylation than the polypeptide from a noncancerous cell or tissue. Changes in glycosylation may be critical because carbohydrate-protein and carbohydrate-carbohydrate interactions are important in cancer cell progression, dissemination and invasion. See, e.g., Barchi, *Curr. Pharm. Des.* 6: 485–501 (2000), Verma, *Cancer Biochem. Biophys*. 14: 151–162 (1994) and Dennis et al., *Bioessays* 5: 412–421 (1999).

Another post-translational modification that may be altered in cancer cells is prenylation. Prenylation is the covalent attachment of a hydrophobic prenyl group (either farnesyl or geranylgeranyl) to a polypeptide. Prenylation is required for localizing a protein to a cell membrane and is often required for polypeptide function. For instance, the Ras superfamily of GTPase signaling proteins must be prenylated for function in a cell. See, e.g., Prendergast et al., *Semin. Cancer Biol*. 10: 443–452 (2000) and Khwaja et al., *Lancet* 355: 741–744 (2000).

Other post-translation modifications that may be altered in cancer cells include, without limitation, polypeptide methylation, acetylation, arginylation or racemization of amino acid residues. In these cases, the polypeptide from the cancerous cell may exhibit either increased or decreased amounts of the post-translational modification compared to the corresponding polypeptides from noncancerous cells.

Other polypeptide alterations in cancer cells include abnormal polypeptide cleavage of proteins and aberrant protein-protein interactions. Abnormal polypeptide cleavage may be cleavage of a polypeptide in a cancerous cell that does not usually occur in a normal cell, or a lack of cleavage in a cancerous cell, wherein the polypeptide is cleaved in a normal cell. Aberrant protein-protein interactions may be either covalent cross-linking or non-covalent binding between proteins that do not normally bind to each other. Alternatively, in a cancerous cell, a protein may fail to bind to another protein to which it is bound in a noncancerous cell. Alterations in cleavage or in protein-protein interactions may be due to over- or underproduction of a polypeptide in a cancerous cell compared to that in a normal cell, or may be due to alterations in post-translational modifications (see above) of one or more proteins in the cancerous cell. See, e.g., Henschen-Edman, *Ann. N.Y. Acad. Sci*. 936: 580–593 (2001).

Alterations in polypeptide post-translational modifications, as well as changes in polypeptide cleavage and protein-protein interactions, may be determined by any method known in the art. For instance, alterations in phosphorylation may be determined by using anti-phosphoserine, anti-phosphothreonine or anti-phosphotyrosine antibodies or by amino acid analysis. Glycosylation alterations may be determined using antibodies specific for different sugar residues, by carbohydrate sequencing, or by alterations in the size of the glycoprotein, which can be determined by, e.g., SDS polyacrylamide gel electrophoresis (PAGE). Other alterations of post-translational modifications, such as prenylation, racemization, methylation, acetylation and arginylation, may be determined by chemical analysis, protein sequencing, amino acid analysis, or by using antibodies specific for the particular post-translational modifications. Changes in protein-protein interactions and in polypeptide cleavage may be analyzed by any method known in the art including, without limitation, non-denaturing PAGE (for non-covalent protein-protein interactions), SDS PAGE (for covalent protein-protein interactions and protein cleavage), chemical cleavage, protein sequencing or immunoassays.

In another embodiment, the invention provides polypeptides that have been post-translationally modified. In one embodiment, polypeptides may be modified enzymatically or chemically, by addition or removal of a post-translational modification. For example, a polypeptide may be glycosylated or deglycosylated enzymatically. Similarly, polypeptides may be phosphorylated using a purified kinase, such as a MAP kinase (e.g, p38, ERK, or JNK) or a tyrosine kinase (e.g., Src or erbB2). A polypeptide may also be modified through synthetic chemistry. Alternatively, one may isolate the polypeptide of interest from a cell or tissue that expresses the polypeptide with the desired post-translational modification. In another embodiment, a nucleic acid molecule encoding the polypeptide of interest is introduced into a host cell that is capable of post-translationally modifying the encoded polypeptide in the desired fashion. If the polypeptide does not contain a motif for a desired post-translational modification, one may alter the post-translational modification by mutating the nucleic acid sequence of a nucleic acid molecule encoding the polypeptide so that it contains a site for the desired post-translational modification. Amino acid sequences that may be post-translationally modified are known in the art. See, e.g., the programs described above on the website www.expasy.org. The nucleic acid molecule is then be introduced into a host cell that is capable of post-translationally modifying the encoded polypeptide. Similarly, one may delete sites that are post-translationally modified by either mutating the nucleic acid sequence so that the encoded polypeptide does not contain the post-translational modification motif, or by introducing the native nucleic acid molecule into a host cell that is not capable of post-translationally modifying the encoded polypeptide.

In selecting an expression control sequence, a variety of factors should also be considered. These include, for example, the relative strength of the sequence, its controllability, and its compatibility with the nucleic acid sequence of this invention, particularly with regard to potential secondary structures. Unicellular hosts should be selected by consideration of their compatibility with the chosen vector, the toxicity of the product coded for by the nucleic acid sequences of this invention, their secretion characteristics, their ability to fold the polypeptide correctly, their fermentation or culture requirements, and the ease of purification from them of the products coded for by the nucleic acid sequences of this invention.

The recombinant nucleic acid molecules and more particularly, the expression vectors of this invention may be used to express the polypeptides of this invention as recombinant polypeptides in a heterologous host cell. The polypeptides of this invention may be full-length or less than full-length polypeptide fragments recombinantly expressed from the nucleic acid sequences according to this invention. Such polypeptides include analogs, derivatives and muteins that may or may not have biological activity.

Vectors of the present invention will also often include elements that permit in vitro transcription of RNA from the inserted heterologous nucleic acid. Such vectors typically include a phage promoter, such as that from T7, T3, or SP6, flanking the nucleic acid insert. Often two different such promoters flank the inserted nucleic acid, permitting separate in vitro production of both sense and antisense strands.

Transformation and other methods of introducing nucleic acids into a host cell (e.g., conjugation, protoplast transformation or fusion, transfection, electroporation, liposome delivery, membrane fusion techniques, high velocity DNA-coated pellets, viral infection and protoplast fusion) can be accomplished by a variety of methods which are well-known in the art (See, for instance, Ausubel, supra, and Sambrook et al., supra). Bacterial, yeast, plant or mammalian cells are transformed or transfected with an expression vector, such as a plasmid, a cosmid, or the like, wherein the expression vector comprises the nucleic acid of interest. Alternatively, the cells may be infected by a viral expression vector comprising the nucleic acid of interest. Depending upon the host cell, vector, and method of transformation used, transient or stable expression of the polypeptide will be constitutive or inducible. One having ordinary skill in the art will be able to decide whether to express a polypeptide transiently or stably, and whether to express the protein constitutively or inducibly.

A wide variety of unicellular host cells are useful in expressing the DNA sequences of this invention. These hosts may include well-known eukaryotic and prokaryotic hosts, such as strains of, fungi, yeast, insect cells such as *Spodoptera frugiperda* (SF9), animal cells such as CHO, as well as plant cells in tissue culture. Representative examples of appropriate host cells include, but are not limited to, bacterial cells, such as *E. coli, Caulobacter crescentus, Streptomyces* species, and *Salmonella typhimurium*; yeast cells, such as *Saccharomyces cerevisiae, Schizosaccharomyces pombe, Pichia pastoris, Pichia methanolica*; insect cell lines, such as those from *Spodoptera frugiperda*, e.g., Sf9 and Sf21 cell lines, and expresSF™ cells (Protein Sciences Corp., Meriden, Conn., USA), *Drosophila* S2 cells, and *Trichoplusia ni* High Five® Cells (Invitrogen, Carlsbad, Calif., USA); and mammalian cells. Typical mammalian cells include BHK cells, BSC 1 cells, BSC 40 cells, BMT 10 cells, VERO cells, COS1 cells, COS7 cells, Chinese hamster ovary (CHO) cells, 3T3 cells, NIH 3T3 cells, 293 cells, HEPG2 cells, HeLa cells, L cells, MDCK cells, HEK293 cells, WI38 cells, murine ES cell lines (e.g., from strains 129/SV, C57/BL6, DBA-1, 129/SVJ), K562 cells, Jurkat cells, and BW5147 cells. Other mammalian cell lines are well-known and readily available from the American Type Culture Collection (ATCC) (Manassas, Va., USA) and the National Institute of General Medical Sciences (NIGMS) Human Genetic Cell Repository at the Coriell Cell Repositories (Camden, N.J., USA). Cells or cell lines derived from breast are particularly preferred because they may provide a more native post-translational processing. Particularly preferred are human breast cells.

Particular details of the transfection, expression and purification of recombinant proteins are well documented and are understood by those of skill in the art. Further details on the various technical aspects of each of the steps used in recombinant production of foreign genes in bacterial cell expression systems can be found in a number of texts and laboratory manuals in the art. See, e.g., Ausubel (1992), supra, Ausubel (1999), supra, Sambrook (1989), supra, and Sambrook (2001), supra, herein incorporated by reference.

Methods for introducing the vectors and nucleic acids of the present invention into the host cells are well-known in the art; the choice of technique will depend primarily upon the specific vector to be introduced and the host cell chosen.

Nucleic acid molecules and vectors may be introduced into prokaryotes, such as *E. coli*, in a number of ways. For instance, phage lambda vectors will typically be packaged using a packaging extract (e.g., Gigapack® packaging extract, Stratagene, La Jolla, Calif., USA), and the packaged virus used to infect *E. coli.*

Plasmid vectors will typically be introduced into chemically competent or electrocompetent bacterial cells. *E. coli* cells can be rendered chemically competent by treatment, e.g., with $CaCl_2$, or a solution of $Mg^{2+}$, $Mn^{2+}$, $Ca^{2+}$, $Rb^+$ or $K^+$, dimethyl sulfoxide, dithiothreitol, and hexamine cobalt (III), Hanahan, *J. Mol. Biol.* 166(4):557–80 (1983), and vectors introduced by heat shock. A wide variety of chemically competent strains are also available commercially (e.g., *Epicurian Coli*® XL10-Gold® Ultracompetent Cells (Stratagene, La Jolla, Calif., USA); DH5α competent cells (Clontech Laboratories, Palo Alto, Calif., USA); and TOP10 Chemically Competent *E. coli* Kit (Invitrogen, Carlsbad, Calif., USA)). Bacterial cells can be rendered electrocompetent, that is, competent to take up exogenous DNA by electroporation, by various pre-pulse treatments; vectors are introduced by electroporation followed by subsequent outgrowth in selected media. An extensive series of protocols is provided online in *Electroprotocols* (BioRad, Richmond, Calif., USA) (http://www.biorad.com/LifeScience/pdf/New_Gene_Pulser.pdf).

Vectors can be introduced into yeast cells by spheroplasting, treatment with lithium salts, electroporation, or protoplast fusion. Spheroplasts are prepared by the action of hydrolytic enzymes such as snail-gut extract, usually denoted Glusulase, or Zymolyase, an enzyme from *Arthrobacter luteus*, to remove portions of the cell wall in the presence of osmotic stabilizers, typically 1 M sorbitol. DNA is added to the spheroplasts, and the mixture is co-precipitated with a solution of polyethylene glycol (PEG) and $Ca^{2+}$. Subsequently, the cells are resuspended in a solution of sorbitol, mixed with molten agar and then layered on the surface of a selective plate containing sorbitol.

For lithium-mediated transformation, yeast cells are treated with lithium acetate, which apparently permeabilizes the cell wall, DNA is added and the cells are co-precipitated with PEG. The cells are exposed to a brief heat shock, washed free of PEG and lithium acetate, and subsequently spread on plates containing ordinary selective medium. Increased frequencies of transformation are obtained by using specially-prepared single-stranded carrier DNA and certain organic solvents. Schiestl et al., *Curr. Genet.* 16(5–6): 339–46 (1989).

For electroporation, freshly-grown yeast cultures are typically washed, suspended in an osmotic protectant, such as sorbitol, mixed with DNA, and the cell suspension pulsed in an electroporation device. Subsequently, the cells are spread on the surface of plates containing selective media. Becker et al., *Methods Enzymol.* 194: 182–187 (1991). The efficiency of transformation by electroporation can be increased over 100-fold by using PEG, single-stranded carrier DNA and cells that are in late log-phase of growth. Larger constructs, such as YACs, can be introduced by protoplast fusion.

Mammalian and insect cells can be directly infected by packaged viral vectors, or transfected by chemical or electrical means. For chemical transfection, DNA can be coprecipitated with $CaPO_4$ or introduced using liposomal and nonliposomal lipid-based agents. Commercial kits are available for $CaPO_4$ transfection (CalPhos™ Mammalian Transfection Kit, Clontech Laboratories, Palo Alto, Calif., USA), and lipid-mediated transfection can be practiced using commercial reagents, such as LIPOFECTAMINE™ 2000, LIPOFECTAMINE™ Reagent, CELLFECTIN™ Reagent, and LIPOFECTIN® Reagent (Invitrogen, Carlsbad, Calif., USA), DOTAP Liposomal Transfection Reagent, FuGENE 6, X-tremeGENE Q2, DOSPER, (Roche Molecular Biochemicals, Indianapolis, Ind. USA), Effectene™, PolyFect®, Superfect® (Qiagen, Inc., Valencia, Calif., USA). Protocols for electroporating mammalian cells can be found online in Electroprotocols (Bio-Rad, Richmond, Calif., USA) (http://www.bio-rad.com/LifeScience/pdf/New_Gene_Pulser.pdf); Norton et al. (eds.), *Gene Transfer Methods: Introducing DNA into Living Cells and Organisms*, BioTechniques Books, Eaton Publishing Co. (2000); incorporated herein by reference in its entirety. Other transfection techniques include transfection by particle bombardment and microinjection. See, e.g., Cheng et al., *Proc. Natl. Acad. Sci. USA* 90(10): 4455–9 (1993); Yang et al., *Proc. Natl. Acad. Sci. USA* 87(24): 9568–72 (1990).

Production of the recombinantly produced proteins of the present invention can optionally be followed by purification.

Purification of recombinantly expressed proteins is now well by those skilled in the art. See, e.g., Thorner et al. (eds.), *Applications of Chimeric Genes and Hybrid Proteins, Part A: Gene Expression and Protein Purification* (Methods in Enzymology, Vol. 326), Academic Press (2000); Harbin (ed.), *Cloning, Gene Expression and Protein Purification: Experimental Procedures and Process Rationale*, Oxford Univ. Press (2001); Marshak et al., *Strategies for Protein Purification and Characterization: A Laboratory Course Manual*, Cold Spring Harbor Laboratory Press (1996); and Roe (ed.), *Protein Purification Applications*, Oxford University Press (2001); the disclosures of which are incorporated herein by reference in their entireties, and thus need not be detailed here.

Briefly, however, if purification tags have been fused through use of an expression vector that appends such tags, purification can be effected, at least in part, by means appropriate to the tag, such as use of immobilized metal affinity chromatography for polyhistidine tags. Other techniques common in the art include ammonium sulfate fractionation, immunoprecipitation, fast protein liquid chromatography (FPLC), high performance liquid chromatography (HPLC), and preparative gel electrophoresis.

Polypeptides

Another object of the invention is to provide polypeptides encoded by the nucleic acid molecules of the instant invention. In a preferred embodiment, the polypeptide is a breast specific polypeptide (BSP). In an even more preferred embodiment, the polypeptide is derived from a polypeptide comprising the amino acid sequence of SEQ ID NO: 82 through 137. A polypeptide as defined herein may be produced recombinantly, as discussed supra, may be isolated from a cell that naturally expresses the protein, or may be chemically synthesized following the teachings of the specification and using methods well-known to those having ordinary skill in the art.

In another aspect, the polypeptide may comprise a fragment of a polypeptide, wherein the fragment is as defined herein. In a preferred embodiment, the polypeptide fragment is a fragment of a BSP. In a more preferred embodiment, the fragment is derived from a polypeptide comprising the amino acid sequence of SEQ ID NO: 82 through 137. A polypeptide that comprises only a fragment of an entire BSP may or may not be a polypeptide that is also a BSP. For instance, a full-length polypeptide may be breast-specific, while a fragment thereof may be found in other tissues as well as in breast. A polypeptide that is not a BSP, whether it is a fragment, analog, mutein, homologous protein or derivative, is nevertheless useful, especially for immunizing animals to prepare anti-BSP antibodies. However, in a preferred embodiment, the part or fragment is a BSP. Methods of determining whether a polypeptide is a BSP are described infra.

Fragments of at least 6 contiguous amino acids are useful in mapping B cell and T cell epitopes of the reference protein. See, e.g., Geysen et al., *Proc. Natl. Acad. Sci. USA* 81: 3998–4002 (1984) and U.S. Pat. Nos. 4,708,871 and 5,595,915, the disclosures of which are incorporated herein by reference in their entireties. Because the fragment need not itself be immunogenic, part of an immunodominant epitope, nor even recognized by native antibody, to be useful in such epitope mapping, all fragments of at least 6 amino acids of the proteins of the present invention have utility in such a study.

Fragments of at least 8 contiguous amino acids, often at least 15 contiguous amino acids, are useful as immunogens for raising antibodies that recognize the proteins of the present invention. See, e.g., Lerner, Nature 299: 592–596 (1982); Shinnick et al., *Annu. Rev. Microbiol.* 37: 425–46 (1983); Sutcliffe et al., *Science* 219: 660–6 (1983), the disclosures of which are incorporated herein by reference in their entireties. As further described in the above-cited references, virtually all 8-mers, conjugated to a carrier, such as a protein, prove immunogenic, meaning that they are capable of eliciting antibody for the conjugated peptide; accordingly, all fragments of at least 8 amino acids of the proteins of the present invention have utility as immunogens.

Fragments of at least 8, 9, 10 or 12 contiguous amino acids are also useful as competitive inhibitors of binding of the entire protein, or a portion thereof, to antibodies (as in epitope mapping), and to natural binding partners, such as subunits in a multimeric complex or to receptors or ligands of the subject protein; this competitive inhibition permits identification and separation of molecules that bind specifically to the protein of interest, U.S. Pat. Nos. 5,539,084 and 5,783,674, incorporated herein by reference in their entireties.

The protein, or protein fragment, of the present invention is thus at least 6 amino acids in length, typically at least 8, 9, 10 or 12 amino acids in length, and often at least 15 amino acids in length. Often, the protein of the present invention, or fragment thereof, is at least 20 amino acids in length, even 25 amino acids, 30 amino acids, 35 amino acids, or 50 amino acids or more in length. Of course, larger fragments having at least 75 amino acids, 100 amino acids, or even 150 amino acids are also useful, and at times preferred.

One having ordinary skill in the art can produce fragments of a polypeptide by truncating the nucleic acid molecule, e.g., a BSNA, encoding the polypeptide and then expressing it recombinantly. Alternatively, one can produce a fragment by chemically synthesizing a portion of the full-length polypeptide. One may also produce a fragment by enzymatically cleaving either a recombinant polypeptide or an isolated naturally-occurring polypeptide. Methods of producing polypeptide fragments are well-known in the art. See, e.g., Sambrook (1989), supra; Sambrook (2001), supra; Ausubel (1992), supra; and Ausubel (1999), supra. In one embodiment, a polypeptide comprising only a fragment of polypeptide of the invention, preferably a BSP, may be produced by chemical or enzymatic cleavage of a polypeptide. In a preferred embodiment, a polypeptide fragment is produced by expressing a nucleic acid molecule encoding a fragment of the polypeptide, preferably a BSP, in a host cell.

By "polypeptides" as used herein it is also meant to be inclusive of mutants, fusion proteins, homologous proteins and allelic variants of the polypeptides specifically exemplified.

A mutant protein, or mutein, may have the same or different properties compared to a naturally-occurring polypeptide and comprises at least one amino acid insertion, duplication, deletion, rearrangement or substitution compared to the amino acid sequence of a native protein. Small deletions and insertions can often be found that do not alter the function of the protein. In one embodiment, the mutein may or may not be breast-specific. In a preferred embodiment, the mutein is breast-specific. In a preferred embodiment, the mutein is a polypeptide that comprises at least one amino acid insertion, duplication, deletion, rearrangement or substitution compared to the amino acid sequence of SEQ ID NO: 82 through 137. In a more preferred embodiment, the mutein is one that exhibits at least 50% sequence identity, more preferably at least 60% sequence identity, even more preferably at least 70%, yet more preferably at least 80% sequence identity to a BSP comprising an amino acid sequence of SEQ ID NO: 82 through 137. In yet a more preferred embodiment, the mutein exhibits at least 85%, more preferably 90%, even more preferably 95% or 96%, and yet more preferably at least 97%, 98%, 99% or 99.5% sequence identity to a BSP comprising an amino acid sequence of SEQ ID NO: 82 through 137.

A mutein may be produced by isolation from a naturally-occurring mutant cell, tissue or organism. A mutein may be produced by isolation from a cell, tissue or organism that has been experimentally mutagenized. Alternatively, a mutein may be produced by chemical manipulation of a polypeptide, such as by altering the amino acid residue to another amino acid residue using synthetic or semi-synthetic chemical techniques. In a preferred embodiment, a mutein may be produced from a host cell comprising an altered nucleic acid molecule compared to the naturally-occurring nucleic acid molecule. For instance, one may produce a mutein of a polypeptide by introducing one or more mutations into a nucleic acid sequence of the invention and then expressing it recombinantly. These mutations may be targeted, in which particular encoded amino acids are altered, or may be untargeted, in which random encoded amino acids within the polypeptide are altered. Muteins with random amino acid alterations can be screened for a particular biological activity or property, particularly whether the polypeptide is breast-specific, as described below. Multiple random mutations can be introduced into the gene by methods well-known to the art, e.g., by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis and site-specific mutagenesis. Methods of producing muteins with targeted or random amino acid alterations are well-known in the art. See, e.g., Sambrook (1989), supra; Sambrook (2001), supra; Ausubel (1992), supra; and Ausubel (1999), U.S. Pat. No. 5,223,408, and the references discussed supra, each herein incorporated by reference.

By "polypeptide" as used herein it is also meant to be inclusive of polypeptides homologous to those polypeptides exemplified herein. In a preferred embodiment, the polypeptide is homologous to a BSP. In an even more preferred embodiment, the polypeptide is homologous to a BSP selected from the group having an amino acid sequence of SEQ ID NO: 82 through 137. In a preferred embodiment, the homologous polypeptide is one that exhibits significant sequence identity to a BSP. In a more preferred embodiment, the polypeptide is one that exhibits significant sequence identity to an comprising an amino acid sequence of SEQ ID NO: 82 through 137. In an even more preferred embodiment, the homologous polypeptide is one that exhibits at least 50% sequence identity, more preferably at least 60% sequence identity, even more preferably at least 70%, yet more preferably at least 80% sequence identity to a BSP comprising an amino acid sequence of SEQ ID NO: 82 through 137. In a yet more preferred embodiment, the homologous polypeptide is one that exhibits at least 85%, more preferably 90%, even more preferably 95% or 96%, and yet more preferably at least 97% or 98% sequence identity to a BSP comprising an amino acid sequence of SEQ ID NO: 82 through 137. In another preferred embodiment, the homologous polypeptide is one that exhibits at least 99%, more preferably 99.5%, even more preferably 99.6%, 99.7%, 99.8% or 99.9% sequence identity to a BSP comprising an amino acid sequence of SEQ ID NO: 82 through 137. In a preferred embodiment, the amino acid substitutions are conservative amino acid substitutions as discussed above.

In another embodiment, the homologous polypeptide is one that is encoded by a nucleic acid molecule that selectively hybridizes to a BSNA. In a preferred embodiment, the homologous polypeptide is encoded by a nucleic acid molecule that hybridizes to a BSNA under low stringency, moderate stringency or high stringency conditions, as defined herein. In a more preferred embodiment, the BSNA is selected from the group consisting of SEQ ID NO: 1 through 81. In another preferred embodiment, the homologous polypeptide is encoded by a nucleic acid molecule that hybridizes to a nucleic acid molecule that encodes a BSP under low stringency, moderate stringency or high stringency conditions, as defined herein. In a more preferred embodiment, the BSP is selected from the group consisting of SEQ ID NO: 82 through 137.

The homologous polypeptide may be a naturally-occurring one that is derived from another species, especially one derived from another primate, such as chimpanzee, gorilla, rhesus macaque, baboon or gorilla, wherein the homologous polypeptide comprises an amino acid sequence that exhibits significant sequence identity to that of SEQ ID NO: 82 through 137. The homologous polypeptide may also be a naturally-occurring polypeptide from a human, when the BSP is a member of a family of polypeptides. The homologous polypeptide may also be a naturally-occurring polypeptide derived from a non-primate, mammalian species, including without limitation, domesticated species, e.g., dog, cat, mouse, rat, rabbit, guinea pig, hamster, cow, horse, goat or pig. The homologous polypeptide may also be a naturally-occurring polypeptide derived from a non-mammalian species, such as birds or reptiles. The naturally-occurring homologous protein may be isolated directly from humans or other species. Alternatively, the nucleic acid molecule encoding the naturally-occurring homologous polypeptide may be isolated and used to express the homologous polypeptide recombinantly. In another embodiment, the homologous polypeptide may be one that is experimentally produced by random mutation of a nucleic acid molecule and subsequent expression of the nucleic acid molecule. In another embodiment, the homologous polypeptide may be one that is experimentally produced by directed mutation of one or more codons to alter the encoded amino acid of a BSP. Further, the homologous protein may or may not encode polypeptide that is a BSP. However, in a preferred embodiment, the homologous polypeptide encodes a polypeptide that is a BSP.

Relatedness of proteins can also be characterized using a second fumctional test, the ability of a first protein competitively to inhibit the binding of a second protein to an antibody. It is, therefore, another aspect of the present invention to provide isolated proteins not only identical in sequence to those described with particularity herein, but also to provide isolated proteins ("cross-reactive proteins") that competitively inhibit the binding of antibodies to all or to a portion of various of the isolated polypeptides of the present invention. Such competitive inhibition can readily be determined using immunoassays well-known in the art.

As discussed above, single nucleotide polymorphisms (SNPs) occur frequently in eukaryotic genomes, and the sequence determined from one individual of a species may differ from other allelic forms present within the population. Thus, by "polypeptide" as used herein it is also meant to be inclusive of polypeptides encoded by an allelic variant of a nucleic acid molecule encoding a BSP. In a preferred embodiment, the polypeptide is encoded by an allelic variant of a gene that encodes a polypeptide having the amino acid sequence selected from the group consisting of SEQ ID NO: 82 through 137. In a yet more preferred embodiment, the polypeptide is encoded by an allelic variant of a gene that has the nucleic acid sequence selected from the group consisting of SEQ ID NO: 1 through 81.

In another embodiment, the invention provides polypeptides which comprise derivatives of a polypeptide encoded by a nucleic acid molecule according to the instant invention. In a preferred embodiment, the polypeptide is a BSP. In a preferred embodiment, the polypeptide has an amino acid sequence selected from the group consisting of SEQ ID NO: 82 through 137, or is a mutein, allelic variant, homologous protein or fragment thereof. In a preferred embodiment, the derivative has been acetylated, carboxylated, phosphorylated, glycosylated or ubiquitinated. In another preferred embodiment, the derivative has been labeled with, e.g., radioactive isotopes such as $^{125}I$, $^{32}P$, $^{35}S$, and $^{3}H$. In another preferred embodiment, the derivative has been labeled with fluorophores, chemiluminescent agents, enzymes, and antiligands that can serve as specific binding pair members for a labeled ligand.

Polypeptide modifications are well-known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance Creighton, *Protein Structure and Molecular Properties*, 2nd ed., W. H. Freeman and Company (1993). Many detailed reviews are available on this subject, such as, for example, those provided by Wold, in Johnson (ed.), *Posttranslational Covalent Modification of Proteins*, pgs. 1–12, Academic Press (1983); Seifter et al., *Meth. Enzymol.* 182: 626–646 (1990) and Rattan et al., *Ann. N.Y. Acad. Sci.* 663: 48–62 (1992).

It will be appreciated, as is well-known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

Useful post-synthetic (and post-translational) modifications include conjugation to detectable labels, such as fluorophores. A wide variety of amine-reactive and thiol-reactive fluorophore derivatives have been synthesized that react under nondenaturing conditions with N-terminal amino groups and epsilon amino groups of lysine residues, on the one hand, and with free thiol groups of cysteine residues, on the other.

Kits are available commercially that permit conjugation of proteins to a variety of amine-reactive or thiol-reactive fluorophores: Molecular Probes, Inc. (Eugene, Oreg., USA), e.g., offers kits for conjugating proteins to Alexa Fluor 350, Alexa Fluor 430, Fluorescein-EX, Alexa Fluor 488, Oregon Green 488, Alexa Fluor 532, Alexa Fluor 546, Alexa Fluor 546, Alexa Fluor 568, Alexa Fluor 594, and Texas Red-X.

A wide variety of other amine-reactive and thiol-reactive fluorophores are available commercially (Molecular Probes, Inc., Eugene, Oreg., USA), including Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA).

The polypeptides of the present invention can also be conjugated to fluorophores, other proteins, and other macromolecules, using bifunctional linking reagents. Common homobifunctional reagents include, e.g., APG, AEDP, BASED, BMB, BMDB, BMH, BMOE, BM[PEO]3, BM[PEO]4, BS3, BSOCOES, DFDNB, DMA, DMP, DMS, DPDPB, DSG, DSP (Lomant's Reagent), DSS, DST, DTBP, DTME, DTSSP, EGS, HBVS, Sulfo-BSOCOES, Sulfo-DST, Sulfo-EGS (all available from Pierce, Rockford, Ill., USA); common heterobifunctional cross-linkers include ABH, AMAS, ANB-NOS, APDP, ASBA, BMPA, BMPH, BMPS, EDC, EMCA, EMCH, EMCS, KMUA, KMUH, GMBS, LC-SMCC, LC-SPDP, MBS, M2C2H, MPBH, MSA, NHS-ASA, PDPH, PMPI, SADP, SAED, SAND, SANPAH, SASD, SATP, SBAP, SFAD, SIA, SIAB, SMCC, SMPB, SMPH, SMPT, SPDP, Sulfo-EMCS, Sulfo-GMBS, Sulfo-HSAB, Sulfo-KMUS, Sulfo-LC-SPDP, Sulfo-MBS, Sulfo-NHS-LC-ASA, Sulfo-SADP, Sulfo-SANPAH, Sulfo-SIAB, Sulfo-SMCC, Sulfo-SMPB, Sulfo-LC-SMPT, SVSB, TFCS (all available Pierce, Rockford, Ill., USA).

The polypeptides, fragments, and fusion proteins of the present invention can be conjugated, using such cross-linking reagents, to fluorophores that are not amine- or thiol-reactive. Other labels that usefully can be conjugated to the polypeptides, fragments, and fusion proteins of the present invention include radioactive labels, echosonographic contrast reagents, and MRI contrast agents.

The polypeptides, fragments, and fusion proteins of the present invention can also usefully be conjugated using cross-linking agents to carrier proteins, such as KLH, bovine thyroglobulin, and even bovine serum albumin (BSA), to increase immunogenicity for raising anti-BSP antibodies.

The polypeptides, fragments, and fusion proteins of the present invention can also usefully be conjugated to polyethylene glycol (PEG); PEGylation increases the serum half-life of proteins administered intravenously for replacement therapy. Delgado et al., *Crit. Rev. Ther. Drug Carrier Syst.* 9(3–4): 249–304 (1992); Scott et al., *Curr. Pharm. Des.* 4(6): 423–38 (1998); DeSantis et al., *Curr. Opin. Biotechnol.* 10(4): 324–30 (1999), incorporated herein by reference in their entireties. PEG monomers can be attached to the protein directly or through a linker, with PEGylation using PEG monomers activated with tresyl chloride (2,2,2-trifluoroethanesulphonyl chloride) permitting direct attachment under mild conditions.

In yet another embodiment, the invention provides analogs of a polypeptide encoded by a nucleic acid molecule according to the instant invention. In a preferred embodiment, the polypeptide is a BSP. In a more preferred embodiment, the analog is derived from a polypeptide having part or all of the amino acid sequence of SEQ ID NO: 82 through 137. In a preferred embodiment, the analog is one that comprises one or more substitutions of non-natural amino acids or non-native inter-residue bonds compared to the naturally-occurring polypeptide. In general, the non-peptide analog is structurally similar to a BSP, but one or more peptide linkages is replaced by a linkage selected from the group consisting of —$CH_2$NH—, —$CH_2$S—, —$CH_2$—$CH_2$—, —CH=CH-(cis and trans), —$COCH_2$—, —CH(OH)$CH_2$— and —$CH_2$SO—. In another embodiment, the non-peptide analog comprises substitution of one or more amino acids of a BSP with a D-amino acid of the same type or other non-natural amino acid in order to generate more stable peptides. D-amino acids can readily be incorporated during chemical peptide synthesis: peptides assembled from D-amino acids are more resistant to proteolytic attack; incorporation of D-amino acids can also be used to confer specific three-dimensional conformations on the peptide. Other amino acid analogues commonly added during chemical synthesis include ornithine, norleucine, phosphorylated amino acids (typically phosphoserine, phosphothreonine, phosphotyrosine), L-malonyltyrosine, a non-hydrolyzable analog of phosphotyrosine (see, e.g., Kole et al., *Biochem. Biophys. Res. Com.* 209: 817–821 (1995)), and various halogenated phenylalanine derivatives.

Non-natural amino acids can be incorporated during solid phase chemical synthesis or by recombinant techniques, although the former is typically more common. Solid phase chemical synthesis of peptides is well established in the art. Procedures are described, inter alia, in Chan et al. (eds.), *Fmoc Solid Phase Peptide Synthesis: A Practical Approach* (Practical Approach Series), Oxford Univ. Press (March 2000); Jones, *Amino Acid and Peptide Synthesis* (Oxford Chemistry Primers, No 7), Oxford Univ. Press (1992); and Bodanszky, *Principles of Peptide Synthesis* (Springer Laboratory), Springer Verlag (1993); the disclosures of which are incorporated herein by reference in their entireties.

Amino acid analogues having detectable labels are also usefully incorporated during synthesis to provide derivatives and analogs. Biotin, for example can be added using biotinoyl-(9-fluorenylmethoxycarbonyl)-L-lysine (FMOC biocytin) (Molecular Probes, Eugene, Oreg., USA). Biotin can also be added enzymatically by incorporation into a fusion protein of a *E. coli* BirA substrate peptide. The FMOC and tBOC derivatives of dabcyl-L-lysine (Molecular Probes, Inc., Eugene, Oreg., USA) can be used to incorporate the dabcyl chromophore at selected sites in the peptide sequence during synthesis. The aminonaphthalene derivative EDANS, the most common fluorophore for pairing with the dabcyl quencher in fluorescence resonance energy transfer (FRET) systems, can be introduced during automated synthesis of peptides by using EDANS-FMOC-L-glutamic acid or the corresponding tBOC derivative (both from Molecular Probes, Inc., Eugene, Oreg., USA). Tetramethylrhodamine fluorophores can be incorporated during automated FMOC synthesis of peptides using (FMOC)-TMR-L-lysine (Molecular Probes, Inc. Eugene, Oreg., USA).

Other useful amino acid analogues that can be incorporated during chemical synthesis include aspartic acid, glutamic acid, lysine, and tyrosine analogues having allyl side-chain protection (Applied Biosystems, Inc., Foster City, Calif., USA); the allyl side chain permits synthesis of cyclic, branched-chain, sulfonated, glycosylated, and phosphorylated peptides.

A large number of other FMOC-protected non-natural amino acid analogues capable of incorporation during chemical synthesis are available commercially, including, e.g., Fmoc-2-aminobicyclo[2.2.1]heptane-2-carboxylic acid, Fmoc-3-endo-aminobicyclo[2.2.1]heptane-2-endo-carboxylic acid, Fmoc-3-exo-aminobicyclo[2.2.1]heptane-2-exo-carboxylic acid, Fmoc-3-endo-amino-bicyclo[2.2.1]hept-5-ene-2-endo-carboxylic acid, Fmoc-3 -exo-amino-bicyclo[2.2.1]hept-5-ene-2-exo-carboxylic acid, Fmoc-cis-2-amino-1-cyclohexanecarboxylic acid, Fmoc-trans-2-amino-1-cyclohexanecarboxylic acid, Fmoc-1-amino-1-cyclopentanecarboxylic acid, Fmoc-cis-2-amino-1-cyclopentanecarboxylic acid, Fmoc-1-amino-1-cyclopropanecarboxylic acid, Fmoc-D-2-amino-4-(ethylthio)butyric acid, Fmoc-L-2-amino-4-(ethylthio) butyric acid, Fmoc-L-buthionine, Fmoc-S-methyl-L-Cysteine, Fmoc-2-aminobenzoic acid (anthranillic acid), Fmoc-3-aminobenzoic acid, Fmoc-4-aminobenzoic acid, Fmoc-2-aminobenzophenone-2'-carboxylic acid, Fmoc-N-(4-aminobenzoyl)-β-alanine, Fmoc-2-amino-4,5-dimethoxybenzoic acid, Fmoc-4-aminohippuric acid, Fmoc-2-amino-3-hydroxybenzoic acid, Fmoc-2-amino-5-hydroxybenzoic acid, Fmoc-3-amino-4-hydroxybenzoic acid, Fmoc-4-amino-3-hydroxybenzoic acid, Fmoc-4-amino-2-hydroxybenzoic acid, Fmoc-5-amino-2-hydroxybenzoic acid, Fmoc-2-amino-3-methoxybenzoic acid, Fmoc-4-amino-3-methoxybenzoic acid, Fmoc-2-amino-3-methylbenzoic acid, Fmoc-2-amino-5-methylbenzoic acid, Fmoc-2-amino-6-methylbenzoic acid, Fmoc-3-amino-2-methylbenzoic acid, Fmoc-3-amino-4-methylbenzoic acid, Fmoc-4-amino-3-methylbenzoic acid, Fmoc-3-amino-2-naphtoic acid, Fmoc-D,L-3-amino-3-phenylpropionic acid, Fmoc-L-Methyldopa, Fmoc-2-amino-4,6-dimethyl-3-pyridinecarboxylic acid, Fmoc-D,L-amino-2-thiophenacetic acid, Fmoc-4-(carboxymethyl)piperazine, Fmoc-4-carboxypiperazine, Fmoc-4-(carboxymethyl) homopiperazine, Fmoc-4-phenyl-4-piperidinecarboxylic acid, Fmoc-L-1,2,3,4-tetrahydronorharman-3-carboxylic acid, Fmoc-L-thiazolidine-4-carboxylic acid, all available from The Peptide Laboratory (Richmond, Calif., USA).

Non-natural residues can also be added biosynthetically by engineering a suppressor tRNA, typically one that recognizes the UAG stop codon, by chemical aminoacylation with the desired unnatural amino acid. Conventional site-directed mutagenesis is used to introduce the chosen stop codon UAG at the site of interest in the protein gene. When the acylated suppressor tRNA and the mutant gene are combined in an in vitro transcription/translation system, the unnatural amino acid is incorporated in response to the UAG codon to give a protein containing that amino acid at the specified position. Liu et al., *Proc. Natl Acad. Sci. USA* 96(9): 4780–5 (1999); Wang et al., *Science* 292(5516): 498–500 (2001).

Fusion Proteins

The present invention further provides fusions of each of the polypeptides and fragments of the present invention to heterologous polypeptides. In a preferred embodiment, the polypeptide is a BSP. In a more preferred embodiment, the polypeptide that is fused to the heterologous polypeptide comprises part or all of the amino acid sequence of SEQ ID NO: 82 through 137, or is a mutein, homologous polypeptide, analog or derivative thereof. In an even more preferred embodiment, the nucleic acid molecule encoding the fusion protein comprises all or part of the nucleic acid sequence of SEQ ID NO: 1 through 81, or comprises all or part of a nucleic acid sequence that selectively hybridizes or is homologous to a nucleic acid molecule comprising a nucleic acid sequence of SEQ ID NO: 1 through 81.

The fusion proteins of the present invention will include at least one fragment of the protein of the present invention, which fragment is at least 6, typically at least 8, often at least 15, and usefully at least 16, 17, 18, 19, or 20 amino acids long. The fragment of the protein of the present to be included in the fusion can usefully be at least 25 amino acids long, at least 50 amino acids long, and can be at least 75, 100, or even 150 amino acids long. Fusions that include the entirety of the proteins of the present invention have particular utility.

The heterologous polypeptide included within the fusion protein of the present invention is at least 6 amino acids in length, often at least 8 amino acids in length, and usefully at least 15, 20, and 25 amino acids in length. Fusions that include larger polypeptides, such as the IgG Fc region, and even entire proteins (such as GFP chromophore-containing proteins) are particular useful.

As described above in the description of vectors and expression vectors of the present invention, which discussion is incorporated here by reference in its entirety, heterologous polypeptides to be included in the fusion proteins of the present invention can usefully include those designed to facilitate purification and/or visualization of recombinantly-expressed proteins. See, e.g., Ausubel, Chapter 16, (1992), supra. Although purification tags can also be incorporated into fusions that are chemically synthesized, chemical synthesis typically provides sufficient purity that further purification by HPLC suffices; however, visualization tags as above described retain their utility even when the protein is produced by chemical synthesis, and when so included render the fusion proteins of the present invention useful as directly detectable markers of the presence of a polypeptide of the invention.

As also discussed above, heterologous polypeptides to be included in the fusion proteins of the present invention can usefully include those that facilitate secretion of recombinantly expressed proteins—into the periplasmic space or extracellular milieu for prokaryotic hosts, into the culture medium for eukaryotic cells—through incorporation of secretion signals and/or leader sequences. For example, a $His^6$ tagged protein can be purified on a Ni affinity column and a GST fusion protein can be purified on a glutathione affinity column. Similarly, a fusion protein comprising the Fc domain of IgG can be purified on a Protein A or Protein G column and a fusion protein comprising an epitope tag such as myc can be purified using an immunoaffinity column containing an anti-c-myc antibody. It is preferable that the epitope tag be separated from the protein encoded by the essential gene by an enzymatic cleavage site that can be cleaved after purification. See also the discussion of nucleic acid molecules encoding fusion proteins that may be expressed on the surface of a cell.

Other useful protein fusions of the present invention include those that permit use of the protein of the present invention as bait in a yeast two-hybrid system. See Bartel et al. (eds.), *The Yeast Two-Hybrid System*, Oxford University Press (1997); Zhu et al., *Yeast Hybrid Technologies*, Eaton Publishing (2000); Fields et al., *Trends Genet*. 10(8): 286–92 (1994); Mendelsohn et al., *Curr. Opin. Biotechnol*. 5(5): 482–6 (1994); Luban et al., *Curr. Opin. Biotechnol*. 6(1): 59–64 (1995); Allen et al., *Trends Biochem. Sci*. 20(12): 511–6 (1995); Drees, *Curr. Opin. Chem. Biol*. 3(1): 64–70 (1999); Topcu et al., *Pharm. Res*. 17(9): 1049–55 (2000); Fashena et al., *Gene* 250(1–2): 1–14 (2000); Colas et al., (1996) Genetic selection of peptide aptarners that recognize and inhibit cyclin-dependent kinase 2. *Nature* 380, 548–550; Norman, T. et al., (1999) Genetic selection of peptide inhibitors of biological pathways. *Science* 285, 591–595, Fabbrizio et al., (1999) Inhibition of mammalian cell proliferation by genetically selected peptide aptarners that functionally antagonize E2F activity. *Oncogene* 18, 4357–4363; Xu et al., (1997) Cells that register logical relationships among proteins. *Proc Natl Acad Sci USA*. 94, 12473–12478; Yang, et al., (1995) Protein-peptide interactions analyzed with the yeast two-hybrid system. *Nuc. Acids Res*. 23, 1152–1156; Kolonin et al., (1998) Targeting cyclin-dependent kinases in *Drosophila* with peptide aptamers. *Proc Natl Acad Sci USA* 95, 14266–14271; Cohen et al., (1998) An artificial cell-cycle inhibitor isolated from a combinatorial library. *Proc Natl Acad Sci USA* 95, 14272–14277; Uetz, P.; Giot, L.; al, e.; Fields, S.; Rothberg, J. M. (2000) A comprehensive analysis of protein-protein interactions in *Saccharomyces cerevisiae*. *Nature* 403, 623–627; Ito, et al., (2001) A comprehensive two-hybrid analysis to explore the yeast protein interactome. *Proc Natl Acad Sci USA* 98, 4569–4574, the disclosures of which are incorporated herein by reference in their entireties. Typically, such fusion is to either *E. coli* LexA or yeast GAL4 DNA binding domains. Related bait plasmids are available that express the bait fused to a nuclear localization signal.

Other useful fusion proteins include those that permit display of the encoded protein on the surface of a phage or cell, fusions to intrinsically fluorescent proteins, such as green fluorescent protein (GFP), and fusions to the IgG Fc region, as described above, which discussion is incorporated here by reference in its entirety.

The polypeptides and fragments of the present invention can also usefully be fused to protein toxins, such as *Pseudomonas* exotoxin A, *diphtheria* toxin, shiga toxin A, anthrax toxin lethal factor, ricin, in order to effect ablation of cells that bind or take up the proteins of the present invention.

Fusion partners include, inter alia, myc, hemagglutinin (HA), GST, immunoglobulins, β-galactosidase, biotin trpE, protein A, β-lactamase, α-amylase, maltose binding protein, alcohol dehydrogenase, polyhistidine (for example, six histidine at the amino and/or carboxyl terminus of the polypeptide), lacZ, green fluorescent protein (GFP), yeast α mating factor, GAL4 transcription activation or DNA binding domain, luciferase, and serum proteins such as ovalbumin, albumin and the constant domain of IgG. See, e.g., Ausubel (1992), supra and Ausubel (1999), supra. Fusion proteins may also contain sites for specific enzymatic cleavage, such as a site that is recognized by enzymes such as Factor XIII, trypsin, pepsin, or any other enzyme known in the art. Fusion proteins will typically be made by either recombinant nucleic acid methods, as described above, chemically synthesized using techniques well-known in the art (e.g., a Merrifield synthesis), or produced by chemical cross-linking.

Another advantage of fusion proteins is that the epitope tag can be used to bind the fusion protein to a plate or column through an affinity linkage for screening binding proteins or other molecules that bind to the BSP.

As further described below, the isolated polypeptides, muteins, fusion proteins, homologous proteins or allelic variants of the present invention can readily be used as specific immunogens to raise antibodies that specifically recognize BSPs, their allelic variants and homologues. The antibodies, in turn, can be used, inter alia, specifically to assay for the polypeptides of the present invention, particularly BSPs, e.g. by ELISA for detection of protein fluid samples, such as serum, by immunohistochemistry or laser scanning cytometry, for detection of protein in tissue samples, or by flow cytometry, for detection of intracellular protein in cell suspensions, for specific antibody-mediated isolation and/or purification of BSPs, as for example by immunoprecipitation, and for use as specific agonists or antagonists of BSPs.

One may determine whether polypeptides including muteins, fusion proteins, homologous proteins or allelic variants are functional by methods known in the art. For instance, residues that are tolerant of change while retaining function can be identified by altering the protein at known residues using methods known in the art, such as alanine scanning mutagenesis, Cunningham et al., *Science* 244 (4908): 1081–5 (1989); transposon linker scanning mutagenesis, Chen et al., *Gene* 263(1–2): 39–48 (2001); combinations of homolog- and alanine-scanning mutagenesis, Jin et al., *J. Mol. Biol*. 226(3): 851–65 (1992); combinatorial alanine scanning, Weiss et al., *Proc. Natl. Acad. Sci USA* 97(16): 8950–4 (2000), followed by functional assay. Transposon linker scanning kits are available commercially (New England Biolabs, Beverly, Mass., USA, catalog. no. E7-102S; EZ::TN™ In-Frame Linker Insertion Kit, catalogue no. EZI04KN, Epicentre Technologies Corporation, Madison, Wis., USA).

Purification of the polypeptides including fragments, homologous polypeptides, muteins, analogs, derivatives and fusion proteins is well-known and within the skill of one having ordinary skill in the art. See, e.g., Scopes, *Protein Purification*, 2d ed. (1987). Purification of recombinantly expressed polypeptides is described above. Purification of chemically-synthesized peptides can readily be effected, e.g., by HPLC.

Accordingly, it is an aspect of the present invention to provide the isolated proteins of the present invention in pure or substantially pure form in the presence of absence of a stabilizing agent. Stabilizing agents include both proteinaceous or non-proteinaceous material and are well-known in the art. Stabilizing agents, such as albumin and polyethylene glycol (PEG) are known and are commercially available.

Although high levels of purity are preferred when the isolated proteins of the present invention are used as therapeutic agents, such as in vaccines and as replacement therapy, the isolated proteins of the present invention are also useful at lower purity. For example, partially purified proteins of the present invention can be used as immunogens to raise antibodies in laboratory animals.

In preferred embodiments, the purified and substantially purified proteins of the present invention are in compositions that lack detectable ampholytes, acrylamide monomers, bis-acrylamide monomers, and polyacrylamide.

The polypeptides, fragments, analogs, derivatives and fusions of the present invention can usefully be attached to a substrate. The substrate can be porous or solid, planar or non-planar; the bond can be covalent or noncovalent.

For example, the polypeptides, fragments, analogs, derivatives and fusions of the present invention can usefully be bound to a porous substrate, commonly a membrane, typically comprising nitrocellulose, polyvinylidene fluoride (PVDF), or cationically derivatized, hydrophilic PVDF; so bound, the proteins, fragments, and fusions of the present invention can be used to detect and quantify antibodies, e.g in serum, that bind specifically to the immobilized protein of the present invention.

As another example, the polypeptides, fragments, analogs, derivatives and fusions of the present invention can usefully be bound to a substantially nonporous substrate, such as plastic, to detect and quantify antibodies, e.g. in serum, that bind specifically to the immobilized protein of the present invention. Such plastics include polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, or mixtures thereof; when the assay is performed in a standard microtiter dish, the plastic is typically polystyrene.

The polypeptides, fragments, analogs, derivatives and fusions of the present invention can also be attached to a substrate suitable for use as a surface enhanced laser desorption ionization source; so attached, the protein, fragment, or fusion of the present invention is useful for binding and then detecting secondary proteins that bind with sufficient affinity or avidity to the surface-bound protein to indicate biologic interaction there between. The proteins, fragments, and fusions of the present invention can also be attached to a substrate suitable for use in surface plasmon resonance detection; so attached, the protein, fragment, or fusion of the present invention is useful for binding and then detecting secondary proteins that bind with sufficient affinity or avidity to the surface-bound protein to indicate biological interaction there between.

Antibodies

In another aspect, the invention provides antibodies, including fragments and derivatives thereof, that bind specifically to polypeptides encoded by the nucleic acid molecules of the invention, as well as antibodies that bind to fragments, muteins, derivatives and analogs of the polypeptides. In a preferred embodiment, the antibodies are specific for a polypeptide that is a BSP, or a fragment, mutein, derivative, analog or fusion protein thereof. In a more preferred embodiment, the antibodies are specific for a polypeptide that comprises SEQ ID NO: 82 through 137, or a fragment, mutein, derivative, analog or fusion protein thereof.

The antibodies of the present invention can be specific for linear epitopes, discontinuous epitopes, or conformational epitopes of such proteins or protein fragments, either as present on the protein in its native conformation or, in some cases, as present on the proteins as denatured, as, e.g., by solubilization in SDS. New epitopes may be also due to a difference in post translational modifications (PTMs) in disease versus normal tissue. For example, a particular site on a BSP may be glycosylated in cancerous cells, but not glycosylated in normal cells or visa versa. In addition, alternative splice forms of a BSP may be indicative of cancer. Differential degradation of the C or N-terminus of a BSP may also be a marker or target for anticancer therapy. For example, a BSP may be N-terminal degraded in cancer cells exposing new epitopes to which antibodies may selectively bind for diagnostic or therapeutic uses.

As is well-known in the art, the degree to which an antibody can discriminate as among molecular species in a mixture will depend, in part, upon the conformational relatedness of the species in the mixture; typically, the antibodies of the present invention will discriminate over adventitious binding to non-BSP polypeptides by at least 2-fold, more typically by at least 5-fold, typically by more than 10-fold, 25-fold, 50-fold, 75-fold, and often by more than 100-fold, and on occasion by more than 500-fold or 1000-fold. When used to detect the proteins or protein fragments of the present invention, the antibody of the present invention is sufficiently specific when it can be used to determine the presence of the protein of the present invention in samples derived from human breast.

Typically, the affinity or avidity of an antibody (or antibody multimer, as in the case of an IgM pentamer) of the present invention for a protein or protein fragment of the present invention will be at least about $1\times10^{-6}$ molar (M), typically at least about $5\times10^{-7}$ M, $1\times10^{-7}$ M, with affinities and avidities of at least $1\times10^{-8}$ M, $5\times10^{-9}$ M, $1\times10^{-10}$ M and up to $1\times10^{-13}$ M proving especially useful.

The antibodies of the present invention can be naturally-occurring forms, such as IgG, IgM, IgD, IgE, IgY, and IgA, from any avian, reptilian, or mammalian species.

Human antibodies can, but will infrequently, be drawn directly from human donors or human cells. In this case, antibodies to the proteins of the present invention will typically have resulted from fortuitous immunization, such as autoimmune immunization, with the protein or protein fragments of the present invention. Such antibodies will typically, but will not invariably, be polyclonal. In addition, individual polyclonal antibodies may be isolated and cloned to generate monoclonals.

Human antibodies are more frequently obtained using transgenic animals that express human immunoglobulin genes, which transgenic animals can be affirmatively immunized with the protein immunogen of the present invention. Human Ig-transgenic mice capable of producing human antibodies and methods of producing human antibodies therefrom upon specific immunization are described, inter alia, in U.S. Pat. Nos. 6,162,963; 6,150,584; 6,114,598; 6,075,181; 5,939,598; 5,877,397; 5,874,299; 5,814,318; 5,789,650; 5,770,429; 5,661,016; 5,633,425; 5,625,126; 5,569,825; 5,545,807; 5,545,806, and 5,591,669, the disclosures of which are incorporated herein by reference in their entireties. Such antibodies are typically monoclonal, and are typically produced using techniques developed for production of murine antibodies.

Human antibodies are particularly useful, and often preferred, when the antibodies of the present invention are to be administered to human beings as in vivo diagnostic or therapeutic agents, since recipient immune response to the administered antibody will often be substantially less than that occasioned by administration of an antibody derived from another species, such as mouse.

IgG, IgM, IgD, IgE, IgY, and IgA antibodies of the present invention can also be obtained from other species, including mammals such as rodents (typically mouse, but also rat, guinea pig, and hamster) lagomorphs, typically rabbits, and also larger mammals, such as sheep, goats, cows, and horses, and other egg laying birds or reptiles such as chickens or alligators. For example, avian antibodies may be generated using techniques described in WO 00/29444, published 25 May 2000, the contents of which are hereby incorporated in their entirety. In such cases, as with the transgenic human-antibody-producing non-human mammals, fortuitous immunization is not required, and the non-human mammal is typically affirmatively immunized, according to standard immunization protocols, with the protein or protein fragment of the present invention.

As discussed above, virtually all fragments of 8 or more contiguous amino acids of the proteins of the present invention can be used effectively as immunogens when conjugated to a carrier, typically a protein such as bovine thyroglobulin, keyhole limpet hemocyanin, or bovine serum albumin, conveniently using a bifunctional linker such as those described elsewhere above, which discussion is incorporated by reference here.

Immunogenicity can also be conferred by fusion of the polypeptide and fragments of the present invention to other moieties. For example, peptides of the present invention can be produced by solid phase synthesis on a branched polylysine core matrix; these multiple antigenic peptides (MAPs) provide high purity, increased avidity, accurate chemical definition and improved safety in vaccine development. Tam et al., *Proc. Natl. Acad. Sci. USA* 85: 5409–5413 (1988); Posnett et al., *J. Biol. Chem.* 263: 1719–1725 (1988).

Protocols for immunizing non-human mammals or avian species are well-established in the art. See Harlow et al. (eds.), *Using Antibodies: A Laboratory Manual*, Cold Spring Harbor Laboratory (1998); Coligan et al. (eds.), *Current Protocols in Immunology*, John Wiley & Sons, Inc. (2001); Zola, *Monoclonal Antibodies: Preparation and Use of Monoclonal Antibodies and Engineered Antibody Derivatives* (*Basics: From Background to Bench*), Springer Verlag (2000); Gross M, Speck *J.Dtsch. Tierarztl. Wochenschr.* 103: 417–422 (1996), the disclosures of which are incorporated herein by reference. Immunization protocols often include multiple immunizations, either with or without adjuvants such as Freund's complete adjuvant and Freund's incomplete adjuvant, and may include naked DNA immunization (Moss, *Semin. Immunol.* 2: 317–327 (1990).

Antibodies from non-human mammals and avian species can be polyclonal or monoclonal, with polyclonal antibodies having certain advantages in immunohistochemical detection of the proteins of the present invention and monoclonal antibodies having advantages in identifying and distinguishing particular epitopes of the proteins of the present invention. Antibodies from avian species may have particular advantage in detection of the proteins of the present invention, in human serum or tissues (Vikinge et al., *Biosens. Bioelectron.* 13: 1257–1262 (1998).

Following immunization, the antibodies of the present invention can be produced using any art-accepted technique. Such techniques are well-known in the art, Coligan, supra; Zola, supra; Howard et al. (eds.), *Basic Methods in Antibody Production and Characterization*, CRC Press (2000); Harlow, supra; Davis (ed.), *Monoclonal Antibody Protocols*, Vol. 45, Humana Press (1995); Delves (ed.), *Antibody Production: Essential Techniques*, John Wiley & Son Ltd (1997); Kenney, *Antibody Solution: An Antibody Methods Manual*, Chapman & Hall (1997), incorporated herein by reference in their entireties, and thus need not be detailed here.

Briefly, however, such techniques include, inter alia, production of monoclonal antibodies by hybridomas and expression of antibodies or fragments or derivatives thereof from host cells engineered to express immunoglobulin genes or fragments thereof. These two methods of production are not mutually exclusive: genes encoding antibodies specific for the proteins or protein fragments of the present invention can be cloned from hybridomas and thereafter expressed in other host cells. Nor need the two necessarily be performed together: e.g., genes encoding antibodies specific for the proteins and protein fragments of the present invention can be cloned directly from B cells known to be specific for the desired protein, as further described in U.S Pat. No. 5,627,052, the disclosure of which is incorporated herein by reference in its entirety, or from antibody-displaying phage.

Recombinant expression in host cells is particularly useful when fragments or derivatives of the antibodies of the present invention are desired.

Host cells for recombinant production of either whole antibodies, antibody fragments, or antibody derivatives can be prokaryotic or eukaryotic.

Prokaryotic hosts are particularly useful for producing phage displayed antibodies of the present invention.

The technology of phage-displayed antibodies, in which antibody variable region fragments are fused, for example, to the gene III protein (pIII) or gene VIII protein (pVIII) for display on the surface of filamentous phage, such as M13, is by now well-established. See, e.g., Sidhu, *Curr. Opin. Biotechnol.* 11(6): 610–6 (2000); Griffiths et al., *Curr. Opin. Biotechnol.* 9(1): 102–8 (1998); Hoogenboom et al., *Immunotechnology*, 4(1): 1–20 (1998); Rader et al., *Current Opinion in Biotechnology* 8: 503–508 (1997); Aujame et al., *Human Antibodies* 8: 155–168 (1997); Hoogenboom, *Trends in Biotechnol.* 15: 62–70 (1997); de Kruif et al., 17: 453–455 (1996); Barbas et al., *Trends in Biotechnol.* 14: 230–234 (1996); Winter et al., *Ann. Rev. Immunol.* 433–455 (1994). Techniques and protocols required to generate, propagate, screen (pan), and use the antibody fragments from such libraries have recently been compiled. See, e.g., Barbas (2001), supra; Kay, supra; Abelson, supra, the disclosures of which are incorporated herein by reference in their entireties.

Typically, phage-displayed antibody fragments are scFv fragments or Fab fragments; when desired, full length antibodies can be produced by cloning the variable regions from the displaying phage into a complete antibody and expressing the full length antibody in a further prokaryotic or a eukaryotic host cell.

Eukaryotic cells are also useful for expression of the antibodies, antibody fragments, and antibody derivatives of the present invention.

For example, antibody fragments of the present invention can be produced in *Pichia pastoris* and in *Saccharomyces cerevisiae*. See, e.g., Takahashi et al., *Biosci. Biotechnol. Biochem.* 64(10): 2138–44 (2000); Freyre et al., J. Biotechnol. 76(2–3):1 57–63 (2000); Fischer et al., *Biotechnol. Appl. Biochem.* 30 (Pt 2): 117–20 (1999); Pennell et al., *Res. Immunol.* 149(6): 599–603 (1998); Eldin et al., *J. Immunol. Methods.* 201(1): 67–75 (1997);, Frenken et al., *Res. Immunol.* 149(6): 589–99 (1998); Shusta et al., *Nature Biotechnol.* 16(8): 773–7 (1998), the disclosures of which are incorporated herein by reference in their entireties.

Antibodies, including antibody fragments and derivatives, of the present invention can also be produced in insect cells. See, e.g., Li et al., *Protein Expr. Purif.* 21(1): 121–8 (2001); Ailor et al., *Biotechnol. Bioeng.* 58(2–3): 196–203 (1998); Hsu et al., *Biotechnol. Prog.* 13(1): 96–104 (1997); Edelman et al., *Immunology* 91(1): 13–9 (1997); and Nesbit et al., *J. Immunol. Methods* 151(1–2): 201–8 (1992), the disclosures of which are incorporated herein by reference in their entireties.

Antibodies and fragments and derivatives thereof of the present invention can also be produced in plant cells, particularly maize or tobacco, Giddings et al., *Nature Biotechnol.* 18(11): 1151–5 (2000); Gavilondo et al., *Biotechniques* 29(1): 128–38 (2000); Fischer et al., *J. Biol. Regul. Homeost. Agents* 14(2): 83–92 (2000); Fischer et al., *Biotechnol. Appl. Biochem.* 30 (Pt 2): 113–6 (1999); Fischer et al., *Biol. Chem.* 380(7–8): 825–39 (1999); Russell, *Curr. Top. Microbiol. Immunol.* 240: 119–38 (1999); and Ma et al., *Plant Physiol.* 109(2): 341–6 (1995), the disclosures of which are incorporated herein by reference in their entireties.

Antibodies, including antibody fragments and derivatives, of the present invention can also be produced in transgenic, non-human, mammalian milk. See, e.g. Pollock et al., *J. Immunol Methods.* 231: 147–57 (1999); Young et al., *Res. Immunol.* 149: 609–10 (1998); Limonta et al., *Immunotechnology* 1: 107–13 (1995), the disclosures of which are incorporated herein by reference in their entireties.

Mammalian cells useful for recombinant expression of antibodies, antibody fragments, and antibody derivatives of the present invention include CHO cells, COS cells, 293 cells, and myeloma cells.

Verma et al., *J. Immunol. Methods* 216(1–2):165–81 (1998), herein incorporated by reference, review and compare bacterial, yeast, insect and mammalian expression systems for expression of antibodies.

Antibodies of the present invention can also be prepared by cell free translation, as further described in Merk et al., *J. Biochem.* (Tokyo) 125(2): 328–33 (1999) and Ryabova et al., *Nature Biotechnol.* 15(1): 79–84 (1997), and in the milk of transgenic animals, as further described in Pollock et al., *J. Immunol. Methods* 231(1–2): 147–57 (1999), the disclosures of which are incorporated herein by reference in their entireties.

The invention further provides antibody fragments that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

Among such useful fragments are Fab, Fab', Fv, $F(ab)'_2$, and single chain Fv (scFv) fragments. Other useful fragments are described in Hudson, *Curr. Opin. Biotechnol.* 9(4): 395–402 (1998).

It is also an aspect of the present invention to provide antibody derivatives that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

Among such useful derivatives are chimeric, primatized, and humanized antibodies; such derivatives are less immunogenic in human beings, and thus more suitable for in vivo administration, than are unmodified antibodies from non-human mammalian species. Another useful derivative is PEGylation to increase the serum half life of the antibodies.

Chimeric antibodies typically include heavy and/or light chain variable regions (including both CDR and framework residues) of immunoglobulins of one species, typically mouse, fused to constant regions of another species, typically human. See, e.g., U.S. Pat. No. 5,807,715; Morrison et al., *Proc. Natl. Acad. Sci USA* .81(21): 6851–5 (1984); Sharon et al., *Nature* 309(5966): 364–7 (1984); Takeda et al., *Nature* 314(6010): 452–4 (1985), the disclosures of which are incorporated herein by reference in their entireties. Primatized and humanized antibodies typically include heavy and/or light chain CDRs from a murine antibody grafted into a non-human primate or human antibody V region framework, usually further comprising a human constant region, Riechmann et al., *Nature* 332(6162): 323–7 (1988); Co et al., *Nature* 351(6326): 501–2 (1991); U.S. Pat. Nos. 6,054,297; 5,821,337; 5,770,196; 5,766,886; 5,821,123; 5,869,619; 6,180,377; 6,013,256; 5,693,761; and 6,180,370, the disclosures of which are incorporated herein by reference in their entireties.

Other useful antibody derivatives of the invention include heteromeric antibody complexes and antibody fusions, such as diabodies (bispecific antibodies), single-chain diabodies, and intrabodies.

It is contemplated that the nucleic acids encoding the antibodies of the present invention can be operably joined to other nucleic acids forming a recombinant vector for cloning or for expression of the antibodies of the invention. The present invention includes any recombinant vector containing the coding sequences, or part thereof, whether for eukaryotic transduction, transfection or gene therapy. Such vectors may be prepared using conventional molecular biology techniques, known to those with skill in the art, and would comprise DNA encoding sequences for the immunoglobulin V-regions including framework and CDRs or parts thereof, and a suitable promoter either with or without a signal sequence for intracellular transport. Such vectors may be transduced or transfected into eukaryotic cells or used for gene therapy (Marasco et al., *Proc. Natl. Acad. Sci.* (*USA*) 90: 7889–7893 (1993); Duan et al., *Proc. Natl. Acad. Sci.* (*USA*) 91: 5075–5079 (1994), by conventional techniques, known to those with skill in the art.

The antibodies of the present invention, including fragments and derivatives thereof, can usefully be labeled. It is, therefore, another aspect of the present invention to provide labeled antibodies that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

The choice of label depends, in part, upon the desired use.

For example, when the antibodies of the present invention are used for immunohistochemical staining of tissue samples, the label is preferably an enzyme that catalyzes production and local deposition of a detectable product.

Enzymes typically conjugated to antibodies to permit their immunohistochemical visualization are well-known, and include alkaline phosphatase, β-galactosidase, glucose oxidase, horseradish peroxidase (HRP), and urease. Typical substrates for production and deposition of visually detectable products include o-nitrophenyl-beta-D-galactopyranoside (ONPG); o-phenylenediamine dihydrochloride (OPD); p-nitrophenyl phosphate (PNPP); p-nitrophenyl-beta-D-galactopryanoside (PNPG); 3',3'-diaminobenzidine (DAB); 3-amino-9-ethylcarbazole (AEC); 4-chloro-1-naphthol (CN); 5-bromo-4-chloro-3-indolyl-phosphate (BCIP); ABTS®; BluoGal; iodonitrotetrazolium (INT); nitroblue tetrazolium chloride (NBT); phenazine methosulfate (PMS); phenolphthalein monophosphate (PMP); tetramethyl benzidine (TMB); tetranitroblue tetrazolium (TNBT); X-Gal; X-Gluc; and X-Glucoside.

Other substrates can be used to produce products for local deposition that are luminescent. For example, in the presence of hydrogen peroxide ($H_2O_2$), horseradish peroxidase (HRP) can catalyze the oxidation of cyclic diacylhydrazides, such as luminol. Immediately following the oxidation, the luminol is in an excited state (intermediate reaction product), which decays to the ground state by emitting light. Strong enhancement of the light emission is produced by enhancers, such as phenolic compounds. Advantages include high sensitivity, high resolution, and rapid detection without radioactivity and requiring only small amounts of antibody. See, e.g., Thorpe et al., *Methods Enzymol.* 133: 331–53 (1986); Kricka et al., *J. Immunoassay* 17(1): 67–83 (1996); and Lundqvist et al., *J. Biolumin. Chemilumin.* 10(6): 353–9 (1995), the disclosures of which are incorporated herein by reference in their entireties. Kits for such enhanced chemiluminescent detection (ECL) are available commercially.

The antibodies can also be labeled using colloidal gold.

As another example, when the antibodies of the present invention are used, e.g., for flow cytometric detection, for scanning laser cytometric detection, or for fluorescent immunoassay, they can usefully be labeled with fluorophores.

There are a wide variety of fluorophore labels that can usefully be attached to the antibodies of the present invention.

For flow cytometric applications, both for extracellular detection and for intracellular detection, common useful fluorophores can be fluorescein isothiocyanate (FITC), allophycocyanin (APC), R-phycoerythrin (PE), peridinin chlorophyll protein (PerCP), Texas Red, Cy3, Cy5, fluorescence resonance energy tandem fluorophores such as PerCP-Cy5.5, PE-Cy5, PE-Cy5.5, PE-Cy7, PE-Texas Red, and APC-Cy7.

Other fluorophores include, inter alia, Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3, Cy3.5, Cy5, Cy5.5, Cy7, all of which are also useful for fluorescently labeling the antibodies of the present invention.

For secondary detection using labeled avidin, streptavidin, captavidin or neutravidin, the antibodies of the present invention can usefully be labeled with biotin.

When the antibodies of the present invention are used, e.g., for Western blotting applications, they can usefully be labeled with radioisotopes, such as $^{33}$P, $^{32}$P, $^{35}$S, $^{3}$H, and $^{125}$I.

As another example, when the antibodies of the present invention are used for radioimmunotherapy, the label can usefully be $^{228}$Th, $^{227}$Ac, $^{225}$Ac, $^{223}$Ra, $^{213}$Bi, $^{212}$Pb, $^{212}$Bi $^{211}$At, $^{203}$Pb, $^{194}$S, $^{188}$Re, $^{186}$Re, $^{153}$Sm, $^{149}$Tb, $^{131}$I, $^{125}$I, $^{111}$In, $^{105}$Rh, $^{99m}$Tc, $^{97}$Ru, $^{90}$Y, $^{90}$Sr, $^{88}$Y, $^{72}$Se, $^{67}$Cu, or $^{47}$Sc.

As another example, when the antibodies of the present invention are to be used for in vivo diagnostic use, they can be rendered detectable by conjugation to MRI contrast agents, such as gadolinium diethylenetriaminepentaacetic acid (DTPA), Lauffer et al., *Radiology* 207(2): 529–38 (1998), or by radioisotopic labeling.

As would be understood, use of the labels described above is not restricted to the application for which they are mentioned.

The antibodies of the present invention, including fragments and derivatives thereof, can also be conjugated to toxins, in order to target the toxin's ablative action to cells that display and/or express the proteins of the present invention. Commonly, the antibody in such immunotoxins is conjugated to *Pseudomonas* exotoxin A, *diphtheria* toxin, *shiga* toxin A, *anthrax* toxin lethal factor, or ricin. See Hall (ed.), *Immunotoxin Methods and Protocols* (Methods in Molecular Biology, vol. 166), Humana Press (2000); and Frankel et al. (eds.), *Clinical Applications of Immunotoxins*, Springer-Verlag (1998), the disclosures of which are incorporated herein by reference in their entireties.

The antibodies of the present invention can usefully be attached to a substrate, and it is, therefore, another aspect of the invention to provide antibodies that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention, attached to a substrate.

Substrates can be porous or nonporous, planar or nonplanar.

For example, the antibodies of the present invention can usefully be conjugated to filtration media, such as NHS-activated Sepharose or CNBr-activated Sepharose for purposes of immunoaffinity chromatography.

For example, the antibodies of the present invention can usefully be attached to paramagnetic microspheres, typically by biotin-streptavidin interaction, which microspheres can then be used for isolation of cells that express or display the proteins of the present invention. As another example, the antibodies of the present invention can usefully be attached to the surface of a microtiter plate for ELISA.

As noted above, the antibodies of the present invention can be produced in prokaryotic and eukaryotic cells. It is, therefore, another aspect of the present invention to provide cells that express the antibodies of the present invention, including hybridoma cells, B cells, plasma cells, and host cells recombinantly modified to express the antibodies of the present invention.

In yet a further aspect, the present invention provides aptamers evolved to bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

In sum, one of skill in the art, provided with the teachings of this invention, has available a variety of methods which may be used to alter the biological properties of the antibodies of this invention including methods which would increase or decrease the stability or half-life, immunogenicity, toxicity, affinity or yield of a given antibody molecule, or to alter it in any other way that may render it more suitable for a particular application.

Transgenic Animals and Cells

In another aspect, the invention provides transgenic cells and non-human organisms comprising nucleic acid molecules of the invention. In a preferred embodiment, the transgenic cells and non-human organisms comprise a nucleic acid molecule encoding a BSP. In a preferred embodiment, the BSP comprises an amino acid sequence selected from SEQ ID NO: 82 through 137, or a fragment, mutein, homologous protein or allelic variant thereof. In another preferred embodiment, the transgenic cells and non-human organism comprise a BSNA of the invention, preferably a BSNA comprising a nucleotide sequence selected from the group consisting of SEQ ID NO: 1 through 81, or a part, substantially similar nucleic acid molecule, allelic variant or hybridizing nucleic acid molecule thereof.

In another embodiment, the transgenic cells and non-human organisms have a targeted disruption or replacement of the endogenous orthologue of the human BSG. The transgenic cells can be embryonic stem cells or somatic cells. The transgenic non-human organisms can be chimeric, nonchimeric heterozygotes, and nonchimeric homozygotes. Methods of producing transgenic animals are well-known in the art. See, e.g., Hogan et al., *Manipulating the Mouse Embryo: A Laboratory Manual*, 2d ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999).

Any technique known in the art may be used to introduce a nucleic acid molecule of the invention into an animal to produce the founder lines of transgenic animals. Such techniques include, but are not limited to, pronuclear microinjection. (see, e.g., Paterson et al., *Appl. Microbiol. Biotechnol.* 40: 691–698 (1994); Carver et al., *Biotechnology* 11: 1263–1270 (1993); Wright et al., *Biotechnology* 9: 830–834 (1991); and U.S. Pat. No. 4,873,191 (1989 retrovirus-mediated gene transfer into germ lines, blastocysts or embryos (see, e.g., Van der Putten et al., *Proc. Natl. Acad. Sci., USA* 82: 6148–6152 (1985)); gene targeting in embryonic stem cells (see, e.g., Thompson et al., *Cell* 56: 313–321 (1989)); electroporation of cells or embryos (see, e.g., Lo, 1983, *Mol. Cell. Biol.* 3: 1803–1814 (1983)); introduction using a gene gun (see, e.g., Ulmer et al., *Science* 259: 1745–49 (1993); introducing nucleic acid constructs into embryonic pleuripotent stem cells and transferring the stem cells back into the blastocyst; and sperm-mediated gene transfer (see, e.g., Lavitrano et al., *Cell* 57: 717–723 (1989)).

Other techniques include, for example, nuclear transfer into enucleated oocytes of nuclei from cultured embryonic, fetal, or adult cells induced to quiescence (see, e.g., Campell et al., *Nature* 380: 64–66 (1996); Wilmut et al., *Nature* 385: 810–813 (1997)). The present invention provides for transgenic animals that carry the transgene (i.e., a nucleic acid molecule of the invention) in all their cells, as well as animals which carry the transgene in some, but not all their cells, i.e., mosaic animals or chimeric animals.

The transgene may be integrated as a single transgene or as multiple copies, such as in concatamers, e.g., head-to-head tandems or head-to-tail tandems. The transgene may also be selectively introduced into and activated in a particular cell type by following, e.g., the teaching of Lasko et al. et al., *Proc. Natl. Acad. Sci. USA* 89: 6232–6236 (1992). The regulatory sequences required for such a cell-type specific activation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (RT-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Methods for creating a transgenic animal with a disruption of a targeted gene are also well-known in the art. In general, a vector is designed to comprise some nucleotide sequences homologous to the endogenous targeted gene. The vector is introduced into a cell so that it may integrate, via homologous recombination with chromosomal sequences, into the endogenous gene, thereby disrupting the function of the endogenous gene. The transgene may also be selectively introduced into a particular cell type, thus inactivating the endogenous gene in only that cell type. See, e.g., Gu et al., *Science* 265: 103–106 (1994). The regulatory sequences required for such a cell-type specific inactivation will depend upon the particular cell type of interest, and will be apparent to those of skill in the art. See, e.g., Smithies et al., *Nature* 317: 230–234 (1985); Thomas et al., *Cell* 51: 503–512 (1987); Thompson et al., *Cell* 5: 313–321 (1989).

In one embodiment, a mutant, non-functional nucleic acid molecule of the invention (or a completely unrelated DNA sequence) flanked by DNA homologous to the endogenous nucleic acid sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene. See, e.g., Thomas, supra and Thompson, supra. However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from an animal or patient or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc.

The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. See, e.g., U.S. Pat. Nos. 5,399,349 and 5,460,959, each of which is incorporated by reference herein in its entirety.

When the cells to be administered are non-autologous or non-MHC compatible cells, they can be administered using well-known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Computer Readable Means

A further aspect of the invention relates to a computer readable means for storing the nucleic acid and amino acid sequences of the instant invention. In a preferred embodiment, the invention provides a computer readable means for storing SEQ ID NO: 1 through 81 and SEQ ID NO: 82 through 137 as described herein, as the complete set of sequences or in any combination. The records of the computer readable means can be accessed for reading and display and for interface with a computer system for the application of programs allowing for the location of data upon a query for data meeting certain criteria, the comparison of sequences, the alignment or ordering of sequences meeting a set of criteria, and the like.

The nucleic acid and amino acid sequences of the invention are particularly useful as components in databases useful for search analyses as well as in sequence analysis algorithms. As used herein, the terms "nucleic acid sequences of the invention" and "amino acid sequences of the invention" mean any detectable chemical or physical characteristic of a polynucleotide or polypeptide of the invention that is or may be reduced to or stored in a computer readable form. These include, without limitation, chromatographic scan data or peak data, photographic data or scan data therefrom, and mass spectrographic data.

This invention provides computer readable media having stored thereon sequences of the invention. A computer readable medium may comprise one or more of the following: a nucleic acid sequence comprising a sequence of a nucleic acid sequence of the invention; an amino acid sequence comprising an amino acid sequence of the invention; a set of nucleic acid sequences wherein at least one of said sequences comprises the sequence of a nucleic acid sequence of the invention; a set of amino acid sequences wherein at least one of said sequences comprises the sequence of an amino acid sequence of the invention; a data set representing a nucleic acid sequence comprising the sequence of one or more nucleic acid sequences of the invention; a data set representing a nucleic acid sequence encoding an amino acid sequence comprising the sequence of an amino acid sequence of the invention; a set of nucleic acid sequences wherein at least one of said sequences comprises the sequence of a nucleic acid sequence of the invention; a set of amino acid sequences wherein at least one of said sequences comprises the sequence of an amino acid sequence of the invention; a data set representing a nucleic acid sequence comprising the sequence of a nucleic acid sequence of the invention; a data set representing a nucleic acid sequence encoding an amino acid sequence comprising the sequence of an amino acid sequence of the invention. The computer readable medium can be any composition of matter used to store information or data, including, for example, commercially available floppy disks, tapes, hard drives, compact disks, and video disks.

Also provided by the invention are methods for the analysis of character sequences, particularly genetic sequences. Preferred methods of sequence analysis include, for example, methods of sequence homology analysis, such as identity and similarity analysis, RNA structure analysis, sequence assembly, cladistic analysis, sequence motif analysis, open reading frame determination, nucleic acid base calling, and sequencing chromatogram peak analysis.

A computer-based method is provided for performing nucleic acid sequence identity or similarity identification. This method comprises the steps of providing a nucleic acid sequence comprising the sequence of a nucleic acid of the invention in a computer readable medium; and comparing said nucleic acid sequence to at least one nucleic acid or amino acid sequence to identify sequence identity or similarity.

A computer-based method is also provided for performing amino acid homology identification, said method comprising the steps of: providing an amino acid sequence comprising the sequence of an amino acid of the invention in a computer readable medium; and comparing said an amino acid sequence to at least one nucleic acid or an amino acid sequence to identify homology.

A computer-based method is still further provided for assembly of overlapping nucleic acid sequences into a single nucleic acid sequence, said method comprising the steps of: providing a first nucleic acid sequence comprising the sequence of a nucleic acid of the invention in a computer readable medium; and screening for at least one overlapping region between said first nucleic acid sequence and a second nucleic acid sequence.

Diagnostic Methods for Breast Cancer

The present invention also relates to quantitative and qualitative diagnostic assays and methods for detecting, diagnosing, monitoring, staging and predicting cancers by comparing expression of a BSNA or a BSP in a human patient that has or may have breast cancer, or who is at risk of developing breast cancer, with the expression of a BSNA or a BSP in a normal human control. For purposes of the present invention, "expression of a BSNA" or "BSNA expression" means the quantity of BSG mRNA that can be measured by any method known in the art or the level of transcription that can be measured by any method known in the art in a cell, tissue, organ or whole patient. Similarly, the term "expression of a BSP" or "BSP expression" means the amount of BSP that can be measured by any method known in the art or the level of translation of a BSG BSNA that can be measured by any method known in the art.

The present invention provides methods for diagnosing breast cancer in a patient, in particular squamous cell carcinoma, by analyzing for changes in levels of BSNA or BSP in cells, tissues, organs or bodily fluids compared with levels of BSNA or BSP in cells, tissues, organs or bodily fluids of preferably the same type from a normal human control, wherein an increase, or decrease in certain cases, in levels of a BSNA or BSP in the patient versus the normal human control is associated with the presence of breast cancer or with a predilection to the disease. In another preferred embodiment, the present invention provides methods for diagnosing breast cancer in a patient by analyzing changes in the structure of the mRNA of a BSG compared to the mRNA from a normal control. These changes include, without limitation, aberrant splicing, alterations in polyadenylation and/or alterations in 5' nucleotide capping. In yet another preferred embodiment, the present invention provides methods for diagnosing breast cancer in a patient by analyzing changes in a BSP compared to a BSP from a normal control. These changes include, e.g., alterations in glycosylation and/or phosphorylation of the BSP or subcellular BSP localization.

In a preferred embodiment, the expression of a BSNA is measured by determining the amount of an mRNA that encodes an amino acid sequence selected from SEQ ID NO: 82 through 137, a homolog, an allelic variant, or a fragment thereof. In a more preferred embodiment, the BSNA expression that is measured is the level of expression of a BSNA mRNA selected from SEQ ID NO: 1 through 81, or a hybridizing nucleic acid, homologous nucleic acid or allelic variant thereof, or a part of any of these nucleic acids. BSNA expression may be measured by any method known in the art, such as those described supra, including measuring mRNA expression by Northern blot, quantitative or qualitative reverse transcriptase PCR (RT-PCR), microarray, dot or slot blots or in situ hybridization. See, e.g., Ausubel (1992), supra; Ausubel (1999), supra; Sambrook (1989), supra; and Sambrook (2001), supra. BSNA transcription may be measured by any method known in the art including using a reporter gene hooked up to the promoter of a BSG of interest or doing nuclear run-off assays. Alterations in mRNA structure, e.g., aberrant splicing variants, may be determined by any method known in the art, including, RT-PCR followed by sequencing or restriction analysis. As necessary, BSNA expression may be compared to a known control, such as normal breast nucleic acid, to detect a change in expression.

In another preferred embodiment, the expression of a BSP is measured by determining the level of a BSP having an amino acid sequence selected from the group consisting of SEQ ID NO: 82 through 137, a homolog, an allelic variant, or a fragment thereof. Such levels are preferably determined in at least one of cells, tissues, organs and/or bodily fluids, including determination of normal and abnormal levels. Thus, for instance, a diagnostic assay in accordance with the invention for diagnosing over- or underexpression of BSNA or BSP compared to normal control bodily fluids, cells, or tissue samples may be used to diagnose the presence of breast cancer. The expression level of a BSP may be determined by any method known in the art, such as those described supra. In a preferred embodiment, the BSP expression level may be determined by radioimmunoassays, competitive-binding assays, ELISA, Western blot, FACS, immunohistochemistry, immunoprecipitation, proteomic approaches: two-dimensional gel electrophoresis (2D electrophoresis) and non-gel-based approaches such as mass spectrometry or protein interaction profiling. See, e.g, Harlow (1999), supra; Ausubel (1992), supra; and Ausubel (1999), supra. Alterations in the BSP structure may be determined by any method known in the art, including, e.g., using antibodies that specifically recognize phosphoserine, phosphothreonine or phosphotyrosine residues, two-dimensional polyacrylamide gel electrophoresis (2D PAGE) and/or chemical analysis of amino acid residues of the protein. Id.

In a preferred embodiment, a radioimmunoassay (RIA) or an ELISA is used. An antibody specific to a BSP is prepared if one is not already available. In a preferred embodiment, the antibody is a monoclonal antibody. The anti-BSP antibody is bound to a solid support and any free protein binding sites on the solid support are blocked with a protein such as bovine serum albumin. A sample of interest is incubated with the antibody on the solid support under conditions in which the BSP will bind to the anti-BSP antibody. The sample is removed, the solid support is washed to remove unbound material, and an anti-BSP antibody that is linked to a detectable reagent (a radioactive substance for RIA and an enzyme for ELISA) is added to the solid support and incubated under conditions in which binding of the BSP to the labeled antibody will occur. After binding, the unbound labeled antibody is removed by washing. For an ELISA, one or more substrates are added to produce a colored reaction product that is based upon the amount of a BSP in the sample. For an RIA, the solid support is counted for radioactive decay signals by any method known in the art. Quantitative results for both RIA and ELISA typically are obtained by reference to a standard curve.

Other methods to measure BSP levels are known in the art. For instance, a competition assay may be employed wherein an anti-BSP antibody is attached to a solid support and an allocated amount of a labeled BSP and a sample of interest are incubated with the solid support. The amount of labeled BSP detected which is attached to the solid support can be correlated to the quantity of a BSP in the sample.

Of the proteomic approaches, 2D PAGE is a well-known technique. Isolation of individual proteins from a sample such as serum is accomplished using sequential separation of proteins by isoelectric point and molecular weight. Typically, polypeptides are first separated by isoelectric point (the first dimension) and then separated by size using an electric current (the second dimension). In general, the second dimension is perpendicular to the first dimension. Because no two proteins with different sequences are identical on the basis of both size and charge, the result of 2D PAGE is a roughly square gel in which each protein occupies a unique spot. Analysis of the spots with chemical or antibody probes, or subsequent protein microsequencing can reveal the relative abundance of a given protein and the identity of the proteins in the sample.

Expression levels of a BSNA can be determined by any method known in the art, including PCR and other nucleic acid methods, such as ligase chain reaction (LCR) and nucleic acid sequence based amplification (NASBA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction.

Hybridization to specific DNA molecules (e.g., oligonucleotides) arrayed on a solid support can be used to both detect the expression of and quantitate the level of expression of one or more BSNAs of interest. In this approach, all or a portion of one or more BSNAs is fixed to a substrate. A sample of interest, which may comprise RNA, e.g., total RNA or polyA-selected mRNA, or a complementary DNA (cDNA) copy of the RNA is incubated with the solid support under conditions in which hybridization will occur between the DNA on the solid support and the nucleic acid molecules in the sample of interest. Hybridization between the substrate-bound DNA and the nucleic acid molecules in the sample can be detected and quantitated by several means, including, without limitation, radioactive labeling or fluorescent labeling of the nucleic acid molecule or a secondary molecule designed to detect the hybrid.

The above tests can be carried out on samples derived from a variety of cells, bodily fluids and/or tissue extracts such as homogenates or solubilized tissue obtained from a patient. Tissue extracts are obtained routinely from tissue biopsy and autopsy material. Bodily fluids useful in the present invention include blood, urine, saliva or any other bodily secretion or derivative thereof. By blood it is meant to include whole blood, plasma, serum or any derivative of blood. In a preferred embodiment, the specimen tested for expression of BSNA or BSP includes, without limitation, breast tissue, fluid obtained by bronchial alveolar lavage (BAL), sputum, breast cells grown in cell culture, blood, serum, lymph node tissue and lymphatic fluid. In another preferred embodiment, especially when metastasis of a primary breast cancer is known or suspected, specimens include, without limitation, tissues from brain, bone, bone marrow, liver, adrenal glands and colon. In general, the tissues may be sampled by biopsy, including, without limitation, needle biopsy, e.g., transthoracic needle aspiration, cervical mediatinoscopy, endoscopic lymph node biopsy, video-assisted thoracoscopy, exploratory thoracotomy, bone marrow biopsy and bone marrow aspiration. See Scott, supra and Franklin, pp. 529–570, in Kane, supra. For early and inexpensive detection, assaying for changes in BSNAs or BSPs in cells in sputum samples may be particularly useful. Methods of obtaining and analyzing sputum samples is disclosed in Franklin, supra.

All the methods of the present invention may optionally include determining the expression levels of one or more other cancer markers in addition to determining the expression level of a BSNA or BSP. In many cases, the use of another cancer marker will decrease the likelihood of false positives or false negatives. In one embodiment, the one or more other cancer markers include other BSNA or BSPs as disclosed herein. Other cancer markers useful in the present invention will depend on the cancer being tested and are known to those of skill in the art. In a preferred embodiment, at least one other cancer marker in addition to a particular BSNA or BSP is measured. In a more preferred embodiment, at least two other additional cancer markers are used. In an even more preferred embodiment, at least three, more preferably at least five, even more preferably at least ten additional cancer markers are used.

Diagnosing

In one aspect, the invention provides a method for determining the expression levels and/or structural alterations of one or more BSNAs and/or BSPs in a sample from a patient suspected of having breast cancer. In general, the method comprises the steps of obtaining the sample from the patient, determining the expression level or structural alterations of a BSNA and/or BSP and then ascertaining whether the patient has breast cancer from the expression level of the BSNA or BSP. In general, if high expression relative to a control of a BSNA or BSP is indicative of breast cancer, a diagnostic assay is considered positive if the level of expression of the BSNA or BSP is at least two times higher, and more preferably are at least five times higher, even more preferably at least ten times higher, than in preferably the same cells, tissues or bodily fluid of a normal human control. In contrast, if low expression relative to a control of a BSNA or BSP is indicative of breast cancer, a diagnostic assay is considered positive if the level of expression of the BSNA or BSP is at least two times lower, more preferably are at least five times lower, even more preferably at least ten times lower than in preferably the same cells, tissues or bodily fluid of a normal human control. The normal human control may be from a different patient or from uninvolved tissue of the same patient.

The present invention also provides a method of determining whether breast cancer has metastasized in a patient. One may identify whether the breast cancer has metastasized by measuring the expression levels and/or structural alterations of one or more BSNAs and/or BSPs in a variety of tissues. The presence of a BSNA or BSP in a certain tissue at levels higher than that of corresponding noncancerous tissue (e.g., the same tissue from another individual) is indicative of metastasis if high level expression of a BSNA or BSP is associated with breast cancer. Similarly, the presence of a BSNA or BSP in a tissue at levels lower than that of corresponding noncancerous tissue is indicative of metastasis if low level expression of a BSNA or BSP is associated with breast cancer. Further, the presence of a structurally altered BSNA or BSP that is associated with breast cancer is also indicative of metastasis.

In general, if high expression relative to a control of a BSNA or BSP is indicative of metastasis, an assay for metastasis is considered positive if the level of expression of the BSNA or BSP is at least two times higher, and more preferably are at least five times higher, even more preferably at least ten times higher, than in preferably the same cells, tissues or bodily fluid of a normal human control. In contrast, if low expression relative to a control of a BSNA or BSP is indicative of metastasis, an assay for metastasis is considered positive if the level of expression of the BSNA or BSP is at least two times lower, more preferably are at least five times lower, even more preferably at least ten times lower than in preferably the same cells, tissues or bodily fluid of a normal human control.

The BSNA or BSP of this invention may be used as element in an array or a multi-analyte test to recognize expression patterns associated with breast cancers or other breast related disorders. In addition, the sequences of either the nucleic acids or proteins may be used as elements in a computer program for pattern recognition of breast disorders.

Staging

The invention also provides a method of staging breast cancer in a human patient. The method comprises identifying a human patient having breast cancer and analyzing cells, tissues or bodily fluids from such human patient for expression levels and/or structural alterations of one or more BSNAs or BSPs. First, one or more tumors from a variety of patients are staged according to procedures well-known in the art, and the expression level of one or more BSNAs or BSPs is determined for each stage to obtain a standard expression level for each BSNA and BSP. Then, the BSNA or BSP expression levels are determined in a biological sample from a patient whose stage of cancer is not known. The BSNA or BSP expression levels from the patient are then compared to the standard expression level. By comparing the expression level of the BSNAs and BSPs from the patient to the standard expression levels, one may determine the stage of the tumor. The same procedure may be followed using structural alterations of a BSNA or BSP to determine the stage of a breast cancer.

Monitoring

Further provided is a method of monitoring breast cancer in a human patient. One may monitor a human patient to determine whether there has been metastasis and, if there has been, when metastasis began to occur. One may also monitor a human patient to determine whether a preneoplastic lesion has become cancerous. One may also monitor a human patient to determine whether a therapy, e.g., chemotherapy, radiotherapy or surgery, has decreased or eliminated the breast cancer. The method comprises identifying a human patient that one wants to monitor for breast cancer, periodically analyzing cells, tissues or bodily fluids from such human patient for expression levels of one or more BSNAs or BSPs, and comparing the BSNA or BSP levels over time to those BSNA or BSP expression levels obtained previously. Patients may also be monitored by measuring one or more structural alterations in a BSNA or BSP that are associated with breast cancer.

If increased expression of a BSNA or BSP is associated with metastasis, treatment failure, or conversion of a preneoplastic lesion to a cancerous lesion, then detecting an increase in the expression level of a BSNA or BSP indicates that the tumor is metastasizing, that treatment has failed or that the lesion is cancerous, respectively. One having ordinary skill in the art would recognize that if this were the case, then a decreased expression level would be indicative of no metastasis, effective therapy or failure to progress to a neoplastic lesion. If decreased expression of a BSNA or BSP is associated with metastasis, treatment failure, or conversion of a preneoplastic lesion to a cancerous lesion, then detecting an decrease in the expression level of a BSNA or BSP indicates that the tumor is metastasizing, that treatment has failed or that the lesion is cancerous, respectively. In a preferred embodiment, the levels of BSNAs or BSPs are determined from the same cell type, tissue or bodily fluid as prior patient samples. Monitoring a patient for onset of breast cancer metastasis is periodic and preferably is done on a quarterly basis, but may be done more or less frequently.

The methods described herein can further be utilized as prognostic assays to identify subjects having or at risk of developing a disease or disorder associated with increased or decreased expression levels of a BSNA and/or BSP. The present invention provides a method in which a test sample is obtained from a human patient and one or more BSNAs and/or BSPs are detected. The presence of higher (or lower) BSNA or BSP levels as compared to normal human controls is diagnostic for the human patient being at risk for developing cancer, particularly breast cancer. The effectiveness of therapeutic agents to decrease (or increase) expression or activity of one or more BSNAs and/or BSPs of the invention can also be monitored by analyzing levels of expression of the BSNAs and/or BSPs in a human patient in clinical trials or in in vitro screening assays such as in human cells. In this way, the gene expression pattern can serve as a marker, indicative of the physiological response of the human patient or cells, as the case may be, to the agent being tested.

Detection of Genetic Lesions or Mutations

The methods of the present invention can also be used to detect genetic lesions or mutations in a BSG, thereby determining if a human with the genetic lesion is susceptible to developing breast cancer or to determine what genetic lesions are responsible, or are partly responsible, for a person's existing breast cancer. Genetic lesions can be detected, for example, by ascertaining the existence of a deletion, insertion and/or substitution of one or more nucleotides from the BSGs of this invention, a chromosomal rearrangement of BSG, an aberrant modification of BSG (such as of the methylation pattern of the genomic DNA), or allelic loss of a BSG. Methods to detect such lesions in the BSG of this invention are known to those having ordinary skill in the art following the teachings of the specification.

Methods of Detecting Noncancerous Breast Diseases

The invention also provides a method for determining the expression levels and/or structural alterations of one or more BSNAs and/or BSPs in a sample from a patient suspected of having or known to have a noncancerous breast disease. In general, the method comprises the steps of obtaining a sample from the patient, determining the expression level or structural alterations of a BSNA and/or BSP, comparing the expression level or structural alteration of the BSNA or BSP to a normal breast control, and then ascertaining whether the patient has a noncancerous breast disease. In general, if high expression relative to a control of a BSNA or BSP is indicative of a particular noncancerous breast disease, a diagnostic assay is considered positive if the level of expression of the BSNA or BSP is at least two times higher, and more preferably are at least five times higher, even more preferably at least ten times higher, than in preferably the same cells, tissues or bodily fluid of a normal human control. In contrast, if low expression relative to a control of a BSNA or BSP is indicative of a noncancerous breast disease, a diagnostic assay is considered positive if the level of expression of the BSNA or BSP is at least two times lower, more preferably are at least five times lower, even more preferably at least ten times lower than in preferably the same cells, tissues or bodily fluid of a normal human control. The normal human control may be from a different patient or from uninvolved tissue of the same patient.

One having ordinary skill in the art may determine whether a BSNA and/or BSP is associated with a particular noncancerous breast disease by obtaining breast tissue from a patient having a noncancerous breast disease of interest and determining which BSNAs and/or BSPs are expressed in the tissue at either a higher or a lower level than in normal breast tissue. In another embodiment, one may determine whether a BSNA or BSP exhibits structural alterations in a particular noncancerous breast disease state by obtaining breast tissue from a patient having a noncancerous breast disease of interest and determining the structural alterations in one or more BSNAs and/or BSPs relative to normal breast tissue.

Methods for Identifying Breast Tissue

In another aspect, the invention provides methods for identifying breast tissue. These methods are particularly useful in, e.g., forensic science, breast cell differentiation and development, and in tissue engineering.

In one embodiment, the invention provides a method for determining whether a sample is breast tissue or has breast tissue-like characteristics. The method comprises the steps of providing a sample suspected of comprising breast tissue or having breast tissue-like characteristics, determining whether the sample expresses one or more BSNAs and/or BSPs, and, if the sample expresses one or more BSNAs and/or BSPs, concluding that the sample comprises breast tissue. In a preferred embodiment, the BSNA encodes a polypeptide having an amino acid sequence selected from SEQ ID NO: 82 through 137, or a homolog, allelic variant or fragment thereof. In a more preferred embodiment, the BSNA has a nucleotide sequence selected from SEQ ID NO: 1 through 81, or a hybridizing nucleic acid, an allelic variant or a part thereof. Determining whether a sample expresses a BSNA can be accomplished by any method known in the art. Preferred methods include hybridization to microarrays, Northern blot hybridization, and quantitative or qualitative RT-PCR. In another preferred embodiment, the method can be practiced by determining whether a BSP is expressed. Determining whether a sample expresses a BSP can be accomplished by any method known in the art. Preferred methods include Western blot, ELISA, RIA and 2D PAGE. In one embodiment, the BSP has an amino acid sequence selected from SEQ ID NO: 82 through 137, or a homolog, allelic variant or fragment thereof. In another preferred embodiment, the expression of at least two BSNAs and/or BSPs is determined. In a more preferred embodiment, the expression of at least three, more preferably four and even more preferably five BSNAs and/or BSPs are determined.

In one embodiment, the method can be used to determine whether an unknown tissue is breast tissue. This is particularly useful in forensic science, in which small, damaged pieces of tissues that are not identifiable by microscopic or other means are recovered from a crime or accident scene. In another embodiment, the method can be used to determine whether a tissue is differentiating or developing into breast tissue. This is important in monitoring the effects of the addition of various agents to cell or tissue culture, e.g., in producing new breast tissue by tissue engineering. These agents include, e.g., growth and differentiation factors, extracellular matrix proteins and culture medium. Other factors that may be measured for effects on tissue development and differentiation include gene transfer into the cells or tissues, alterations in pH, aqueous:air interface and various other culture conditions.

Methods for Producing and Modifying Breast Tissue

In another aspect, the invention provides methods for producing engineered breast tissue or cells. In one embodiment, the method comprises the steps of providing cells, introducing a BSNA or a BSG into the cells, and growing the cells under conditions in which they exhibit one or more properties of breast tissue cells. In a preferred embodiment, the cells are pluripotent. As is well-known in the art, normal breast tissue comprises a large number of different cell types. Thus, in one embodiment, the engineered breast tissue or cells comprises one of these cell types. In another embodiment, the engineered breast tissue or cells comprises more than one breast cell type. Further, the culture conditions of the cells or tissue may require manipulation in order to achieve full differentiation and development of the breast cell tissue. Methods for manipulating culture conditions are well-known in the art.

Nucleic acid molecules encoding one or more BSPs are introduced into cells, preferably pluripotent cells. In a preferred embodiment, the nucleic acid molecules encode BSPs having amino acid sequences selected from SEQ ID NO: 82 through 137, or homologous proteins, analogs, allelic variants or fragments thereof. In a more preferred embodiment, the nucleic acid molecules have a nucleotide sequence selected from SEQ ID NO: 1 through 81, or hybridizing nucleic acids, allelic variants or parts thereof. In another highly preferred embodiment, a BSG is introduced into the cells. Expression vectors and methods of introducing nucleic acid molecules into cells are well-known in the art and are described in detail, supra.

Artificial breast tissue may be used to treat patients who have lost some or all of their breast function.

Pharmaceutical Compositions

In another aspect, the invention provides pharmaceutical compositions comprising the nucleic acid molecules, polypeptides, antibodies, antibody derivatives, antibody fragments, agonists, antagonists, and inhibitors of the present invention. In a preferred embodiment, the pharmaceutical composition comprises a BSNA or part thereof. In a more preferred embodiment, the BSNA has a nucleotide sequence selected from the group consisting of SEQ ID NO: 1 through 81, a nucleic acid that hybridizes thereto, an allelic variant thereof, or a nucleic acid that has substantial sequence identity thereto. In another preferred embodiment, the pharmaceutical composition comprises a BSP or fragment thereof In a more preferred embodiment, the BSP having an amino acid sequence that is selected from the group consisting of SEQ ID NO: 82 through 137, a polypeptide that is homologous thereto, a fusion protein comprising all or a portion of the polypeptide, or an analog or derivative thereof. In another preferred embodiment, the pharmaceutical composition comprises an anti-BSP antibody, preferably an antibody that specifically binds to a BSP having an amino acid that is selected from the group consisting of SEQ ID NO: 82 through 137, or an antibody that binds to a polypeptide that is homologous thereto, a fusion protein comprising all or a portion of the polypeptide, or an analog or derivative thereof.

Such a composition typically contains from about 0.1 to 90% by weight of a therapeutic agent of the invention formulated in and/or with a pharmaceutically acceptable carrier or excipient.

Pharmaceutical formulation is a well-established art, and is further described in Gennaro (ed.), *Remington: The Science and Practice of Pharmacy*, 20$^{th}$ ed., Lippincott, Williams & Wilkins (2000); Ansel et al., *Pharmaceutical Dosage Forms and Drug Delivery Systems*, 7$^{th}$ ed., Lippincott Williams & Wilkins (1999); and Kibbe (ed.), *Handbook of Pharmaceutical Excipients* American Pharmaceutical Association, 3$^{rd}$ ed. (2000), the disclosures of which are incorporated herein by reference in their entireties, and thus need not be described in detail herein.

Briefly, formulation of the pharmaceutical compositions of the present invention will depend upon the route chosen for administration. The pharmaceutical compositions utilized in this invention can be administered by various routes including both enteral and parenteral routes, including oral, intravenous, intramuscular, subcutaneous, inhalation, topical, sublingual, rectal, intra-arterial, intramedullary, intrathecal, intraventricular, transmucosal, transdermal, intranasal, intraperitoneal, intrapulmonary, and intrauterine.

Oral dosage forms can be formulated as tablets, pills, dragees, capsules, liquids, gels, syrups, slurries, suspensions, and the like, for ingestion by the patient.

Solid formulations of the compositions for oral administration can contain suitable carriers or excipients, such as carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, sodium carboxymethylcellulose, or microcrystalline cellulose; gums including arabic and tragacanth; proteins such as gelatin and collagen; inorganics, such as kaolin, calcium carbonate, dicalcium phosphate, sodium chloride; and other agents such as acacia and alginic acid.

Agents that facilitate disintegration and/or solubilization can be added, such as the cross-linked polyvinyl pyrrolidone, agar, alginic acid, or a salt thereof, such as sodium alginate, microcrystalline cellulose, corn starch, sodium starch glycolate, and alginic acid.

Tablet binders that can be used include acacia, methylcellulose, sodium carboxymethylcellulose, polyvinylpyrrolidone (Povidone™), hydroxypropyl methylcellulose, sucrose, starch and ethylcellulose.

Lubricants that can be used include magnesium stearates, stearic acid, silicone fluid, talc, waxes, oils, and colloidal silica.

Fillers, agents that facilitate disintegration and/or solubilization, tablet binders and lubricants, including the aforementioned, can be used singly or in combination.

Solid oral dosage forms need not be uniform throughout. For example, dragee cores can be used in conjunction with suitable coatings, such as concentrated sugar solutions, which can also contain gum arabic, talc, polyvinylpyrrolidone, carbopol gel, polyethylene glycol, and/or titanium dioxide, lacquer solutions, and suitable organic solvents or solvent mixtures.

Oral dosage forms of the present invention include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Additionally, dyestuffs or pigments can be added to the tablets or dragee coatings for product identification or to characterize the quantity of active compound, i.e., dosage.

Liquid formulations of the pharmaceutical compositions for oral (enteral) administration are prepared in water or other aqueous vehicles and can contain various suspending agents such as methylcellulose, alginates, tragacanth, pectin, kelgin, carrageenan, acacia, polyvinylpyrrolidone, and polyvinyl alcohol. The liquid formulations can also include solutions, emulsions, syrups and elixirs containing, together with the active compound(s), wetting agents, sweeteners, and coloring and flavoring agents.

The pharmaceutical compositions of the present invention can also be formulated for parenteral administration. Formulations for parenteral administration can be in the form of aqueous or non-aqueous isotonic sterile injection solutions or suspensions.

For intravenous injection, water soluble versions of the compounds of the present invention are formulated in, or if provided as a lyophilate, mixed with, a physiologically acceptable fluid vehicle, such as 5% dextrose ("D5"), physiologically buffered saline, 0.9% saline, Hanks' solution, or Ringer's solution. Intravenous formulations may include carriers, excipients or stabilizers including, without limitation, calcium, human serum albumin, citrate, acetate, calcium chloride, carbonate, and other salts.

Intramuscular preparations, e.g. a sterile formulation of a suitable soluble salt form of the compounds of the present invention, can be dissolved and administered in a pharmaceutical excipient such as Water-for-Injection, 0.9% saline, or 5% glucose solution. Alternatively, a suitable insoluble form of the compound can be prepared and administered as a suspension in an aqueous base or a pharmaceutically acceptable oil base, such as an ester of a long chain fatty acid (e.g., ethyl oleate), fatty oils such as sesame oil, triglycerides, or liposomes.

Parenteral formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like).

Aqueous injection suspensions can also contain substances that increase the viscosity of the suspension, such as sodium carboxymethyl cellulose, sorbitol, or dextran. Non-lipid polycationic amino polymers can also be used for delivery. Optionally, the suspension can also contain suitable stabilizers or agents that increase the solubility of the compounds to allow for the preparation of highly concentrated solutions.

Pharmaceutical compositions of the present invention can also be formulated to permit injectable, long-term, deposition. Injectable depot forms may be made by forming microencapsulated matrices of the compound in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in microemulsions that are compatible with body tissues.

The pharmaceutical compositions of the present invention can be administered topically.

For topical use the compounds of the present invention can also be prepared in suitable forms to be applied to the skin, or mucus membranes of the nose and throat, and can take the form of lotions, creams, ointments, liquid sprays or inhalants, drops, tinctures, lozenges, or throat paints. Such topical formulations further can include chemical compounds such as dimethylsulfoxide (DMSO) to facilitate surface penetration of the active ingredient. In other transdermal formulations, typically in patch-delivered formulations, the pharmaceutically active compound is formulated with one or more skin penetrants, such as 2-N-methyl-pyrrolidone (NMP) or Azone. A topical semi-solid ointment formulation typically contains a concentration of the active ingredient from about 1 to 20%, e.g., 5 to 10%, in a carrier such as a pharmaceutical cream base.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Inhalation formulations can also readily be formulated. For inhalation, various powder and liquid formulations can be prepared. For aerosol preparations, a sterile formulation of the compound or salt form of the compound may be used in inhalers, such as metered dose inhalers, and nebulizers. Aerosolized forms may be especially useful for treating respiratory disorders.

Alternatively, the compounds of the present invention can be in powder form for reconstitution in the appropriate pharmaceutically acceptable carrier at the time of delivery.

The pharmaceutically active compound in the pharmaceutical compositions of the present invention can be provided as the salt of a variety of acids, including but not limited to hydrochloric, sulfuric, acetic, lactic, tartaric, malic, and succinic acid. Salts tend to be more soluble in aqueous or other protonic solvents than are the corresponding free base forms.

After pharmaceutical compositions have been prepared, they are packaged in an appropriate container and labeled for treatment of an indicated condition.

The active compound will be present in an amount effective to achieve the intended purpose. The determination of an effective dose is well within the capability of those skilled in the art.

A "therapeutically effective dose" refers to that amount of active ingredient, for example BSP polypeptide, fusion protein, or fragments thereof, antibodies specific for BSP, agonists, antagonists or inhibitors of BSP, which ameliorates the signs or symptoms of the disease or prevents progression thereof; as would be understood in the medical arts, cure, although desired, is not required.

The therapeutically effective dose of the pharmaceutical agents of the present invention can be estimated initially by in vitro tests, such as cell culture assays, followed by assay in model animals, usually mice, rats, rabbits, dogs, or pigs. The animal model can also be used to determine an initial preferred concentration range and route of administration.

For example, the ED50 (the dose therapeutically effective in 50% of the population) and LD50 (the dose lethal to 50% of the population) can be determined in one or more cell culture of animal model systems. The dose ratio of toxic to therapeutic effects is the therapeutic index, which can be expressed as LD50/ED50. Pharmaceutical compositions that exhibit large therapeutic indices are preferred.

The data obtained from cell culture assays and animal studies are used in formulating an initial dosage range for human use, and preferably provide a range of circulating concentrations that includes the ED50 with little or no toxicity. After administration, or between successive administrations, the circulating concentration of active agent varies within this range depending upon pharmacokinetic factors well-known in the art, such as the dosage form employed, sensitivity of the patient, and the route of administration.

The exact dosage will be determined by the practitioner, in light of factors specific to the subject requiring treatment. Factors that can be taken into account by the practitioner include the severity of the disease state, general health of the subject, age, weight, gender of the subject, diet, time and frequency of administration, drug combination(s), reaction sensitivities, and tolerance/response to therapy. Long-acting pharmaceutical compositions can be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Where the therapeutic agent is a protein or antibody of the present invention, the therapeutic protein or antibody agent typically is administered at a daily dosage of 0.01 mg to 30 mg/kg of body weight of the patient (e.g., 1 mg/kg to 5 mg/kg). The pharmaceutical formulation can be administered in multiple doses per day, if desired, to achieve the total desired daily dose.

Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Conventional methods, known to those of ordinary skill in the art of medicine, can be used to administer the pharmaceutical formulation(s) of the present invention to the patient. The pharmaceutical compositions of the present invention can be administered alone, or in combination with other therapeutic agents or interventions.

Therapeutic Methods

The present invention further provides methods of treating subjects having defects in a gene of the invention, e.g., in expression, activity, distribution, localization, and/or solubility, which can manifest as a disorder of breast finction. As used herein, "treating" includes all medically-acceptable types of therapeutic intervention, including palliation and prophylaxis (prevention) of disease. The term "treating" encompasses any improvement of a disease, including minor improvements. These methods are discussed below.

Gene Therapy and Vaccines

The isolated nucleic acids of the present invention can also be used to drive in vivo expression of the polypeptides of the present invention. In vivo expression can be driven from a vector, typically a viral vector, often a vector based upon a replication incompetent retrovirus, an adenovirus, or an adeno-associated virus (AAV), for purpose of gene therapy. In vivo expression can also be driven from signals endogenous to the nucleic acid or from a vector, often a plasmid vector, such as pVAX1 (Invitrogen, Carlsbad, Calif., USA), for purpose of "naked" nucleic acid vaccination, as further described in U.S. Pat. Nos. 5,589,466; 5,679,647; 5,804,566; 5,830,877; 5,843,913; 5,880,104; 5,958,891; 5,985,847; 6,017,897; 6,110,898; and 6,204,250, the disclosures of which are incorporated herein by reference in their entireties. For cancer therapy, it is preferred that the vector also be tumor-selective. See, e.g., Doronin et al., *J. Virol.* 75: 3314–24 (2001).

In another embodiment of the therapeutic methods of the present invention, a therapeutically effective amount of a pharmaceutical composition comprising a nucleic acid of the present invention is administered. The nucleic acid can be delivered in a vector that drives expression of a BSP, fusion protein, or fragment thereof, or without such vector. Nucleic acid compositions that can drive expression of a BSP are administered, for example, to complement a deficiency in the native BSP, or as DNA vaccines. Expression vectors derived from virus, replication deficient retroviruses, adenovirus, adeno-associated (AAV) virus, herpes virus, or vaccinia virus can be used as can plasmids. See, e.g., Cid-Arregui, supra. In a preferred embodiment, the nucleic acid molecule encodes a BSP having the amino acid sequence of SEQ ID NO: 82 through 137, or a fragment, fusion protein, allelic variant or homolog thereof.

In still other therapeutic methods of the present invention, pharmaceutical compositions comprising host cells that express a BSP, fusions, or fragments thereof can be administered. In such cases, the cells are typically autologous, so as to circumvent xenogeneic or allotypic rejection, and are administered to complement defects in BSP production or activity. In a preferred embodiment, the nucleic acid molecules in the cells encode a BSP having the amino acid sequence of SEQ ID NO: 82 through 137, or a fragment, fusion protein, allelic variant or homolog thereof.

Antisense Administration

Antisense nucleic acid compositions, or vectors that drive expression of a BSG antisense nucleic acid, are administered to downregulate transcription and/or translation of a BSG in circumstances in which excessive production, or production of aberrant protein, is the pathophysiologic basis of disease.

Antisense compositions useful in therapy can have a sequence that is complementary to coding or to noncoding regions of a BSG. For example, oligonucleotides derived from the transcription initiation site, e.g., between positions −10 and +10 from the start site, are preferred.

Catalytic antisense compositions, such as ribozymes, that are capable of sequence-specific hybridization to BSG transcripts, are also useful in therapy. See, e.g., Phylactou, *Adv. Drug Deliv. Rev.* 44(2–3): 97–108 (2000); Phylactou et al., *Hum. Mol. Genet.* 7(10): 1649–53 (1998); Rossi, *Ciba Found. Symp.* 209: 195–204 (1997); and Sigurdsson et al., *Trends Biotechnol.* 13(8): 286–9 (1995), the disclosures of which are incorporated herein by reference in their entireties.

Other nucleic acids useful in the therapeutic methods of the present invention are those that are capable of triplex helix formation in or near the BSG genomic locus. Such triplexing oligonucleotides are able to inhibit transcription. See, e.g., Intody et al., *Nucleic Acids Res.* 28(21): 4283–90 (2000); McGuffie et al., *Cancer Res.* 60(14): 3790–9 (2000), the disclosures of which are incorporated herein by reference. Pharmaceutical compositions comprising such triplex forming oligos (TFOs) are administered in circumstances in which excessive production, or production of aberrant protein, is a pathophysiologic basis of disease.

In a preferred embodiment, the antisense molecule is derived from a nucleic acid molecule encoding a BSP, preferably a BSP comprising an amino acid sequence of SEQ ID NO: 82 through 137, or a fragment, allelic variant or homolog thereof. In a more preferred embodiment, the antisense molecule is derived from a nucleic acid molecule having a nucleotide sequence of SEQ ID NO: 1 through 81, or a part, allelic variant, substantially similar or hybridizing nucleic acid thereof.

Polypeptide Administration

In one embodiment of the therapeutic methods of the present invention, a therapeutically effective amount of a pharmaceutical composition comprising a BSP, a fusion protein, fragment, analog or derivative thereof is administered to a subject with a clinically-significant BSP defect.

Protein compositions are administered, for example, to complement a deficiency in native BSP. In other embodiments, protein compositions are administered as a vaccine to elicit a humoral and/or cellular immune response to BSP. The immune response can be used to modulate activity of BSP or, depending on the immunogen, to immunize against aberrant or aberrantly expressed forms, such as mutant or inappropriately expressed isoforms. In yet other embodiments, protein fusions having a toxic moiety are administered to ablate cells that aberrantly accumulate BSP.

In a preferred embodiment, the polypeptide is a BSP comprising an amino acid sequence of SEQ ID NO: 82 through 137, or a fusion protein, allelic variant, homolog, analog or derivative thereof. In a more preferred embodiment, the polypeptide is encoded by a nucleic acid molecule having a nucleotide sequence of SEQ ID NO: 1 through 81, or a part, allelic variant, substantially similar or hybridizing nucleic acid thereof.

Antibody, Agonist and Antagonist Administration

In another embodiment of the therapeutic methods of the present invention, a therapeutically effective amount of a pharmaceutical composition comprising an antibody (including fragment or derivative thereof) of the present invention is administered. As is well-known, antibody compositions are administered, for example, to antagonize activity of BSP, or to target therapeutic agents to sites of BSP presence and/or accumulation. In a preferred embodiment, the antibody specifically binds to a BSP comprising an amino acid sequence of SEQ ID NO: 82 through 137, or a fusion protein, allelic variant, homolog, analog or derivative thereof. In a more preferred embodiment, the antibody specifically binds to a BSP encoded by a nucleic acid molecule having a nucleotide sequence of SEQ ID NO: 1 through 81, or a part, allelic variant, substantially similar or hybridizing nucleic acid thereof.

The present invention also provides methods for identifying modulators which bind to a BSP or have a modulatory effect on the expression or activity of a BSP. Modulators which decrease the expression or activity of BSP (antagonists) are believed to be useful in treating breast cancer. Such screening assays are known to those of skill in the art and include, without limitation, cell-based assays and cell-free assays. Small molecules predicted via computer imaging to specifically bind to regions of a BSP can also be designed, synthesized and tested for use in the imaging and treatment of breast cancer. Further, libraries of molecules can be screened for potential anticancer agents by assessing the ability of the molecule to bind to the BSPs identified herein. Molecules identified in the library as being capable of binding to a BSP are key candidates for further evaluation for use in the treatment of breast cancer. In a preferred embodiment, these molecules will downregulate expression and/or activity of a BSP in cells.

In another embodiment of the therapeutic methods of the present invention, a pharmaceutical composition comprising a non-antibody antagonist of BSP is administered. Antagonists of BSP can be produced using methods generally known in the art. In particular, purified BSP can be used to screen libraries of pharmaceutical agents, often combinatorial libraries of small molecules, to identify those that specifically bind and antagonize at least one activity of a BSP.

In other embodiments a pharmaceutical composition comprising an agonist of a BSP is administered. Agonists can be identified using methods analogous to those used to identify antagonists.

In a preferred embodiment, the antagonist or agonist specifically binds to and antagonizes or agonizes, respectively, a BSP comprising an amino acid sequence of SEQ ID NO: 82 through 137, or a fusion protein, allelic variant, homolog, analog or derivative thereof. In a more preferred embodiment, the antagonist or agonist specifically binds to and antagonizes or agonizes, respectively, a BSP encoded by a nucleic acid molecule having a nucleotide sequence of SEQ ID NO: 1 through 81, or a part, allelic variant, substantially similar or hybridizing nucleic acid thereof.

Targeting Breast Tissue

The invention also provides a method in which a polypeptide of the invention, or an antibody thereto, is linked to a therapeutic agent such that it can be delivered to the breast or to specific cells in the breast. In a preferred embodiment, an anti-BSP antibody is linked to a therapeutic agent and is administered to a patient in need of such therapeutic agent. The therapeutic agent may be a toxin, if breast tissue needs to be selectively destroyed. This would be useful for targeting and killing breast cancer cells. In another embodiment, the therapeutic agent may be a growth or differentiation factor, which would be useful for promoting breast cell function.

In another embodiment, an anti-BSP antibody may be linked to an imaging agent that can be detected using, e.g., magnetic resonance imaging, CT or PET. This would be useful for determining and monitoring breast function, identifying breast cancer tumors, and identifying noncancerous breast diseases.

EXAMPLES

Example 1

Gene Expression analysis

BSGs were identified by a systematic analysis of gene expression data in the LIFESEQ® Gold database available from Incyte Genomics Inc (Palo Alto, Calif.) using the data mining software package CLASP™ (Candidate Lead Automatic Search Program). CLASP™ is a set of algorithms that interrogate Incyte's database to identify genes that are both specific to particular tissue types as well as differentially expressed in tissues from patients with cancer. LifeSeq® Gold contains information about which genes are expressed in various tissues in the body and about the dynamics of expression in both normal and diseased states. CLASP™ first sorts the LifeSeq® Gold database into defined tissue types, such as breast, ovary and prostate. CLASP™ categorizes each tissue sample by disease state. Disease states include "healthy," "cancer," "associated with cancer," "other disease" and "other." Categorizing the disease states improves our ability to identify tissue and cancer-specific molecular targets. CLASP™ then performs a simultaneous parallel search for genes that are expressed both (1) selectively in the defined tissue type compared to other tissue types and (2) differentially in the "cancer" disease state compared to the other disease states affecting the same, or different, tissues. This sorting is accomplished by using mathematical and statistical filters that specify the minimum change in expression levels and the minimum frequency that the differential expression pattern must be observed across the tissue samples for the gene to be considered statistically significant. The CLASP™ algorithm quantifies the relative abundance of a particular gene in each tissue type and in each disease state.

To find the BSGs of this invention, the following specific CLASP™ profiles were utilized: tissue-specific expression (CLASP 1), detectable expression only in cancer tissue (CLASP 2), highest differential expression for a given cancer (CLASP 4); differential expression in cancer tissue (CLASP 5), and. cDNA libraries were divided into 60 unique tissue types (early versions of LifeSeq® had 48 tissue types). Genes or ESTs were grouped into "gene bins," where each bin is a cluster of sequences grouped together where they share a common contig. The expression level for each gene bin was calculated for each tissue type. Differential expression significance was calculated with rigorous statistical significant testing taking into account variations in sample size and relative gene abundance in different libraries and within each library (for the equations used to determine statistically significant expression see Audic and Claverie "The significance of digital gene expression profiles," Genome Res 7(10): 986–995 (1997), including Equation 1 on page 987 and Equation 2 on page 988, the contents of which are incorporated by reference). Differentially expressed tissue-specific genes were selected based on the percentage abundance level in the targeted tissue versus all the other tissues (tissue-specificity). The expression levels for each gene in libraries of normal tissues or non-tumor tissues from cancer patients were compared with the expression levels in tissue libraries associated with tumor or disease (cancer-specificity). The results were analyzed for statistical significance.

The selection of the target genes meeting the rigorous CLASP™ profile criteria were as follows:

(a) CLASP 1: tissue-specific expression: To qualify as a CLASP 1 candidate, a gene must exhibit statistically significant expression in the tissue of interest compared to all other tissues. Only if the gene exhibits such differential expression with a 90% of confidence level is it selected as a CLASP 1 candidate.

(b) CLASP 2: detectable expression only in cancer tissue: To qualify as a CLASP 2 candidate, a gene must exhibit detectable expression in tumor tissues and undetectable expression in libraries from normal individuals and libraries from normal tissue obtained from diseased patients. In addition, such a gene must also exhibit further specificity for the tumor tissues of interest.

(c) CLASP 5: differential expression in cancer tissue: To qualify as a CLASP 5 candidate, a gene must be differentially expressed in tumor libraries in the tissue of interest compared to normal libraries for all tissues. Only if the gene exhibits such differential expression with a 90% of confidence level is it selected as a CLASP 5 candidate.

DEX0269 CLASP expression level for SEQ ID NO: 1–80 are listed below:

| | | | | | | | | | |
|---|---|---|---|---|---|---|---|---|---|
| DEX0269_28 | SEQ ID NO: 28 | | | GLB | .0139 | SPL | .0313 | | |
| DEX0269_29 | SEQ ID NO: 29 | | | GLB | .0139 | SPL | .0313 | | |
| DEX0269_30 | SEQ ID NO: 30 | | | CON | .0011 | LIV | .0019 | | |
| DEX0269_31 | SEQ ID NO: 31 | CON | .0011 | LIV | .0019 | | | | |
| DEX0269_32 | SEQ ID NO: 32 | INL | .0006 | OVR | .001 | CON | .0011 | LNG | .0011 |
| DEX0269_33 | SEQ ID NO: 33 | INL | .0006 | OVR | .001 | CON | .0011 | LNG | .0011 |
| DEX0269_34 | SEQ ID NO: 34 | UTR | .0013 | PRO | .0017 | OVR | .0021 | ADR | .0045 |
| DEX0269_35 | SEQ ID NO: 35 | UTR | .0013 | PRO | .0017 | OVR | .0021 | ADR | .0045 |
| DEX0269_36 | SEQ ID NO: 36 | THR | .0091 | BMR | .0129 | LMN | .0139 | | |
| DEX0269_38 | SEQ ID NO: 38 | PAN | .0047 | NOS | .0073 | GLB | .0139 | | |
| DEX0269_42 | SEQ ID NO: 42 | CON | .0045 | BLD | .008 | | | | |
| DEX0269_44 | SEQ ID NO: 44 | LNG | .0039 | | | | | | |
| DEX0269_45 | SEQ ID NO: 45 | LNG | .0039 | | | | | | |
| DEX0269_49 | SEQ ID NO: 49 | INL | .0006 | MAN | .0009 | LMN | .0028 | | |
| DEX0269_51 | SEQ ID NO: 51 | BLV | .0016 | PRO | .0017 | MAN | .0019 | PNS | .0023 |
| DEX0269_53 | SEQ ID NO: 53 | BLD | .0016 | | | | | | |
| DEX0269_54 | SEQ ID NO: 54 | SPL | .0042 | PAN | .0071 | MAN | .0132 | LMN | .0167 |
| DEX0269_56 | SEQ ID NO: 56 | CRD | .0068 | OVR | .0092 | THR | .0136 | URE | .0225 |
| DEX0269_59 | SEQ ID NO: 59 | OVR | .0021 | PAN | .0024 | CON | .0045 | LIV | .0057 |
| DEX0269_60 | SEQ ID NO: 60 | OVR | .0021 | PAN | .0024 | CON | .0045 | LIV | .0057 |
| DEX0269_61 | SEQ ID NO: 61 | OVR | .001 | CON | .0011 | UNC | .004 | | |
| DEX0269_62 | SEQ ID NO: 62 | OVR | .001 | CON | .0011 | UNC | .004 | | |
| DEX0269_63 | SEQ ID NO: 63 | INL | .0032 | LNG | .0067 | | | | |
| DEX0269_65 | SEQ ID NO: 65 | CRD | .0023 | | | | | | |
| DEX0269_66 | SEQ ID NO: 66 | CRD | .0023 | | | | | | |
| DEX0269_69 | SEQ ID NO: 69 | SAG | .079 | SAG | .079 | PIT | .3246 | PIT | .3246 |
| DEX0269_70 | SEQ ID NO: 70 | SAG | .079 | SAG | .079 | PIT | .3246 | PIT | .3246 |
| DEX0269_77 | SEQ ID NO: 77 | PRO | .0011 | PAN | .0012 | BRN | .0017 | LMN | .0028 |
| DEX0269_79 | SEQ ID NO: 79 | CRD | .0023 | MAM | .0024 | FAL | .0063 | NOS | .0073 |
| DEX0269_80 | SEQ ID NO: 80 | INS | .001 | KID | .0013 | BLD | .0032 | INL | .0032 |

Abbreviations for tissues:
BLO Blood; BRN Brain; CON Connective Tissue; CRD Heart; FTS Fetus; INL Intestine, Large; INS Intestine, Small; KID Kidney; LIV Liver; LNG Lung; MAM Breast; MSL Muscles; NRV Nervous Tissue; OVR Ovary; PRO Prostate; STO Stomach; THR Thyroid Gland; TNS Tonsil/Adenoids; UTR Uterus

Example 2

Relative Quantitation of Gene Expression

Real-Time quantitative PCR with fluorescent Taqman probes is a quantitation detection system utilizing the 5'–3' nuclease activity of Taq DNA polymerase. The method uses an internal fluorescent oligonucleotide probe (Taqman) labeled with a 5' reporter dye and a downstream, 3' quencher dye. During PCR, the 5'–3' nuclease activity of Taq DNA polymerase releases the reporter, whose fluorescence can then be detected by the laser detector of the Model 7700 Sequence Detection System (PE Applied Biosystems, Foster City, Calif., USA). Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH), ATPase, or 18S ribosomal RNA (rRNA) is used as this endogenous control. To calculate relative quantitation between all the samples studied, the target RNA levels for one sample were used as the basis for comparative results (calibrator). Quantitation relative to the "calibrator" can be obtained using the standard curve method or the comparative method (User Bulletin #2: ABI PRISM 7700 Sequence Detection System).

The tissue distribution and the level of the target gene are evaluated for every sample in normal and cancer tissues. Total RNA is extracted from normal tissues, cancer tissues, and from cancers and the corresponding matched adjacent tissues. Subsequently, first strand cDNA is prepared with reverse transcriptase and the polymerase chain reaction is done using primers and Taqman probes specific to each target gene. The results are analyzed using the ABI PRISM 7700 Sequence Detector. The absolute numbers are relative levels of expression of the target gene in a particular tissue compared to the calibrator tissue.

One of ordinary skill can design appropriate primers. The relative levels of expression of the BSNA versus normal tissues and other cancer tissues can then be determined. All the values are compared to a normal tissue (calibrator). These RNA samples are commercially available pools, originated by pooling samples of a particular tissue from different individuals.

The relative levels of expression of the BSNA in pairs of matching samples and 1 cancer and 1 normal/normal adjacent of tissue may also be determined. All the values are compared to a normal tissue (calibrator). A matching pair is formed by mRNA from the cancer sample for a particular tissue and mRNA from the normal adjacent sample for that same tissue from the same individual.

In the analysis of matching samples, BSNAs show a high degree of tissue specificity for the tissue of interest. These results confirm the tissue specificity results obtained with normal pooled samples.

Further, the level of mRNA expression in cancer samples and the isogenic normal adjacent tissue from the same individual are compared. This comparison provides an indication of specificity for the cancer stage (e.g. higher levels of mRNA expression in the cancer sample compared to the normal adjacent).

Altogether, the high level of tissue specificity, plus the mRNA overexpression in matching samples tested are indicative of SEQ ID NO: 1 through 81 being diagnostic markers for cancer.

The chromosomal locations were determined for several of the sequences. Specifically:

DEX0269_6 chromosome 1
DEX0269_10 chromosome 14
DEX0269_11 chromosome 1
DEX0269_28 chromosome 9
DEX0269_29 chromosome 9
DEX0269_34 chromosome 5
DEX0269_39 chromosome 11
DEX0269_40 chromosome 3
DEX0269_43 chromosome 1
DEX0269_46 chromosome 10
DEX0269_47 chromosome 10
DEX0269_52 chromosome 12
DEX0269_53 chromosome 9
DEX0269_54 chromosome 3
DEX0269_55 chromosome 3
DEX0269_56 chromosome 3
DEX0269_62 chromosome 3
DEX0269_64 chromosome 2
DEX0269_71 chromosome 3
DEX0269_72 chromosome X
DEX0269_75 chromosome 3
DEX0269_77 chromosome 2
DEX0269_80 chromosome 8
DEX0269_81 chromosome 8

Many of the nucleotide sequences found from RNA subtractions were extended. The source nucleotide and predicted amino acid sequences are listed below:

| | | |
|---|---|---|
| DEX0269_1 | DEX0121_1 | DEX0269_82 |
| DEX0269_2 | DEX0121_2 | DEX0269_83 |
| DEX0269_3 | DEX0121_3 | DEX0269_84 |
| DEX0269_4 | DEX0121_4 | DEX0269_85 |
| DEX0269_5 | DEX0121_5 | |
| DEX0269_6 | DEX0121_6 | DEX0269_86 |
| DEX0269_7 | DEX0121_7 | DEX0269_87 |
| DEX0269_8 | DEX0121_8 | DEX0269_88 |
| DEX0269_9 | DEX0121_9 | |
| DEX0269_10 | DEX0121_10 | DEX0269_89 |
| DEX0269_11 | DEX0121_11 | DEX0269_90 |
| DEX0269_12 | DEX0121_12 | DEX0269_91 |
| DEX0269_13 | DEX0121_13 | DEX0269_92 |
| DEX0269_14 | DEX0121_14 | DEX0269_93 |
| DEX0269_15 | DEX0121_15 | DEX0269_94 |
| DEX0269_16 | DEX0121_16 | DEX0269_95 |
| DEX0269_17 | DEX0121_17 | DEX0269_96 |
| DEX0269_18 | DEX0121_18 | DEX0269_97 |
| DEX0269_19 | DEX0121_19 | DEX0269_98 |
| DEX0269_20 | DEX0121_20 | |
| DEX0269_21 | DEX0121_21 | DEX0269_99 |
| DEX0269_22 | DEX0121_22 | DEX0269_100 |
| DEX0269_23 | DEX0121_23 | DEX0269_101 |
| DEX0269_24 | DEX0121_24 | |
| DEX0269_25 | DEX0121_25 | DEX0269_102 |
| DEX0269_26 | DEX0121_26 | |
| DEX0269_27 | DEX0121_27 | DEX0269_103 |
| DEX0269_28 | DEX0132_1 | DEX0269_104 |
| DEX0269_29 | flex DEX0132_1 | DEX0269_105 |
| DEX0269_30 | DEX0132_2 | DEX0269_106 |
| DEX0269_31 | flex DEX0132_2 | |
| DEX0269_32 | DEX0132_3 | DEX0269_107 |
| DEX0269_33 | flex DEX0132_3 | DEX0269_108 |
| DEX0269_34 | DEX0132_4 | DEX0269_109 |
| DEX0269_35 | flex DEX0132_4 | |
| DEX0269_36 | DEX0132_5 | DEX0269_110 |
| DEX0269_37 | flex DEX0132_5 | |
| DEX0269_38 | DEX0132_6 | DEX0269_111 |
| DEX0269_39 | flex DEX0132_6 | |
| DEX0269_40 | DEX0132_7 | DEX0269_112 |
| DEX0269_41 | flex DEX0132_7 | |
| DEX0269_42 | DEX0132_8 | DEX0269_113 |
| DEX0269_43 | flex DEX0132_8 | DEX0269_114 |
| DEX0269_44 | DEX0132_9 | DEX0269_115 |
| DEX0269_45 | flex DEX0132_9 | |
| DEX0269_46 | DEX0132_10 | DEX0269_116 |
| DEX0269_47 | flex DEX0132_10 | |
| DEX0269_48 | DEX0132_11 | DEX0269_117 |
| DEX0269_49 | DEX0132_12 | DEX0269_118 |
| DEX0269_50 | flex DEX0132_12 | |
| DEX0269_51 | DEX0132_13 | DEX0269_119 |
| DEX0269_52 | flex DEX0132_13 | DEX0269_120 |
| DEX0269_53 | DEX0132_14 | DEX0269_121 |
| DEX0269_54 | DEX0132_15 | DEX0269_122 |
| DEX0269_55 | flex DEX0132_15 | |
| DEX0269_56 | DEX0132_16 | |
| DEX0269_57 | flex DEX0132_16 | |
| DEX0269_58 | DEX0132_17 | |
| DEX0269_59 | DEX0132_18 | DEX0269_123 |
| DEX0269_60 | flex DEX0132_18 | |
| DEX0269_61 | DEX0132_19 | DEX0269_124 |
| DEX0269_62 | flex DEX0132_19 | DEX0269_125 |
| DEX0269_63 | DEX0132_20 | DEX0269_126 |
| DEX0269_64 | flex DEX0132_20 | DEX0269_127 |
| DEX0269_65 | DEX0132_21 | DEX0269_128 |
| DEX0269_66 | flex DEX0132_21 | |
| DEX0269_67 | DEX0132_22 | DEX0269_129 |
| DEX0269_68 | flex DEX0132_22 | |
| DEX0269_69 | DEX0132_23 | DEX0269_130 |
| DEX0269_70 | flex DEX0132_23 | |
| DEX0269_71 | DEX0132_24 | DEX0269_131 |
| DEX0269_72 | flex DEX0132_24 | |
| DEX0269_73 | DEX0132_25 | DEX0269_132 |
| DEX0269_74 | DEX0132_26 | DEX0269_133 |
| DEX0269_75 | flex DEX0132_26 | |
| DEX0269_76 | DEX0132_27 | DEX0269_134 |
| DEX0269_77 | DEX0132_28 | DEX0269_135 |
| DEX0269_78 | DEX0132_29 | DEX0269_136 |
| DEX0269_79 | flex DEX0132_29 | |
| DEX0269_80 | DEX0132_30 | DEX0269_137 |
| DEX0269_81 | flex DEX0132_30 | |

The predicted antigenicity for the amino acid sequences is as follows:

| positions | AI avg | length |
|---|---|---|
| DEX0269_85 Antigenicity Index(Jameson-Wolf) | | |
| 51–99 | 1.19 | 49 |
| DEX0269_89 Antigenicity Index(Jameson-Wolf) | | |
| 10–43 | 1.04 | 34 |
| DEX0269_92 Antigenicity Index(Jameson-Wolf) | | |
| 101–126 | 1.08 | 26 |
| DEX0269_93 Antigenicity Index(Jameson-Wolf) | | |
| 41–50 | 1.39 | 10 |
| 57–66 | 1.03 | 10 |
| DEX0269_94 Antigenicity Index(Jameson-Wolf) | | |
| 11–38 | 1.11 | 28 |
| 45–67 | 1.00 | 23 |
| DEX0269_97 Antigenicity Index(Jameson-Wolf) | | |
| 3–20 | 1.02 | 18 |
| DEX0269_103 Antigenicity Index(Jameson-Wolf) | | |
| 89–106 | 1.11 | 18 |

-continued

| positions | AI avg | length |
|---|---|---|
| DEX0269_106 Antigenicity Index(Jameson-Wolf) | | |
| 15–32 | 1.10 | 18 |
| DEX0269_108 Antigenicity Index(Jameson-Wolf) | | |
| 256–266 | 1.25 | 11 |
| 271–293 | 1.20 | 23 |
| 224–242 | 1.19 | 19 |
| 107–146 | 1.18 | 40 |
| 301–323 | 1.07 | 23 |
| 9–100 | 1.04 | 92 |
| 527–543 | 1.04 | 17 |
| 581–596 | 1.02 | 16 |
| 340–374 | 1.02 | 35 |
| 180–213 | 1.00 | 34 |
| DEX0269_118 Antigenicity Index(Jameson-Wolf) | | |
| 5–14 | 1.21 | 10 |
| DEX0269_120 Antigenicity Index(Jameson-Wolf) | | |
| 25–36 | 1.20 | 12 |
| DEX0269_125 Antigenicity Index(Jameson-Wolf) | | |
| 39–53 | 1.29 | 15 |
| 20–32 | 1.06 | 13 |
| DEX0269_135 Antigenicity Index(Jameson-Wolf) | | |
| 32–58 | 1.04 | 27 |
| 14–25 | 1.01 | 12 |
| DEX0269_137 Antigenicity Index(Jameson-Wolf) | | |
| 5–25 | 1.25 | 21 |

The predicted helicity for the amino acid sequences is listed below:

| | | |
|---|---|---|
| DEX0269_86 | PredHel = 5 | Topology = o15-37i58-80o90-112i148-170o185-207i |
| DEX0269_96 | PredHel = 2 | Topology = i72-94o124-146i |
| DEX0269_98 | PredHel = 1 | Topology = i21-38o |
| DEX0269_113 | PredHel = 1 | Topology = o15-37i |
| DEX0269_118 | PredHel = 1 | Topology = i52-74o |
| DEX0269_119 | PredHel = 1 | Topology = i5-22o |
| DEX0269_121 | PredHel = 1 | Topology = i13-32o |
| DEX0269_122 | PredHel = 1 | Topology = o10-32i |
| DEX0269_124 | PredHel = 1 | Topology = o20-39i |
| DEX0269_132 | PredHel = 1 | Topology = o10-29i |
| DEX0269_133 | PredHel = 1 | Topology = o24-46i |

Example 3

Protein Expression

The BSNA is amplified by polymerase chain reaction (PCR) and the amplified DNA fragment encoding the BSNA is subcloned in pET-21d for expression in *E. coli*. In addition to the BSNA coding sequence, codons for two amino acids, Met-Ala, flanking the $NH_2$-terminus of the coding sequence of BSNA, and six histidines, flanking the COOH-terminus of the coding sequence of BSNA, are incorporated to serve as initiating Met/restriction site and purification tag, respectively.

An over-expressed protein band of the appropriate molecular weight may be observed on a Coomassie blue stained polyacrylamide gel. This protein band is confirmed by Western blot analysis using monoclonal antibody against 6× Histidine tag.

Large-scale purification of BSP was achieved using cell paste generated from 6-liter bacterial cultures, and purified using immobilized metal affinity chromatography (IMAC). Soluble fractions that had been separated from total cell lysate were incubated with a nickle chelating resin. The column was packed and washed with five column volumes of wash buffer. BSP was eluted stepwise with various concentration imidazole buffers.

Example 4

Protein Fusions

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 2, is ligated into this BamHI site. Note that the polynucleotide is cloned without a stop codon, otherwise a fusion protein will not be produced. If the naturally occurring signal sequence is used to produce the secreted protein, pC4 does not need a second signal peptide. Alternatively, if the naturally occurring signal sequence is not used, the vector can be modified to include a heterologous signal sequence. See, e.g., WO 96/34891.

Example 5

Production of an Antibody from a Polypeptide

In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100, $\mu$g/ml of streptomycin. The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al., *Gastroenterology* 80: 225–232 (1981).

The hybridoma cells obtained through such a selection are then assayed to identify clones which secrete antibodies capable of binding the polypeptide. Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein specific antibody and can be used to immunize an animal to induce formation of further protein-specific antibodies. Using the Jameson-Wolf methods the following epitopes were predicted. (Jameson and Wolf, CABIOS, 4(1), 181–186, 1988, the contents of which are incorporated by reference).

Example 6

Method of Determining Alterations in a Gene Corresponding to a Polynucleotide RNA is isolated from individual patients or from a family of individuals that have a phenotype of interest. cDNA is then generated from these RNA samples using protocols known in the art. See, Sambrook (2001), supra. The cDNA is then used as a template for PCR, employing primers surrounding regions of interest in SEQ ID NO: 1 through 81. Suggested PCR conditions consist of 35 cycles at 95° C. for 30 seconds; 60–120 seconds at 52–58° C.; and 60–120 seconds at 70° C., using buffer solutions described in Sidransky et al., *Science* 252(5006): 706–9 (1991). See also Sidransky et al., *Science* 278(5340): 1054–9 (1997).

PCR products are then sequenced using primers labeled at their 5' end with T4 polynucleotide kinase, employing SequiTherm Polymnerase. (Epicentre Technologies). The intron-exon borders of selected exons is also determined and genomic PCR products analyzed to confirm the results. PCR products harboring suspected mutations are then cloned and sequenced to validate the results of the direct sequencing. PCR products is cloned into T-tailed vectors as described in Holton et al., *Nucleic Acids Res.,* 19: 1156 (1991) and sequenced with T7 polymerase (United States Biochemical). Affected individuals are identified by mutations not present in unaffected individuals.

Genomic rearrangements may also be determined. Genomic clones are nick-translated with digoxigenin deoxyuridine 5' triphosphate (Boehringer Manheim), and FISH is performed as described in Johnson et al., *Methods Cell Biol.* 35: 73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C-and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. Id. Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 7

Method of Detecting Abnormal Levels of a Polypeptide in a Biological Sample

Antibody-sandwich ELISAs are used to detect polypeptides in a sample, preferably a biological sample. Wells of a microtiter plate are coated with specific antibodies, at a final concentration of 0.2 to 10 μg/ml. The antibodies are either monoclonal or polyclonal and are produced by the method described above. The wells are blocked so that non-specific binding of the polypeptide to the well is reduced. The coated wells are then incubated for >2 hours at RT with a sample containing the polypeptide. Preferably, serial dilutions of the sample should be used to validate results. The plates are then washed three times with deionized or distilled water to remove unbound polypeptide. Next, 50 μl of specific antibody-alkaline phosphatase conjugate, at a concentration of 25–400 ng, is added and incubated for 2 hours at room temperature. The plates are again washed three times with deionized or distilled water to remove unbound conjugate. 75 μl of 4-methylumbelliferyl phosphate (MUP) or p-nitrophenyl phosphate (NPP) substrate solution are added to each well and incubated 1 hour at room temperature.

The reaction is measured by a microtiter plate reader. A standard curve is prepared, using serial dilutions of a control sample, and polypeptide concentrations are plotted on the X-axis (log scale) and fluorescence or absorbance on the Y-axis (linear scale). The concentration of the polypeptide in the sample is calculated using the standard curve.

Example 8

Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1, μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 μg/kg/hour to about 50 mg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The secreted polypeptide is also suitably administered by sustained-release systems. Suitable examples of sustained-release compositions include semipermeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22: 547–556 (1983)), poly (2-hydroxyethyl methacrylate) (R. Langer et al., J. Biomed. Mater. Res. 15: 167–277 (1981), and R. Langer, Chem. Tech. 12: 98–105 (1982)), ethylene vinyl acetate (R. Langer et al.) or poly-D-(−)-3-hydroxybutyric acid (EP 133,988). Sustained-release compositions also include liposomally entrapped polypeptides. Liposomes containing the secreted polypeptide are prepared by methods known per se: DE Epstein et al., Proc. Natl. Acad. Sci. USA 82: 3688–3692 (1985); Hwang et al., Proc. Natl. Acad. Sci. USA 77: 4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, the secreted polypeptide is formulated generally by mixing it at the desired degree of purity, in a unit dosage injectable form (solution, suspension, or emulsion), with a pharmaceutically acceptable carrier, I.e., one that is non-toxic to recipients at the dosages and concentrations employed and is compatible with other ingredients of the formulation.

For example, the formulation preferably does not include oxidizing agents and other compounds that are known to be deleterious to polypeptides. Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The secreted polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container (s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 9

Method of Treating Decreased Levels of the Polypeptide

It will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1–100 $\mu$g/kg of the polypeptide for six consecutive days. Preferably, the polypeptide is in the secreted form. The exact details of the dosing scheme, based on administration and formulation, are provided above.

Example 10

Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided above.

Example 11

Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks. pMV-7 (Kirschmeier, P. T. et al., DNA, 7: 219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1. Preferably, the 5' primer contains an EcoRi site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB 101, which are then plated onto agar containing kanamycin for the purpose of confirming that the vector has the gene of interest properly inserted.

The amphotropic pA317 or GP+aml2 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media.

If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 12

Method of Treatment Using Gene Therapy-In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide.

The polynucleotide of the present invention may be operatively linked to a promoter or any other genetic elements necessary for the expression of the polypeptide by the target tissue. Such gene therapy and delivery techniques and methods are known in the art, see, for example, WO 90/11092, WO 98/11779; U.S. Pat. Nos. 5,693,622; 5,705,151; 5,580,859; Tabata H. et al. (1997) Cardiovasc. Res. 35 (3): 470–479, Chao J et al. (1997) Pharmacol. Res. 35 (6): 517–522, Wolff J. A. (1997) Neuromuscul. Disord. 7 (5): 314–318, Schwartz B. et al. (1996) Gene Ther. 3 (5): 405–411, Tsurumi Y. et al. (1996) Circulation 94 (12): 3281–3290 (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772: 126–139 and Abdallah B. et al. (1995) Biol. Cell 85 (1): 1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 μg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice.

The results of the above experimentation in mice can be use to extrapolate proper dosages and other treatment parameters in humans and other animals using naked DNA.

Example 13

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40: 691–698 (1994); Carver et al., Biotechnology (NY) 11: 1263–1270 (1993); Wright et al., Biotechnology (NY) 9: 830–834 (1991); and Hoppe et al., U.S. Pat. No. 4,873,191 (1989)); retrovirus mediated gene transfer into germ lines (Van der Putten et al., Proc. Natl. Acad. Sci., USA 82: 6148–6152 (1985)), blastocysts or embryos; gene targeting in embryonic stem cells (Thompson et al., Cell 56: 313–321 (1989)); electroporation of cells or embryos (Lo, 1983, Mol Cell. Biol. 3: 1803–1814 (1983)); introduction of the polynucleotides of the invention using a gene gun (see, e.g., Ulmer et al., Science 259: 1745 (1993); introducing nucleic acid constructs into embryonic pleuripotent stem cells and transferring the stem cells back into the blastocyst; and sperm mediated gene transfer (Lavitrano et al., Cell 57: 717–723 (1989); etc. For a review of such techniques, see Gordon, "Transgenic Animals," Intl. Rev. Cytol. 115: 171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380: 64–66 (1996); Wilmut et al., Nature 385: 810813 (1997)).

The present invention provides for transgenic animals that carry the transgene in all their cells, as well as animals which carry the transgene in some, but not all their cells, I.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89: 6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265: 103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Example 14

Knock-Out Animals

Endogenous gene expression can also be reduced by inactivating or "knocking out" the gene and/or its promoter using targeted homologous recombination. (E.g., see Smithies et al., Nature 317: 230–234 (1985); Thomas & Capecchi, Cell 51: 503512 (1987); Thompson et al., Cell 5: 313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (I.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc.

The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological finction of polypeptides of the present invention, studying conditions and/or disorders associated with aberrant expression, and in screening for compounds effective in ameliorating such conditions and/or disorders.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

We claim:

1. An isolated nucleic acid molecule comprising (a) a nucleic acid molecule comprising a nucleic acid Sequence that encodes an amino acid sequence of SEQ ID NO:127;

(b) a nucleic acid molecule comprising a nucleic acid sequence of SEQ ID NO:63 or 64; or (c) a nucleic acid molecule which is an allelic variant of a nucleic acid of SEQ ID NO:63 or 64 encoding an amino acid sequence of SEQ ID NO:127;

wherein said nucleic acid molecule is detectably expressed in breast tumor tissues.

2. The nucleic acid molecule according to claim 1, wherein the nucleic acid molecule is a cDNA.

3. The nucleic acid molecule according to claim 1, wherein the nucleic acid molecule is a mammalian nucleic acid molecule.

4. The nucleic acid molecule according to claim 3, wherein the nucleic acid molecule is a human nucleic acid molecule.

5. A vector comprising the nucleic acid molecule of claim 1.

6. A host cell comprising the vector according to claim 5.

7. A method for producing a polypeptide encoded by the nucleic acid molecule according to claim 1, comprising the steps of (a) providing a host cell comprising the nucleic acid molecule operably linked to one or more expression control sequences, and (b) incubating the host cell under conditions in which the polypeptide is produced.

8. The nucleic acid molecule of claim 1 comprising a nucleic acid molecule that encodes an amino acid sequence comprieing amino acids residues 230 through 1088 of SEQ ID NO:127.

* * * * *